US012637714B2

(12) United States Patent
Lefkowitz et al.

(10) Patent No.: US 12,637,714 B2
(45) Date of Patent: May 26, 2026

(54) METHODS, AND SYSTEMS TO DETECT TRANSPLANT REJECTION

(71) Applicant: SEQUENOM, INC., San Diego, CA (US)

(72) Inventors: Roy Brian Lefkowitz, San Diego, CA (US); John Allen Tynan, San Diego, CA (US); Chen Xu, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 1372 days.

(21) Appl. No.: 17/268,732

(22) PCT Filed: Sep. 6, 2019

(86) PCT No.: PCT/US2019/050059
§ 371 (c)(1),
(2) Date: Feb. 16, 2021

(87) PCT Pub. No.: WO2020/051529
PCT Pub. Date: Mar. 12, 2020

(65) Prior Publication Data
US 2021/0301342 A1     Sep. 30, 2021

Related U.S. Application Data

(60) Provisional application No. 62/728,479, filed on Sep. 7, 2018.

(51) Int. Cl.
| | |
|---|---|
| *G16H 10/40* | (2018.01) |
| *C12Q 1/6881* | (2018.01) |
| *G16B 20/20* | (2019.01) |
| *G16B 30/10* | (2019.01) |
| *G16H 10/60* | (2018.01) |
| *G16H 50/30* | (2018.01) |
| *G16H 50/70* | (2018.01) |

(52) U.S. Cl.
CPC ........... *C12Q 1/6881* (2013.01); *G16B 20/20* (2019.02); *G16B 30/10* (2019.02); *G16H 10/40* (2018.01); *G16H 10/60* (2018.01); *G16H 50/30* (2018.01); *G16H 50/70* (2018.01); *C12Q 2600/118* (2013.01); *C12Q 2600/156* (2013.01)

(58) Field of Classification Search
CPC ........... C12Q 1/6881; C12Q 2600/118; C12Q 2600/156; C12Q 1/6883; G16B 20/20; G16B 30/10; G16H 10/40; G16H 10/60; G16H 50/30; G16H 50/70
See application file for complete search history.

(56) References Cited

U.S. PATENT DOCUMENTS

| | | | |
|---|---|---|---|
| 8,703,652 | B2 | 4/2014 | Quake et al. |
| 9,732,390 | B2 | 8/2017 | Lo et al. |
| 9,845,497 | B2 | 12/2017 | Quake et al. |
| 10,174,375 | B2 | 1/2019 | Lo et al. |
| 10,329,607 | B2 | 6/2019 | Quake et al. |
| 10,385,396 | B2 | 8/2019 | Mitchell et al. |
| 10,435,750 | B2 | 10/2019 | Goossens et al. |
| 10,494,669 | B2 | 12/2019 | Quake et al. |
| 10,526,658 | B2 | 1/2020 | Babiarz et al. |
| 10,557,172 | B2 | 2/2020 | Babiarz et al. |
| 10,570,443 | B2 | 2/2020 | Schutz et al. |
| 10,597,709 | B2 | 3/2020 | Zimmermann et al. |
| 10,793,912 | B2 | 10/2020 | Babiarz et al. |
| 10,947,582 | B2 | 3/2021 | Myers et al. |
| 10,968,479 | B2 | 4/2021 | Quake et al. |
| 11,155,872 | B2 | 10/2021 | Schutz et al. |
| 11,384,389 | B2 | 7/2022 | Quake et al. |
| 11,597,966 | B2 | 3/2023 | Quake et al. |
| 2012/0264121 | A1 * | 10/2012 | Rava ...................... G16B 30/00 702/20 |
| 2014/0127688 | A1 * | 5/2014 | Umbarger ............ C12Q 1/6881 435/6.11 |
| 2014/0336056 | A1 * | 11/2014 | Erlich .................. C12Q 1/6881 506/2 |

(Continued)

FOREIGN PATENT DOCUMENTS

| | | |
|---|---|---|
| CN | 107841548 A | 3/2018 |
| JP | 2013509883 A | 3/2013 |

(Continued)

OTHER PUBLICATIONS

US 11,525,159 B2, 12/2022, Moshkevich et al. (withdrawn)

(Continued)

*Primary Examiner* — Soren Harward
*Assistant Examiner* — Dawn Bickham
(74) *Attorney, Agent, or Firm* — Kilpatrick Townsend & Stockton LLP

(57) ABSTRACT

This application provides methods and systems for determining transplant status. In some embodiments, the method comprises obtaining a biological sample from an organ transplant recipient who has received an organ; isolating cell-free nucleic acids from the biological sample; measuring the amount of each allele of one or more polymorphic nucleic acid targets in the biological sample; identifying the donor specific allele using a computer algorithm based on the measurements of the one or more polymorphic nucleic acid targets, whereby detecting one or more donor-specific circulating cell-free nucleic acids, detecting tissue injury based on the presence or amount of said one or more donor-specific nucleic acids, thereby determining transplant status.

24 Claims, 12 Drawing Sheets

Specification includes a Sequence Listing.

(56) References Cited

U.S. PATENT DOCUMENTS

| | | | |
|---|---|---|---|
| 2016/0145682 A1* | 5/2016 | Woodward | C12Q 1/6876 |
| | | | 506/4 |
| 2018/0142296 A1 | 5/2018 | Mitchell et al. | |
| 2019/0177792 A1 | 6/2019 | Liu et al. | |
| 2019/0367972 A1 | 12/2019 | Mitchell et al. | |
| 2020/0048713 A1 | 2/2020 | De Vlaminck et al. | |
| 2021/0020314 A1 | 1/2021 | Ehrich et al. | |
| 2021/0062264 A1 | 3/2021 | Favalli | |
| 2021/0115506 A1 | 4/2021 | De Vlaminck et al. | |
| 2021/0139983 A1 | 5/2021 | Mitchell et al. | |
| 2022/0042100 A1 | 2/2022 | Zhang et al. | |
| 2022/0073989 A1 | 3/2022 | Sarwal et al. | |
| 2022/0081715 A1 | 3/2022 | Naesens et al. | |
| 2023/0203573 A1 | 6/2023 | Swenerton et al. | |
| 2023/0352144 A1 | 11/2023 | Zhang et al. | |
| 2024/0392359 A1 | 11/2024 | Gale et al. | |
| 2024/0409989 A1 | 12/2024 | Mitchell et al. | |
| 2025/0011871 A1 | 1/2025 | Clark-Langone et al. | |

FOREIGN PATENT DOCUMENTS

| | | | |
|---|---|---|---|
| WO | 2011057061 A1 | 5/2011 | |
| WO | 2015069933 A1 | 5/2015 | |
| WO | 2015138997 A1 | 9/2015 | |
| WO | 2022182878 A1 | 9/2022 | |
| WO | 2022197864 A1 | 9/2022 | |
| WO | 2023009757 A1 | 2/2023 | |
| WO | 2023043956 A1 | 3/2023 | |

OTHER PUBLICATIONS

US 11,725,234 B2, 08/2023, Mitchell et al. (withdrawn)

Ma, Lijiang, and Wendy K Chung. "Quantitative analysis of copy number variants based on real-time LightCycler PCR." Current protocols in human genetics vol. 80 7.21.1-7.21.8. Jan. 21, 2014 (Year: 2014).*

JP2021-512435 , "Office Action", May 30, 2023, 8 pages.

PCT/US2019/050059, International Preliminary Report on Patentability, Mar. 18, 2021, 10 pages.

International Search Report and Written Opinion, Dec. 13, 2019, 15 pages.

Wang et al., "An Integrative Variant Analysis Pipeline for Accurate Genotype/Haplotype Inference in Population NGS Data", Genome Research, vol. 23, No. 5, 2013, pp. 833-842.

Application No. JP2024-74763, Office Action, Mailed on Jun. 23, 2025, 2 pages.

* cited by examiner

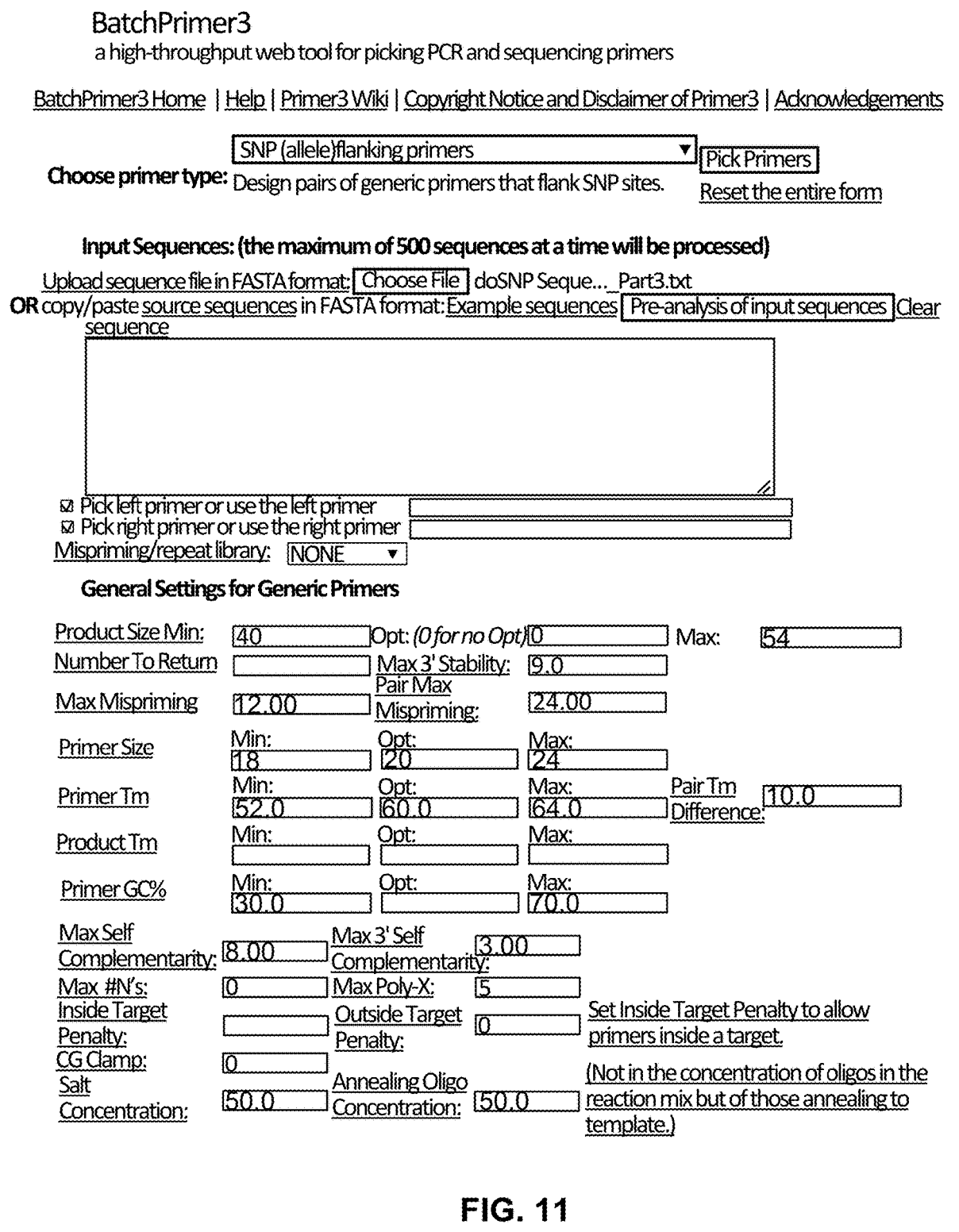

BatchPrimer3
a high-throughput web tool for picking PCR and sequencing primers BatchPrimer3 Home | Help | Primer3 Wiki | Copyright Notice and Disclaimer of Primer3 | Acknowledgements

Choose primer type: [ SNP (allele)flanking primers ▼ ] [Pick Primers]
Design pairs of generic primers that flank SNP sites.     Reset the entire form

Input Sequences: (the maximum of 500 sequences at a time will be processed)

Upload sequence file in FASTA format: [Choose File] doSNP Seque..._Part3.txt
OR copy/paste source sequences in FASTA format:Example sequences [Pre-analysis of input sequences] Clear
sequence ☑ Pick left primer or use the left primer [                    ]
☑ Pick right primer or use the right primer [                    ]
Mispriming/repeat library: [NONE ▼]

General Settings for Generic Primers

Product Size Min: [40] Opt: *(0 for no Opt)* [0] Max: [54]
Number To Return [     ] Max 3' Stability: [9.0]
Max Mispriming [12.00] Pair Max Mispriming: [24.00]

Primer Size
Min: [18]  Opt: [20]  Max: [24]

Primer Tm
Min: [52.0]  Opt: [60.0]  Max: [64.0]  Pair Tm Difference: [10.0]

Product Tm
Min: [     ]  Opt: [     ]  Max: [     ]

Primer GC%
Min: [30.0]  Opt: [     ]  Max: [70.0]

Max Self Complementarity: [8.00]  Max 3' Self Complementarity: [3.00]
Max #N's: [0]  Max Poly-X: [5]
Inside Target Penalty: [     ]  Outside Target Penalty: [0]  Set Inside Target Penalty to allow primers inside a target.
CG Clamp: [0]
Salt Concentration: [50.0]  Annealing Oligo Concentration: [50.0]  (Not in the concentration of oligos in the reaction mix but of those annealing to template.)

FIG. 11

SEQUENCE LISTING

<160> NUMBER OF SEQ ID NOS: 1342

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
aaaaactgct tgccttcttc tt                                          22

<210> SEQ ID NO 2
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tctatgggtt ctcacaactc aac                                         23

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
tggacaaaaa taccatcatc a                                           21

<210> SEQ ID NO 4
<211> LENGTH: 21
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
agatcatcct gaacataagg t                                              21

<210> SEQ ID NO 5
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
catctaaata catgaaaaag gag                                            23

<210> SEQ ID NO 6
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tcaagtatcc aggacttgtt cg                                             22

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
ggacccaaga tctgattcta gc                                             22

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
agggtgagct gttctcagga                                                20

<210> SEQ ID NO 9
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tccccagact aattatggaa aaa                                            23
```

```
<210> SEQ ID NO 10
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tcactttact gttcaccaaa cg                                          22

<210> SEQ ID NO 11
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ggattttagg gcactaggaa gg                                          22

<210> SEQ ID NO 12
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
gagagttttt aaagagtgtc gtt                                         23

<210> SEQ ID NO 13
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tgtatttgcc taaaagtaag agg                                         23

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ggcagagttc tcttgacgtg                                             20

<210> SEQ ID NO 15
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 15
cagctaaagg aaaactatta atgc                                               24

<210> SEQ ID NO 16
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
tctctttgtc tgttagggtt tt                                                 22

<210> SEQ ID NO 17
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
tcatctgtga aatagggaca cc                                                 22

<210> SEQ ID NO 18
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gctcttaaaa ctcatcccaa gc                                                 22

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
agaaattatt caggacacag aga                                                23

<210> SEQ ID NO 20
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
tcctgacaag acagttatca tct                                                23

<210> SEQ ID NO 21
<211> LENGTH: 23

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
gagaagaatg attagacctt gct                                            23

<210> SEQ ID NO 22
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
acaagagtac acgagagaaa aa                                             22

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tgatgtggaa tagtttaggt ga                                             22

<210> SEQ ID NO 24
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
tccaaaaggt aattccaata tgc                                            23

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
ggatatgccg cttttcctct                                               20

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
```
gctaagtaaa taatttggca gtt                                                    23

<210> SEQ ID NO 27
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
tcacagtgtt tctcatagtt tta                                                    23

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
cagcagctag tgttgcacta at                                                     22

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ggttcacaga gcccaagtta c                                                      21

<210> SEQ ID NO 30
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tgagtctctt actgatcctg tgac                                                   24

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gagtcactct tggggtatca                                                        20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gatgcccagc ctcttctctc                                        20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
agagatctcc gcatcctgtg                                        20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gggggccaat aactatgctc                                        20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
agtgtgatgt ttgagtgagg                                        20

<210> SEQ ID NO 36
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
gtcctatcat cttttatttc caa                                    23

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
ttccttggca ttttagtttc c                                      21

<210> SEQ ID NO 38

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
tcccatgtaa cacctttcag a                                                      21

<210> SEQ ID NO 39
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
tcacccattc ttcatactct ttg                                                    23

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40 aactttcag gtcggcagtg                                                         20

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
ggagagaatc ccttaccctt g                                                      21

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
ggaattttat tagatgttga gg                                                     22

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
```

-continued cagcccagat tttctctttc a                                                    21

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tcgaggtaaa taggcccaca                                                      20

<210> SEQ ID NO 45
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
ttcagctctt ctactctgga ctg                                                  23

<210> SEQ ID NO 46
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
tgaaacaaga gaagactgga tttg                                                 24

<210> SEQ ID NO 47
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gttatatctc ttttgtttct ctcc                                                 24

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
ttggattgtt agagaataac g                                                    21

<210> SEQ ID NO 49
<211> LENGTH: 22
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic primer"

<400> SEQUENCE: 49
tggacaagag agacttcagg ag                                               22

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gctgagcctt ttagatagtg ctg                                              23

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tccaactgga aaacacctca                                                  20

<210> SEQ ID NO 52
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
gagccacctt caagactctt tc                                               22

<210> SEQ ID NO 53
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
tttaaatctt tccagggggt tt                                               22

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
tgattctcag cctggagttt                                                  20
```

-continued

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
aggattcagc catccatctg                                                        20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tctgccatgg gaggtataga                                                        20

<210> SEQ ID NO 57
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
aaaacataat tgaacaccta gca                                                    23

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
aataggaggc tgctctatgc                                                        20

<210> SEQ ID NO 59
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
tgattcactt ccagttcttg aca                                                    23

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 60
agtgaccttg ctggtttgtg                                                    20

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
gggtaccata tgaggccagt t                                                  21

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
tcttcttccc aatgtcatgg a                                                  21

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ccaggcttcc aagattattg t                                                  21

<210> SEQ ID NO 64
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
aaggcatctc aggtgttatt tt                                                 22

<210> SEQ ID NO 65
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
cctcgctgtc cctgcatac                                                     19

<210> SEQ ID NO 66
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 66
aagtgctgac tctgttctgg                                             20

<210> SEQ ID NO 67
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
gaatatctgt ctcggaatac ca                                          22

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
gggatgtgtg atttctgaag g                                           21

<210> SEQ ID NO 69
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
gaacaacatc tatcattcat ctct                                        24

<210> SEQ ID NO 70
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
caccactcta aagtagacca ttg                                         23

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
gctttggggt tatagctgga                                             20
```

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
agatggccat tagctaggaa                                                    20

<210> SEQ ID NO 73
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
gcacatagag gtctctctct tct                                                23

<210> SEQ ID NO 74
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
ctatattaga acactcagca gcta                                               24

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
agggctgaac aaggaactga                                                    20

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
ctcatcctga gctctcgtgt a                                                  21

<210> SEQ ID NO 77
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 77
tcactcatgt tttacctttt agc                                        23

<210> SEQ ID NO 78
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
tgagtcagat tcttcataac ttt                                        23

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
tactgccaac agacaactcg                                            20

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
ttagaccgca gacctttaga a                                          21

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
ggggcagatc agaaatgttg                                            20

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
ggctgttctc aatggtgtca                                            20

<210> SEQ ID NO 83
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
ccccatatgt aacccatcac a                                    21

<210> SEQ ID NO 84
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
tctttggaag agaaatgtga ttct                                 24

<210> SEQ ID NO 85
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
ggaatgtatt tctgctgtgc tg                                   22

<210> SEQ ID NO 86
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
tcactattcc ttactccagg tga                                  23

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
ccattcacgt ggcacttttt                                      20

<210> SEQ ID NO 88
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
caccttactg cttcctgcta cc                                   22
```

-continued

```
<210> SEQ ID NO 89
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
ccaaaggctg tattatttat gc                                          22

<210> SEQ ID NO 90
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
gtgttgaagt gatgtaattc ag                                          22

<210> SEQ ID NO 91
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
tgaacatatc agctggccat t                                           21

<210> SEQ ID NO 92
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
aaagcccaga attgacttgg                                             20

<210> SEQ ID NO 93
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
caaacctcca gggtagtaga ca                                          22

<210> SEQ ID NO 94
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
        Synthetic primer"

<400> SEQUENCE: 94
ggggttcata agggaaacca                                                20

<210> SEQ ID NO 95
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 95
tctcagagca acatgtacca aaa                                            23

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 96
gcccaatcag acatcaatcc                                                20

<210> SEQ ID NO 97
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 97
gtttcccagc aaattcccta                                                20

<210> SEQ ID NO 98
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 98
tcatcaaaat ggatcataac ag                                             22

<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 99
tttggagtgg gtctcttcac t                                              21

<210> SEQ ID NO 100
<211> LENGTH: 22
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
aaagagtaca ttctgccttg ct                                            22

<210> SEQ ID NO 101
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
gctcactgtt accctactac tctc                                          24

<210> SEQ ID NO 102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
accacacaaa tgattatggt a                                             21

<210> SEQ ID NO 103
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
ccacacactg aaaagaattt gtg                                           23

<210> SEQ ID NO 104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
agtgggctgg atatatgaaa a                                             21

<210> SEQ ID NO 105
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
```

-continued aggcatgtgt taaactagaa aaa                                                              23

<210> SEQ ID NO 106
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
ggaggaagct gtgttctttt ca                                                              22

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
ggggatctta aaagcaccaa                                                                 20

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gacactccca cttctgccta                                                                 20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
cagcctaaat ttccagtctt                                                                 20

<210> SEQ ID NO 110
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
agttatgagt aatgaaggaa gg                                                              22

<210> SEQ ID NO 111
<211> LENGTH: 23
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic primer"

<400> SEQUENCE: 111
atttcttcaa gtgtatacag agc                                                          23

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
caggcaaaca ttcccttgta                                                              20

<210> SEQ ID NO 113
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
tgtctttgct cagttatgaa gaga                                                         24

<210> SEQ ID NO 114
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
ttgtaaattt ttctctaggt gtg                                                          23

<210> SEQ ID NO 115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
ggcatggcaa tactcttctg a                                                            21

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
gattttcaca tctaattttc acc                                                          23

<210> SEQ ID NO 117

-continued

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
acaatgagct attttaactc ca                                              22

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
actaactttg caagatacag att                                             23

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
tggccacttg cttatttgaa                                                 20

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
tgttcttaag ttgcccataa                                                 20

<210> SEQ ID NO 121
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
cccactttca caatttgaat cc                                              22

<210> SEQ ID NO 122
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
```

-continued

```
gaagaaatac aaagcagttg ctaa                                        24

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
gcttaggaag gtgtggagag c                                           21

<210> SEQ ID NO 124
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
ccactattta tgtttattga gtgc                                        24

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
gagtcatttt gtccaccaac c                                           21

<210> SEQ ID NO 126
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
gctcatagtt agaagtggca gca                                         23

<210> SEQ ID NO 127
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
gcaatgataa caagaacaca gca                                         23

<210> SEQ ID NO 128
<211> LENGTH: 20
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
      Synthetic primer"

<400> SEQUENCE: 128
tggagccaaa gggagtaata                                                    20

<210> SEQ ID NO 129
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
ttgctggctt acattcattc c                                                  21

<210> SEQ ID NO 130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
tacagctcag ccagttctgc                                                    20

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
gaaagggatg atggttccaa                                                    20

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
cccatgaaca cattcacagc                                                    20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
gtctgtccct gggccattat                                                    20

```
<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
cacgattcag taaatggctt g                                                21

<210> SEQ ID NO 135
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
tggagacatg acactatgaa ttt                                              23

<210> SEQ ID NO 136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
ccatcctggg attaccaatc t                                                21

<210> SEQ ID NO 137
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
ttctgtgttc tacaatgtct aggg                                             24

<210> SEQ ID NO 138
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
tcatccattt gagttttcca a                                                21

<210> SEQ ID NO 139
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 139
tatgagctgt ggccaatgaa                                                  20

<210> SEQ ID NO 140
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
cctgaagtgt cccctagaag g                                                21

<210> SEQ ID NO 141
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
tttgcagaca ggttaagatg c                                                21

<210> SEQ ID NO 142
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
tgcaccaaga tgtgttctgt c                                                21

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 143
cctacagtcc agggggtctt                                                  20

<210> SEQ ID NO 144
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
tctagataag gagaatctgg tg                                               22

<210> SEQ ID NO 145
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 145
cggaattgag ctaaccgtct                                           20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
cactggcctg aggctacttc                                           20

<210> SEQ ID NO 147
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
aagtcctgga tttcaccaga g                                         21

<210> SEQ ID NO 148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
tcccaagatc tgcactaaac g                                         21

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
ccctccagag ctaactgcat                                           20

<210> SEQ ID NO 150
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
tggatttatt cttcatgttg ctt                                       23
```

-continued

```
<210> SEQ ID NO 151
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
tttccaggag tataaaggag tgaa                                           24

<210> SEQ ID NO 152
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 152
aaccaacact taggaaaaca aatg                                           24

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 153
gaagcttctg tcccttctgt                                               20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 154
cctgctgatt tcatccttcc                                               20

<210> SEQ ID NO 155
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155
tcacatcagt aacctccttc ttg                                           23

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 156
tccagaagcc tttcttcctg                                                      20

<210> SEQ ID NO 157
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157
ggcataggaa ccatattatt gtca                                                 24

<210> SEQ ID NO 158
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158
ccttctcaac atagttctaa ttcc                                                 24

<210> SEQ ID NO 159
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159
ccacaagctc atcatctatt cg                                                   22

<210> SEQ ID NO 160
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 160
tttctgaggc tgataactga a                                                    21

<210> SEQ ID NO 161
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 161
gaaggaacat caaacaagga aa                                                   22

<210> SEQ ID NO 162
<211> LENGTH: 21
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
tgcatatcac agtctccaag g                                                            21

<210> SEQ ID NO 163
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
gagcaggtag ctacaatgac a                                                            21

<210> SEQ ID NO 164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 164
tgccacccag atctcttttc                                                              20

<210> SEQ ID NO 165
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
cctgatctgg aaactcatga aa                                                           22

<210> SEQ ID NO 166
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166
tggggatgtg ggtaagttaa t                                                            21

<210> SEQ ID NO 167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167
gcaactggtc ttgttccaca                                                              20

```
<210> SEQ ID NO 168
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168
gctaagccaa tgtctacatc ttc                                              23

<210> SEQ ID NO 169
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 169
tggtgtgtta gggatctgga g                                                21

<210> SEQ ID NO 170
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 170
tgacattggt tattggcaga                                                  20

<210> SEQ ID NO 171
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 171
cgtattcatt atccacaggg act                                              23

<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
tgcagtgaag gattgcaaag                                                  20

<210> SEQ ID NO 173
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 173
cccttcctgg acttcacata g                                          21

<210> SEQ ID NO 174
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174
gcatctagat ctttaccatt gc                                         22

<210> SEQ ID NO 175
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
ggagaacatt tagtgcctct gc                                         22

<210> SEQ ID NO 176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
acactcggaa cgatctctgc                                            20

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 177
aaacccacgg aggtcatttt                                            20

<210> SEQ ID NO 178
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178
tgggtctcct atttctgtgt cc                                         22

<210> SEQ ID NO 179
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
tgttaggact accttatgca gtt                                          23

<210> SEQ ID NO 180
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180
tggtatgtct cctttgatct tt                                           22

<210> SEQ ID NO 181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181
ctgagcggga gcttgtagat                                              20

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
gctcctgacg accaataacc                                              20

<210> SEQ ID NO 183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183
ggaccactgt ctagaccaag c                                            21

<210> SEQ ID NO 184
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
```

-continued tgtgtctggt gaggaagatg a                                                              21

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185
gggatgaaac caaacctcct                                                                20

<210> SEQ ID NO 186
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186
ttttaggaaa cctcaccagg ac                                                             22

<210> SEQ ID NO 187
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
tctctgttcg tgtctctgtc ttg                                                            23

<210> SEQ ID NO 188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 188
ttgagttggc ctaaaaccag a                                                              21

<210> SEQ ID NO 189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
cccgaccact aaaaggcata                                                                20

<210> SEQ ID NO 190
<211> LENGTH: 24
<212> TYPE: DNA
<213> ORGANISM: Artificial Sequence
<220> FEATURE:
<221> NAME/KEY: source -continued
<223> OTHER INFORMATION: /note="Description of Artificial Sequence:
       Synthetic primer"

<400> SEQUENCE: 190
ttgcctctaa aatctagaat agcc                                                          24

<210> SEQ ID NO 191
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 191
tcttaggaat gactcacact ggtc                                                          24

<210> SEQ ID NO 192
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 192
cactgaatat tgaaaactaa tgg                                                           23

<210> SEQ ID NO 193
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 193
gcatgttata attttacaag ctc                                                           23

<210> SEQ ID NO 194
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 194
tcacacaggt taggatgttt gtg                                                           23

<210> SEQ ID NO 195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 195
gcaccctagg agcaaactga                                                               20

<210> SEQ ID NO 196

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 196
gcagttgcct tgaaaggagt                                                  20

<210> SEQ ID NO 197
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 197
gcaaataaaa tgactctggg aac                                              23

<210> SEQ ID NO 198
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198
ggggttgaga tacaacatct tca                                              23

<210> SEQ ID NO 199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 199
gattcttggg gcatcaagtg                                                  20

<210> SEQ ID NO 200
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 200
ggacgtgggt gactatcagg                                                  20

<210> SEQ ID NO 201
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
```

-continued

```
tctagctcct aagttgattg attc                                         24

<210> SEQ ID NO 202
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
tccattatag ttcagtcttc aat                                          23

<210> SEQ ID NO 203
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 203
caggagaaaa gcagagacca a                                            21

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
agcgagagca ggctcataat                                              20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 205
tgacaaggga ttagggcaaa                                              20

<210> SEQ ID NO 206
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
gaaactacct ctgagtgtta caga                                         24

<210> SEQ ID NO 207
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 207
gaatcctgga cggtcagaaa                                              20

<210> SEQ ID NO 208
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
tgaaaatgag tagtggacat ctg                                         23

<210> SEQ ID NO 209
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209
aaaatgtgaa gataagtgaa cagc                                        24

<210> SEQ ID NO 210
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210
ccctaactta ttcaacatca ctgc                                        24

<210> SEQ ID NO 211
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 211
acatattcca ggagcatgac                                             20

<210> SEQ ID NO 212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 212
cattgagttc attggcctgt                                             20
```

-continued

```
<210> SEQ ID NO 213
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 213
ctctcgtggt ggattgaaca                                                   20

<210> SEQ ID NO 214
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 214
ccaacaagta ctctgaacca attt                                              24

<210> SEQ ID NO 215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 215
aaggagggct tagctagttg                                                   20

<210> SEQ ID NO 216
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 216
gctctttctc atcttaaggc ttc                                               23

<210> SEQ ID NO 217
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 217
gttaaaatta ctgttccagt tgt                                               23

<210> SEQ ID NO 218
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 218
caggcaacca ataataaca aaa                                            23

<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 219
cccatttcca tttaccgttt t                                             21

<210> SEQ ID NO 220
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 220
ttgtatttac aatagccatc ca                                            22

<210> SEQ ID NO 221
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 221
tgaaagtatc aggaaaaatg gatg                                          24

<210> SEQ ID NO 222
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 222
agcagtcaaa gtgaggatat gtt                                           23

<210> SEQ ID NO 223
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223
gcagtaacaa ataaccccaa cag                                           23

<210> SEQ ID NO 224
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 224
accagccttt gttgttgagc                                                20

<210> SEQ ID NO 225
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
gggttccagc aatattctac ctt                                            23

<210> SEQ ID NO 226
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226
ggtaatgaag aaagacaaaa ca                                             22

<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
tctaatgcct caccaagcaa                                                20

<210> SEQ ID NO 228
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
gcacagcaga aacccagatt                                                20

<210> SEQ ID NO 229
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
cactagtccg gcttgtgtaa aa                                             22
```

```
<210> SEQ ID NO 230
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230
tggtgattac agaataccac cag                                             23

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231
acaggagcgg acaatgagag                                                 20

<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
tgatgtgcat gtgtctcagc                                                 20

<210> SEQ ID NO 233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 233
tggtcctctg cttccctaag                                                 20

<210> SEQ ID NO 234
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234
catacatgag gtgactacca cca                                             23

<210> SEQ ID NO 235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 235
catcagattc ccaacattgc t                                                              21

<210> SEQ ID NO 236
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 236
agctcatccc aatcatcaca                                                                20

<210> SEQ ID NO 237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
aagggccatg agggtacttt                                                                20

<210> SEQ ID NO 238
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 238
aacccaaacg tctaacaaga taca                                                           24

<210> SEQ ID NO 239
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 239
catcgatagt attaggccca ca                                                             22

<210> SEQ ID NO 240
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 240
tgtgatttct ttctatagga ggtt                                                           24

<210> SEQ ID NO 241
<211> LENGTH: 21
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
ggaaggaaag ctcttttgga a                                            21

<210> SEQ ID NO 242
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
ttccagccct gaataacaac tt                                           22

<210> SEQ ID NO 243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
tgatcattgc tgtgatgtat t                                            21

<210> SEQ ID NO 244
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
aggataccat gattttgtag tgc                                          23

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
cttccctgca catccttttg                                              20

<210> SEQ ID NO 246
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
ctgtttagga agagtcatgt aacc                                         24
```

<210> SEQ ID NO 247
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 247
aactgttttg tcagctgctc at                                        22

<210> SEQ ID NO 248
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 248
aaaagaccac ttgattcagc tt                                        22

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 249
tgagcacaca catatggaag c                                         21

<210> SEQ ID NO 250
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 250
tgcaatgtac atgtggagaa tc                                        22

<210> SEQ ID NO 251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 251
cccgttctcc attctggtta                                           20

<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 252
cccagggaag aaaattggta                                          20

<210> SEQ ID NO 253
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 253
tgaaatagtg cttattgcat cg                                       22

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 254
agccactcca gcattcactt                                          20

<210> SEQ ID NO 255
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 255
ccacatgttt ctgagtgaag ga                                       22

<210> SEQ ID NO 256
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 256
ggagttacag ttatcaaatg caga                                     24

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
ggaaagaagg gagaatggtc a                                        21

<210> SEQ ID NO 258
<211> LENGTH: 22

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
ttgcatattc tggacctcat ct                                                    22

<210> SEQ ID NO 259
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
ggaggcaaag aagttaggga gt                                                    22

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
ttttacctcc ctgccctagt                                                       20

<210> SEQ ID NO 261
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
aggaaatgta gtcaggtcta gga                                                   23

<210> SEQ ID NO 262
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
gcagcttgaa aacagccagt                                                       20

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
```

-continued

--- catggtaagt atgctgttaa atc                                                          23

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
gctgagcaga aaacataagc a                                                            21

<210> SEQ ID NO 265
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 265
caaacccaca ctgtgttagc tg                                                           22

<210> SEQ ID NO 266
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 266
agctaatctt tggtacttca atct                                                         24

<210> SEQ ID NO 267
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 267
caagcatctt gctgaatttc c                                                            21

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 268
agtgcaaagt gaagataatg aca                                                          23

<210> SEQ ID NO 269
<211> LENGTH: 20
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic primer"

<400> SEQUENCE: 269
agtgtctgtc ttccagttcc                                              20

<210> SEQ ID NO 270
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 270
cattcatccc atcttctaac ttca                                         24

<210> SEQ ID NO 271
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 271
gcaaacatgt aaagtgtgag ag                                           22

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 272
gcagtcttct gtgattttat att                                          23

<210> SEQ ID NO 273
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 273
cagaaggaag gggtaagaca ca                                           22

<210> SEQ ID NO 274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 274
tcccctcagg taacttccat c                                            21

<210> SEQ ID NO 275

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 275
gatttctgtg ttgtgccaca gt                                                    22

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 276
ttggtgtctt acatgtattg tga                                                   23

<210> SEQ ID NO 277
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 277
gctgtagcac atccaaaaac c                                                     21

<210> SEQ ID NO 278
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 278
gaactgaaaa aggaataaag tagg                                                  24

<210> SEQ ID NO 279
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 279
ggcataagca gatacagaca gc                                                    22

<210> SEQ ID NO 280
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 280

-continued

```
tgaaacctat aagccactga gc                                          22

<210> SEQ ID NO 281
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 281
tccaaaaaga cagctgaaag aa                                          22

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 282
aagccatgca gtgggtatct                                             20

<210> SEQ ID NO 283
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 283
tccatacagg aagatccatt aaga                                        24

<210> SEQ ID NO 284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 284
gtgcagtttg ggctacaaga                                             20

<210> SEQ ID NO 285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 285
tcacacatca ttggtgaagg                                             20

<210> SEQ ID NO 286
<211> LENGTH: 24
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 286
aagtgtcaga gggttagtga ttcc                                        24

<210> SEQ ID NO 287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 287
cacctaaaga tttccccaca a                                           21

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 288
gacttacggc ctaacccttt                                             20

<210> SEQ ID NO 289
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 289
gaacaagtat actagcaaaa cgaa                                        24

<210> SEQ ID NO 290
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 290
tttgtctaaa gaatttgaca gtgg                                        24

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 291
tcttgagaag ccttttctta cca                                         23
```

-continued

```
<210> SEQ ID NO 292
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 292
gcatgagtgt gtgtctatgc ag                                               22

<210> SEQ ID NO 293
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 293
ttctggactc tccactctat ttca                                            24

<210> SEQ ID NO 294
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 294
tggcataaga tagacatatt cacc                                            24

<210> SEQ ID NO 295
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 295
gcatctatgt caccaagcat tt                                               22

<210> SEQ ID NO 296
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 296
gccgttaagc actgagctgt                                                 20

<210> SEQ ID NO 297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 297
tccactactt cttggagttc a                                              21

<210> SEQ ID NO 298
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 298
tcttgaatag cacccacaag ag                                             22

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 299
gacactactg tcctcaaacg                                                20

<210> SEQ ID NO 300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 300
gcccaaagac caagttttag a                                              21

<210> SEQ ID NO 301
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 301
cgtgtctgtg agctcctttc t                                              21

<210> SEQ ID NO 302
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 302
aggttgtgaa agacactgat gg                                             22

<210> SEQ ID NO 303
<211> LENGTH: 22
<212> TYPE: DNA
<213> ORGANISM: Artificial Sequence
```

-continued

---

```
<220> FEATURE:
<221> NAME/KEY: source
<223> OTHER INFORMATION: /note="Description of Artificial Sequence:
      Synthetic primer"

<400> SEQUENCE: 303
tccaagctgt ttctcatgtt tg                                              22

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 304
cagtgggctc acagtaatgg                                                 20

<210> SEQ ID NO 305
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 305
gcaattccag atatctcttt at                                              22

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 306
ttatctaccc atgcttctct c                                               21

<210> SEQ ID NO 307
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 307
aacagatcac ttaccgcttt g                                               21

<210> SEQ ID NO 308
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 308
ccctacatgc attatctcct tt                                              22
```

<210> SEQ ID NO 309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 309
tggtgccatc ctagagttct g                                              21

<210> SEQ ID NO 310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 310
agtgtgcact tgctcatgac t                                              21

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 311
ccagggattt catcttcacc                                                20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
atgtctatgc cctgcctcat                                                20

<210> SEQ ID NO 313
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313
tgtagtcgaa gcaatgagat gtg                                            23

<210> SEQ ID NO 314
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314
tttcactccc ttctgtattt agcc                                            24

<210> SEQ ID NO 315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 315
aaatgctttg ctgcatgtct                                                 20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 316
tcaatggcaa tttgaggaga                                                 20

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 317
tgaggaagtg acaagttcag a                                               21

<210> SEQ ID NO 318
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 318
ttttctcccc atctgttact a                                               21

<210> SEQ ID NO 319
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 319
caattttaca tccaacagaa ga                                              22

<210> SEQ ID NO 320
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 320
tgggattata aggaggtcaa gaa                                          23

<210> SEQ ID NO 321
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 321
tggtgagttt cttccctagg tt                                           22

<210> SEQ ID NO 322
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 322
cttgacacca tagtggtcac ct                                           22

<210> SEQ ID NO 323
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 323
tttacttctg agctgaaggt actc                                         24

<210> SEQ ID NO 324
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 324
cacgcaggca atagtaggaa                                              20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 325
agcaccaaag gcaagttcaa                                              20

-continued

```
<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 326
ggatgccaag attgcaaata                                                   20

<210> SEQ ID NO 327
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 327
ttctttctac ccaggtactt atca                                              24

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 328
tttcaagatg caaaggcttg                                                   20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 329
cgaaatccat aggacctaca                                                   20

<210> SEQ ID NO 330
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 330
agctacacta tttccatgtg ac                                                22

<210> SEQ ID NO 331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 331
cgtcggttgt tttatcattg c                                        21

<210> SEQ ID NO 332
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 332
ggacaggttg tgcataacta aga                                      23

<210> SEQ ID NO 333
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 333
cctcacttaa ggagaacagt taga                                     24

<210> SEQ ID NO 334
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334
tgctaatcat cccttattat tgc                                      23

<210> SEQ ID NO 335
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 335
tgacctacta gacatcaagc ctta                                     24

<210> SEQ ID NO 336
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 336
tgccagtaac ttaatccata gc                                       22

<210> SEQ ID NO 337
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 337
ccagacaggc acatacagtc a                                              21

<210> SEQ ID NO 338
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 338
gggaactgag tatctctgtg tga                                            23

<210> SEQ ID NO 339
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 339
gaggtcgaag ttgtaggctt g                                              21

<210> SEQ ID NO 340
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 340
tcaacttagt tacaggtcac aca                                            23

<210> SEQ ID NO 341
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 341
tcaatttttg ttgtggttta cct                                            23

<210> SEQ ID NO 342
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 342

-continued

```
aggtttttcct ataagactg ct                                                22

<210> SEQ ID NO 343
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 343
tcagagtagg aatgaacaat tt                                                22

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 344
ctcagggcct aaacttgcac                                                   20

<210> SEQ ID NO 345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 345
gcactcatgt gagtttgcac                                                   20

<210> SEQ ID NO 346
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 346
cacagtgaag tatgtataaa ttgc                                              24

<210> SEQ ID NO 347
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 347
gcctagctgt gcgattcttc                                                   20

<210> SEQ ID NO 348
<211> LENGTH: 20
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 348
tgataccagt tgatgccaca                                                20

<210> SEQ ID NO 349
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 349
tgactgaact caattcaaac agc                                            23

<210> SEQ ID NO 350
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 350
tggcatctag ggtataggaa ga                                             22

<210> SEQ ID NO 351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 351
ggccaccatc tcctgttcta                                                20

<210> SEQ ID NO 352
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 352
ccttgtttgt ctgtatctga gc                                             22

<210> SEQ ID NO 353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 353
ccaactctga ttgtgcgact                                                20

<210> SEQ ID NO 354
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 354
gctccaagcc atagatccag                                               20

<210> SEQ ID NO 355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 355
ggtgtgtgta tgaggcttgg                                               20

<210> SEQ ID NO 356
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 356
aaccgccagc atagcttct                                                19

<210> SEQ ID NO 357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 357
ggtaggaagg ggttgtcgtt                                               20

<210> SEQ ID NO 358
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 358
tttctttcta cttctcatca ctct                                          24

<210> SEQ ID NO 359
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 359
```

-continued

```
ggacatcagc actaactgaa gtg                                                        23

<210> SEQ ID NO 360
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 360
ttctcttgtg tgaaccatcc tc                                                         22

<210> SEQ ID NO 361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 361
gccagcgtgt aagacacaag                                                            20

<210> SEQ ID NO 362
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 362
tggcatttgt ttacagactt atc                                                        23

<210> SEQ ID NO 363
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 363
tcctccacat tggtaattag gg                                                         22

<210> SEQ ID NO 364
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 364
ggtgtccccc tcaaattgta                                                            20

<210> SEQ ID NO 365
<211> LENGTH: 22
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
      Synthetic primer"

<400> SEQUENCE: 365
caagtttgta cctcagcttt ca                                                   22

<210> SEQ ID NO 366
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 366
tgagatactg ttgtcctctg c                                                    21

<210> SEQ ID NO 367
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 367
ttcccttctt atgtaatctc c                                                    21

<210> SEQ ID NO 368
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 368
gagggttact gaactaggat aatg                                                 24

<210> SEQ ID NO 369
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 369
tcctgagagc atggtaagat gt                                                   22

<210> SEQ ID NO 370
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 370
tgcagggcat tctatgtgaa                                                      20

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 371
tacagctgag caataacgtg                                                    20

<210> SEQ ID NO 372
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 372
tggctggcca aatctttcta                                                    20

<210> SEQ ID NO 373
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 373
aaactataaa aggacctagg aaa                                                 23

<210> SEQ ID NO 374
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 374
aagtctagtg aatttcttgt tagg                                                24

<210> SEQ ID NO 375
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 375
cttaatgatt ttgtaatgtc agg                                                 23

<210> SEQ ID NO 376
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 376
atttgagagg ttgccagagc                                          20

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 377
gaggttctca ttccctcacc                                          20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 378
agaggggctc acctgagagt                                          20

<210> SEQ ID NO 379
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 379
cacactagtg ggtcctgatt aga                                      23

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 380
ttgcggtttc ctcattcttc                                          20

<210> SEQ ID NO 381
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 381
cgtgatgggt aggtcagtcc                                          20

<210> SEQ ID NO 382
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 382
cgcctctggg gataactaaa                                            20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 383
ggaattgcca ctctggagaa                                            20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 384
agtggtcccc aacaacttga                                            20

<210> SEQ ID NO 385
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 385
ataacaatgt ctagcaacag g                                          21

<210> SEQ ID NO 386
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 386
gatcaacact tcaaaattat ggt                                        23

<210> SEQ ID NO 387
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 387
tcagataaaa caattccagt tac                                        23
```

-continued

```
<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 388
acccacagag gaaagccttg                                               20

<210> SEQ ID NO 389
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 389
cagcatatat tacctttct ttg                                            23

<210> SEQ ID NO 390
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 390
tgtgcccaga aagttttagc a                                             21

<210> SEQ ID NO 391
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 391
tcaactgaca ctggtgtttc tc                                            22

<210> SEQ ID NO 392
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 392
gtgaagggag gacaaaatcg                                               20

<210> SEQ ID NO 393
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 393
caagtgatct gatggggtga                                                             20

<210> SEQ ID NO 394
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 394
tgctgagttt gagaaacttg gt                                                          22

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 395
gtaggactta gggcgctcat                                                             20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 396
gcattactgc cgagggatct                                                             20

<210> SEQ ID NO 397
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 397
tgacaaagcc tagagtgaac tga                                                         23

<210> SEQ ID NO 398
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 398
tcctagagta ctcctctttg tcca                                                        24

<210> SEQ ID NO 399
<211> LENGTH: 21
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 399
gtacagagtc cctgtctcac a                                           21

<210> SEQ ID NO 400
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 400
catgatctgt ctctctcact gaa                                         23

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 401
gcattttctc acagccacag                                             20

<210> SEQ ID NO 402
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 402
tggcctaaaa attcaccact g                                           21

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 403
aacatttgca cattatcagc                                             20

<210> SEQ ID NO 404
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 404
gcaaggatca gtcagactac ga                                          22
```

-continued

<210> SEQ ID NO 405
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 405
tgtccatcaa tctcaaaagt cg                                          22

<210> SEQ ID NO 406
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 406
ctgatttcta ccagttactt acca                                        24

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 407
gcatgagcca ccctaaatct                                             20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 408
tgcagaccat gaggaatgtt                                             20

<210> SEQ ID NO 409
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 409
aggattcctt atacactgac ctc                                         23

<210> SEQ ID NO 410
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 410
accaaataat ggtctactcc t                                                21

<210> SEQ ID NO 411
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 411
aagacattct ctgcctttct ca                                               22

<210> SEQ ID NO 412
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 412
ggctctacta tggggaaaat tca                                              23

<210> SEQ ID NO 413
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 413
gcaaatcact aggaaagctc a                                                21

<210> SEQ ID NO 414
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 414
gaggttcact ctatttctgt tcc                                              23

<210> SEQ ID NO 415
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 415
ctagaaacgg ctgccaggta                                                  20

<210> SEQ ID NO 416
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 416
ccctgcactt gtaccagctt                                              20

<210> SEQ ID NO 417
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 417
aggacattct tttgtgtatt caag                                         24

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 418
atcccatata ggcacttgct                                              20

<210> SEQ ID NO 419
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 419
caaataatca ccccaataca atca                                         24

<210> SEQ ID NO 420
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 420
gctttcagtg ccctcatctc                                              20

<210> SEQ ID NO 421
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 421
```
aagatgatca aagttttgag agca                                                       24

<210> SEQ ID NO 422
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 422
cactcctaaa gaacaagatg tcaa                                                       24

<210> SEQ ID NO 423
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 423
gacaagaact gaaggcaaag g                                                          21

<210> SEQ ID NO 424
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 424
gggaggaaca gaacaacctt c                                                          21

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 425
cccttgcaat acccagcata                                                           20

<210> SEQ ID NO 426
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 426
agttatctga gttggcttac c                                                          21

<210> SEQ ID NO 427
<211> LENGTH: 20
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 427
tcgcagtctt ttgcatcatt                                               20

<210> SEQ ID NO 428
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 428
tccaatagct accttcacca gaa                                           23

<210> SEQ ID NO 429
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 429
tggaaaaaca caggcatatt ctc                                           23

<210> SEQ ID NO 430
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 430
ccaaaagcat ctaaaaacag ga                                            22

<210> SEQ ID NO 431
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 431
caaatatact gattctgtgg caaa                                          24

<210> SEQ ID NO 432
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 432
tgatgcattg agattttgat ga                                            22

<210> SEQ ID NO 433
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 433
tagcctttgg ataacagtcc                                                   20

<210> SEQ ID NO 434
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 434
gagggaggaa atggtcaact t                                                 21

<210> SEQ ID NO 435
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 435
aggcaaagaa ctagacaact ct                                                22

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 436
agacgtgctg ggttcctaga                                                   20

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 437
ggcatgaaga tgttaaccta cca                                               23

<210> SEQ ID NO 438
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 438
```

-continued

```
ttgtctggtc ttcatcaagt ctct                                        24

<210> SEQ ID NO 439
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 439
ttgccatgca gcagtactta g                                           21

<210> SEQ ID NO 440
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 440
tgacttttca ttgctagtat cca                                         23

<210> SEQ ID NO 441
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 441
gcaacaagaa caggaaccaa g                                           21

<210> SEQ ID NO 442
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 442
tgttttgaca ttgtcctgtg tg                                          22

<210> SEQ ID NO 443
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 443
cagtgaggtg tgatgtataa agag                                        24

<210> SEQ ID NO 444
<211> LENGTH: 24
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 444
gagaacacat attcattcct ctcc                                          24

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 445
gtggggtcca gcagtaaatc                                               20

<210> SEQ ID NO 446
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 446
gaacttctca catcacctca agc                                           23

<210> SEQ ID NO 447
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 447
tctattaacc ctaatcaatc tcct                                          24

<210> SEQ ID NO 448
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 448
ttgctaaatt tcaggcacct c                                             21

<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 449
cctttgactc tggcctcatc                                               20
```

-continued

```
<210> SEQ ID NO 450
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 450
agtgaataac cagccttagt tg                                          22

<210> SEQ ID NO 451
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 451
aaataaggac atctggaaaa caa                                         23

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 452
gtgccagcta caaacaatgg                                             20

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 453
gtgcctcatc aaaatgcaac                                             20

<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 454
acacagatga cttcagctgg                                             20

<210> SEQ ID NO 455
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 455
aactcaaacc taagtgcccc                                             20

<210> SEQ ID NO 456
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 456
ggaatggaat agtgtgtggg                                             20

<210> SEQ ID NO 457
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 457
acactggtct caagctccc                                              19

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 458
cacacctgta attctagccc                                             20

<210> SEQ ID NO 459
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 459
agaaggaagg atcagagaag                                             20

<210> SEQ ID NO 460
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 460
agctttcctc cccacactg                                              19

<210> SEQ ID NO 461
<211> LENGTH: 20
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic primer"

<400> SEQUENCE: 461
gctgtgtgga gccctataaa                                                          20

<210> SEQ ID NO 462
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 462
gaatgaaatg gagtttgcag                                                          20

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 463
cctcagccac cacttgttag                                                          20

<210> SEQ ID NO 464
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 464
gtgttggtca gacagaaagg                                                          20

<210> SEQ ID NO 465
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 465
gccaattacc ccataattag                                                          20

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 466
atgcacactt acacacgcac                                                          20

-continued

```
<210> SEQ ID NO 467
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 467
aaggaagtaa aggtatgtgc                                               20

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 468
aggctaactc taacatcctg                                               20

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 469
aagagtgtct cctccctctg                                               20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 470
aactggaggc tgtgttagac                                               20

<210> SEQ ID NO 471
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 471
cgctcttttc tgactagtcc                                               20

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 472
ttgcagcagt cacaggaaac                                               20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 473
ctctctgtgc acaaaaaacc                                               20

<210> SEQ ID NO 474
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 474
ggaagacact gccttcaaac                                               20

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 475
aaaaacccca ggctccattg                                               20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 476
atgtccagct gcttcttttc                                               20

<210> SEQ ID NO 477
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 477
tccaagtcag aagctatggg                                               20

<210> SEQ ID NO 478
<211> LENGTH: 20
<212> TYPE: DNA
```

-continued

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 478
agtctgcaga cctaacatgg                                                20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 479
atggcttgta cttcctcctc                                                20

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 480
ttcggtggaa tagcagcaag                                                20

<210> SEQ ID NO 481
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 481
cataatctca gggctacat                                                 19

<210> SEQ ID NO 482
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 482
ttcacctggc cttgagggtc                                                20

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 483
gtttattgat gaactggtgc                                                20

-continued

```
<210> SEQ ID NO 484
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 484
gggcagagtg atatcacag                                                      19

<210> SEQ ID NO 485
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 485
actggcaagt ccaggtcttc                                                     20

<210> SEQ ID NO 486
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 486
aaggctcagg gcagaagcac                                                     20

<210> SEQ ID NO 487
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 487
tcctcatccg gtgtggcaa                                                      19

<210> SEQ ID NO 488
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 488
cagcaaagag agagaggttc c                                                   21

<210> SEQ ID NO 489
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 489
agtatgccat catgaaagcc                                               20

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 490
cttctttgac taaggctgac                                               20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 491
ctctgcctat tctcctcttc                                               20

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 492
tagacctcaa ggcctagagc                                               20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 493
agtaagagct cccttggttg                                               20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 494
gctcataaca atctctcccc                                               20

<210> SEQ ID NO 495
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 495
tcccctctac cccttgaagc                                                  20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 496
cagcactgat gacatctggg                                                  20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 497
aagaacacag gcctggttgg                                                  20

<210> SEQ ID NO 498
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 498
tatggctctg gggctctata                                                  20

<210> SEQ ID NO 499
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 499
aacagagaga atgaggaggg                                                  20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 500
```
tcattctaaa agggctgccg                                          20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 501
gaaaggtatt cagggtggtg                                         20

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 502
gatgctctga gacaatcctg                                         20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 503
ttaactgtga ggcgttcacc                                         20

<210> SEQ ID NO 504
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 504
gatcatggga ctatccacac                                         20

<210> SEQ ID NO 505
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 505
ccagccctgc tcctttaatc                                         20

<210> SEQ ID NO 506
<211> LENGTH: 20
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 506
ggagaagatc ctacactcag                                            20

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 507
ccaacttctt cccagtctgt                                            20

<210> SEQ ID NO 508
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 508
ctggagctga aggacccca                                             19

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 509
ggagaaatcc ttccctagag                                            20

<210> SEQ ID NO 510
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 510
ttcaaggtgc tgcaggtttg                                            20

<210> SEQ ID NO 511
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 511
ccccctctac aggaaaattc                                            20

<210> SEQ ID NO 512
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 512
ttctgaattc ttcagccagc                                                   20

<210> SEQ ID NO 513
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 513
catcctacct ctaggtacac                                                   20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 514
ggtgtcttag ttacatgtgc                                                   20

<210> SEQ ID NO 515
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 515
tggtgacgca aggactggac                                                   20

<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 516
atactgtgct gctcttcagg                                                   20

<210> SEQ ID NO 517
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 517
```

-continued

```
cagctgctgt tccctcaga                                  19

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 518
ccaaaaaacc atgccctctg                                 20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 519
taattggtac aggaggtggg                                 20

<210> SEQ ID NO 520
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 520
aggcatggga ctcagcttg                                  19

<210> SEQ ID NO 521
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 521
gtgcaggtca ttgtgctgag                                 20

<210> SEQ ID NO 522
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 522
aaacactcca cgttaaaggg                                 20

<210> SEQ ID NO 523
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 523
cagctgagaa aactgagacc                                              20

<210> SEQ ID NO 524
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 524
tttacagact agcgtgacgg                                              20

<210> SEQ ID NO 525
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 525
tgctgctccg ccatgaaagt                                              20

<210> SEQ ID NO 526
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 526
atgcagggag agcagcagcc                                              20

<210> SEQ ID NO 527
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 527
gctgagagtt aagtggccaa                                              20

<210> SEQ ID NO 528
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 528
ctgtggccat atttctgctg                                              20
```

-continued

```
<210> SEQ ID NO 529
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 529
gcaatcaggc ccagcttatg                                               20

<210> SEQ ID NO 530
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 530
ttgtctggac tctcttcatc                                               20

<210> SEQ ID NO 531
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 531
cgcctaattt ccagcaagaa                                               20

<210> SEQ ID NO 532
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 532
gacttgcaaa agctctctgg                                               20

<210> SEQ ID NO 533
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 533
gtctggctga ggaatgctac                                               20

<210> SEQ ID NO 534
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 534
aagggcagca tgagcttggg                                            20

<210> SEQ ID NO 535
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 535
gtctacttca aatcatgcct c                                          21

<210> SEQ ID NO 536
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 536
ctacatgcat atctggagac                                            20

<210> SEQ ID NO 537
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 537
cagagatgca agcagccaag                                            20

<210> SEQ ID NO 538
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 538
aggaatgggg ctgccatct                                             19

<210> SEQ ID NO 539
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 539
gagacaggca aagatgcaac                                            20

<210> SEQ ID NO 540
<211> LENGTH: 19
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 540
accacgcctg gccagaact                                                      19

<210> SEQ ID NO 541
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 541
gggtttagtc tccttacccc                                                     20

<210> SEQ ID NO 542
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 542
aatgtccctg gcacagctca                                                     20

<210> SEQ ID NO 543
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 543
gcttcagttg tcactgtgag                                                     20

<210> SEQ ID NO 544
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 544
ctcagatgat gtcccttctt                                                     20

<210> SEQ ID NO 545
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 545
cgatgcaagc ttccattcta                                                     20
```

<210> SEQ ID NO 546
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 546
ggacagagaa tggcctgcta                                                    20

<210> SEQ ID NO 547
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 547
ttaaaacagc cctgcaacc                                                     19

<210> SEQ ID NO 548
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 548
tgatgagaac agagctgag                                                     19

<210> SEQ ID NO 549
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 549
ctgaagctat gtcctgttag                                                    20

<210> SEQ ID NO 550
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 550
aggtggcacg gcacgttcat                                                    20

<210> SEQ ID NO 551
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 551
ctgaagtgca ggaagcttgg                                              20

<210> SEQ ID NO 552
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 552
accctagaac ttgacactgc                                              20

<210> SEQ ID NO 553
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 553
aaggagctgg caaggcccta                                              20

<210> SEQ ID NO 554
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 554
acataggcac aatgagatgg                                              20

<210> SEQ ID NO 555
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 555
tacctttcaa gctcaagtgc                                              20

<210> SEQ ID NO 556
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 556
tttggatgga acgtttgcag                                              20

<210> SEQ ID NO 557
<211> LENGTH: 20
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 557
gctacccttt aatgtgtctc                                                       20

<210> SEQ ID NO 558
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 558
atgaagagca gctggtcaac                                                       20

<210> SEQ ID NO 559
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 559
cagcccttgt gtgcataaag                                                       20

<210> SEQ ID NO 560
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 560
tacagtggtg gacaaggtgg                                                       20

<210> SEQ ID NO 561
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 561
cttgttttgc aggctgattg                                                       20

<210> SEQ ID NO 562
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 562
tcaatcatcc ccatccccac                                                       20

-continued

```
<210> SEQ ID NO 563
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 563
gcacatcaca agttaagagg                                                        20

<210> SEQ ID NO 564
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 564
ccccagtagg gaacacactt                                                        20

<210> SEQ ID NO 565
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 565
caggatgcac tttttggatg                                                        20

<210> SEQ ID NO 566
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 566
ggcttctccc agaaaatctc                                                        20

<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 567
actgcagtgc cgggaaaagt                                                        20

<210> SEQ ID NO 568
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 568
tttgctcacc ctaccccac                                                                19

<210> SEQ ID NO 569
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 569
tgataacagc ctccatttcc                                                               20

<210> SEQ ID NO 570
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 570
tagggatgca agatgaaagg                                                               20

<210> SEQ ID NO 571
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 571
gatgcaggag ggcgtccca                                                                19

<210> SEQ ID NO 572
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 572
tccagccact ctgagctgc                                                                19

<210> SEQ ID NO 573
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 573
tctgctgttt gatggatgtg                                                               20

<210> SEQ ID NO 574
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 574
tgggagatca gctaggaatg                                              20

<210> SEQ ID NO 575
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 575
gctgggatcc catctcaaag                                              20

<210> SEQ ID NO 576
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 576
tgaatgtctt gcttgagacc                                              20

<210> SEQ ID NO 577
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 577
ttcccttgtt tggaaccctg                                              20

<210> SEQ ID NO 578
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 578
cagcttccac cctctccac                                               19

<210> SEQ ID NO 579
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 579
```

-continued

```
tggccttaaa catgcatgct                                        20

<210> SEQ ID NO 580
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 580
ggtgacaatc tagagaggtg                                        20

<210> SEQ ID NO 581
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 581
aggtcagctc agggtgaagt                                        20

<210> SEQ ID NO 582
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 582
gctccattga agggtaaagg                                        20

<210> SEQ ID NO 583
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 583
gagggtacct ttctttctcc                                        20

<210> SEQ ID NO 584
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 584
gctcagtgtc tgacaaaagc                                        20

<210> SEQ ID NO 585
<211> LENGTH: 20
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 585
agccatgttt cagggttcag                                              20

<210> SEQ ID NO 586
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 586
cagtgcctga cagggaaagt                                              20

<210> SEQ ID NO 587
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 587
ctgttttctc agaagggact tt                                           22

<210> SEQ ID NO 588
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 588
tcgaaagaaa acactgagaa tcaa                                         24

<210> SEQ ID NO 589
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 589
tggacaaaaa taccatcatc a                                            21

<210> SEQ ID NO 590
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 590
agatcatcct gaacataagg t                                            21

<210> SEQ ID NO 591
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 591
ttccctcttc agtttacctg ttt                                                      23

<210> SEQ ID NO 592
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 592
caccaagaag ggaatgaaaa t                                                        21

<210> SEQ ID NO 593
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 593
tgaagaaagc aagggacaga a                                                        21

<210> SEQ ID NO 594
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 594
aagccgcgtg ttattgaaac                                                          20

<210> SEQ ID NO 595
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 595
ttcagtgctt tccgttgga                                                           19

<210> SEQ ID NO 596
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 596
```

-continued

```
cacacacacg cactaagcaa                                           20

<210> SEQ ID NO 597
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 597
tcacctcata catgttttct ttt                                       23

<210> SEQ ID NO 598
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 598
aatacctcaa aggactgtaa tg                                        22

<210> SEQ ID NO 599
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 599
tgctgcattc atttgtcaac                                           20

<210> SEQ ID NO 600
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 600
gaactctggt gttcctagtg                                           20

<210> SEQ ID NO 601
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 601
tgtatttgcc taaaagtaag agg                                       23

<210> SEQ ID NO 602
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 602
ggcagagttc tcttgacgtg                                           20

<210> SEQ ID NO 603
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 603
aaggaagtaa aggtatgtgc                                           20

<210> SEQ ID NO 604
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 604
aggctaactc taacatcctg                                           20

<210> SEQ ID NO 605
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 605
acttaaaacc aaaccctca                                            19

<210> SEQ ID NO 606
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 606
ttattgggtg ttgcaagtgt                                           20

<210> SEQ ID NO 607
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 607
gtttattgat gaactggtgc                                           20
```

-continued

```
<210> SEQ ID NO 608
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 608
gggcagagtg atatcacag                                                    19

<210> SEQ ID NO 609
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 609
tcccctctac cccttgaagc                                                   20

<210> SEQ ID NO 610
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 610
cagcactgat gacatctggg                                                   20

<210> SEQ ID NO 611
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 611
acggggtctt atggttcctc                                                   20

<210> SEQ ID NO 612
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 612
gcctgagaag caattaacct g                                                 21

<210> SEQ ID NO 613
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 613
tgctaacctg tgaagtccat tc                                      22

<210> SEQ ID NO 614
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 614
tttatttgca ttggtctttg c                                       21

<210> SEQ ID NO 615
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 615
gcataatttg aaagctctgt ttg                                     23

<210> SEQ ID NO 616
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 616
cgattatgcc cattgatatt ttt                                     23

<210> SEQ ID NO 617
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 617
tcaagggatt gctccaatgt                                         20

<210> SEQ ID NO 618
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 618
ctccaaacca atacctaaaa a                                       21

<210> SEQ ID NO 619
<211> LENGTH: 20
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 619
ccagccctgc tcctttaatc                                              20

<210> SEQ ID NO 620
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 620
ggagaagatc ctacactcag                                              20

<210> SEQ ID NO 621
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 621
gcttctcatc tgtgtgcatt t                                            21

<210> SEQ ID NO 622
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 622
cctagaatat gatgcccaaa ca                                           22

<210> SEQ ID NO 623
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 623
cctcctctac tagacctctg acg                                          23

<210> SEQ ID NO 624
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 624
tgtagaataa gaaggcagtc caa                                          23
```

-continued

<210> SEQ ID NO 625
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 625
acctagggaa ggggtcac                                                        18

<210> SEQ ID NO 626
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 626
aagccagggt tcatctgc                                                        18

<210> SEQ ID NO 627
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 627
catcctacct ctaggtacac                                                      20

<210> SEQ ID NO 628
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 628
ggtgtcttag ttacatgtgc                                                      20

<210> SEQ ID NO 629
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 629
tccaaaattc cttgatgtgt ca                                                   22

<210> SEQ ID NO 630
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

<400> SEQUENCE: 630
tcaacctcct acagcaacaa aa                                            22

<210> SEQ ID NO 631
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 631
ggttcactac agagcgtctc aa                                            22

<210> SEQ ID NO 632
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 632
atgtaccttt tgggccttgc                                              20

<210> SEQ ID NO 633
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 633
ccaccaacct gcctctgg                                                18

<210> SEQ ID NO 634
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 634
tgatttgtga tcagtcttcc tctt                                         24

<210> SEQ ID NO 635
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 635
attcttcctc ctgcaatcca                                              20

<210> SEQ ID NO 636
<211> LENGTH: 20
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 636
tttggaagtc ggtgctaacc                                                    20

<210> SEQ ID NO 637
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 637
ggcttgctta acatgtgctg                                                    20

<210> SEQ ID NO 638
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 638
caaagattgc agataaagtg ct                                                 22

<210> SEQ ID NO 639
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 639
ttccttggca ttttagtttc c                                                  21

<210> SEQ ID NO 640
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 640
tcccatgtaa cacctttcag a                                                  21

<210> SEQ ID NO 641
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 641
tttgcattct cctgtctctt ttt                                                23

```
<210> SEQ ID NO 642
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 642
ggaaccacta caggaaacga a                                              21

<210> SEQ ID NO 643
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 643
ttttgccaag ctattcacag                                               20

<210> SEQ ID NO 644
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 644
ctccatcgag ggattatcag a                                              21

<210> SEQ ID NO 645
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 645
gcacctattc acagacagtt tga                                            23

<210> SEQ ID NO 646
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 646
agaatcttcc gattctgcat                                               20

<210> SEQ ID NO 647
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 647
gcccctataa tccttggagt c                                                      21

<210> SEQ ID NO 648
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 648
gaggagccaa agagctgaaa                                                        20

<210> SEQ ID NO 649
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 649
ggtttcatta ctctatgctt cttc                                                   24

<210> SEQ ID NO 650
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 650
aggagatgtg catttcagca                                                        20

<210> SEQ ID NO 651
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 651
caggacagga attagtgttg c                                                      21

<210> SEQ ID NO 652
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 652
ttttaaatac tacggagtca aac                                                    23

<210> SEQ ID NO 653
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 653
gcccttgaaa agagggctta                                               20

<210> SEQ ID NO 654
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 654
gcaggatatt ctctgactgc aa                                            22

<210> SEQ ID NO 655
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 655
aaagagtata gggatggaca ctga                                          24

<210> SEQ ID NO 656
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 656
cgtgtagtag tcacccggtt t                                             21

<210> SEQ ID NO 657
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 657
gaaagcctac acgcccaag                                                19

<210> SEQ ID NO 658
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 658
```

-continued

```
ttttcagtgt cctcacctct ga                                              22

<210> SEQ ID NO 659
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 659
tccaactgga aaacacctca                                                 20

<210> SEQ ID NO 660
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 660
gagccacctt caagactctt tc                                              22

<210> SEQ ID NO 661
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 661
caaaatttcc agcgcattct                                                 20

<210> SEQ ID NO 662
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 662
actgattcct cgcagccttg                                                 20

<210> SEQ ID NO 663
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 663
actgcattgt ggcggtatct                                                 20

<210> SEQ ID NO 664
<211> LENGTH: 23
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 664
aaaagtacat gatgcattta agc                                    23

<210> SEQ ID NO 665
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 665
aaaacataat tgaacaccta gca                                    23

<210> SEQ ID NO 666
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 666
aataggaggc tgctctatgc                                        20

<210> SEQ ID NO 667
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 667
cgctggtaaa tacttagaga taaa                                   24

<210> SEQ ID NO 668
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 668
acatgttccc cattgctca                                         19

<210> SEQ ID NO 669
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 669
cagtcttgtt gtattcccta aaga                                   24

<210> SEQ ID NO 670
```

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 670
gcaactgaga ggatgaggtt g                                                    21

<210> SEQ ID NO 671
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 671
gacctaagac tagtgccgtg aa                                                   22

<210> SEQ ID NO 672
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 672
gtgcaaagga aaccaggaga                                                      20

<210> SEQ ID NO 673
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 673
ggaataatat atgtggactg ctt                                                  23

<210> SEQ ID NO 674
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 674
ttacccttaa aaattccttg g                                                    21

<210> SEQ ID NO 675
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 675
```

-continued

```
aaagcaaatg gttaaatagc aga                                          23

<210> SEQ ID NO 676
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 676
ttggttcttt ctctttaatt gtg                                          23

<210> SEQ ID NO 677
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 677
cagagagaaa gcagtttgaa tttg                                         24

<210> SEQ ID NO 678
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 678
ccaagatacc ttgccttctg a                                            21

<210> SEQ ID NO 679
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 679
catcatattc ctaactgtgc tcat                                         24

<210> SEQ ID NO 680
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 680
tccttggtaa agagggtaaa gaaa                                         24

<210> SEQ ID NO 681
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 681
tactgccaac agacaactcg                                                20

<210> SEQ ID NO 682
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 682
ttagaccgca gacctttaga a                                              21

<210> SEQ ID NO 683
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 683
gtctacttca aatcatgcct c                                              21

<210> SEQ ID NO 684
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 684
ctacatgcat atctggagac                                                20

<210> SEQ ID NO 685
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 685
actgaggagt aattcatgag g                                              21

<210> SEQ ID NO 686
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 686 tggtttttacc tttctgaaaa aca                                           23
```

-continued

```
<210> SEQ ID NO 687
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 687
cacctcctaa gacaaaatgg cta                                            23

<210> SEQ ID NO 688
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 688
cctaatccag cagaccatgt                                                20

<210> SEQ ID NO 689
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 689
ggaggcagaa attgcatcag                                                20

<210> SEQ ID NO 690
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 690
gcatagccag ccattagcat                                                20

<210> SEQ ID NO 691
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 691
tctcagagca acatgtacca aaa                                            23

<210> SEQ ID NO 692
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 692
gcccaatcag acatcaatcc                                               20

<210> SEQ ID NO 693
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 693
cctcaaggcc tctccattg                                                19

<210> SEQ ID NO 694
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 694
gaagagtttt gactttttct gagg                                          24

<210> SEQ ID NO 695
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 695
atccccaagc ccaagaag                                                 18

<210> SEQ ID NO 696
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 696
acagccatga acgaagcatt                                               20

<210> SEQ ID NO 697
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 697
ggctcatgaa ctaagatagt ttgg                                          24

<210> SEQ ID NO 698
<211> LENGTH: 23
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 698
aagaaagatt gtgggattag aca                                          23

<210> SEQ ID NO 699
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 699
ccatcagagc ttagggttga a                                            21

<210> SEQ ID NO 700
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 700
ttggaggaga aaggcatcag                                              20

<210> SEQ ID NO 701
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 701
ccatcttagt tggaaatagc aacc                                         24

<210> SEQ ID NO 702
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 702
ccatcttctt ttcccaagca                                              20

<210> SEQ ID NO 703
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 703
acatgctcct agggtgcttc                                              20
```

-continued

<210> SEQ ID NO 704
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 704
ttcttgacgg tgttctgttt tt                                              22

<210> SEQ ID NO 705
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 705
cccttgttgg ggaaataaca                                                 20

<210> SEQ ID NO 706
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 706
ccctatttcc tactgaacgc tta                                             23

<210> SEQ ID NO 707
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 707
ttggaatgtc catcctttga g                                               21

<210> SEQ ID NO 708
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 708
caaacccatg gccttgaa                                                   18

<210> SEQ ID NO 709
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 709
ggtatgtatg tgggaaggga at                                        22

<210> SEQ ID NO 710
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 710
aaggttatgt aagaaagatg tca                                       23

<210> SEQ ID NO 711
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 711
aaggaagaat tctcaatgac ct                                        22

<210> SEQ ID NO 712
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 712
tggggctaaa agtcagacca                                           20

<210> SEQ ID NO 713
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 713
tttaagatat gctctctcct gact                                      24

<210> SEQ ID NO 714
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 714
ctattagtta ggtttccagt tga                                       23

<210> SEQ ID NO 715
<211> LENGTH: 24
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 715
aggaaatctg tgagtaacta tcat                                          24

<210> SEQ ID NO 716
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 716
cctaatagac ctaacaagga tgc                                           23

<210> SEQ ID NO 717
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 717
gcaatgataa caagaacaca gca                                           23

<210> SEQ ID NO 718
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 718
tggagccaaa gggagtaata                                               20

<210> SEQ ID NO 719
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 719
tctctccacc tttccacact g                                             21

<210> SEQ ID NO 720
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 720
tgtgtgaaac ctgtgacttg c                                             21

-continued

```
<210> SEQ ID NO 721
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 721
catattcata ccttcaagcc aac                                      23

<210> SEQ ID NO 722
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 722
tgtggaaaca cagcccatt                                           19

<210> SEQ ID NO 723
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 723
gaaagggatg atggttccaa                                          20

<210> SEQ ID NO 724
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 724
cccatgaaca cattcacagc                                          20

<210> SEQ ID NO 725
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 725
caggaactcg ctgaataccc                                          20

<210> SEQ ID NO 726
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
        Synthetic primer"

<400> SEQUENCE: 726
cagaggagca ccagcctatg                                        20

<210> SEQ ID NO 727
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 727
gccatgaatt aggagccttg                                        20

<210> SEQ ID NO 728
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 728
caatccaacg aagatgacca                                        20

<210> SEQ ID NO 729
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 729
accatgacct ggcttgaagt                                        20

<210> SEQ ID NO 730
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 730
ggacgatcag gttacaccta aaa                                    23

<210> SEQ ID NO 731
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 731
tccacctcct aaccaaggac                                        20

<210> SEQ ID NO 732
<211> LENGTH: 21
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 732
cagctgaaca ctgagatttt t                                               21

<210> SEQ ID NO 733
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 733
aagccctgtt tccctgtttt                                                 20

<210> SEQ ID NO 734
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 734
catctgcaga agacagactc                                                 20

<210> SEQ ID NO 735
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 735
atcattcccg gagctcaca                                                  19

<210> SEQ ID NO 736
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 736
gacacaatgt gccttgaaa                                                  19

<210> SEQ ID NO 737
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 737
```

-continued gtacagctgg aatggccaag                                              20

<210> SEQ ID NO 738
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 738
cccagtttcc atcctcagtc                                              20

<210> SEQ ID NO 739
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 739
aacaatttgc tctgagaacc tc                                           22

<210> SEQ ID NO 740
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 740
tcttggcctt cagggtttc                                               19

<210> SEQ ID NO 741
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 741
cctttgttac taagaattga agtg                                         24

<210> SEQ ID NO 742
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 742
tcgtttctta ttgtcttctg tt                                           22

<210> SEQ ID NO 743
<211> LENGTH: 20
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 743
ctcccaatat ccgacagctc                                             20

<210> SEQ ID NO 744
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 744
ccacctcagg acaggagagt                                             20

<210> SEQ ID NO 745
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 745
tggattgatg gcagaacatt                                             20

<210> SEQ ID NO 746
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 746
ctgagggctt tttggctaac                                             20

<210> SEQ ID NO 747
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 747
ttttattttt ctcacaagcc tga                                         23

<210> SEQ ID NO 748
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 748
tcagagagat aaagaaggaa agga                                        24

<210> SEQ ID NO 749
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 749
tctaattaag ccatgactcc                                              20

<210> SEQ ID NO 750
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 750
ggctgtggta tggctagcag                                              20

<210> SEQ ID NO 751
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 751
cacagagaaa gaacagaatc tgaa                                         24

<210> SEQ ID NO 752
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 752
aggcagacag atggacacat                                              20

<210> SEQ ID NO 753
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 753
gagctttgca tgcagtaggg                                              20

<210> SEQ ID NO 754
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 754
```

-continued

```
cccagcctct ctgtctatgg                                                    20

<210> SEQ ID NO 755
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 755
tgacttctat cacccctacc                                                    20

<210> SEQ ID NO 756
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 756
gtgcaggaga ggaaagcaga                                                    20

<210> SEQ ID NO 757
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 757
gttgatgaca cccacattca                                                    20

<210> SEQ ID NO 758
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 758
gcacgacgta cgaatgagtc                                                    20

<210> SEQ ID NO 759
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 759
agcaccaggc tttggctat                                                     19

<210> SEQ ID NO 760
<211> LENGTH: 22
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
      Synthetic primer"

<400> SEQUENCE: 760
gaaggatgtg agaaaagacc tg                                            22

<210> SEQ ID NO 761
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 761
gcatggtcac tgagttttgc                                               20

<210> SEQ ID NO 762
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 762
caagccacaa gaggtgatga                                               20

<210> SEQ ID NO 763
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 763
cacagaacag cttgtgaaaa tca                                           23

<210> SEQ ID NO 764
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 764
tggtactaag acccaccaaa a                                             21

<210> SEQ ID NO 765
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 765
aaaaccctct aactaggcat tgaa                                          24

```
<210> SEQ ID NO 766
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 766
gcttgctctt attattttga cgtt                                              24

<210> SEQ ID NO 767
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 767
agaatttgga actcactttg g                                                 21

<210> SEQ ID NO 768
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 768
aaacagatcc tattgtgtct ggaa                                              24

<210> SEQ ID NO 769
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 769
acctcatgca ccagccctta                                                   20

<210> SEQ ID NO 770
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 770
aagtgttgct ccctgctgtc                                                   20

<210> SEQ ID NO 771
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 771
aaaggtcttt caggagaatt tg                                            22

<210> SEQ ID NO 772
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 772
aggtggccat acacatgctt                                               20

<210> SEQ ID NO 773
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 773
ggttgtccat gtccccaag                                                19

<210> SEQ ID NO 774
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 774
tttgcagtgt ttatgccaca                                               20

<210> SEQ ID NO 775
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 775
tcatggcaat ttaaatgatg ag                                            22

<210> SEQ ID NO 776
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 776
tttaaatggt gccttgtttc tt                                            22

<210> SEQ ID NO 777
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 777
cagggcacta actgaaaaat                                                20

<210> SEQ ID NO 778
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 778
gggatatgga ttatctttct cat                                            23

<210> SEQ ID NO 779
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 779
agccccaaac taagtgctga                                                20

<210> SEQ ID NO 780
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 780
cccagagcca gtgcattta                                                 19

<210> SEQ ID NO 781
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 781
tgatgagaaa acacagaaat gc                                             22

<210> SEQ ID NO 782
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 782
cctggctgaa tcaaggaaga                                                20
```

<210> SEQ ID NO 783
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 783
cagtgacagt tttctcatta agc                                 23

<210> SEQ ID NO 784
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 784
taggaacaat ccccaatcca                                    20

<210> SEQ ID NO 785
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 785
tgagaaactc acttggggtc a                                   21

<210> SEQ ID NO 786
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 786
tgacagcaat tctggtctgc                                    20

<210> SEQ ID NO 787
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 787
aggcttgaag aaaagcttca t                                   21

<210> SEQ ID NO 788
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

-continued

```
<400> SEQUENCE: 788
ctttttcata tccagtattt cag                                               23

<210> SEQ ID NO 789
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 789
cagctagaat ctatacaagg aagg                                              24

<210> SEQ ID NO 790
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 790
ggatacaaca ggaactagga tcaa                                              24

<210> SEQ ID NO 791
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 791
cccattatta tgctgttatg ctg                                               23

<210> SEQ ID NO 792
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 792
tctgagagtt aaatccttgg tga                                               23

<210> SEQ ID NO 793
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 793
cacctcttaa cagtttcatt tt                                                22

<210> SEQ ID NO 794
<211> LENGTH: 20
<212> TYPE: DNA
```

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 794
ggccgacagc ttctacttta                                          20

<210> SEQ ID NO 795
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 795
aaggagggct tagctagttg                                          20

<210> SEQ ID NO 796
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 796
gctctttctc atcttaaggc ttc                                      23

<210> SEQ ID NO 797
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 797
gttaaaatta ctgttccagt tgt                                      23

<210> SEQ ID NO 798
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 798
caggcaacca ataataaca aaa                                       23

<210> SEQ ID NO 799
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 799
ggattctgca gaccctcagt                                          20
```

<210> SEQ ID NO 800
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 800
caccttgcca ctcactgttg                                                20

<210> SEQ ID NO 801
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 801
gggttccagc aatattctac ctt                                            23

<210> SEQ ID NO 802
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 802
ggtaatgaag aaagacaaaa ca                                             22

<210> SEQ ID NO 803
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 803
ctgtgtggct ggggaagc                                                  18

<210> SEQ ID NO 804
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 804
gcacataacc tcagaaccag                                                20

<210> SEQ ID NO 805
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
            Synthetic primer"

<400> SEQUENCE: 805
ggagccccaa ccctaattt                                            19

<210> SEQ ID NO 806
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 806
atcctcatcc tccgcaca                                             18

<210> SEQ ID NO 807
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 807
cggtagctaa gtatctgctt ttt                                       23

<210> SEQ ID NO 808
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 808
gggcaggaat tattatgttc ca                                        22

<210> SEQ ID NO 809
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 809
ggatgttttt gcagtttatt                                           20

<210> SEQ ID NO 810
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 810
acttgctctg atacctaaat ga                                        22

<210> SEQ ID NO 811
<211> LENGTH: 20
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 811
cggctctctc ctcattctgt                                          20

<210> SEQ ID NO 812
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 812
gcattgccac tgagacatga                                          20

<210> SEQ ID NO 813
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 813
aagaggaggg ctttgagtcc                                          20

<210> SEQ ID NO 814
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 814
tttagtagag ctactgatca ttcc                                     24

<210> SEQ ID NO 815
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 815
caattaagtc aggtaataat gctg                                     24

<210> SEQ ID NO 816
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 816
```

-continued

```
aagccattca tttgggtttg                                          20

<210> SEQ ID NO 817
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 817
ttgattccta ttgagctttc a                                        21

<210> SEQ ID NO 818
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 818
ggcctctgac atcactctca                                          20

<210> SEQ ID NO 819
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 819
ggcaagggtt taggacttgg                                          20

<210> SEQ ID NO 820
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 820
ggattgcgcc tcaaaataaa                                          20

<210> SEQ ID NO 821
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 821
cttccctgca catccttttg                                          20

<210> SEQ ID NO 822
<211> LENGTH: 24
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 822
ctgtttagga agagtcatgt aacc                                              24

<210> SEQ ID NO 823
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 823
tggcctattt ctcaaatgca g                                                 21

<210> SEQ ID NO 824
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 824
ctgcaaggca cgatctatga                                                   20

<210> SEQ ID NO 825
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 825
gtgattctaa caggtatgta atga                                              24

<210> SEQ ID NO 826
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 826
tgcatgttaa caccacattg ag                                                22

<210> SEQ ID NO 827
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 827
ggagaccata ctgaagttat ttt                                               23

<210> SEQ ID NO 828
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 828
tttcgagttg gtggtaattt                                                    20

<210> SEQ ID NO 829
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 829
tcgaaggtag aattaaatgt ttc                                                23

<210> SEQ ID NO 830
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 830
gatagtgact tataacaact ccaa                                               24

<210> SEQ ID NO 831
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 831
tgaattgaag ggttttggac                                                    20

<210> SEQ ID NO 832
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 832
gcacacgtta agatggtttg aa                                                 22

<210> SEQ ID NO 833
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 833
```

```
ggggagggag acgtaaaaac                                                  20

<210> SEQ ID NO 834
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 834
tccagatttt cctgttcatg att                                              23

<210> SEQ ID NO 835
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 835
gcacatcaca agttaagagg                                                  20

<210> SEQ ID NO 836
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 836
ccccagtagg gaacacactt                                                  20

<210> SEQ ID NO 837
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 837
caggatgcac tttttggatg                                                  20

<210> SEQ ID NO 838
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 838
ggcttctccc agaaaatctc                                                  20

<210> SEQ ID NO 839
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 839
ggggaggccc tacaagttat                                              20

<210> SEQ ID NO 840
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 840
gaagggaggg gcatcttta                                               19

<210> SEQ ID NO 841
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 841
aaaatcacat ctgctaaata tcc                                          23

<210> SEQ ID NO 842
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 842
tggacgatag aacttgttag tgc                                          23

<210> SEQ ID NO 843
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 843
ccattaagca gacacaccta cg                                           22

<210> SEQ ID NO 844
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 844
ctcctttgaa agtggatcaa a                                            21
```

-continued

```
<210> SEQ ID NO 845
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 845
tctgaaaatg gggctaaaac tt                                              22

<210> SEQ ID NO 846
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 846
tccttaaagc agccctaaaa                                                 20

<210> SEQ ID NO 847
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 847
agtttagatt tcagtctatg caa                                             23

<210> SEQ ID NO 848
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 848
tggagaatag ctcctgcagt t                                               21

<210> SEQ ID NO 849
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 849
tctttctgga gacactcagg                                                 20

<210> SEQ ID NO 850
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 850
ctggaatcta gaaagaaaaa gaa                                          23

<210> SEQ ID NO 851
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 851
caaagataga tgagatgctt tt                                           22

<210> SEQ ID NO 852
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 852
ctgacattga aaacttgaaa gaa                                          23

<210> SEQ ID NO 853
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 853
agccctcctc caccgttag                                               19

<210> SEQ ID NO 854
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 854
gcccagctac gatttctcct                                              20

<210> SEQ ID NO 855
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 855
ttttatgcag cctgtgatgg                                              20

<210> SEQ ID NO 856
<211> LENGTH: 22
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 856
cccttagttc aatcaagcca ac                                          22

<210> SEQ ID NO 857
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 857
cactcttgca atctccctca g                                           21

<210> SEQ ID NO 858
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 858
ctgacccttg tgggattcat                                             20

<210> SEQ ID NO 859
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 859
cttttatgat atccaccaag act                                         23

<210> SEQ ID NO 860
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 860
tggatcatct gtccaaagtc a                                           21

<210> SEQ ID NO 861
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 861
ccaaaacctg ctctccaaga                                             20
```

-continued

```
<210> SEQ ID NO 862
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 862
aagactactg aggttgtgca aaga                                          24

<210> SEQ ID NO 863
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 863
ttcaacttgg taccctgaaa aa                                            22

<210> SEQ ID NO 864
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 864
agtcagttag tatgcagtac ttgg                                          24

<210> SEQ ID NO 865
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 865
tcttaaaagt gtcttgactg aaa                                           23

<210> SEQ ID NO 866
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 866
ggtcaatggc taaatcattc g                                             21

<210> SEQ ID NO 867
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 867
gcaattccag atatctcttt at                                                                22

<210> SEQ ID NO 868
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 868
ttatctaccc atgcttctct c                                                                 21

<210> SEQ ID NO 869
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 869
gcataaacaa atgtgtaacg tggt                                                              24

<210> SEQ ID NO 870
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 870
tgttttcgta gtctttattg ct                                                                22

<210> SEQ ID NO 871
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 871
tgctagctat atgtaggtca gtt                                                               23

<210> SEQ ID NO 872
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 872
cgttagttcc ctggaaagat ca                                                                22

<210> SEQ ID NO 873
<211> LENGTH: 23
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 873
ttgcatagat gtagcagtat ttc                                        23

<210> SEQ ID NO 874
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 874
gactttctta aagctgcaca atca                                       24

<210> SEQ ID NO 875
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 875
gtttgcttgc ttttactttg                                            20

<210> SEQ ID NO 876
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 876
tgtgaagcac catttctgtt t                                          21

<210> SEQ ID NO 877
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 877
aacagtgagg ctctcctgta gc                                         22

<210> SEQ ID NO 878
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 878
cccattgtca ccgaggata                                             19
```

-continued

```
<210> SEQ ID NO 879
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 879
cagagagctc acttctagtt ctgc                                          24

<210> SEQ ID NO 880
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 880
gctatcttgg gtcatgaatt tg                                            22

<210> SEQ ID NO 881
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 881
cctcatgcaa ttcaaaggaa                                               20

<210> SEQ ID NO 882
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 882
catttcccct aggtttgtgc                                               20

<210> SEQ ID NO 883
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 883
gtggggcaca cagtgtctt                                                19

<210> SEQ ID NO 884
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
       Synthetic primer"

<400> SEQUENCE: 884
cttagatttg ttcatctgat ggt                                        23

<210> SEQ ID NO 885
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 885
ttgggtagat gcaatgcaag                                            20

<210> SEQ ID NO 886
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 886
aacccatatg actaaggtga a                                          21

<210> SEQ ID NO 887
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 887
gctgaaaatt cacactgtgg tc                                         22

<210> SEQ ID NO 888
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 888
tgtcataatg aagagctagt tgc                                        23

<210> SEQ ID NO 889
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 889
gagaggtaag agagagtatc tttg                                       24

<210> SEQ ID NO 890
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 890
gagttatttc ccttaaaaac cag                                                     23

<210> SEQ ID NO 891
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 891
gctacgcttg acacccttac a                                                       21

<210> SEQ ID NO 892
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 892
ggatgctgtg agtgctaaat ga                                                      22

<210> SEQ ID NO 893
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 893
ggcactgcgt cagcatacta                                                         20

<210> SEQ ID NO 894
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 894
ctggctcctt gccatcat                                                           18

<210> SEQ ID NO 895
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 895
```
taggcctcag aaagaacgag                                          20

<210> SEQ ID NO 896
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 896
tgctaggctt acttcgtttt c                                        21

<210> SEQ ID NO 897
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 897
aaaataattc cctttggtat gc                                       22

<210> SEQ ID NO 898
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 898
catcatgaat tctcccaatg c                                        21

<210> SEQ ID NO 899
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 899
ttgggtaaat gtgtgactac gc                                       22

<210> SEQ ID NO 900
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 900
tacctggggc cctgatttat                                          20

<210> SEQ ID NO 901
<211> LENGTH: 21
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 901
gcactgaaaa tgttagtgat t                                           21

<210> SEQ ID NO 902
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 902
ccttagtgag gtatttaggt taca                                        24

<210> SEQ ID NO 903
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 903
agggagttat gatgccaagg                                             20

<210> SEQ ID NO 904
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 904
tgatcagggg tagaagagat tt                                          22

<210> SEQ ID NO 905
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 905
cggcttccaa tcgtatcttg                                             20

<210> SEQ ID NO 906
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 906
gacaagtcag agaacaagct g                                           21

<210> SEQ ID NO 907
```

-continued

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 907
tcatctgtaa ctaatgaacc ttg                                              23

<210> SEQ ID NO 908
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 908
tcaggaaaga atgctactca                                                  20

<210> SEQ ID NO 909
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 909
aattggatgc tgttttaacc                                                  20

<210> SEQ ID NO 910
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 910
tgccacatga caaattatca ca                                               22

<210> SEQ ID NO 911
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 911
ccaaggttta gctacatgta taa                                              23

<210> SEQ ID NO 912
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 912
```

-continued

```
ctgatagaaa aatttctgtt gtg                                            23

<210> SEQ ID NO 913
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 913
attccttccc gccttgct                                                  18

<210> SEQ ID NO 914
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 914
attcctgcac aggctcagac                                                20

<210> SEQ ID NO 915
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 915
aaatgttcag tgtaaaaggc taca                                           24

<210> SEQ ID NO 916
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 916
aaaggactag cagcatgtaa ctc                                            23

<210> SEQ ID NO 917
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 917
cactacttcc ccttcccaaa                                                20

<210> SEQ ID NO 918
<211> LENGTH: 23
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 918
aagatctggt agaaataaat gga                                           23

<210> SEQ ID NO 919
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 919
gcttccaggc taaaagaagg                                               20

<210> SEQ ID NO 920
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 920
aaaaagaaaa gctggttagg                                               20

<210> SEQ ID NO 921
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 921
cacctctatg gtttagtcca ctcc                                          24

<210> SEQ ID NO 922
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 922
cctgggattg aaagcaccta                                               20

<210> SEQ ID NO 923
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 923
ggaattgcca ctctggagaa                                               20
```

-continued

```
<210> SEQ ID NO 924
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 924
agtggtcccc aacaacttga                                                  20

<210> SEQ ID NO 925
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 925
tcagataaaa caattccagt tac                                              23

<210> SEQ ID NO 926
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 926
acccacagag gaaagccttg                                                  20

<210> SEQ ID NO 927
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 927
cctgctggca cacgtaagtt                                                  20

<210> SEQ ID NO 928
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 928
ccatgggaat ttgaaccact                                                  20

<210> SEQ ID NO 929
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 929
aaccacaatc cacctcttgc                                                     20

<210> SEQ ID NO 930
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 930
gccaagtcat taacacaaag tga                                                 23

<210> SEQ ID NO 931
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 931
cccactcttc tgctttactc ca                                                  22

<210> SEQ ID NO 932
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 932
gagaagggga aagagaacaa a                                                   21

<210> SEQ ID NO 933
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 933 ggcttttttcc acccagctta                                                    20

<210> SEQ ID NO 934
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 934
agtgggcaat aataaacctt                                                     20

<210> SEQ ID NO 935
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 935
ggtggctgga gaaattgaga                                                  20

<210> SEQ ID NO 936
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 936
aaagacaatt tggctggtgt tt                                               22

<210> SEQ ID NO 937
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 937
gctaagttgc ctccaagctg                                                  20

<210> SEQ ID NO 938
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 938
ttccctattt ctgccaaagc                                                  20

<210> SEQ ID NO 939
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 939
ttcatggaga tttgaccagt g                                                21

<210> SEQ ID NO 940
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 940
cagatactcc tttttggaga gtca                                             24
```

-continued

```
<210> SEQ ID NO 941
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 941
cagctaatgc ataagggaga tg                                            22

<210> SEQ ID NO 942
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 942
ccagaacatt tcatcactcc aa                                            22

<210> SEQ ID NO 943
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 943
gtacagagtc cctgtctcac a                                             21

<210> SEQ ID NO 944
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 944
catgatctgt ctctctcact gaa                                           23

<210> SEQ ID NO 945
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 945
gtggcagaac tgacatgcaa                                               20

<210> SEQ ID NO 946
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 946
tgtgggggca gacagact                                                      18

<210> SEQ ID NO 947
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 947
tccaccagaa accctttgg                                                     19

<210> SEQ ID NO 948
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 948
cctctgtgga aggaaggaa                                                     20

<210> SEQ ID NO 949
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 949
cccgctccag gttattctc                                                     19

<210> SEQ ID NO 950
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 950
aagaaatctg aaaagcagag g                                                  21

<210> SEQ ID NO 951
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 951
aactgattca catgaggttg c                                                  21

<210> SEQ ID NO 952
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 952
tttgagaggc aacattaaca a                                              21

<210> SEQ ID NO 953
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 953
agtctgtaca aggggccaca                                                20

<210> SEQ ID NO 954
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 954
taaggctcct gtggtagacg                                                20

<210> SEQ ID NO 955
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 955
catcatggaa ggtccctcac                                                20

<210> SEQ ID NO 956
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 956
caagatcaag gcattggtag                                                20

<210> SEQ ID NO 957
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 957
aggttcagat tctatttctg tca                                            23

-continued

```
<210> SEQ ID NO 958
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 958
ccttgcctaa gataacacaa cca                                             23

<210> SEQ ID NO 959
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 959
tgttttgtaa ttcctttcag tca                                             23

<210> SEQ ID NO 960
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 960
cctcaaatac tgaagatagc aagc                                            24

<210> SEQ ID NO 961
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 961
gacaagaact gaaggcaaag g                                               21

<210> SEQ ID NO 962
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 962
gggaggaaca gaacaacctt c                                               21

<210> SEQ ID NO 963
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 963
tcgcagtctt ttgcatcatt                                          20

<210> SEQ ID NO 964
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 964
tccaatagct accttcacca gaa                                      23

<210> SEQ ID NO 965
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 965
ggttaaattc tacttcgcaa cca                                      23

<210> SEQ ID NO 966
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 966
gcagtgtagt ctaactagct gtgt                                     24

<210> SEQ ID NO 967
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 967
cagcttccca gtttctcaca                                          20

<210> SEQ ID NO 968
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 968
aattgctaca ttcctgtcta ttg                                      23

<210> SEQ ID NO 969
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 969
gcggaaagac attccatgtt                                                        20

<210> SEQ ID NO 970
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 970
tgcatctcaa tgatattgct ttt                                                    23

<210> SEQ ID NO 971
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 971
tctctgagag caaagacact                                                        20

<210> SEQ ID NO 972
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 972
tgtgcaatag taataatggg tct                                                    23

<210> SEQ ID NO 973
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 973
gagggtacct ttctttctcc                                                        20

<210> SEQ ID NO 974
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 974
```

-continued

```
gctcagtgtc tgacaaaagc                                        20

<210> SEQ ID NO 975
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 975
tggctgccta aaattattta cga                                    23

<210> SEQ ID NO 976
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 976
aagcaaataa ggccatctaa gaa                                    23

<210> SEQ ID NO 977
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 977
tcaaacaaaa acagtgtagg catt                                   24

<210> SEQ ID NO 978
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 978
gaaaagttaa gtcagaggct atcg                                   24

<210> SEQ ID NO 979
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 979
aagtcaccta aatggcatga                                        20

<210> SEQ ID NO 980
<211> LENGTH: 20
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 980
agacacagca agatgcaaaa                                            20

<210> SEQ ID NO 981
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 981
cagcaaccct ttgaagcaat                                            20

<210> SEQ ID NO 982
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 982
tgttttctct tcaaatgcaa                                            20

<210> SEQ ID NO 983
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 983
tgactcagtg gtgaactgtc t                                          21

<210> SEQ ID NO 984
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 984
gcagcccatt aatactagca ca                                         22

<210> SEQ ID NO 985
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 985
tgcattcaag aggaagaaag g                                          21

<210> SEQ ID NO 986
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 986
tcaggacgaa ttcacaggat                                               20

<210> SEQ ID NO 987
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 987
atgaaggcca ggctgtagg                                                19

<210> SEQ ID NO 988
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 988
gaacattcac tgccttactc tca                                           23

<210> SEQ ID NO 989
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 989
ttcagtgaag ggatggacct                                               20

<210> SEQ ID NO 990
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 990
ggccacagga tctcctatct                                               20

<210> SEQ ID NO 991
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 991
```

-continued

```
ccaagtaatc acttcaaccc tct                                        23

<210> SEQ ID NO 992
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 992
gctagctacg cccacgagat                                            20

<210> SEQ ID NO 993
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 993
aactcaaacc taagtgcccc                                            20

<210> SEQ ID NO 994
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 994
ggaatggaat agtgtgtggg                                            20

<210> SEQ ID NO 995
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 995
acactggtct caagctccc                                             19

<210> SEQ ID NO 996
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 996
cacacctgta attctagccc                                            20

<210> SEQ ID NO 997
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 997
agaaggaagg atcagagaag                                                    20

<210> SEQ ID NO 998
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 998
agctttcctc cccacactg                                                     19

<210> SEQ ID NO 999
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 999
taacaaattt gcatgtcatc                                                    20

<210> SEQ ID NO 1000
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1000
agaagccagg tgctgaagtg                                                    20

<210> SEQ ID NO 1001
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1001
gctgtgtgga gccctataaa                                                    20

<210> SEQ ID NO 1002
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1002
gaatgaaatg gagtttgcag                                                    20
```

-continued

```
<210> SEQ ID NO 1003
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1003
ggcagtgttt aaggtgttgg                                                    20

<210> SEQ ID NO 1004
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1004
aggtagtgat ttctaggctt atca                                              24

<210> SEQ ID NO 1005
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1005
cctggaagta ttcattcatg tgg                                               23

<210> SEQ ID NO 1006
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1006
gggacatctg ggtagcactg                                                   20

<210> SEQ ID NO 1007
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1007
aagagtgtct cctccctctg                                                   20

<210> SEQ ID NO 1008
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1008
aactggaggc tgtgttagac                                          20

<210> SEQ ID NO 1009
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1009
aaaaacccca ggctccattg                                          20

<210> SEQ ID NO 1010
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1010
atgtccagct gcttcttttc                                          20

<210> SEQ ID NO 1011
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1011
atggcttgta cttcctcctc                                          20

<210> SEQ ID NO 1012
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1012
ttcggtggaa tagcagcaag                                          20

<210> SEQ ID NO 1013
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1013
agtatgccat catgaaagcc                                          20

<210> SEQ ID NO 1014
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 1014
cttctttgac taaggctgac                                              20

<210> SEQ ID NO 1015
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1015
gatcttccag ggggcact                                                18

<210> SEQ ID NO 1016
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1016
tcattttggt ttcgttcatt                                              20

<210> SEQ ID NO 1017
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1017
ccttttgtgg cttttcctca                                              20

<210> SEQ ID NO 1018
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1018
ggcattccaa catgaaaagg                                              20

<210> SEQ ID NO 1019
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1019
cagctgctgt tccctcaga                                               19
```

```
<210> SEQ ID NO 1020
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1020
ccaaaaaacc atgccctctg                                                   20

<210> SEQ ID NO 1021
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1021
ggttcacaga gcccaagtta c                                                 21

<210> SEQ ID NO 1022
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1022
tgagtctctt actgatcctg tgac                                              24

<210> SEQ ID NO 1023
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1023
cttccctctg cctcttttag a                                                 21

<210> SEQ ID NO 1024
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1024
ccaaagagct caggtctcca                                                   20

<210> SEQ ID NO 1025
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 1025
aggtgagcat ggggttgata                                        20

<210> SEQ ID NO 1026
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1026
acctcttcct tcctcaccaa                                        20

<210> SEQ ID NO 1027
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1027
ggcagctcca cacaccttag                                        20

<210> SEQ ID NO 1028
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1028
tcatcttttg gttttagatt gtg                                    23

<210> SEQ ID NO 1029
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1029
caactgcccg cttatcctt                                         19

<210> SEQ ID NO 1030
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1030
aagacagctt gaagattctg g                                      21

<210> SEQ ID NO 1031
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1031
aaggtctaag ggggcacaag                                                20

<210> SEQ ID NO 1032
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1032
atggccacgc tctttgtc                                                  18

<210> SEQ ID NO 1033
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1033
ccagattatc ttcttcgccc ta                                             22

<210> SEQ ID NO 1034
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1034
tgattagggt tgggaagtgg                                                20

<210> SEQ ID NO 1035
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1035
ttcagctctt ctactctgga ctg                                            23

<210> SEQ ID NO 1036
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1036
tgaaacaaga gaagactgga tttg                                           24

-continued

```
<210> SEQ ID NO 1037
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1037
caagttagtg agaaacagag tcg                                              23

<210> SEQ ID NO 1038
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1038
ggcctctact ccaagaaagc                                                  20

<210> SEQ ID NO 1039
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1039
gttatatctc ttttgtttct ctcc                                            24

<210> SEQ ID NO 1040
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1040
ttggattgtt agagaataac g                                               21

<210> SEQ ID NO 1041
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1041
gtccagctgt gtgattatct                                                 20

<210> SEQ ID NO 1042
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 1042
agagggagat ggaataaaaa                                                    20

<210> SEQ ID NO 1043
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1043
aaaaataaac atccctgtgg                                                    20

<210> SEQ ID NO 1044
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1044
acatagccac cagccacact                                                    20

<210> SEQ ID NO 1045
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1045
tgctcttttt ctcacaaatg a                                                  21

<210> SEQ ID NO 1046
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1046
atattggtca gtggggcaaa                                                    20

<210> SEQ ID NO 1047
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1047
gcacatgagc tgagactgga                                                    20

<210> SEQ ID NO 1048
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1048
tggcagtatt acctgagcaa                                                                    20

<210> SEQ ID NO 1049
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1049
gcagcgtctt gcctcctt                                                                      18

<210> SEQ ID NO 1050
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1050
gcccagctct taacacaaca                                                                    20

<210> SEQ ID NO 1051
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1051
aaaaggctgg aggatgaagg                                                                    20

<210> SEQ ID NO 1052
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1052
tcagaaggca cctctgtcac                                                                    20

<210> SEQ ID NO 1053
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1053
```
tgcaaccaaa actcagttat cta                                                    23

<210> SEQ ID NO 1054
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1054
tcccttgcct atcattgctt                                                        20

<210> SEQ ID NO 1055
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1055
ttcccagcct tccaggag                                                          18

<210> SEQ ID NO 1056
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1056
tacaatggct gactgagcac                                                        20

<210> SEQ ID NO 1057
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1057
tgatttaaac ctgatcttgg tga                                                    23

<210> SEQ ID NO 1058
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1058
attcctgtcc accctggtc                                                         19

<210> SEQ ID NO 1059
<211> LENGTH: 20
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic primer"

<400> SEQUENCE: 1059
cctttgatca caagcaacca                                                                    20

<210> SEQ ID NO 1060
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1060
ttactcttgg gtcaggtgca t                                                                  21

<210> SEQ ID NO 1061
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1061
atggcagaag agcccagag                                                                     19

<210> SEQ ID NO 1062
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1062
cgatgctgac cttctggagt                                                                    20

<210> SEQ ID NO 1063
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1063
gctgaaaaac ccaggaatca                                                                    20

<210> SEQ ID NO 1064
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1064
ggagttgagg gagagggtct                                                                    20

<210> SEQ ID NO 1065

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1065
gacagaatga aatgctgtgt                                                    20

<210> SEQ ID NO 1066
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1066
ctttctaatc cagcagcctc t                                                  21

<210> SEQ ID NO 1067
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1067
ctgatccccg taagatcagc                                                    20

<210> SEQ ID NO 1068
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1068
caggatgaaa cggtgcag                                                      18

<210> SEQ ID NO 1069
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1069
tctctgacct gcttcctcgt                                                    20

<210> SEQ ID NO 1070
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1070
```

```
taaggcaata ggcaccaagc                                                  20

<210> SEQ ID NO 1071
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1071
agcaatgggg tcagagtcc                                                   19

<210> SEQ ID NO 1072
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1072
agctgattcc ttccctggat                                                  20

<210> SEQ ID NO 1073
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1073
cctgatggag gatccacttg                                                  20

<210> SEQ ID NO 1074
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1074
ctgcaaagct tcccatcct                                                   19

<210> SEQ ID NO 1075
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1075
ggggatctta aaagcaccaa                                                  20

<210> SEQ ID NO 1076
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 1076
gacactccca cttctgccta                                           20

<210> SEQ ID NO 1077
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1077
atttcttcaa gtgtatacag agc                                       23

<210> SEQ ID NO 1078
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1078
caggcaaaca ttcccttgta                                           20

<210> SEQ ID NO 1079
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1079
cactgttgac tccaaaacaa aaa                                       23

<210> SEQ ID NO 1080
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1080
cttcccacaa caatgagctg                                           20

<210> SEQ ID NO 1081
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1081
gcagctaaga aagactctcc aa                                        22
```

-continued

```
<210> SEQ ID NO 1082
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1082
tctttgctcc ccacctatt                                                19

<210> SEQ ID NO 1083
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1083
tgaattcaac tgatggcaca                                               20

<210> SEQ ID NO 1084
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1084
aagatttaat cctttgagat gc                                            22

<210> SEQ ID NO 1085
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1085
tgaaaggacc caccaaatgt                                               20

<210> SEQ ID NO 1086
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1086
ttttgttgtg tgtttgcttt                                               20

<210> SEQ ID NO 1087
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1087
ttgctggctt acattcattc c                                           21

<210> SEQ ID NO 1088
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1088
tacagctcag ccagttctgc                                             20

<210> SEQ ID NO 1089
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1089
tggttggtat ggttattatt gg                                          22

<210> SEQ ID NO 1090
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1090
gccttagttt ctctttctgt aaaa                                        24

<210> SEQ ID NO 1091
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1091
ggccagcaca aacacacc                                               18

<210> SEQ ID NO 1092
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1092
tcctaggact ctccctttag a                                           21

<210> SEQ ID NO 1093
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 1093
aatgggcaga tgagagcaag                                              20

<210> SEQ ID NO 1094
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1094
ccagtaccta ccccatgtcc                                              20

<210> SEQ ID NO 1095
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1095
tccttttgac aggtccacat c                                            21

<210> SEQ ID NO 1096
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1096
tggcccaatt ttcagtaact tc                                           22

<210> SEQ ID NO 1097
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1097
caccaggggt agaagtaaga cg                                           22

<210> SEQ ID NO 1098
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1098
gagtatccat gcccagaacc                                              20
```

```
<210> SEQ ID NO 1099
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1099
tgcatgtctg tatgtgtgtt gg                                              22

<210> SEQ ID NO 1100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1100
atgctcccac tgcatcctta                                                20

<210> SEQ ID NO 1101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1101
aaatgaagag ccagcagcat                                                20

<210> SEQ ID NO 1102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1102
cccaccaaca ctaacctagc a                                              21

<210> SEQ ID NO 1103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1103
acatctagct gaggtcagaa                                                20

<210> SEQ ID NO 1104
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 1104
tgtgcagatt tatgcaaatc aa                                                   22

<210> SEQ ID NO 1105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1105
gggaatttct ctggttggag                                                      20

<210> SEQ ID NO 1106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1106
aaacacagct tcatgacaag                                                      20

<210> SEQ ID NO 1107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1107
ggactgagca tatgtggaaa                                                      20

<210> SEQ ID NO 1108
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1108
cctgaatttt tacttctttg ctt                                                  23

<210> SEQ ID NO 1109
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1109
ttgctgagta acaggaaaac aa                                                   22

<210> SEQ ID NO 1110
<211> LENGTH: 23
<212> TYPE: DNA
```

-continued

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1110
tgctaaacca ttaaataatc tgg                                            23

<210> SEQ ID NO 1111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1111
gatgctaagc ccatctcctg                                                20

<210> SEQ ID NO 1112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1112
agggtaggaa ggatgcaatg                                                20

<210> SEQ ID NO 1113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1113
ggagcgacca ctcttcattt                                                20

<210> SEQ ID NO 1114
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1114
ctgaagggct cccaggcta                                                 19

<210> SEQ ID NO 1115
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1115
gaagattttg tagctggtct tgg                                            23
```

-continued

```
<210> SEQ ID NO 1116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1116
ccacaatggt ttgtaagatt t                                             21

<210> SEQ ID NO 1117
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1117
tgcgttcttt ggagataaga cc                                            22

<210> SEQ ID NO 1118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1118
cacatttctc acccatgtca a                                             21

<210> SEQ ID NO 1119
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1119
gttccctcat ctgcccttc                                                19

<210> SEQ ID NO 1120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1120
tgtgagatga gtggagagca a                                             21

<210> SEQ ID NO 1121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 1121
taaatgtgcc tggcttgatg                                                   20

<210> SEQ ID NO 1122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1122
ccctttcctt ccttggatgt                                                   20

<210> SEQ ID NO 1123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1123
tgcaaggaca ccagaacaga                                                   20

<210> SEQ ID NO 1124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1124
catttgcaca gcatctgacc                                                   20

<210> SEQ ID NO 1125
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1125
gggtgagatc aaattcttag gc                                                22

<210> SEQ ID NO 1126
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1126
ttctaatatg tatttgggag agag                                              24

<210> SEQ ID NO 1127
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1127
gccatgtttt catcttgtgg                                               20

<210> SEQ ID NO 1128
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1128
tctgtaaagg acttcatgtt tcat                                          24

<210> SEQ ID NO 1129
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1129
tcctgccatc ttaatagtct caca                                          24

<210> SEQ ID NO 1130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1130
cttgtggcct ctcattctcc                                               20

<210> SEQ ID NO 1131
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1131
tgttaatgta aaattgcctc gat                                           23

<210> SEQ ID NO 1132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1132
```

```
gagctctggc atttctctgc                                          20

<210> SEQ ID NO 1133
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1133
tgctggaaag tcattttga                                           19

<210> SEQ ID NO 1134
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1134
ttggcattat ttgtgatcc                                           19

<210> SEQ ID NO 1135
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1135
ccacactccc cagaccag                                            18

<210> SEQ ID NO 1136
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1136
gggaagacca gaacttcaga aa                                       22

<210> SEQ ID NO 1137
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1137
ctcttgcctt ctcattcaca a                                        21

<210> SEQ ID NO 1138
<211> LENGTH: 20
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic primer"

<400> SEQUENCE: 1138
ctttcctccc tttgggactc                                              20

<210> SEQ ID NO 1139
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1139
cccacgcact gtaccaca                                                18

<210> SEQ ID NO 1140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1140
tcagggcgag atacaccttt                                              20

<210> SEQ ID NO 1141
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1141
gccagctcag ctcctctct                                               19

<210> SEQ ID NO 1142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1142
gagggaaatt cgagcatcag                                              20

<210> SEQ ID NO 1143
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1143
ggcactcaat aaacattgac aca                                          23

<210> SEQ ID NO 1144

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1144
gggagagagg tgttctcagc                                              20

<210> SEQ ID NO 1145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1145
cgcaatacct tcaacagcag                                              20

<210> SEQ ID NO 1146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1146
ggtgggctgc attcataaag                                              20

<210> SEQ ID NO 1147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1147
tgccaagaat ccactccaag                                              20

<210> SEQ ID NO 1148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1148
ggggagggag aattggacta                                              20

<210> SEQ ID NO 1149
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1149
```

-continued

```
caaagaaaca gaatgaaaaa gtgg                                              24

<210> SEQ ID NO 1150
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1150
caccaacctg gaatgcttac t                                                21

<210> SEQ ID NO 1151
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1151
tgactgctct aaaatctttg tca                                              23

<210> SEQ ID NO 1152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1152
atacgccaaa cagtgagatg                                                  20

<210> SEQ ID NO 1153
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1153
tgacctatct ataacctgtc cac                                              23

<210> SEQ ID NO 1154
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1154
tgggaatttt agtttctctg tct                                              23

<210> SEQ ID NO 1155
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 1155
attgatctat gtgtctgtag ctt                                            23

<210> SEQ ID NO 1156
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1156
aattaagaca gtgtggtatt gg                                             22

<210> SEQ ID NO 1157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1157
ttcagagagg gacacccttg                                                20

<210> SEQ ID NO 1158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1158
ttcttcgcaa ccacactttg                                                20

<210> SEQ ID NO 1159
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1159
gaggctctct ggggcttg                                                  18

<210> SEQ ID NO 1160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1160
agccttccac ctgattgaaa                                                20
```

```
<210> SEQ ID NO 1161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1161
agagtcatgc atccttcatt                                                      20

<210> SEQ ID NO 1162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1162
tggtggagac acagatccaa                                                      20

<210> SEQ ID NO 1163
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1163
gcagcaggaa ccattcaca                                                       19

<210> SEQ ID NO 1164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1164
cacttgtgtc ctccaacatt                                                      20

<210> SEQ ID NO 1165
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1165
cccctcagag tgatgactgg                                                      20

<210> SEQ ID NO 1166
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1166
ctcctgaccc agccacttt                                              19

<210> SEQ ID NO 1167
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1167
gaaaatcttg tggagcctga a                                           21

<210> SEQ ID NO 1168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1168
agagaggaga tgggggaaag                                             20

<210> SEQ ID NO 1169
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1169
tgagcctaca ctaacacatc a                                           21

<210> SEQ ID NO 1170
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1170
gccctaatgt aaactaaaga cgtt                                        24

<210> SEQ ID NO 1171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1171
ggaaatgtga ccctcacagg                                             20

<210> SEQ ID NO 1172
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 1172
ttttccatac ctaaagaacg                                                20

<210> SEQ ID NO 1173
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1173
catcatctct tccttatgtt ctcc                                           24

<210> SEQ ID NO 1174
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1174
ggcctggggg tgctaatg                                                  18

<210> SEQ ID NO 1175
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1175
gggtggtctg gtgatgtgtt                                                20

<210> SEQ ID NO 1176
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1176
gctatgccaa gggaacctag a                                              21

<210> SEQ ID NO 1177
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1177
gggagtactc tccaaagc                                                  18
```

```
<210> SEQ ID NO 1178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1178
cctcctgtca ctttccctca                                                 20

<210> SEQ ID NO 1179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1179
tgctccacag atgacacagt                                                 20

<210> SEQ ID NO 1180
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1180
tggaatgtga tggatgaga                                                  19

<210> SEQ ID NO 1181
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1181
agccctgctt cagcttctg                                                  19

<210> SEQ ID NO 1182
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1182
ttgactactg gaacttggag agg                                             23

<210> SEQ ID NO 1183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1183
tggaaacttc ttgtggacct                                              20

<210> SEQ ID NO 1184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1184
gtgggtggaa gacttgctct                                              20

<210> SEQ ID NO 1185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1185
tttctgggcc acctacaagt                                              20

<210> SEQ ID NO 1186
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1186
cccaaggttc tgggctaag                                               19

<210> SEQ ID NO 1187
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1187
cctcctcctc acactgcttc                                              20

<210> SEQ ID NO 1188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1188
ccctttctta gctcctgacc a                                            21

<210> SEQ ID NO 1189
<211> LENGTH: 24
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1189
ggtctaaagg gagagtagga ggtc                                                 24

<210> SEQ ID NO 1190
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1190
gaatggtctt ttcgtcattc c                                                    21

<210> SEQ ID NO 1191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1191
ctttcccaaa accccacact                                                      20

<210> SEQ ID NO 1192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1192
cacacacaag gaaaaacagg a                                                    21

<210> SEQ ID NO 1193
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1193
gctggatgga gggtgagg                                                        18

<210> SEQ ID NO 1194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1194
tgcctgcctg ttagaacatc                                                      20
```

```
<210> SEQ ID NO 1195
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1195
ggcaatccga agtctaagag a                                            21

<210> SEQ ID NO 1196
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1196
tggaaccaac aacctatcat ca                                           22

<210> SEQ ID NO 1197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1197
gactggtact tccccaagga                                              20

<210> SEQ ID NO 1198
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1198
tgaaaatcca tttggtagtt gct                                          23

<210> SEQ ID NO 1199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1199
aaaatgactg tcccctatct                                              20

<210> SEQ ID NO 1200
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
        Synthetic primer"

<400> SEQUENCE: 1200
tggtaagtgg gatgatactg agc                                    23

<210> SEQ ID NO 1201
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 1201
aagcatagaa ggaaaaacag attg                                   24

<210> SEQ ID NO 1202
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 1202
cccctgaatg aaactattga gc                                     22

<210> SEQ ID NO 1203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 1203
agcaagggag ggaagacacc                                        20

<210> SEQ ID NO 1204
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 1204
ttgtcaatcc ttgctctacc c                                      21

<210> SEQ ID NO 1205
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic primer"

<400> SEQUENCE: 1205
tgaagggtag atatgaagtt tttc                                   24

<210> SEQ ID NO 1206
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1206
taatctttgg actccttgaa                                                20

<210> SEQ ID NO 1207
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1207
tgatcccatg tatttaaacc t                                              21

<210> SEQ ID NO 1208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1208
cccctgaaat gagagtcacc                                                20

<210> SEQ ID NO 1209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1209
caaaataaac ccaggcaaaa a                                              21

<210> SEQ ID NO 1210
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1210
ctttaacaaa tatagggcga ttt                                            23

<210> SEQ ID NO 1211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1211
```

-continued aagtaccaaa aaggcacatc g                                           21

<210> SEQ ID NO 1212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1212
tccccctaag atcaggaaca                                             20

<210> SEQ ID NO 1213
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1213
tggaacagca acttgcaaac                                             20

<210> SEQ ID NO 1214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1214
aagagtgtaa atgggtcctg a                                           21

<210> SEQ ID NO 1215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1215
ctcccctgaa cctgagtgac                                             20

<210> SEQ ID NO 1216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1216
tgctcacatt tcattgacca g                                           21

<210> SEQ ID NO 1217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1217
tgaggtggga agaaacacaa                                             20

<210> SEQ ID NO 1218
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1218
tgcgactgga tactattttt gg                                          22

<210> SEQ ID NO 1219
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1219
agttgcatgg agtggctga                                              19

<210> SEQ ID NO 1220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1220
tgttggtgca ttcagagagc                                             20

<210> SEQ ID NO 1221
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1221
caagtaattc ttaccagcct tt                                          22

<210> SEQ ID NO 1222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1222
aggctacaaa aaggcagcag                                             20

<210> SEQ ID NO 1223

-continued

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1223
aaggaaacgg ccccagag                                               18

<210> SEQ ID NO 1224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1224
gaccctgtgg actgagaacc                                             20

<210> SEQ ID NO 1225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1225
tcagagcact ctgcattcca                                             20

<210> SEQ ID NO 1226
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1226
ctttttaaag ccagaaaaat gg                                          22

<210> SEQ ID NO 1227
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1227
agaatcatat gacacatgga a                                           21

<210> SEQ ID NO 1228
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1228
```

-continued

```
cagcttatct ttatctgttt gctt                                        24

<210> SEQ ID NO 1229
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1229
cactttgcag ccaatccata                                             20

<210> SEQ ID NO 1230
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1230
cagatctgat ttcctggag                                              19

<210> SEQ ID NO 1231
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1231
tccatacagg aagatccatt aaga                                        24

<210> SEQ ID NO 1232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1232
gtgcagtttg ggctacaaga                                             20

<210> SEQ ID NO 1233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1233
tgctgccaga agcaacctac                                             20

<210> SEQ ID NO 1234
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 1234
agaaagttgt gccaagtgct                                                 20

<210> SEQ ID NO 1235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1235
tgtctggaaa tcattgcttc a                                               21

<210> SEQ ID NO 1236
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1236
cataaagcta aaagattgga ca                                              22

<210> SEQ ID NO 1237
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1237
caaatcagtg tgccccaac                                                  19

<210> SEQ ID NO 1238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1238
gttttgccca gaggtcatgt                                                 20

<210> SEQ ID NO 1239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1239
gctcttccct cagtggctta                                                 20
```

-continued

```
<210> SEQ ID NO 1240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1240
ctatcatttc tccccaacac a                                                21

<210> SEQ ID NO 1241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1241
ctggatttca aattgtttca                                                  20

<210> SEQ ID NO 1242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1242
tcaagtatct agttgtgata gcc                                              23

<210> SEQ ID NO 1243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1243
tagagcagct aggggactgc                                                  20

<210> SEQ ID NO 1244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1244
cgagactgtt caccctttgg                                                  20

<210> SEQ ID NO 1245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 1245
atgccagact tcaccactgc                                          20

<210> SEQ ID NO 1246
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1246
tttcagtttt gttatgtggc ta                                       22

<210> SEQ ID NO 1247
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1247
ttgaagttag ttctttgtgg atgg                                     24

<210> SEQ ID NO 1248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1248
atcaactccc cacctggaag                                          20

<210> SEQ ID NO 1249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1249
ttttccctca ttagctgcat t                                        21

<210> SEQ ID NO 1250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1250
tgattccagt tcacagtagt cca                                      23

<210> SEQ ID NO 1251
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 1251
catttccagc tgactggtta                                               20

<210> SEQ ID NO 1252
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1252
accctgagga ggggctagt                                                19

<210> SEQ ID NO 1253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1253
gcccagtagc actgctcttc                                               20

<210> SEQ ID NO 1254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1254
agatcaccaa ggcagaaacc                                               20

<210> SEQ ID NO 1255
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1255
ccgagaacgc tctgagttg                                                19

<210> SEQ ID NO 1256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1256
ggcagcaaca ggaaatagca                                               20
```

-continued

```
<210> SEQ ID NO 1257
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1257
acaggagtgg ctcggtca                                                 18

<210> SEQ ID NO 1258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1258
cactgcagga aatgcagctt                                               20

<210> SEQ ID NO 1259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1259
cgaaatccat aggacctaca                                               20

<210> SEQ ID NO 1260
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1260
agctacacta tttccatgtg ac                                            22

<210> SEQ ID NO 1261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1261
aacaagaaag gcagggaagg                                               20

<210> SEQ ID NO 1262
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1262
ctgggtcacg cctcttga                                              18

<210> SEQ ID NO 1263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1263
tacaaacagt ggggcaacaa                                            20

<210> SEQ ID NO 1264
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1264
gccaggcatg ggcttaat                                              18

<210> SEQ ID NO 1265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1265
ttcgtctttc agcaatttga                                            20

<210> SEQ ID NO 1266
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1266
aacagaaaga gagttacatc taca                                       24

<210> SEQ ID NO 1267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1267
cctcatgacc taaccacctc                                            20

<210> SEQ ID NO 1268
<211> LENGTH: 19
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1268
cccccaatgc aagagtgtt                                                19

<210> SEQ ID NO 1269
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1269
tttcacagtg gaatgaatcg                                               20

<210> SEQ ID NO 1270
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1270
gcccaggaca cacaaaaa                                                 18

<210> SEQ ID NO 1271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1271
ctggtcctct gtgaattgaa                                               20

<210> SEQ ID NO 1272
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1272
caccgaatct atatctgtga gg                                            22

<210> SEQ ID NO 1273
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1273
tctttatgtg gccttcactt g                                             21
```

<210> SEQ ID NO 1274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1274
tatgctgaag ctgccatcct                                             20

<210> SEQ ID NO 1275
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1275
gggcaggaaa cagggacta                                              19

<210> SEQ ID NO 1276
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1276
gctgtcctat ttcaggttgc at                                          22

<210> SEQ ID NO 1277
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1277
tccactggaa ttggtagaca ga                                          22

<210> SEQ ID NO 1278
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1278
agcaatcatc ctaggaggtc a                                           21

<210> SEQ ID NO 1279
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 1279
ttctgacttc acagagggta                                                    20

<210> SEQ ID NO 1280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1280
gggcaagtca cttagcattt                                                    20

<210> SEQ ID NO 1281
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1281
ttctcagact tcaaagcaaa gg                                                  22

<210> SEQ ID NO 1282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1282
tgaaaagata cctaaaatca agg                                                 23

<210> SEQ ID NO 1283
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1283
gagaagaacc agacagaaca cg                                                  22

<210> SEQ ID NO 1284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1284
atttctgcag ccctgtgact                                                    20

<210> SEQ ID NO 1285
<211> LENGTH: 23

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1285
catgaaaaat aaggaaatgc tga                                        23

<210> SEQ ID NO 1286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1286
tcctaagttt ttctgatctg tgg                                        23

<210> SEQ ID NO 1287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1287
gcctcagttt cctcctcaga                                            20

<210> SEQ ID NO 1288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1288
cctctcaaca acccaggtac t                                          21

<210> SEQ ID NO 1289
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1289
actgtggctc cagcatgaa                                             19

<210> SEQ ID NO 1290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1290
```

-continued agtccaggca ccactgctac                                          20

<210> SEQ ID NO 1291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1291
gctggaagga gagaaacacg                                          20

<210> SEQ ID NO 1292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1292
atggccacta gaggggagtc                                          20

<210> SEQ ID NO 1293
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1293
gcatcctgtg gtgggaag                                            18

<210> SEQ ID NO 1294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1294
tggtcaataa gcctgttcca                                          20

<210> SEQ ID NO 1295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1295
ggtcaggacc tgttttctca a                                        21

<210> SEQ ID NO 1296
<211> LENGTH: 22
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 1296
tcaataactg ctggagatgt gg                                          22

<210> SEQ ID NO 1297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1297
gcccaatcta atcatgtgag g                                           21

<210> SEQ ID NO 1298
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1298
gcagccaaga aaggctgt                                               18

<210> SEQ ID NO 1299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1299
ggaaagcagt gaagacagca                                             20

<210> SEQ ID NO 1300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1300
tcctcttccc cagaacttga                                             20

<210> SEQ ID NO 1301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1301
gttggggcag tactcagcag                                             20

<210> SEQ ID NO 1302
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1302
tcctttacta catcatgggt ca                                               22

<210> SEQ ID NO 1303
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1303
ggcctcccct tcattcaa                                                    18

<210> SEQ ID NO 1304
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1304
ttgaactagt ttatacaccc agaa                                             24

<210> SEQ ID NO 1305
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1305
cacacataca caaaataaag gt                                               22

<210> SEQ ID NO 1306
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1306
caaagaagaa ggagcaagg                                                   19

<210> SEQ ID NO 1307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1307
```

-continued ttatccagga caggaagctg                                                  20

<210> SEQ ID NO 1308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1308
cccggtgata acagaacgat                                                  20

<210> SEQ ID NO 1309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1309
catgggactc tagaggtaga a                                                21

<210> SEQ ID NO 1310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1310
ttttaatctc tcttgctctc c                                                21

<210> SEQ ID NO 1311
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1311
tcatagagta agccagatat aagc                                             24

<210> SEQ ID NO 1312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1312
tttaccagcc agctcagtcc                                                  20

<210> SEQ ID NO 1313
<211> LENGTH: 20
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic primer"

<400> SEQUENCE: 1313
tcctgaaggg taagcaggaa                                                20

<210> SEQ ID NO 1314
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1314
accaaggtct tccctctgc                                                 19

<210> SEQ ID NO 1315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1315
aggtcagctc agggtgaagt                                                20

<210> SEQ ID NO 1316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1316
gctccattga agggtaaagg                                                20

<210> SEQ ID NO 1317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1317
tggaatagaa tgcaatcctg a                                              21

<210> SEQ ID NO 1318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1318
agcccacaca ggttggtaag                                                20
```

-continued

```
<210> SEQ ID NO 1319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1319
cagatgctgc aggaaacaga                                                    20

<210> SEQ ID NO 1320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1320
gtggatcaca gggtcacctc                                                    20

<210> SEQ ID NO 1321
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1321
cctcaagctg gcctgcaa                                                      18

<210> SEQ ID NO 1322
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1322
aaggcaggca agacgtagc                                                     19

<210> SEQ ID NO 1323
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1323
caaatatact gattctgtgg caaa                                               24

<210> SEQ ID NO 1324
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 1324
tgatgcattg agattttgat ga                                              22

<210> SEQ ID NO 1325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1325
cgtctcccac attcttttgg                                                 20

<210> SEQ ID NO 1326
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1326
ggtaggcttt gtaacttgca ctg                                             23

<210> SEQ ID NO 1327
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1327
tgaatcctgg ctgggaaa                                                   18

<210> SEQ ID NO 1328
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1328
gcctcaccta caaagcttat tca                                             23

<210> SEQ ID NO 1329
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1329
tgcagtttgc tatgcagtct tt                                              22

<210> SEQ ID NO 1330
<211> LENGTH: 22
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 1330
tgaagctaca cagataagaa gc                                              22

<210> SEQ ID NO 1331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1331
tcattctggg ttaccctttt g                                               21

<210> SEQ ID NO 1332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1332
gccaggaaaa gacagtgcat                                                 20

<210> SEQ ID NO 1333
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1333
tctcagcaca gagaaggtgc t                                               21

<210> SEQ ID NO 1334
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1334
gcacatttat tcactcagca aa                                              22

<210> SEQ ID NO 1335
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1335
tgtcctctgt aaaccagaca a                                               21
```

<210> SEQ ID NO 1336
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1336
cattttccaa ggttgtttct gt                                         22

<210> SEQ ID NO 1337
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1337
tctttcccta cacgacgctc ttccgatctc tcccacatgt aatgtgttg             49

<210> SEQ ID NO 1338
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1338
gtgactggag ttcagacgtg tgctcttccg atctcatact tggagaacaa aggac       55

<210> SEQ ID NO 1339
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1339
ctcccacatg taatgtgttg aaaaagcatg gataacggtg tcctttgttc tccaagtatg   60

<210> SEQ ID NO 1340
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1340
tctttcccta cacgacgctc ttccgatctc caggaatgtg accagcaac             49

<210> SEQ ID NO 1341
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 1341
gtgactggag ttcagacgtg tgctcttccg atctcaatca caggcaggaa gatg          54

<210> SEQ ID NO 1342
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1342
ccaggaatgt gaccagcaac gcagcccaca aaaccttcat cttcctgcct gtgattg          57
```

METHODS, AND SYSTEMS TO DETECT TRANSPLANT REJECTION

RELATED APPLICATION

This application is a U.S. national phase International Application PCT/US2019/050059, filed on Sep. 6, 2019, which claims priority to U.S. Provisional Patent Application 62/728,479, filed on Sep. 7, 2018, the entire contents of both the aforementioned applications are herein incorporated by reference for all purposes.

SEQUENCE LISTING

The instant application contains a Sequence Listing which has been submitted electronically in ASCII format and is hereby incorporated by reference in its entirety. Said ASCII copy, created on Sep. 25, 2019, is named 057618-1152448_(SEQ-7010-PCT)_SL.txt and is 336,307 bytes in size.

FIELD

The technology in part relates to methods and systems used for detecting transplant rejection.

BACKGROUND

During the past sixty years, solid organ transplantation has progressed from being classified as a clinical experiment to being considered a routine and reliable medical procedure. It is now possible to transplant many solid organs including heart, lungs, kidney, and liver, and thousands of successful solid organ transplantations are performed in the United States each year. Unfortunately, sometimes the recipient's immune system recognizes the transplanted organ as foreign to the body and activates various immune system mechanisms to reject the organ. When the transplanted organ is rejected by the recipient, it creates a life-threatening situation that is difficult to detect in its early stages. Monitoring the patient for rejection is challenging and expensive, often requiring invasive procedures; furthermore, current surveillance methods lack adequate sensitivity.

The present invention resolves these problems by providing non-invasive methods of monitoring organ transplant patients for rejection that are sensitive, rapid, and inexpensive.

SUMMARY OF THE INVENTION

In one aspect, this disclosure provides a method of determining transplant status comprising:
- (a) obtaining a biological sample from an organ transplant recipient who has received an organ;
- (b) isolating cell-free nucleic acids from the biological sample;
- (c) measuring the amount of each allele of one or more polymorphic nucleic acid targets in the biological sample;
- (d) identifying the donor specific allele using a computer algorithm based on the measurements of the one or more polymorphic nucleic acid targets, whereby detecting one or more donor-specific circulating cell-free nucleic acids,
- (e) detecting tissue injury based on the presence or amount of said one or more donor-specific nucleic acids, thereby determining transplant status.

In some embodiments, the organ is a solid organ from an allogeneic source. In some embodiments, the solid organ is one of a kidney, a heart, a lung, a pancreas, an intestine, a stomach, or a liver.

In some embodiments, the polymorphic nucleic acid targets comprises (i) one or more SNPs, (ii) one or more restriction fragment length polymorphisms (RFLPs), (iii) one or more short tandem repeat (STRs), (iv) one or more variable number of tandem repeats (VNTRs), (v) one or more copy number variants, (vi) one or more insertion/deletion variants, or (vii) a combination of any of (i)-(vii). The combination of any of items (i) to (vii) can be deletion insertion variant(s) combined with a short tandem repeat (DIP-STR). In some embodiments, the polymorphic nucleic acid targets comprises one or more SNPs. In some embodiments, each polymorphic nucleic acid target has a minor population allele frequency of 15%-49%. In some embodiments, the SNPs comprise at least one, two, three, or four or more SNPs of SEQ ID NOs: in Table 1 or Table 6.

In some embodiments, the one or more SNPs do not comprise a SNP, the reference allele and alternate allele combination of which is selected from the group consisting of A_G, G_A, C_T, and T_C.

In some embodiments, the organ donor's genotype is not known for the one or more polymorphic nucleic acid targets prior to the transplant status determination, wherein the recipient's genotype is known for the one or more polymorphic nucleic acid targets prior to the transplant status determination, the method step of identifying donor-specific allele and/or determining the donor-specific nucleic acid fraction comprises:
- I) filtering out 1) polymorphic nucleic acid targets which are present in the recipient and the donor in a genotype combination of $AB_{recipient}/AB_{donor}$, $AB_{recipient}/AA_{donor}$, and $AB_{recipient}/BB_{donor}$;
- II) performing the computer algorithm on a data set consisting of measurements of the remaining polymorphic nucleic acid targets to form a first cluster and a second cluster,
  - wherein the first cluster comprises polymorphic nucleic acid targets that are present in the recipient and the donor in a genotype combination of $AA_{recipient}/AB_{donor}$, or $BB_{recipient}/AB_{donor}$, and
  - wherein the second cluster comprises SNPs that are present in the recipient and the donor in a genotype combination of $AA_{recipient}/BB_{donor}$ or $BB_{recipient}/AA_{donor}$; and
- III) detecting the donor specific allele based on the presence of the remaining polymorphic nucleic acid targets in the one or more polymorphic nucleic acid targets in the biological sample.

In some embodiments, the recipient's genotype for the one or more polymorphic nucleic acid targets prior to the transplant status determination is not known, wherein the donor's genotype for the one or more polymorphic nucleic acid targets is known prior to the transplant status determination, the method step of detecting the donor specific allele comprise:
- I) filtering out 1) polymorphic nucleic acid targets which are present in the recipient and the donor in a genotype combination of $AA_{recipient}/AA_{donor}$ or $AB_{recipient}/AA_{donor}$ and the donor allele frequency is less than 0.5, and 2) SNPs which are present in the recipient and the donor in a genotype combination of $BB_{recipient}/BB_{donor}$, and $AB_{recipient}/BB_{donor}$, and the donor allele frequency is larger than 0.5; and II) detecting the donor specific alleles based on the presence of the remaining polymorphic nucleic acid targets in the biological sample.

In some embodiments, neither the recipient nor the organ donor are genotyped for the one or more polymorphic nucleic acid targets prior to the transplant status determination, the method step of detecting donor-specific allele and/or determining donor-specific nucleic acid fraction comprises:

I) performing the computer algorithm on a data set consisting of measurements of the amounts of the one or more polymorphic nucleic acid targets to form a first cluster and a second cluster, wherein the first cluster comprises polymorphic nucleic acid targets that are present in the recipient and the donor in a genotype combination of $AA_{recipient}/AB_{donor}$, $BB_{recipient}/AB_{donor}$, $AA_{recipient}/BB_{donor}$, or $BB_{recipient}/AA_{donor}$, and wherein the second cluster comprises polymorphic nucleic acid targets that are present in the recipient and the donor in a genotype combination of $AB_{recipient}/AB_{donor}$, $AB_{recipient}/AA_{donor}$, or $AB_{recipient}/BB_{donor}$; and II) detecting the donor specific allele based on the presence of the polymorphic nucleic acid targets in the first cluster.

In some embodiments, the biological sample from an organ transplant recipient is a bodily fluid. For example, the bodily fluid may be one or more of blood, serum, plasma, saliva, tears, urine, cerebralspinal, fluid, mucosal secretion, peritoneal fluid, ascitic fluid, vaginal secretion, breast fluid, breast milk, lymph fluid, cerebrospinal fluid, sputum, and stool.

In some embodiments, the organ donor is not genotyped for the one or more polymorphic nucleic acid targets. In some embodiments, neither the recipient nor the organ donor is genotyped for the one or more polymorphic nucleic acid targets prior to the transplant status determination.

The computer algorithm that can be used in the methods disclosed herein can comprise one or more of the following: (i) a fixed cutoff, (ii) a dynamic clustering, and (iii) an individual polymorphic nucleic acid target threshold. For example, in certain embodiments, the fixed cutoff algorithm can detect donor-specific nucleic acids if the deviation between the measured frequency of a reference allele of the one or more polymorphic nucleic acid targets in the cell-free nucleic acids in the sample and the expected frequency of the reference allele in a reference population is greater than a fixed cutoff, wherein the expected frequency for the reference allele is in the range of:

0.00-0.03 if the recipient is homozygous for the alternate allele, 0.40-0.60 if the recipient is heterozygous for the alternate allele, or 0.97-1.00 if the recipient is homozygous for the reference allele.

In some embodiments, the recipient is homozygous for the reference allele, and the fixed cutoff algorithm detects donor-specific nucleic acids if the measured allele frequency of the reference allele of the one or more polymorphic nucleic acid targets is less than the fixed cutoff. In some embodiments, the recipient is homozygous for the alternate allele, and the fixed cutoff algorithm detects donor-specific nucleic acids if the measured allele frequency of the reference allele of the one or more polymorphic nucleic acid targets is greater than the fixed cutoff.

In some embodiments, the fixed cutoff is based on the homozygous allele frequency of the reference and/or alternate allele of the one or more polymorphic nucleic acid targets in a reference population. In some embodiments, the fixed cutoff is based on a percentile value of distribution of the homozygous allele frequency of the reference and/or alternate allele of the one or more polymorphic nucleic acid targets in the reference population. In some embodiments, the fixed cutoff the percentile is at least 90.

In some embodiments, identifying one or more cell-free nucleic acids as donor-specific nucleic acids using the dynamic clustering algorithm comprises (i) stratifying the one or more polymorphic nucleic acid targets in the cell-free nucleic acids into recipient homozygous group and recipient heterozygous group based on the measured allele frequency for a reference allele and/or an alternate allele of each of the polymorphic nucleic acid targets; (ii) further stratifying recipient homozygous groups into non-informative and informative groups; and (iii) measuring the amounts of one or more polymorphic nucleic acid targets in the informative groups. In some embodiments, the dynamic clustering algorithm is a dynamic K-means algorithm. The informative groups comprise or consist of informative polymorphic nucleic acid targets (e.g., informative SNPs) and the non-informative groups comprise or consist of non-informative polymorphic nucleic acid targets.

The individual polymorphic nucleic acid target threshold algorithm used in the method identifies the one or more nucleic acids as donor-specific nucleic acids if the allele frequency of each of the one or more of the polymorphic nucleic acid targets is greater than a threshold. In some embodiments, the threshold is based on the homozygous allele frequency of each of the one or more polymorphic nucleic acid targets in a reference population. In some embodiments, the threshold is a percentile value of a distribution of the homozygous allele frequency of each of the one or more polymorphic nucleic acid targets in the reference population.

In some embodiments, the method further comprises determining a donor-specific nucleic acid fraction based on the amount of the polymorphic nucleic acid targets that are donor-specific as compared to the total amount of the polymorphic nucleic acid targets in circulating cell-free nucleic acids in the biological sample. In some embodiments, the determining of the amount of one or more circulating cell-free nucleic acids from the transplant donor is performed by measuring the one or more polymorphic nucleic acid targets in at least one assay, and wherein the at least one assay comprises at least one of high-throughput sequencing, capillary electrophoresis or digital polymerase chain reaction (dPCR). In some embodiments, the high-throughput sequencing comprises targeted amplification using a forward and a reverse primer designed specifically for the SNP or targeted hybridization using a probe sequence that contains the SNP. In some embodiments, the amount of one or more polymorphic nucleic acid targets is determined based on sequence reads for each allele of each of the one or more polymorphic nucleic acid targets. In some embodiments, the transplant status is determined as rejection if the donor-specific nucleic acid fraction is greater than a predetermined threshold; and the transplant status is determined as acceptance if the donor-specific nucleic acid fraction is less than a predetermined threshold.

In some embodiments, the method further comprises targeted amplification using a forward and a reverse primer designed specifically for a native genomic nucleic acid and a variant oligonucleotide (i.e., oligo) that contains a single nucleotide substitution as compared to the native sequence, and wherein the method further comprises: determining the ratio of the amount of the amplified native genomic nucleic acid to the amount of the amplified variant oligo, determining the total copy number of genomic DNA by multiplying the ratio with the amount of the variant oligo added to the amplification reaction. In some embodiments, the method further comprises determining total copy number of genomic DNA in circulating cell-free nucleic acids in the biological sample and determining the copy number of the donor-specific nucleic acid by multiplying the donor-specific nucleic acid fraction and the total copy number of genomic DNA. In some embodiments, the transplant status is determined as rejection if the copy number of the donor-specific nucleic acid is greater than a predetermined threshold; and/or the transplant status is determined as acceptance if the copy number of the donor-specific nucleic acid is less than a predetermined threshold.

In some embodiments, the method of detecting transplant status comprises determining the donor-specific circulating cell-free nucleic acid fraction and/or as a copy number of donor-specific circulating cell-free nucleic acid in the transplant recipient at one or more time points comprising an earlier time point and a later time point after the earlier time point, wherein for all time points post-transplantation an increase in donor-specific circulating cell-free nucleic acid fraction or an increase in the copy number of donor-specific circulating cell-free nucleic acid from the earlier time point to later time point is indicative of developing transplant rejection. A variety of timepoints may be monitored and variations may depend upon the nature of the organ transplanted, the health of the recipient or other factors. In some embodiments, the time interval between the earlier time point and the later time point is at least 7 days. In some embodiments, the earlier time point is between 0 days to one year following transplantation. In some embodiments, the later time point is between 7 days to five years following transplantation.

In some embodiments, the method further comprises providing a therapy based on the results of the determination of donor nucleic acid in the sample. For example, the method may further comprise advising administration or administering immunosuppressive therapy to the organ transplant recipient or advising the modification of or modifying the organ transplant recipient's immunosuppressive therapy.

Also provided herein are systems to perform any of the embodiments of the methods disclosed herein. In some embodiments, the system for determining transplant status may comprise one or more processors; and a memory coupled to the one or more processors, wherein the memory is encoded with a set of instructions. The process may, in some embodiments, comprise:

(a) obtaining measurements of one or more polymorphic nucleic acid targets within the circulating cell-free nucleic acids isolated from a biological sample, wherein the biological sample is obtained from an organ transplant recipient who has received an organ from an allogeneic donor; (b) detecting, a presence or absence of one or more donor-specific circulating cell-free nucleic acids based at least on the measurements of the one or more polymorphic nucleic acid targets from (a); and (c) determining a transplant status of the organ transplant recipient based at least on the determined presence or amount of said one or more donor-specific nucleic acids.

Also provided in this disclosure is a non-transitory machine readable storage medium comprising program instructions that when executed by one or more processors cause the one or more processors to perform a method in any one of the embodiments disclosed herein. In some embodiments, the non-transitory machine readable storage medium may comprise program instructions that when executed by one or more processors cause the one or more processors to perform a method comprising the steps of: (a) obtaining measurements of one or more polymorphic nucleic acid targets present as circulating cell-free nucleic acid isolated from a biological sample, wherein the biological sample is obtained from an organ transplant recipient who has received an organ from an allogeneic donor; (b) detecting, by a computing system, one or more donor-specific circulating cell-free nucleic acids based on the measurements from (a); and (c) determining transplant status based on the presence or amount of said one or more donor-specific nucleic acids.

Certain embodiments are described further in the following description, examples, claims and drawings.

BRIEF DESCRIPTION OF THE DRAWINGS

The drawings illustrate embodiments of the technology herein and are not limiting. For clarity and ease of illustration, the drawings are not made to scale and, in some instances, various aspects may be shown exaggerated or enlarged to facilitate an understanding of particular embodiments.

FIG. 6A shows that Informative SNPs that are included in the calculation of donor fraction are SNPs where the recipient is homozygous and the donor is heterozygous ($AA_{recipient}/AB_{donor}$ or $BB_{recipient}/AB_{donor}$ combinations) or SNPs where the recipient is homozygous and the donor is opposite homozygous ($AA_{recipient}/BB_{donor}$, $BB_{recipient}/AA_{donor}$ combinations). Informative SNPs that are excluded from the donor fraction calculation are cases where the recipient is heterozygous and the donor is homozygous ($AB_{recipient}/AA_{donor}$ or $AB_{recipient}/BB_{donor}$). Uninformative SNPs are SNPs where the donor and recipient have a matching genotype ($AA_{recipient}/AA_{donor}$, $BB_{recipient}/BB_{donor}$, $AB_{recipient}/AB_{donor}$). After testing each approach, SNPs are classified as either informative or non-informative. This is designated by "o" and "+" symbols, respectively. FIG. 6B is a figure in which the FIG. 6A is re-plotted to highlight misclassified SNPs visible in panels for Approach 1 and 2 at low and high donor fractions (see data points that have been circled).

FIG. 11 shows the parameters used for primer design.

DEFINITIONS

Figure 1:
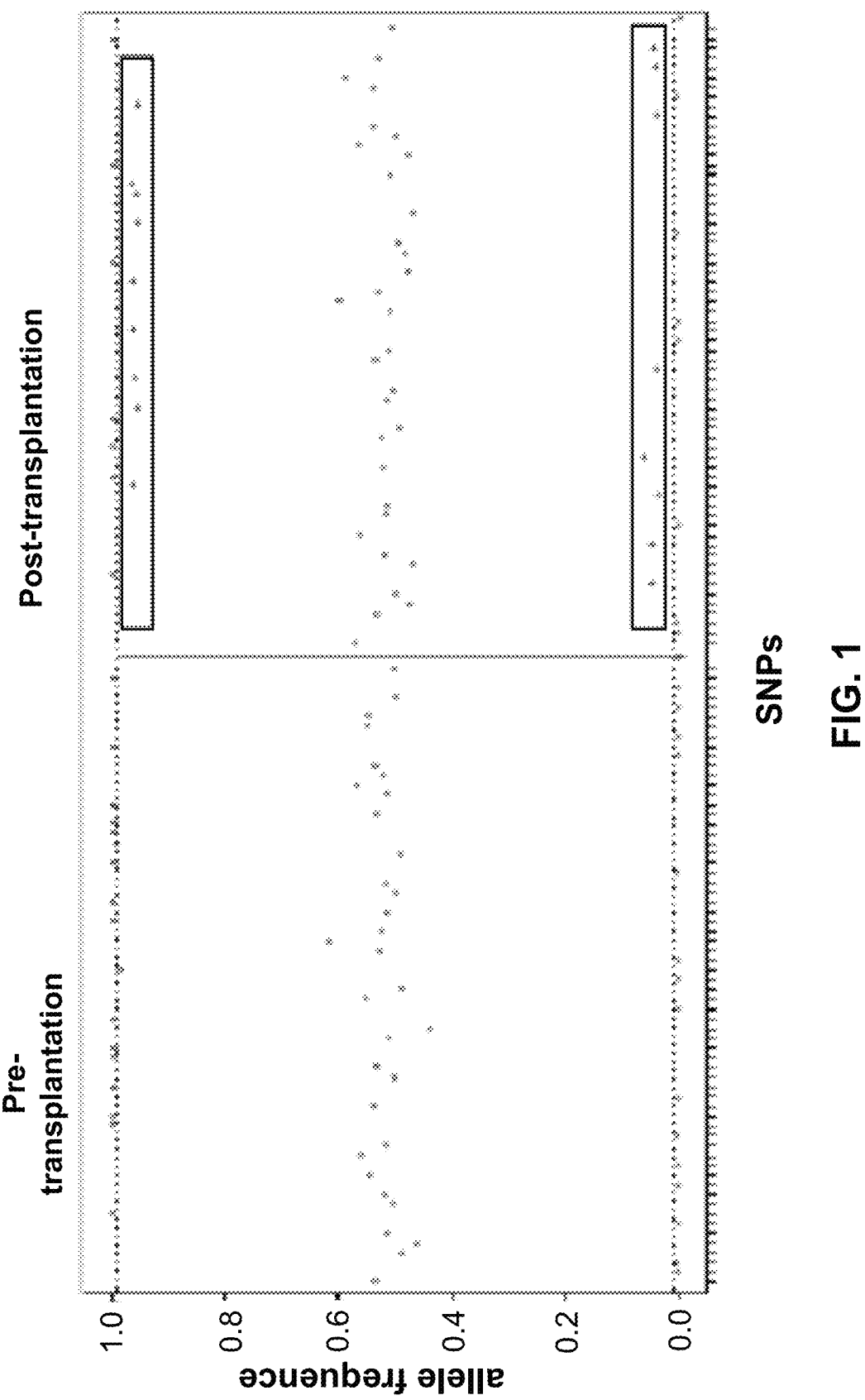
FIG. 1 shows an illustrative example of SNP allele frequencies in a pre-transplant patient and a post-transplant patient. Horizontal dotted black lines represent fixed cutoffs of 0.01 and 0.99, respectively. The boxed regions represent SNPs with allele frequency contribution due to the donor cfDNA.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), transfer RNA (tRNA), microRNA), DNA or RNA analogs (e.g., containing base analogs, sugar analogs and/or a non-native backbone and the like), and/or RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. Nucleic acids can be in any form useful for conducting processes herein (e.g., linear, circular, super-coiled, single-stranded, double-stranded and the like) or may include variations (e.g., insertions, deletions or substitutions) that do not alter their utility as part of the present technology. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

The term "polymorphism" or "polymorphic nucleic acid target" as used herein refers to a sequence variation within different alleles of the same genomic sequence. A sequence that contains a polymorphism is considered a "polymorphic sequence". Detection of one or more polymorphisms allows differentiation of different alleles of a single genomic sequence or between two or more individuals. As used herein, the term "polymorphic marker", "polymorphic sequence", "polymorphic nucleic acid target" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), variable number of tandem repeats (VNTRs), copy number variants, insertions, deletions, duplications, and the like. Polymorphic markers according to the present technology can be used to specifically differentiate between a recipient and donor allele in the enriched donor-specific nucleic acid sample and may include one or more of the markers described above.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production.

Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria. A polymorphic nucleic acid target disclosed herein may have two, three, four, or more alternate forms of a gene or non-coding regions of DNA that occupy the same position on a chromosome. A polymorphic nucleic acid target that has two alternate forms is commonly referred to bialleilic polymorphic nucleic acid target. For the purpose of this disclosure, one allele is referred to as the reference allele, and the others are referred to alternate alleles. In some embodiments, the reference allele is an allele present in one or more of the reference genomes, as released by the Genome Reference Consortium (www.ncbi.nlm.nih.gov/ grc). In some embodiments, the reference allele is an allele reprenst in reference genome GRCh38. See www.ncbi.nlm.nih.gov/grc/human. In some embodiments, the reference allele is not an allele present in the one or more of the reference genomes, for example, the reference allele is an alternate allele of an allele found in the one or more of the reference genomes.

The terms "ratio of the alleles" or "allelic ratio" as used herein refer to the ratio of the amount of one allele and the amount of the other allele in a sample.

The term "Ref_Alt" combination with regard to an SNP refers to the reference allele and alternate allele combination for the SNP. For example, a Ref_Alt of C_G refers to that the reference allele is C and the alternate allele is G for the SNP.

The terms "amount" or "copy number" as used herein refers to the amount or quantity of an analyte (e.g., total nucleic acid or donor-specific nucleic acid). The present technology provides compositions and processes for determining the absolute amount of donor-specific nucleic acid in a mixed recipient sample. The amount or copy number represents the number of molecules available for detection, and may be expressed as the genomic equivalents per unit.

The term "fraction" refers to the proportion of a substance in a mixture or solution (e.g., the proportion of donor-specific nucleic acid in a recipient sample that comprises a mixture of recipient and donor-specific nucleic acid). The fraction may be expressed as a percentage, which is used to express how large/small one quantity is, relative to another quantity as a fraction of 100.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, sputum, cerebrospinal fluid or mucosa secretion), or other body exudate, fecal matter (e.g., stool), an individual cell or extract of the such sources that contain the nucleic acid of the same, and subcellular structures such as mitochondria, using protocols well established within the art.

The term "blood" as used herein refers to a blood sample or preparation from a subject. The term encompasses whole blood or any fractions of blood, such as serum and plasma as conventionally defined.

The term "target nucleic acid" as used herein refers to a nucleic acid examined using the methods disclosed herein to determine if the nucleic acid is donor or recipient-derived cell free nucleic acid.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), where the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Primers" as used herein refer to oligonucleotides that can be used in an amplification method, such as a polymerase chain reaction (PCR), to amplify a nucleotide sequence based on the polynucleotide sequence corresponding to a particular genomic sequence. At least one of the PCR primers for amplification of a polynucleotide sequence is sequence-specific for the sequence.

The term "template" refers to any nucleic acid molecule that can be used for amplification in the technology herein. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplification reaction" as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction. In some embodiments, a single molecule of nucleic acid is amplified, for example, by digital PCR.

As used herein, "reads" are short nucleotide sequences produced by any sequencing process described herein or known in the art. Reads can be generated from one end of nucleic acid fragments ("single-end reads"), and sometimes are generated from both ends of nucleic acids ("double-end reads"). In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

The term "cutoff value" or "threshold" as used herein means a numerical value whose value is used to arbitrate between two or more states (e.g. diseased and non-diseased) of classification for a biological sample. For example, if a parameter is greater than the cutoff value, a first classification of the quantitative data is made (e.g. the donor cell-free nucleic acid is present in the sample derived from the transplant recipient and/or transplant is rejected); or if the parameter is less than the cutoff value, a different classification of the quantitative data is made (e.g. the donor-specific cell-free nucleic acid is absent in the sample derived from the transplant recipient, and/or the transplant is accepted).

Unless explicitly stated otherwise, the term "transplant" or "transplantation" refers to the transfer of a tissue from a donor to a recipient. In some cases, the transplant is an allotransplantation, i.e., organ transplant to a recipient from a genetically non-identical donor of the same species. The donor and/or recipient of the organ transplant can be a human or an animal. For example, the animal can be a mammal, a primate (e.g., a monkey), a livestock animal (e.g., a horse, a cow, a sheep, a pig, or a goat), a companion animal (e.g., a dog, or a cat), a laboratory test animal (e.g., a mouse, a rat, a guinea pig, or a bird), an animal of veterinary significance or economic significance. In some embodiments, the organ being transplanted is a solid organ. Non-limiting examples of solid organs include kidney, liver, heart, pancreas, intestine, and lung.

The term "allogeneic" refers to tissues or cells that are genetically dissimilar and hence immunologically incompatible, although from individuals of the same species. An allogeneic transplant is also referred to as an allograft.

The term "expected allele frequency" refers to allele frequency in the recipient before transplantation. Expected allele frequency can be extrapolated from the allele frequencies found in a group of individuals having a single diploid genome, e.g., non-pregnant female and male who have not received a transplant. In some cases, the expected allele frequency is the median or mean of the allele frequencies in the group of individuals. The expected allele frequency is typically around 0.5 for homozygous, and around 0 for homozygous for the alternate allele, and around 1 if homozygous for the reference allele. When the donor and recipient are of the same genotype, the allele frequency in the post-transplantation sample from the recipient is equal to the expected allele frequency.

The term "transplant status" refers the health status of the organ after it has been removed from the donor and implanted into the recipient. Transplant status includes transplant rejection and transplant acceptance. During transplant rejection, the recipient mounts an immune response against the donated organ, e.g., the allograft, which results in tissue injury of the donated organ. This injury may be detected by detecting the presence of donor-specific cell-free nucleic acid. Transplant acceptance means no tissue injury associated with the donated organ is detected after the organ has been implanted in the recipient.

One or more "prediction algorithms" may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent donor genetic contribution tested, or percent recipient genetic contribution tested. The term "independent" as used herein refers to not being influenced or not being controlled by another. The term "dependent" as used herein refers to being influenced or controlled by another. Such prediction algorithms may be implemented using a computer as disclosed in more detail herein.

One of skill in the art may use any type of method or prediction algorithm to give significance to the data of the present technology within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present technology. And one or more methods or prediction algorithms may be determined not to give significance to the data having different independent and/or dependent variables of the present technology. One may design or change parameters of the different variables of methods described herein based on results of one or more prediction algorithms (e.g., number of sets analyzed, types of nucleotide species in each set). For example, applying the Chi-squared test to detection data may suggest that specific ranges of donor-specific cell free nucleic acids are correlated to a higher likelihood of having a transplant rejection.

In certain embodiments, several algorithms may be chosen to be tested. These algorithms can be trained with raw data. For each new raw data sample, the trained algorithms will assign a classification to that sample (e.g., transplant rejection or transplant acceptance). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

Overview

The present technology relates to analyzing donor DNA found in recipient blood as a non-invasive means to monitor the progress of a transplantation-associated condition, e.g., transplant rejection. This disclosure provides methods of detecting the amount of the one or more cell-free nucleic acids that are produced as a result of transplant rejection.

In some embodiments, the transplant is a solid organ transplant and the cell-free nucleic acids produced during tissue injury are donor-specific cell-free nucleic acids. In some embodiments, the cell-free nucleic acids are donor-specific nucleic acids based on measurements of one or more polymorphic nucleic acid targets using one or more of a fixed cutoff approach, a dynamic clustering approach, or an individual polymorphic nucleic acids target threshold approach. These approaches advantageously allow the donor-specific nucleic acids to be identified without the need of genotyping the donor or recipient for the one or more nucleic acid targets before the transplant status determination.

Therefore the methods disclosed herein can be used to conveniently and accurately determine the status of a transplant, i.e., whether the transplant is rejected or accepted.

Specific Embodiments

Practicing the technology herein utilizes routine techniques in the field of molecular biology. Basic texts disclosing the general methods of use in the technology herein include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22:1859-1862 (1981), using an automated synthesizer, as described in Van Devanter et. al., Nucleic Acids Res. 12:6159-6168 (1984). Purification of oligonucleotides is performed using any art-recognized strategy, e.g., native acrylamide gel electrophoresis or anion-exchange high performance liquid chromatography (HPLC) as described in Pearson & Reanier, J. Chrom. 255:137-149 (1983).

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, donor vs. recipient origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female.

Nucleic acid may be isolated from any type of suitable biological specimen or sample. Non-limiting examples of samples include, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), lymph fluid, cerebrospinal fluid, mucosa secretion, or other body exudate, fecal matter (e.g., stool), an individual cell or extract of the such sources that contain the nucleic acid of the same, and subcellular structures such as mitochondria, using protocols well established within the art. As used herein, the term "blood" encompasses whole blood or any fractions of blood, such as serum and plasma as conventionally defined, for example. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation. A fluid or tissue sample from which nucleic acid is extracted may be acellular. In some embodiments, a fluid or tissue sample may contain cellular elements or cellular remnants. In some embodiments, fetal cells or cancer cells may be included in the sample.

A sample often is heterogeneous, by which is meant that more than one type of nucleic acid species is present in the sample. For example, a heterogeneous nucleic acid sample can include, but is not limited to, (i) donor derived and recipient derived nucleic acid, (ii) cancer and non-cancer nucleic acid, (iii) pathogen and host nucleic acid, and more generally, or (iv) mutated and wild-type nucleic acid. A sample may be heterogeneous because more than one cell type is present, such as a donor cell and a recipient cell, a cancer and non-cancer cell, or a pathogenic and host cell. In some embodiments, a minority nucleic acid species and a majority nucleic acid species is present.

In some embodiments, the samples are typically taken for monitoring the transplant status at one or more time points post-transplantation. The time points may be days or months after the transplantation. In some embodiments, the time points are between 7 days to 1 year after transplantation, e.g., between 10 days to 8 months after transplantation, or between 1 month to 6 months after transplantation. In some embodiments, the time points are on or after the one year anniversary of the transplantation. In some embodiments, one or more samples are taken pre-transplant as a baseline of the SNP allele frequencies and additional samples are taken post-transplant, and the polymorphic nucleic acid targets frequencies in the pre-transplant and post-transplant samples are compared to determine the transplant status.

In some embodiments, multiple samples from the same recipient that has received the organ transplant are taken over a period of time. The frequency of sampling may vary. For examples, samples may be taken every week, once every two weeks, once every 3 weeks, once a month, once every two months, once every three months, once every four months, once every five months, once every six months, once every year.

Preparation of Samples

Blood Samples

In some embodiments, the samples that are used for detecting transplant status is a blood sample from an organ transplant recipient who has received an organ from an allogeneic source. Collection of blood from a subject is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

Serum or Plasma Samples

In some embodiments, the sample is a serum sample or a plasma sample. The methods for preparing serum or plasma from recipient blood are well known among those of skill in the art. For example, a transplant recipient's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used, it is typically, though not exclusively, conducted at an appropriate speed, e.g., 1,500-3,000 times g. Plasma or serum may be subjected to additional centrifugation steps before being transferred to a fresh tube for DNA extraction.

Methods for preparing serum or plasma from blood obtained from a subject (e.g., a transplant recipient) are known. For example, a subject's blood (e.g., a transplant recipient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

In some embodiments, the sample may first be enriched or relatively enriched for donor-specific nucleic acid by one or more methods. For example, the discrimination of donor and recipient DNA can be performed using the compositions and processes of the present technology alone or in combination with other discriminating factors. Examples of these factors include, but are not limited to, single nucleotide differences between polymorphisms located in the genome.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, recipient nucleic acid is selectively removed (either partially, substantially, almost completely or completely) from the sample. Cellular Nucleic Acid Isolation and Processing Various methods for extracting DNA from a biological sample are known and can be used in the methods of determining transplant status. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a subject. Combinations of more than one of these methods may also be used.

In some cases, cellular nucleic acids from samples are isolated. Samples containing cells are typically lysed in order to isolate cellular nucleic acids. Cell lysis procedures and reagents are known in the art and may generally be performed by chemical, physical, or electrolytic lysis methods. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 µg/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Isolating Cell Free DNA from Transplant Recipients

In some embodiments, the cell-free nucleic acids are isolated from a sample. The term "cell-free DNA", also referred to as "cell-free circulating nucleic acid" or "extracellular nucleic acid", refers to nucleic acid isolated from a source having no detectable cells, although the source may contain cellular elements or cellular remnants. As used herein, the term "obtain cell-free circulating sample nucleic acid" includes obtaining a sample directly (e.g., collecting a sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Cell-free nucleic acids isolated from a transplant recipient who has received an organ from an allogeneic source can include different nucleic acid species, and therefore is referred to herein as "heterogeneous" in certain embodiments. For example, blood serum or plasma from a transplant recipient can include recipient cell-free nucleic acid (also referred to as recipient-specific nucleic acid) and donor cell-free nucleic acid (also referred to as donor-specific nucleic acid). In some instances, donor cell-free nucleic acid sometimes is about 5% to about 50% of the overall cell-free nucleic acid (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total cell-free nucleic acid is donor-specific nucleic acid). In some embodiments, the fraction of donor cell-free nucleic acid in a test sample is less than about 10%. In some embodiments, the fraction of donor cell-free nucleic acid in a test sample is less than about 5%. In some embodiments, the majority of donor-specific cell-free nucleic acid in nucleic acid is of a length of about 500 base pairs or less (e.g., about 80, 85, 90, 91, 92, 93, 94, 95, 96, 97, 98, 99 or 100% of donor-specific nucleic acid is of a length of about 500 base pairs or less). In some embodiments, the majority of donor-specific nucleic acid in nucleic acid is of a length of about 250 base pairs or less (e.g., about 80, 85, 90, 91, 92, 93, 94, 95, 96, 97, 98, 99 or 100% of donor-specific nucleic acid is of a length of about 250 base pairs or less). In some embodiments, the majority of donor-specific cell-free nucleic acid in nucleic acid is of a length of about 200 base pairs or less (e.g., about 80, 85, 90, 91, 92, 93, 94, 95, 96, 97, 98, 99 or 100% of donor-specific nucleic acid is of a length of about 200 base pairs or less). In some embodiments, the majority of donor-specific cell-free nucleic acid in nucleic acid is of a length of about 150 base pairs or less (e.g., about 80, 85, 90, 91, 92, 93, 94, 95, 96, 97, 98, 99 or 100% of donor-specific cell-free nucleic acid is of a length of about 150 base pairs or less). In some embodiments, the majority of donor-specific cell-free nucleic acid is of a length of about 100 base pairs or less (e.g., about 80, 85, 90, 91, 92, 93, 94, 95, 96, 97, 98, 99 or 100% of donor-specific nucleic acid is of a length of about 100 base pairs or less).

Methods for isolating cell-free DNA from liquid biological samples, such as blood or serum samples, are well known. In one illustrative example, magnetic beads are used to bind the cfDNA and then bead-bound cfDNA is washed and eluted from the magnetic beads. An exemplary method of isolating cell-free DNA is described in WO2017074926, the entire content of which is hereby incorporated by reference. Commercial kits for isolating cell free DNA are also available, for example, MagNA Pure Compact (MPC) Nucleic Acid Isolation Kit I, Maxwell RSC (MR) ccfDNA Plasma Kit, the QIAamp Circulating Nucleic Acid (QCNA) kit.

The cell-free nucleic acids may be isolated at a different time points as compared to another nucleic acid, where each of the samples is from the same or a different source. In some embodiments, the cell-free nucleic acids are isolated from the same recipient at different time points post transplantation. The donor cell-free nucleic acid fractions are determined for each of the time points as described above, and a comparison between the time points can often reveal the transplant status. For example, an increase in donor-specific cell-free nucleic acid fractions indicates transplant rejection. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples). In some embodiments, the pooled samples may be from the same patient, e.g., transplant recipient, but are taken at different time points, or are of different tissue type. In some embodiments, the pooled samples may be from different patients. As described further below, in some embodiments, identifiers are attached to the nucleic acids derived from the each of the one or more samples to distinguish the sources of the sample.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. An isolated nucleic acid is provided with fewer non-nucleic acid components (e.g., protein, lipid) than the amount of components present in a source sample. A composition comprising isolated nucleic acid can be about 90%, 91%, 92%, 93%, 94%, 95%, 96%, 97%, 98%, 99% or greater than 99% free of non-nucleic acid components. The term "purified" as used herein refers to nucleic acid provided that contains fewer nucleic acid species than in the sample source from which the nucleic acid is derived. A composition comprising nucleic acid may be about 90%, 91%, 92%, 93%, 94%, 95%, 96%, 97%, 98%, 99% or greater than 99% free of other nucleic acid species. The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Nucleic acid may be single or double stranded. Single stranded DNA, for example, can be generated by denaturing double stranded DNA by heating or by treatment with alkali, for example. In some cases, nucleic acid is in a D-loop structure, formed by strand invasion of a duplex DNA molecule by an oligonucleotide or a DNA-like molecule such as peptide nucleic acid (PNA). D loop formation can be facilitated by addition of E. coli RecA protein and/or by alteration of salt concentration, for example, using methods known in the art.

In some cases nucleic acids may be fragmented using either physical or enzymatic methods known in the art.

Genomic DNA Target Sequences

In some embodiments of the methods provided herein, one or more nucleic acid species, and sometimes one or more nucleotide sequence species, are targeted for amplification and quantification. In some embodiments, the targeted nucleic acids are genomic DNA sequences. Certain genomic DNA target sequences are used, for example, because they can allow for the determination of a particular feature for a given assay. Genomic DNA target sequences can be referred to herein as markers for a given assay. In some cases, genomic target sequences are polymorphic, as described herein. In some embodiments, more than one genomic DNA target sequence or marker can allow for the determination of a particular feature for a given assay. Such genomic DNA target sequences are considered to be of a particular "region". As used herein, a "region" is not intended to be limited to a description of a genomic location, such as a particular chromosome, stretch of chromosomal DNA or genetic locus. Rather, the term "region" is used herein to identify a collection of one or more genomic DNA target sequences or markers that can be indicative of a particular assay. Such assays can include, but are not limited to, assays for the detection and quantification of donor-specific nucleic acid, assays for the detection and quantification of recipient nucleic acid, assays for the detection and quantification of total DNA, assays for the detection and quantification of methylated DNA, assays for the detection and quantification of donor-specific nucleic acid, and assays for the detection and quantification of digested and/or undigested DNA, as an indicator of digestion efficiency. In some embodiments, the genomic DNA target sequence is described as being within a particular genomic locus. As used herein, a genomic locus can include any or a combination of open reading frame DNA, non-transcribed DNA, intronic sequences, extronic sequences, promoter sequences, enhancer sequences, flanking sequences, or any sequences considered by one of skill in the art to be associated with a given genomic locus Methods for Determining Donor-Specific Cell-Free Nucleic Acid Content In some embodiments, the amount of donor-specific cell free nucleic acids in a sample is determined. In some cases, the amount of donor-specific nucleic acid is determined based on a quantification of sequence read counts described herein. Quantification may be achieved by direct counting of sequence reads covering particular target sites, or by competitive PCR (i.e., co-amplification of competitor oligo-nucleotides of known quantity, as described herein). The term "amount" as used herein with respect to nucleic acids refers to any suitable measurement, including, but not limited to, absolute amount (e.g. copy number), relative amount (e.g. fraction or ratio), weight (e.g., grams), and concentration (e.g., grams per unit volume (e.g., milliliter); molar units). As used herein, when an action such as a determination of something is "triggered by", "according to", or "based on" something, this means the action is triggered, according to, or based at least in part on at least a part of the something.

In some embodiments, the relative amount or the proportion of donor-specific cell-free nucleic acid is determined according to allelic ratios of polymorphic sequences, or according to one or more markers specific to donor-specific nucleic acid and not recipient nucleic acid. In some cases, the amount of donor-specific cell-free nucleic acid relative to the total cell-free nucleic acid in a sample is referred to as "donor-specific nucleic acid fraction".

Polymorphism-Based Donor Quantifier Assay

Determination of donor-specific nucleic acid content (e.g., donor-specific nucleic acid fraction) sometimes is performed using a polymorphism-based donor quantifier assay, as described herein. This type of assay allows for the detection and quantification of donor-specific nucleic acid in a sample from a transplant recipient based on allelic ratios of polymorphic nucleic acid target sequences (e.g., single nucleotide polymorphisms (SNPs)).

In some cases, donor-specific alleles are identified, for example, by their relative minor contribution to the mixture of donor and recipient cell-free nucleic acids in the sample when compared to the major contribution to the mixture by the recipient nucleic acids. In some cases, donor-specific alleles are identified by a deviation of the measured allele frequency in the total cell-free nucleic acids from an expected allele frequency, as described below. In some cases, the relative amount of donor-specific cell-free nucleic acid in a recipient sample can be determined as a parameter of the total number of unique sequence reads mapped to a target nucleic acid sequence on a reference genome for each of the two alleles (a reference allele and an alternate allele) of a polymorphic site. In some cases, the relative amount of donor-specific cell-free nucleic acid in a recipient sample can be determined as a parameter of the relative number of sequence reads for each allele from an enriched sample.

Selecting Polymorphic Nucleic Acid Targets

In some embodiments, the polymorphic nucleic acid targets are one or more of a: (i) single nucleotide polymorphism (SNP); (ii) insertion/deletion polymorphism, (iii) restriction fragment length polymorphism (RFLPs), (iv) short tandem repeat (STR), (v) variable number of tandem repeats (VNTR), (vi) a copy number variant, (vii) an insertion/deletion variant, or (viii) a combination of any of (i)-(vii) thereof.

A polymorphic marker or site is the locus at which divergence occurs. Polymorphic forms also are manifested as different alleles for a gene. In some embodiments, there are two alleles for a polymorphic nucleic acid target and these polymorphic nucleic acid targets are called biallelic polymorphic nucleic acid targets. In some embodiments, there are three, four, or more alleles for a polymorphic nucleic acid target.

In some embodiments, one of these alleles is referred to as a reference allele and the others are referred to as alternate alleles. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transplantation. Accordingly, it is highly desirable to develop rapid, sensitive, and accurate methods for determining the identity of allelic variants of polymorphic regions of genes or genetic lesions.

In some embodiments, the polymorphic nucleic acid targets are single nucleotide polymorphisms (SNPs). Single nucleotide polymorphisms (SNPs) are generally biallelic systems, that is, there are two alleles that an individual can have for any particular marker, one of which is referred to as a reference allele and the other referred to as an alternate allele. This means that the information content per SNP marker is relatively low when compared to microsatellite markers, which can have upwards of 10 alleles. SNPs also tend to be very population-specific; a marker that is polymorphic in one population sometimes is not very polymorphic in another. SNPs, found approximately every kilobase (see Wang et al. (1998) Science 280:1077-1082), offer the potential for generating very high density genetic maps, which will be extremely useful for developing haplotyping systems for genes or regions of interest, and because of the nature of SNPS, they can in fact be the polymorphisms associated with the disease phenotypes under study. The low mutation rate of SNPs also makes them excellent markers for studying complex genetic traits.

Much of the focus of genomics has been on the identification of SNPs, which are important for a variety of reasons. SNPs allow indirect testing (association of haplotypes) and direct testing (functional variants). SNPs are the most abundant and stable genetic markers. Common diseases are best explained by common genetic alterations, and the natural variation in the human population aids in understanding disease, therapy and environmental interactions.

In some embodiments, the polymorphic nucleic acid marker targets comprises at least one, two, three, four or more SNPs in Table 1 or Table 6. These SNPs have alternative alleles occurring frequently in individuals within a population. As well, these SNPs are diverse and present in multiple populations. Informative analysis indicates that possibility to design specific nucleic acid primers to these SNPs with low potential for off-target non-specific amplification.

TABLE 1

Exemplary SNPs

| | |
|---|---|
| Panel A | rs10737900, rs1152991, rs10914803, rs4262533, rs686106, rs3118058, rs4147830, rs12036496, rs1281182, rs863368, rs765772, rs6664967, rs12045804, rs1160530, rs11119883, rs751128, rs7519121, rs9432040, rs7520974, rs1879744, rs6739182, rs4074280, rs7608890, rs6758291, rs13026162, rs2863205, rs11126021, rs9678488, rs10168354, rs13383149, rs955105, rs2377442, rs13019275, rs967252, rs16843261, rs2049711, rs2389557, rs6434981, rs1821662, rs1563127, rs7422573, rs6802060, rs9879945, rs7652856, rs1030842, rs614004, rs1456078, rs6599229, rs1795321, rs4928005, rs9870523, rs7612860, rs11925057, rs792835, rs9867153, rs602763, rs12630707, rs2713575, rs9682157, rs13095064, rs2622744, rs12635131, rs7650361, rs16864316, rs9810320, rs9841174, rs7626686, rs9864296, rs2377769, rs4687051, rs1510900, rs6788448, rs11941814, rs4696758, rs7440228, rs13145150, rs17520130, rs11733857, rs6828639, rs6834618, rs16996144, rs376293, rs11098234, rs975405, rs1346065, rs1992695, rs6849151, rs11099924, rs6857155, rs10033133, rs7673939, rs7700025, rs6850094, rs11132383, rs7716587, rs38062, rs582991, rs2388129, rs9293030, rs11738080, rs13171234, rs309622, rs253229, rs11744596, rs4703730, rs10040600, rs11953653, rs163446, rs4920944, rs11134897, rs226447, rs12194118, rs4959364, rs4712253, rs2457322, rs7767910, rs2814122, rs6930785, rs1145814, rs1341111, rs2615519, rs1894642, rs6570404, rs9479877, rs9397828, rs6927758, rs6461264, rs6947796, rs1347879, rs10246622, rs10232758, rs756668, rs2709480, rs1983496, rs1665105, rs11785007, rs10089460, rs1390028, rs4738223, rs6981577, rs10958016, rs9298424, rs517811, rs1442330, rs1002142, rs2922446, rs1514221, rs387413, rs10758875, rs10759102, rs2183830, rs1566838, rs12553648, rs10781432, rs11141878, rs2756921, rs1885968, rs10980011, rs1002607, rs10987505, rs1334722, rs723211, rs4335444, rs7917095, rs10509211, rs10881838, rs2286732, rs4980204, rs12286769, rs4282978, rs7112050, rs7932189, rs7124405, rs7111400, rs1938985, rs7925970, rs7104748, rs10790402, rs2509616, rs4609618, rs12321766, rs2920833, rs10133739, rs10134053, rs71159423, rs2064929, rs1298730, rs2400749, rs12902281, rs11074843, rs9924912, rs1562109, rs2051985, rs8067791, rs12603144, rs16950913, rs1486748, rs2570054, rs2215006, rs4076588, rs7229946, rs9945902, rs1893691, rs930189, rs3745009, rs1646594, rs7254596, rs511654, rs427982, rs10518271, rs1452321, rs6080070, rs6075517, rs6075728, rs6023939, rs3092601, rs6069767, rs2426800, rs2826676, rs2251381, rs2833579, rs1981392, rs1399591, rs2838046, rs8130292, rs241713 |
| Panel B | rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, rs9909561, rs10839598, rs10875295, rs12102760, rs12335000, rs12346725, rs12579042, rs12582518, rs17167582, rs1857671, rs2027963, rs2037921, rs2074292, rs2662800, rs2682920, rs2695572, rs2713594, rs2838361, rs315113, rs3735114, rs3784607, rs3817, rs3850890, rs3934591, rs4027384, rs405667, rs4263667, rs4328036, rs4399565, rs4739272, rs4750494, rs4790519, rs4805406, rs4815533, rs483081, rs4940791, rs4948196, rs582111, rs596868, rs6010063, rs6014601, rs6050798, rs6131030, rs631691, rs6439563, rs6554199, rs6585677, rs6682717, rs6720135, rs6727055, rs6744219, rs6768281, rs681836, rs6940141, rs6974834, rs718464, rs7222829, rs7310931, rs732478, rs7422573, rs7639145, rs7738073, rs7844900, rs7997656, rs8069699, rs8078223, rs8080167, rs8103778, rs8128, rs8191288, rs886984, rs896511, rs931885, rs9426840, rs9920714, rs9976123, rs999557, rs9997674 |

In some embodiments, the polymorphic nucleic acid targets selected for determining transplant rejection are a combination of any of the polymorphic nucleic acid targets in Table 1 (Panel A, and/or panel B) or Table 6.

A plurality of polymorphic nucleic acid targets is sometimes referred to as a collection or a panel (e.g., target panel, SNP panel, SNP collection). A plurality of polymorphic targets can comprise two or more targets. For example, a plurality of polymorphic targets can comprise 2, 3, 4, 5, 6, 7, 8, 9, 10, 20, 30, 40, 50, 60, 70, 80, 90, 100, 200, 300, 400, 500, 600, 700, 800, 900, 1000, or more targets.

In some cases, 10 or more polymorphic nucleic acid targets are enriched using the methods described herein. In some cases, 50 or more polymorphic nucleic acid targets are enriched. In some cases, 100 or more polymorphic nucleic acid targets are enriched. In some cases, 500 or more polymorphic nucleic acid targets are enriched. In some cases, about 10 to about 500 polymorphic nucleic acid targets are enriched. In some cases, about 20 to about 400 polymorphic nucleic acid targets are enriched. In some cases, about 30 to about 200 polymorphic nucleic acid targets are enriched. In some cases, about 40 to about 100 polymorphic nucleic acid targets are enriched. In some cases, about 60 to about 90 polymorphic nucleic acid targets are enriched. For example, in certain embodiments, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 polymorphic nucleic acid targets are enriched.

Identifying the Informative Polymorphic Nucleic Acid Targets

In some embodiments, at least one polymorphic nucleic acid target of the plurality of polymorphic nucleic acid targets is informative for determining donor-specific nucleic acid fraction in a given sample. A polymorphic nucleic acid target that is informative for determining donor-specific nucleic acid fraction, sometimes referred to as an informative target, informative polymorphism (e.g., informative SNP), typically differs in some aspect between the donor and the recipient. For example, an informative target may have one allele for the donor and a different allele for the recipient (e.g., the recipient has allele A at the polymorphic target and the donor has allele B at the polymorphic target site).

In some cases, polymorphic nucleic acid targets are informative in the context of certain donor/recipient genotype combinations. For a biallelic polymorphic target (i.e., two possible alleles (e.g., A and B, wherein A is a reference allele and B is an alternate allele, or vice versa)), possible recipient/donor genotype combinations include: 1) recipient AA, donor AA; 2) recipient AA, donor AB; 3) recipient AA, donor BB; 4) recipient AB, donor AA; 5) recipient AB, donor AB; 6) recipient AB; donor BB; 7) recipient BB, donor AA; 8) recipient BB, donor AB; and 9) recipient BB, donor BB. Genotypes AA and BB are considered homozygous genotypes and genotype AB is considered a heterozygous genotype. In some cases, informative genotype combinations (i.e., genotype combinations for a polymorphic nucleic acid target that may be informative for determining donor-specific nucleic acid fraction) include combinations where the recipient is homozygous and the donor is heterozygous or homozygous for the altenate allele (e.g., recipient AA, donor AB; or recipient BB, donor AB; or recipient AA, donor BB). Such genotype combinations may be referred to as Type 1 informative genotypes. In some cases, informative genotype combinations (i.e., genotype combinations for a polymorphic nucleic acid target that may be informative for determining donor-specific nucleic acid fraction) include combinations where the recipient is heterozygous and the donor is homozygous (e.g., recipient AB, donor AA; or recipient AB, donor BB). Such genotype combinations may be referred to as Type 2 informative genotypes. In some cases, non-informative genotype combinations (i.e., genotype combinations for a polymorphic nucleic acid target that may not be informative for determining donor-specific nucleic acid fraction) include combinations where the recipient is heterozygous and the donor is heterozygous (e.g., recipient AB, donor AB). Such genotype combinations may be referred to as non-informative genotypes or non-informative heterozygotes. In some cases, non-informative genotype combinations (i.e., genotype combinations for a polymorphic nucleic acid target that may not be informative for determining donor-specific nucleic acid fraction) include combinations where the recipient is homozygous and the donor is homozygous (e.g., recipient AA, donor AA; or recipient BB, donor BB). Such genotype combinations may be referred to as non-informative genotypes or non-informative homozygotes. In some embodiments, both the recipient's genotype and the donor's genotype for the polymorphic nucleic acid targets are determined prior to transplantation. The presence of donor-specific cell-free nucleic acids can be readily determined by selecting the informative polymorphic nucleic acid targets as described above, and detecting and/or quantifying the donor-specific alleles of the polymorphic nucleic acid targets using the assays described herein.

In some embodiments, individual polymorphic nucleic acid targets and/or panels of polymorphic nucleic acid targets are selected based on certain criteria, such as, for example, minor allele frequency, variance, coefficient of variance, MAD value, and the like. In some cases, polymorphic nucleic acid targets are selected so that at least one polymorphic nucleic acid target within a panel of polymorphic targets has a high probability of being informative for a majority of samples tested. Additionally, in some cases, the number of polymorphic nucleic acid targets (i.e., number of targets in a panel) is selected so that at least one polymorphic nucleic acid target has a high probability of being informative for a majority of samples tested. For example, selection of a larger number of polymorphic targets generally increases the probability that least one polymorphic nucleic acid target will be informative for a majority of samples tested. In some cases, the polymorphic nucleic acid targets and number thereof (e.g., number of polymorphic targets selected for enrichment) result in at least about 2 to about 50 or more polymorphic nucleic acid targets being informative for determining the donor-specific nucleic acid fraction for at least about 80% to about 100% of samples. For example, the polymorphic nucleic acid targets and number thereof result in at least about 5, 10, 15, 20, 25, 30, 35, 40, 45, 50 or more polymorphic nucleic acid targets being informative for determining the donor-specific nucleic acid fraction for at least about 81%, 82%, 83%, 84%, 85%, 86%, 87%, 88%, 89%, 90%, 91%, 92%, 93%, 94%, 95%, 96%, 97%, 98%, or 99% of samples. In some cases, the polymorphic nucleic acid targets and number thereof result in at least five polymorphic nucleic acid targets being informative for determining the donor-specific nucleic acid fraction for at least 90% of samples. In some cases, the polymorphic nucleic acid targets and number thereof result in at least five polymorphic nucleic acid targets being informative for determining the donor-specific nucleic acid fraction for at least 95% of samples. In some cases, the polymorphic nucleic acid targets and number thereof result in at least five polymorphic nucleic acid targets being informative for determining the donor-specific nucleic acid fraction for at least 99% of samples. In some cases, the polymorphic nucleic acid targets and number thereof result in at least ten polymorphic nucleic acid targets being informative for determining the donor-specific nucleic acid fraction for at least 90% of samples. In some cases, the polymorphic nucleic acid targets and number thereof result in at least ten polymorphic nucleic acid targets being informative for determining the donor-specific nucleic acid fraction for at least 95% of samples. In some cases, the polymorphic nucleic acid targets and number thereof result in at least ten polymorphic nucleic acid targets being informative for determining the donor-specific nucleic acid fraction for at least 99% of samples.

In some embodiments, individual polymorphic nucleic acid targets are selected based, in part, on minor allele frequency. In some cases, polymorphic nucleic acid targets having minor allele frequencies of about 10% to about 50% are selected. For example, polymorphic nucleic acid targets having minor allele frequencies that ranges between 15-49%, e.g., 20-49%, 25-45%, 35-49%, or 40-40%. In some embodiments, the polymorphic nucleic acid target has a minor allele allele frequency of about 15%, 20%, 25%, 30%, 35%, 36%, 37%, 38%, 39%, 40%, 41%, 42%, 43%, 44%, 45%, 46%, 47%, 48%, or 49% are selected. In some embodiments, polymorphic nucleic acid targets having a minor allele frequency of about 40% or more are selected. In some cases, the minor allele frequencies of the polymorphic nucleic acid targets can be identified from published databases or based on study results from a reference population.

By analyzing a panel of multiple polymorphic nucleic acid targets (e.g., SNPs) (for instance on the order of 100, 200, 300, etc.) with high minor allele frequencies (for instance from 0.4-0.5), a significant number of 'informative' donor and recipient's genotype combinations (with donor's genotypes differing from recipient's genotype) may be seen (represent in FIG. 1 right panel). In some embodiments, polymorphic nucleic acid targets of the type 1 Informative genotypes, where the recipient is homozygous for one allele and the donor is heterozygous or homozygous for the other allele (compared to the recipient's genotype), are used to determine a change in allele frequency due to the minimal impact of molecular sampling error on the background recipient homozygous allele frequency. In some embodiments, about 25% of the polymorphic nucleic acid targets in a panel are informative where the recipient is homozygous for one reference allele or one alternate allele and the donor is heterozygous. In cases of non-related donor/recipient pairs, the rate of informative polymorphic nucleic acid targets would be expected to be higher. Monozygotic twin donor/recipient pairs would be the exception with no informative genotype combinations present.

In some embodiments, the polymorphic nucleic acid targets are selected based on the GC content of the region surrounding the polymorphic nucleic acid targets and the amplification efficiency of the polymorphic nucleic acid targets. In some embodiments, the GC content is in a range of 10% to 80%, e.g., 20% to 70%, or 25% to 70%, 21% to 61% or 30% to 61%.

In some embodiments, individual polymorphic nucleic acid targets and/or panels of polymorphic nucleic acid targets are selected based, in part, on degree of variance for an individual polymorphic target or a panel of polymorphic targets. Variance, in some cases, can be specific for certain polymorphic targets or panels of polymorphic targets and can be from systematic, experimental, procedural, and or inherent errors or biases (e.g., sampling errors, sequencing errors, PCR bias, and the like). Variance of an individual polymorphic target or a panel of polymorphic targets can be determined by any method known in the art for assessing variance and may be expressed, for example, in terms of a calculated variance, an error, standard deviation, p-value, mean absolute deviation, median absolute deviation, median adjusted deviation (MAD score), coefficient of variance (CV), and the like. In some embodiments, measured allele frequency variance (i.e., background allele frequency) for certain SNPs (when homozygous, for example) can be from about 0.001 to about 0.01 (i.e., 0.1% to about 1.0%). For example, measured allele frequency variance can be about 0.002, 0.003, 0.004, 0.005, 0.006, 0.007, 0.008, or 0.009. In some cases, measured allele frequency variance is about 0.007.

In some cases, noisy polymorphic targets are excluded from a panel of polymorphic nucleic acid targets selected for determining donor-specific nucleic acid fraction. The term "noisy polymorphic targets" or "noisy SNPs" refers to (a) targets or SNPs that have significant variance between data points (e.g., measured donor-specific nucleic acid fraction, measured allele frequency) when analyzed or plotted, (b) targets or SNPs that have significant standard deviation (e.g., greater than 1, 2, or 3 standard deviations), (c) targets or SNPs that have a significant standard error of the mean, the like, and combinations of the foregoing. Noise for certain polymorphic targets or SNPs sometimes occurs due to the quantity and/or quality of starting material (e.g., nucleic acid sample), sometimes occurs as part of processes for preparing or replicating DNA used to generate sequence reads, and sometimes occurs as part of a sequencing process. In certain embodiments, noise for some polymorphic targets or SNPs results from certain sequences being over represented when prepared using PCR-based methods. In some cases, noise for some polymorphic targets or SNPs results from one or more inherent characteristics of the site such as, for example, certain nucleotide sequences and/or base compositions surrounding, or being adjacent to, a polymorphic target or SNP. A SNP having a measured allele frequency variance (when homozygous, for example) of about 0.005 or more may be considered noisy. For example, a SNP having a measured allele frequency variance of about 0.006, 0.007, 0.008, 0.009, 0.01 or more may be considered noisy.

Figure 9:
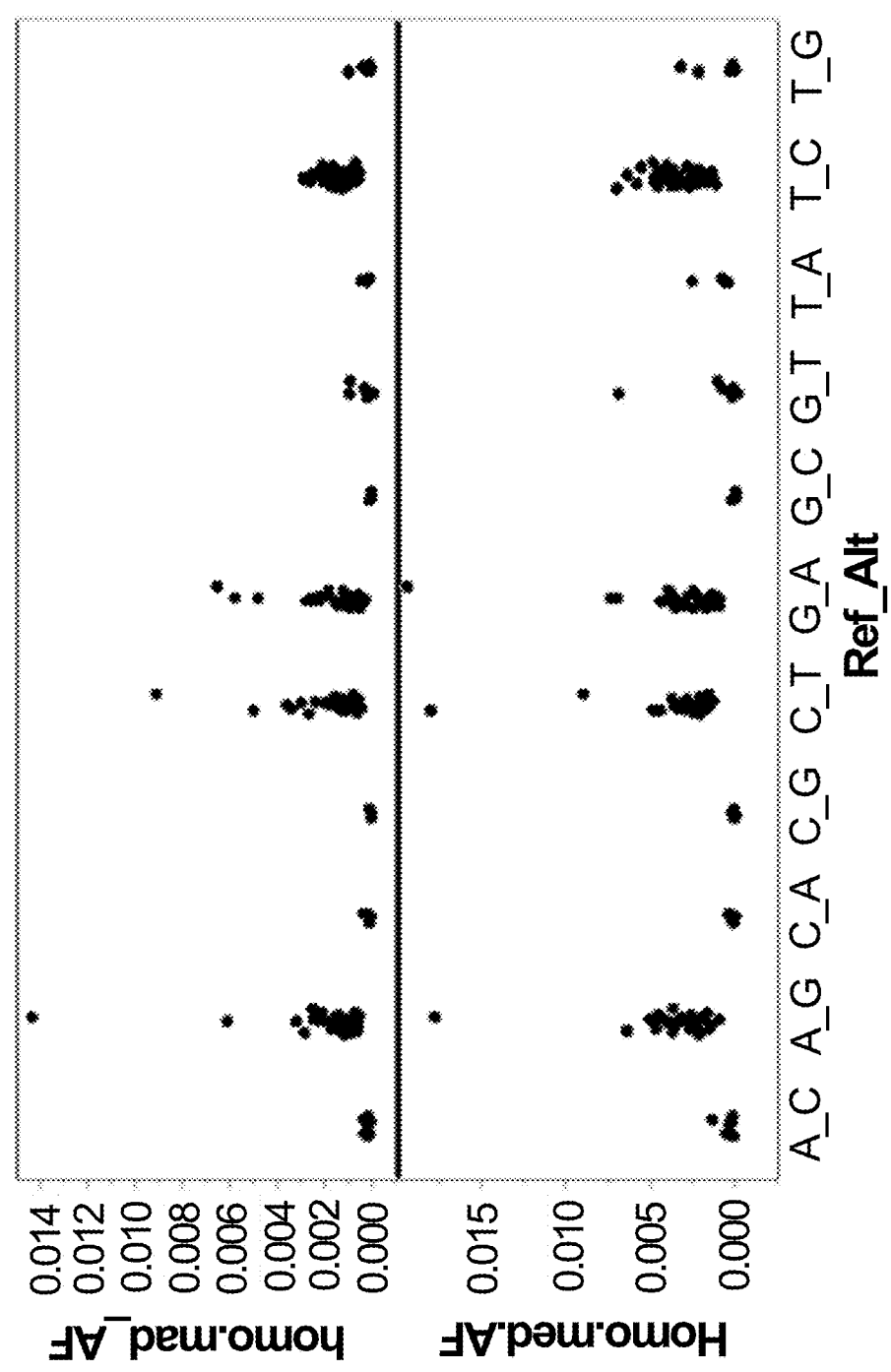
FIG. 9 shows Median and MAD for homozygous allele frequencies of SNPs having different reference allele and alternate allele combination ("Ref_Alt combination"). A higher median and a higher MAD for SNPs having A_G, G_A, C_T, or T_C combinations were observed.

In some embodiments, the reference allele and alternate allele combination of one or more SNPs selected for determining the transplant status is not any one of A_G, G_A, C_T, and T_C (the first letter refers to the reference allele and the second letter refers to the alternate allele). As shown in FIG. 9 and Example 2, SNPs having the above reference allele and alternate allele combination showed higher amount of bias and variability and thus they are not suitable for use in the method disclosed herein for determining the donor fraction and transplant status.

In some embodiments, the one or more SNPs selected for determining the transplant status meet one or more, or all of the following criteria:
1. Biallelic.
2. The SNP is not located within the primer annealing regions.
3. Validated by the 1000 Genomes Project.
4. The ref_alt combination is not any of the A_G, G_A, C_T or T_C.
5. Minor allele frequency is at least 0.3.
6. The sequence for amplified target region is unique and cannot be found elsewhere in the genome.

In some embodiments, variance of an individual polymorphic target or a panel of polymorphic targets can be represented using coefficient of variance (CV). Coefficient of variance (i.e., standard deviation divided by the mean) can be determined, for example, by determining donor-specific nucleic acid fraction for several aliquots of a single recipient sample comprising recipient and donor-specific nucleic acid, and calculating the mean donor-specific nucleic acid fraction and standard deviation. In some cases, individual polymorphic nucleic acid targets and/or panels of polymorphic nucleic acid targets are selected so that donor-specific nucleic acid fraction is determined with a coefficient of variance (CV) of 0.30 or less. For example, donor-specific nucleic acid fraction may be determined with a coefficient of variance (CV) of 0.25, 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01 or less, in some embodiments. In some cases, donor-specific nucleic acid fraction is determined with a coefficient of variance (CV) of 0.20 or less. In some cases, donor-specific nucleic acid fraction is determined with a coefficient of variance (CV) of 0.10 or less. In some cases, donor-specific nucleic acid fraction is determined with a coefficient of variance (CV) of 0.05 or less.

In some embodiments, an allele frequency is determined for one or more alleles of the polymorphic nucleic acid targets in a sample. This sometimes is referred to as measured allele frequency. Allele frequency can be determined, for example, by counting the number of sequence reads for an allele (e.g., allele B) and dividing by the total number of sequence reads for that locus (e.g., allele B+allele A). In some cases, an allele frequency average, mean or median is determined. In some cases, donor-specific nucleic acid fraction can be determined based on the allele frequency mean (e.g., allele frequency mean multiplied by two).

In some embodiments, quantification data (e.g., sequencing data) covering the polymorphic nucleic acid target are used to count the number of times the genomic positions of the polymorphic nucleic acid target (e.g., an SNP) are sequenced. The number of sequencing reads containing the reference allele and the alternate allele of the polymorphic nucleic acid target, respectively, can be determined. For example, in a sample homozygous for the reference allele of a SNP, there would ideally be a reference SNP allele frequency of about 1.0 (e.g. 0.99-1.00) where all sequencing reads covering the SNP contain the reference SNP allele (FIG. 1 left panel, top group of allele frequencies). When the sample is heterozygous for both the reference and alternate allele, the expected allele frequency for the reference SNP allele is about 0.5 (e.g., 0.46-0.53) (FIG. 1 left panel, middle group of allele frequencies). When the sample is homozygous for the alternate allele, the expected reference SNP allele frequency would be 0 (FIG. 1 left panel, bottom group of allele frequencies). These values of 1.0, 0.5, and 0 are idealized though, and while measurements will generally approach these values, real-world SNP allele frequency measurement will be influenced by biochemical, sequencing, and process error. In the case of heterozygous allele frequencies, these will also be influenced by molecular sampling error.

While in some embodiments, both the recipient's genotype and the donor's genotype are determined prior to transplantation, and the presence of donor-specific allele can be readily detected and quantified, however, in some cases, genotyping of the donor and recipient may not be possible or practical. Thus, in some embodiments, donor and/or recipient's genotypes of the one or more polymorphic nucleic acid targets are not determined prior to the transplant status determination. In some cases, the recipient's genotype for one or more polymorphic targets is not determined prior to transplant status determination. In some cases, the donor's genotype for one or more polymorphic targets is not determined prior to transplant status determination. In some cases, the recipient's genotype and the donor's genotype for one or more polymorphic targets are not determined prior to transplant status determination. In some embodiments, donor and recipient's genotypes are not determined for any of the polymorphic nucleic acid targets prior to transplant status determination. In some cases, the recipient's genotype for each of the polymorphic targets is not determined prior to transplantation. In some cases, the donor's genotype for each of the polymorphic targets is not determined prior to transplant status determination. In some cases, the recipient's genotype and the donor's genotype for each of the polymorphic targets are not determined prior to transplant status determination.

In some embodiments, this disclosure provides methods and systems that can be used to detect and/or quantify donor-specific cell free nucleic acids even in the absence of donor's genotype information. The advantage of not having to genotype the recipient before the transplant and not having to genotype the donor is tremendous especially in situations where the patient is not submitted to testing until after transplantation, at which point the donor cannot be located and no pre-transplant samples from recipient was accessible for gentyping. Dispensing the need for genotyping before transplantation also saves costs in tracking the patient information. Without being bound to a particular theory, the present invention can determine the recipient's genotype before transplant from a mixture of cell free DNA that include both donor and recipient cell free DNA from post-transplant samples. This is based on the fact that each of the SNPs allele frequencies before transplantation will cluster around heterozygous (0.5) or homozygous (0 or 1). When there is a difference in donor & recipient's genotype, there'll be a deviation (proportional to donor fraction) from heterozygous or homozygous. When there is a match in donor & recipient's genotype, the allele frequency in the mixed cell free DNA will be the same as the allele frequency in the genotype of the recipient before transplantation. These two categories of recipient-donor genotype combinations are further illustrated below. Donor & recipient's genotypes are different (results in a donor-specific deviation of the allele frequency):

$$AA_{recipient}/AB_{donor}$$
$$AA_{recipient}/BB_{donor}$$
$$AB_{recipient}/AA_{donor}$$
$$AB_{recipient}/BB_{donor}$$
$$BB_{recipient}/AA_{donor}$$
$$BB_{recipient}/AB_{donor}$$

Donor & recipient's genotypes are the same (so the resulting allele frequency is the "expected" recipient's genotype):

$$AA_{recipient}/AA_{donor}$$
$$AB_{recipient}/AB_{donor}$$
$$BB_{recipient}/BB_{donor}$$

(the genotype on the left represents the recipient and the genotype on the right represents the donor. A represents the reference allele and B represents the alternate allele.)

The deviation is the difference between the allele frequency in the cell free DNA sample from the recipient where the donor's genotype matches with the recipient's genotype (i.e., the expected allele frequency) and the allele frequency in the cell free DNA sample where the donor's genotype does not match the recipient's genotype (i.e., the measured allele frequency). In some cases, an allele frequency average, mean or median is determined for the expected allele frequency and measured allele frequency and used for calculation of the deviation. Thus, for SNPs where the recipient is homozygous for the alternate allele (the reference allele frequency is about 0, or is in the range of 0.00-0.03, 0.00-0.02, e.g., 0.00-0.01), the deviation is the difference in mean or median of allele frequencies where the donor is homozygous for the alternate allele (matching recipient's genotype) vs. the mean or median of allele frequencies where the donor is either heterozygous or homozygous for the reference allele (differing form recipient's genotype).

For SNPs where the recipient is heterozygous for the alternate allele (the reference allele frequency is about 0.5, or is in the range of 0.40-0.60, 0.42-0.56, or 0.46-0.53), the deviation is the difference in mean or median of allele frequencies where the donor is heterozygous for the alternate allele (matching recipient's genotype) vs. the mean or median of allele frequencies where the donor is either homozygous for the alternate allele or homozygous for the reference allele (differing form recipient's genotype).

For SNPs where the recipient is homozygous for the reference allele (the reference allele frequency is about 1.00, or in the range of 0.97-1.00, or 0.98-1.00, e.g., 0.99-1.00), the deviation is the difference in mean or median of allele frequencies where the donor is homozygous for the reference allele (matching recipient's genotype) vs. the mean or median of allele frequencies where the donor is either heterozygous or homozygous for the alternate allele (differing form recipient's genotype)."

Whether a particular transplant donor/recipient belong to one or another category can be determined based on a single sample, without gentyping the donor or genotyping the recipient before receiving the transplant by using the methods as described below.

In these cases, these methods assume that normal SNP allele frequencies (allele frequencies associated with homozygous alternate allele genotypes, heterozygous alternate and reference allele genotypes, or homozygous reference allele genotypes) are present from recipient allele background In these cases, the donor-specific nucleic acids can be identified using, for example, one or more of a fixed cutoff approach, a dynamic clustering approach, and an individual polymorphic nucleic acid target threshold approach, as described below. Table 2 shows the features of the various exemplary approaches that can be used for these purposes. In general, such approaches are performed by a processor, a micro-processor, a computer system, in conjunction with memory and/or by a microprocessor controlled apparatus. In various embodiments, the approaches are performed as a sequence of events or steps (e.g., a method or process) in the operating environment 110 described with respect to FIG. 2 herein.

TABLE 2

| Methods | Description |
|---|---|
| Quality filtering of sequencing reads | Monitor and filter sequence read quality scores with exclusion of low quality sequence reads, Decreases background noise in SNP allele frequency measurement<br>Does not contribute directly to detection of donor alleles, but will enable a more precise genotype frequency calculation |
| Fixed cutoff for homozygous variance | Establish a fixed cutoff level for homozygous allele frequencies defined as a fixed percentile of homozygous SNP allele frequencies<br>Easily established by analysis of a moderate sized cohort<br>Does not allow for differences in variance across SNPs within a panel |
| Dynamic k-means clustering | Use clustering algorithm (k-means) on a per sample basis<br>Two tiered approach to dynamically stratify SNPs based on recipient homozygous or heterozygous genotype and then stratify recipient homozygous SNPs into non-informative and informative groups |
| SNP specific variance threshold | Establish specific homozygous allele frequencies threshold for each individual SfNP in the panel<br>Established by analysis of a large cohort of genome DNA to collect data on homozygous SNP genotypes<br>Allows for differences in variance across SNPs within a panel |

The Fixed Cutoff Method

In some embodiments, determining whether a polymorphic nucleic acid target is informative and/or detect donor-specific cell free nucleic acids comprises comparing its measured allele frequency in a recipient to a fixed cutoff frequency. In some cases, determining which polymorphic nucleic acid targets are informative comprises identifying informative genotypes by comparing each allele frequency to one or more fixed cutoff frequencies. Fixed cutoff frequencies may be predetermined threshold values based on one or more qualifying data sets from a population of subjects who have not received transplant, for example, and represent the variance of the measured allele frequencies in subjects who have not received transplant.

In some cases, the fixed cutoff for identifying informative genotypes from non-informative genotypes is expressed as a percent (%) shift in allele frequency from an expected allele frequency. Generally, expected allele frequencies for a given allele (e.g., allele A) are 0 (for a BB genotype), 0.5 (for an AB genotype) and 1.0 (for an AA genotype), or equivalent values on any numerical scale. If a polymorphic nucleic acid target allele frequency in the recipient deviate from an expected allele frequency and such deviation is beyond one or more fixed cutoff frequencies, the polymorphic nucleic acid target may be considered informative. The degree of deviation generally is proportional to donor-specific nucleic acid fraction (i.e., large deviations from expected allele frequency may be observed in samples having high donor-specific nucleic acid fraction). The deviation between the expected allele frequency and measured allele frequency can be determined as described above.

In some cases, the polymorphic nucleic acid targets in the recipient before transplantation are homozygous and the expected allele frequency, either the reference allele or the alternate allele, is, e.g., 0. In these circumstances, the deviation between the measured allele frequency in transplant recipient and expected allele frequency is equal to the measured allele frequency. The polymorphic nucleic acid targets are identified as informative if the measured allele frequency is greater than the fixed cutoff.

In some cases, the fixed cutoff is a percentile value of the measure allele frequencies of all the polymorphic nucleic acid targets used in the assay. In some embodiments, the percentile value is a 90, 95 or 98 percentile value.

In some cases, the fixed cutoff for identifying informative genotypes from non-informative homozygotes is about a 0.5% or greater shift in allele frequency from the median of expected allele frequencies. For example, a fixed cutoff may be about a 0.6%, 0.7%, 0.8%, 0.9%, 1%, 1.5%, 2%, 3%, 4%, 5%, 10% or greater shift in allele frequency. In some cases, the fixed cutoff for identifying informative genotypes from non-informative homozygotes is about a 1% or greater shift in allele frequency. In some cases, the fixed cutoff for identifying informative genotypes from non-informative homozygotes is about a 2% or greater shift in allele frequency. In some embodiments, the fixed cutoff for identifying informative genotypes from non-informative heterozygotes is about a 10% or greater shift in allele frequency. For example, a fixed cutoff may be about a 10%, 15%, 20%, 21%, 22%, 23%, 24%, 25%, 26%, 27%, 28%, 29%, 30%, 35%, 40%, 45%, 50%, 55%, 60%, 70%, 80% or greater shift in allele frequency. In some cases, the fixed cutoff for identifying informative genotypes from non-informative heterozygotes is about a 25% or greater shift in allele frequency. In some cases, the fixed cutoff for identifying informative genotypes from non-informative heterozygotes is about a 50% or greater shift in allele frequency.

Target-Specific Threshold Method

In some embodiments, determining whether a polymorphic nucleic acid target is informative and/or detecting the donor-specific allele comprises comparing its measured allele frequency to a target-specific threshold (e.g., a cutoff value). In some embodiments, target-specific threshold frequencies are determined for each polymorphic nucleic acid target. Typically, target-specific threshold frequency is determined based on the allele frequency variance for the corresponding polymorphic nucleic acid target. In some embodiments, variance of individual polymorphic targets can be represented by a median absolute deviation (MAD), for example. In some cases, determining a MAD value for each polymorphic nucleic acid target can generate unique (i.e., target-specific) threshold values. To determine median absolute deviation, measured allele frequency can be determined, for example, for multiple replicates (e.g., 5, 6, 7, 8, 9, 10, 15, 20 or more replicates) of a recipient only nucleic acid sample (e.g., buffy coat sample). Each polymorphic target in each replicate will typically have a slightly different measured allele frequency due to PCR and/or sequencing errors, for example. A median allele frequency value can be identified for each polymorphic target. A deviation from the median for the remaining replicates can be calculated (i.e., the difference between the observed allele frequency and the median allele frequency). The absolute value of the deviations (i.e., negative values become positive) is taken and the median value of the absolute deviations is calculated to provide a median absolute deviation (MAD) for each polymorphic nucleic acid target. A target-specific threshold can be assigned, for example, as a multiple of the MAD (e.g., 1×MAD, 2×MAD, 3×MAD, 4×MAD or 5×MAD). Typically, polymorphic targets having less variance have a lower MAD and therefore a lower threshold value than more variable targets.

In some embodiments, the target-specific threshold is a percentile value of the measured allele frequencies of the polymorphic nucleic acid target used in the assay. In some embodiments, the percentile value is a 90, 95 or 98 percentile value.

Dynamic Clustering Algorithm

In some embodiments, determining whether a polymorphic nucleic acid target is informative and/or detecting the donor-specific allele comprises a dynamic clustering algorithm. Non-limiting examples of dynamic clustering algorithms include K-means, affinity propagation, mean-shift, spectral clustering, ward hierarchical clustering, agglomerative clustering, DBSCAN, Gaussian mixtures, and Birch. See, http://scikit-learn.org/stable/modules/clustering.html#k-means. Such algorithms may be implemented with a processor, a micro-processor, a computer system, in conjunction with memory and/or by a microprocessor controlled apparatus.

In some embodiments, the dynamic clustering algorithm is a k-means clustering. The k-means algorithm divides a set of samples into disjoint clusters, each described by the mean position of the samples in the cluster. The means are commonly referred to as cluster "centroids". The k-means algorithm aims to choose centroids that minimize the inertia, or within-cluster sum of squares criterion. k-means is often referred to as Lloyd's algorithm. In basic terms, the algorithm has three steps. The first step chooses the initial centroids, with the most basic method being to choose k samples from a dataset X. After initialization, k-means consists of looping between the two other steps. The first step assigns each sample to its nearest centroid. The second step creates new centroids by taking the mean value of all of the samples assigned to each previous centroid. The difference between the old and the new centroids are computed and the algorithm repeats these last two steps until this value is less than a threshold. In other words, it repeats until the centroids do not move significantly.

In some embodiments, the dynamic clustering comprises stratifying the one or more polymorphic nucleic acid targets in the cell-free nucleic acids into recipient homozygous group and recipient heterozygous group based on the measured allele frequency for a reference allele or an alternate allele for each of the polymorphic nucleic acid targets. Homozygous groups are clustered having a mean position of close to 0 or 1, and heterozygous group are clustered having a mean position of close to 0.5.

The method may further comprise stratifying recipient homozygous groups into non-informative and informative groups; and measuring the amounts of one or more polymorphic nucleic acid targets in the informative groups. In some embodiments, stratifying the recipient homozygous groups into non-informative and informative groups is based on whether the group contains donor-specific alleles-informative groups are the groups that comprise distinct donor alleles derived from the donor that are not present in the recipients genome and non-informative groups comprise alleles from the donor, where the informative SNPs are those within the cluster with higher mean or median allele frequency. These informative SNPs can be used to determine the fractional concentration of donor derived cfDNA.

In some embodiments, the k-means clustering process is repeated as described above to identify a cutoff for the informative SNPS. To find a cutoff, clustering is performed on SNPs with allele frequencies in the range of (0, 0.25). This results in 2 clusters where cluster 1 (the lower cluster) are non-informative SNPs (donor & recipient alleles match) and cluster 2 (the higher cluster) are informative SNPs (donor has at least one different allele than the recipient). The cutoff is calculated as the average of the maximum of the first/lower cluster and the minimum of the second/upper cluster.

In some embodiments, the informative SNPs are determined substantially as follows: As a first step in calculating donor fraction, allele frequencies are first mirrored to generate mirrored allele frequencies. A mirrored allele frequency is the lesser value of the allele frequency of an allele and (1—the allele frequency). This mirrors allele frequencies larger than 0.5 into a range of [0,0.5] and groups similar donor-recipient genotype combinations together (e.g. $AA_{recipient}/AB_{donor}$ with $BB_{recipient}/AB_{donor}$). Next, an "informative" SNPs is identified as an SNP where the donor's genotype and the recipient's genotype for the SNP are different. Defining the reference alleles as A and alternate alleles as B, there are 3 categories of informative SNPs (FIG. 3 and FIG. 4):

1) Informative category 1 refers to the "Homo-Het" category, in which the recipient is homozygous and the donor is heterozygous (e.g. $AA_{recipient}/AB_{donor}$ or $BB_{recipient}/AB_{donor}$).

2) Informative category 2 refers to the "Homo-Opp Homo" category, in which the recipient is homozygous and the donor is homozygous for the opposite allele (e.g. $AA_{recipient}/BB_{donor}$ or $BB_{recipient}/AA_{donor}$). This occurs when the donor and recipient are unrelated.

3) Informative category 3 refers to the "Het-Homo" category, in which the recipient is heterozygous and the donor is homozygous (e.g. $AB_{recipient}/AA_{donor}$ or $AB_{recipient}/BB_{donor}$).

In some embodiments, the informative SNPs selected for detecting donor specific nucleic acid and/or determining the donor specific nucleic acid fraction do not include the category 3 SNPs.

Figure 3:
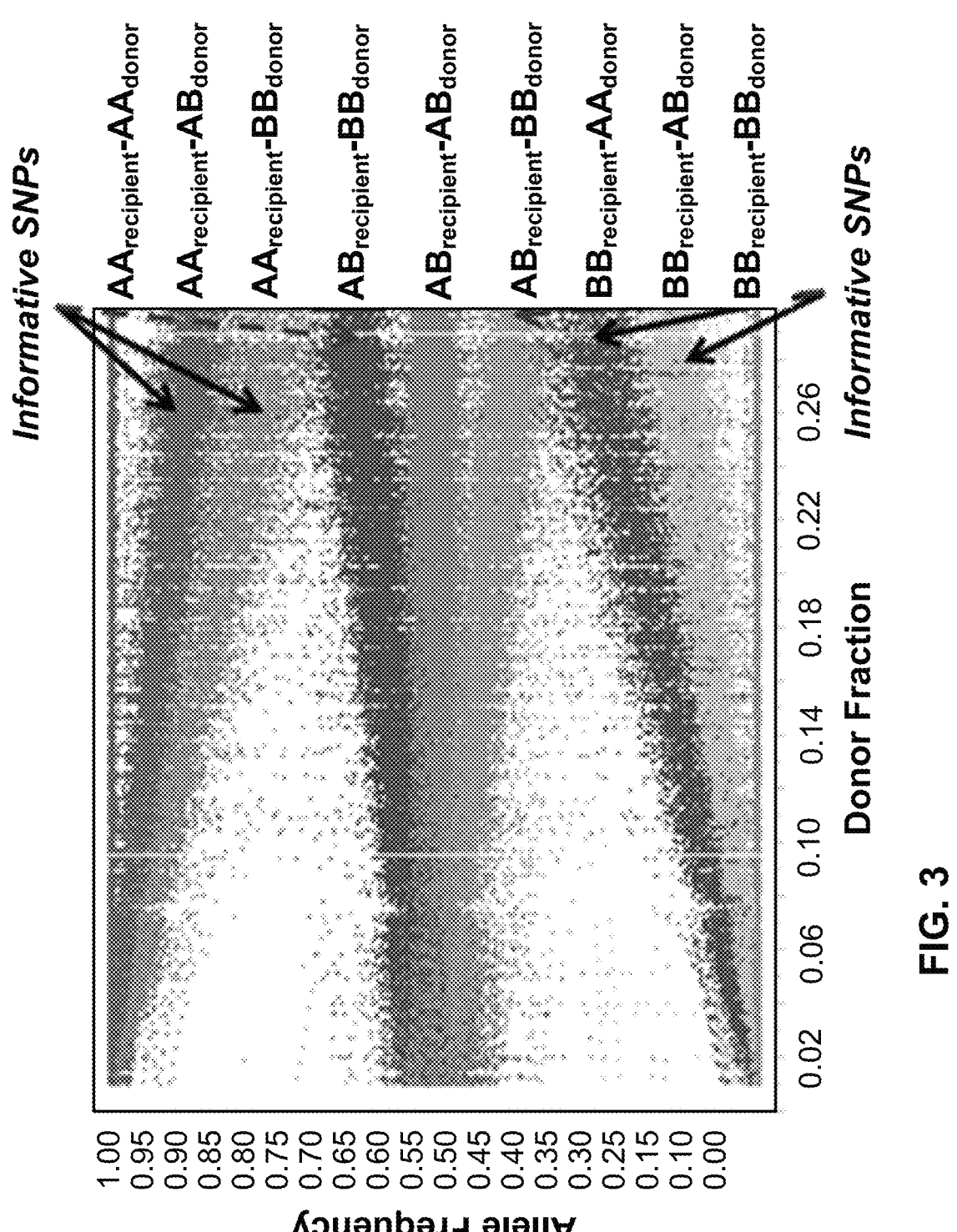
FIG. 3 illustrates types of informative SNPs in a model of transplant patient cfDNA. Solid arrows point to informative clusters of SNPs that are used for the calculation of donor fraction. The dashed arrow points to excluded informative clusters which are not included in donor fraction calculation.
Figure 4:
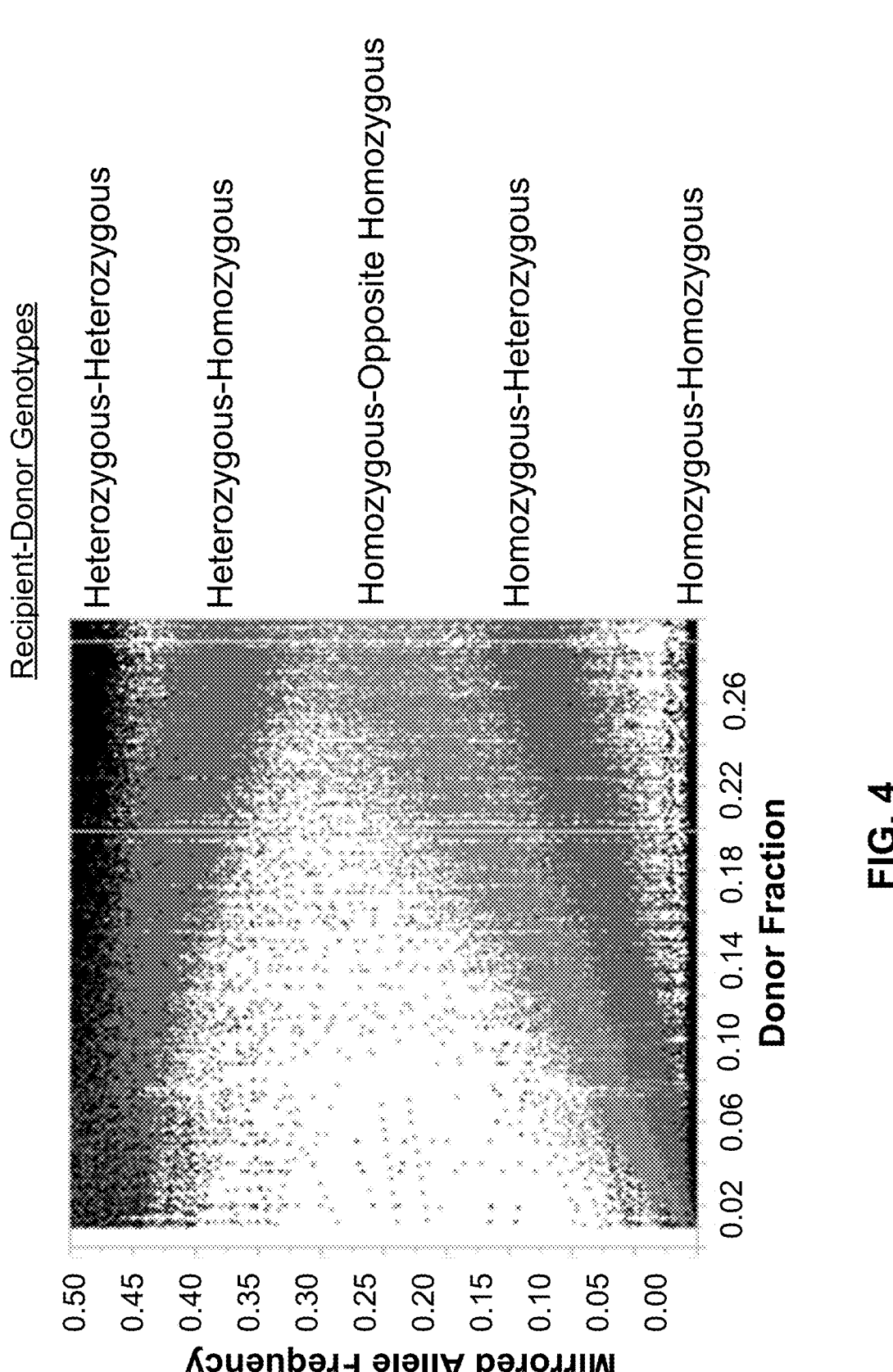
FIG. 4 shows mirrored allele frequency of informative SNPs. The data are informative clusters used in the calculation of donor fraction. The second cluster from the bottom is SNPs where the recipient is homozygous and the donor is heterozygous. The third cluster from the bottom is SNPs where the recipient is homozygous for one allele and the donor is homozygous for the opposite allele.

The data shown in FIG. 3 and FIG. 4 utilize 91 mixtures of genomic DNA and non-pregnant plasma cfDNA to simulate donor-recipient mixtures. The mirrored allele frequencies increase with higher donor fraction for SNPs in category 1 and 2, but decreases for category 3 SNPs (FIG. 4). To focus on a positive correlation, the category 3 SNPs are excluded and re-classified as non-informative for the sake of calculating donor fraction (FIG. 3 and FIG. 4). The non-informative SNPs can then be identified and removed by different approaches, some of which depend on a two-step clustering analysis. When clustering is employed, the first step is an iteration of fuzzy K-means in the range of mirrored allele frequencies between 0 and 0.3 in order to determine a lower cutoff separating non-informative SNPs (e.g. $AA_{recipient}/AA_{donor}$) from informative SNPs (e.g. $AA_{recipient}/AB_{donor}$, $AA_{recipient}/BB_{donor}$). In a second round of clustering, hard K-means clustering is performed between this lower cutoff and an allele frequency of 0.49 to determine the upper bound of the desired informative SNPs (e.g. separating $AA_{recipient}/AB_{donor}$ and $AA_{recipient}/BB_{donor}$ from $AB_{recipient}/AA_{donor}$ and $AB_{recipient}/AB_{donor}$).

Four different approaches are detailed as follows, depending on availability of the genotype for the donor or recipient:

1) Approach 1 ("DF1"):

If neither donor nor recipient's genotype are known, use K-means clustering to identify and remove non-informative SNPs ($AA_{recipient}/AA_{donor}$, $BB_{recipient}/BB_{donor}$, and $AB_{recipient}/AB_{donor}$, $AB_{recipient}/AA_{donor}$, and $AB_{recipient}/BB_{donor}$ combinations). The 2 clusters are expected to contain the following recipient/donor's genotype combinations:

a. Cluster 1=($AA_{recipient}/AB_{donor}$, $BB_{recipient}/AB_{donor}$, $AA_{recipient}/BB_{donor}$, $BB_{recipient}/AA_{donor}$).

b. Cluster 2=($AB_{recipient}/AB_{donor}$, $AB_{recipient}/AA_{donor}$, $AB_{recipient}/BB_{donor}$).

Retain only the SNPs in the cluster 1 as those are relevant to the donor fraction calculation.

Accordingly, using the DF1 approach, under the circumstances where neither the donor nor the recipient's genotype is known, the method of determining transplant status comprises:

I) isolating cell-free nucleic acids from a biological sample;

II) measuring the amount of each allele of the one or more SNPs in the biological sample to generate a data set consisting of measurements of the amounts of the one or more SNPs; an "informative" SNPs is identified as an SNP where the donor's genotype and the recipient's genotype for the SNP are different.

III) performing a computer algorithm on the data set to form a first cluster and a second cluster, wherein the first cluster comprising informative SNPs and the second cluster comprising non-informative SNPs, wherein the informative SNPs are present in the recipient and the donor in a genotype combination of $AA_{recipient}/AB_{donor}$, $BB_{recipient}/AB_{donor}$, $AA_{recipient}/BB_{donor}$, or $BB_{recipient}/AA_{donor}$, and wherein the non-informative SNPs are present in the recipient and the donor in a genotype combination of $AB_{recipient}/AB_{donor}$, $AB_{recipient}/AA_{donor}$, or $AB_{recipient}/BB_{donor}$; and IV) detecting the donor specific allele based on the presence of the informative SNPs. In some embodiments, the method further comprises determining the donor-specific nucleic acid fraction based on the amount of the donor specific alleles.

2) Approach 2 ("DF2"):

If only the donor's genotype is known, filter out cases where the donor is homozygous for the alternate allele for (non-mirrored) allele frequencies less than 0.5 and homozygous for the reference allele for allele frequencies larger than 0.5. This excludes $BB_{recipient}/BB_{donor}$, and $AB_{recipient}/BB_{donor}$ in the [0,0.5) allele frequency range and $AA_{recipient}/AA_{donor}$ and $AB_{recipient}/AA_{donor}$ clusters in the (0.5, 1] allele frequency range.

Accordingly, using the DF2 approach, under the circumstances where the donor's genotype is known but the recipient's genotype is unknown, the disclosure provides a method of determining transplant status comprises:

I) isolating cell-free nucleic acids from a biological sample;

II) measuring the amount of each allele of the one or more SNPs in the biological sample to generate a data set consisting of measurements of the amounts of the one or more SNPs;

III) filtering out 1) SNPs which are present in the recipient and the donor in a genotype combination of $AA_{recipient}/AA_{donor}$ or $AB_{recipient}/AA_{donor}$ and the donor allele frequency is less than 0.5, and 2) SNPs which are present in the recipient and the donor in a genotype combination of $BB_{recipient}/BB_{donor}$, and $AB_{recipient}/BB_{donor}$, and the donor allele frequency is larger than 0.5; and IV) detecting the donor specific alleles based on the presence of the remaining SNPs in the one or more SNPs in the biological sample. In some embodiments, the method further comprises determining the donor-specific nucleic acid fraction based on the amount of the donor specific alleles.

3) Approach 3 ("DF3"):

If only the recipient's genotype is known, filter out cases where the recipient is heterozygous (so $AB_{recipient}/AB_{donor}$, $AB_{recipient}/AA_{donor}$, and $AB_{recipient}/BB_{donor}$ are excluded). Then perform clustering on the remaining SNPs to remove uninformative SNPs. The 2 clusters are expected to contain the following genotype combinations:

a. Cluster 1: $AA_{recipient}/AB_{donor}$, $BB_{recipient}/AB_{donor}$.

b. Cluster 2: $AA_{recipient}/BB_{donor}$, $BB_{recipient}/AA_{donor}$.

SNPs in both clusters are relevant to the donor fraction calculation and should be combined.

Accordingly, using the DF3 approach, under the circumstances where the recipient's genotype is known but the donor's genotype is unknown, the disclosure provides a method of determining transplant status comprises:

I) isolating cell-free nucleic acids from a biological sample; measuring the amount of each allele of the one or more SNPs in the biological sample to generate a data set consisting of measurements of the amounts of the one or more SNPs;

II) filtering out 1) SNPs which are present in the recipient and the donor in a genotype combination of $AB_{recipient}/AB_{donor}$, $AB_{recipient}/AA_{donor}$, and $AB_{recipient}/BB_{donor}$;

III) performing a computer algorithm on the data set of the remaining SNPs to form a first cluster and a second cluster, both comprising informative SNPs. The first cluster comprises SNPs that are present in the recipient and the donor in a genotype combination of $AA_{recipient}/AB_{donor}$, or $BB_{recipient}/AB_{donor}$. The second cluster comprises SNPs that are present in the recipient and the donor in a genotype combination of $AA_{recipient}/BB_{donor}$ or $BB_{recipient}/AA_{donor}$; and IV) detecting the donor specific allele based on the presence of the remaining SNPs in the one or more SNPs in the biological sample.

In some embodiments, the method further comprises determining donor-specific nucleic acid fraction in the biological sample based on the amount of the donor specific alleles.

4) Approach 4 ("DF4"):

If both donor and recipient's genotypes are known, all informative SNPs are known. Non-informative SNPs are precisely identified and excluded.

Once non-informative SNPs are removed, the median is calculated on the remaining informative SNPs. Donor fraction is then estimated as a correction factor K times the median of the mirrored allele frequencies (Donor fraction=K*median (mirrored allele frequency)) for informative SNPs. The correction factor K is then used in cases where there is a 1 allele difference between the donor and the recipient (informative categories 1 and 3). K is then set to 2 to correct for there being 2 alleles in a diploid genome while the allele frequency only counts the fraction of alleles that are the reference allele. As an example, a 10% donor fraction would have 10 copies of donor AB for every 90 copies of recipient AA, but the allele frequency is 5% ($10\,A_{donor}/(10\,A_{donor}+10\,B_{donor}+90\,A_{recipient}+90\,A_{recipient})$) and needs to be multiplied by 2 in order to obtain the donor fraction.

Ideally, K should be set to 1 for category 2 SNPs, which have a 2 allele difference between the donor and recipient. Given the potential challenge of resolving category 1 and 2 informative SNPs, the correction factor is applied to the grouping of both categories 1 and 2. This should not result in much error in the calculation of donor fraction as there should be a higher proportion of SNPs in category 1. Furthermore, it's not the absolute value of donor fraction that's important for transplant monitoring, but the measure of donor fraction increasing over the time elapsed since a transplant procedure.

Figure 5:
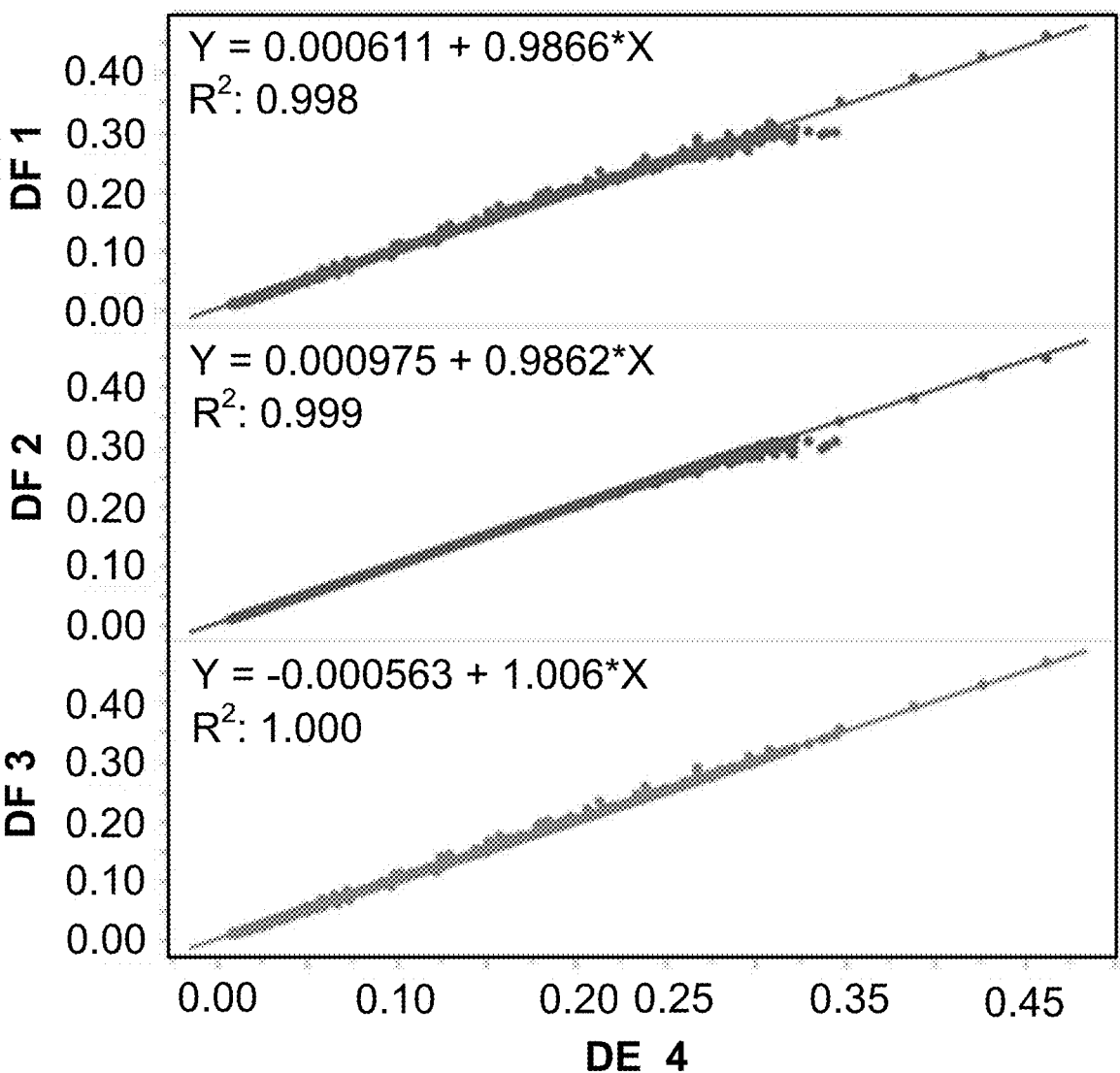
FIG. 5 shows approaches for calculating donor fraction (DF) based on knowledge of donor or recipient's genotype. Donor fraction is calculated using approach 1 (DF1) disclosed herein if neither genotype is known, using approach 2 (DF2) disclosed herein if given the donor's genotype, using approach 3 (DF3) disclosed herein if given the recipient's genotype, and using approach 4 (DF4) disclosed herein if given both genotypes. Since DF4 represents the most accurate identification of the informative SNPs, it's placed on the X-axis to serve as the ground truth to which all other approaches are correlated.

The data shown in FIG. 5 (as well as in FIG. 7 and FIG. 8) utilize 86 mixtures of genomic DNA and non-pregnant plasma cfDNA to simulate donor-recipient mixtures. FIG. 5 compares the donor fraction calculated by Approaches 1-3 with that of the most accurate determination using Approach 4. Approaches 1-3 correlate highly ($R^2 > 0.97$) and match closely in value (slope=0.971-0.996), indicating overall excellent agreement between all the strategies for measuring moderate levels (e.g. 5%-25%) of donor fraction. It also indicates that K-means clustering of SNP allele frequencies is sufficient to identify informative SNPs in such a range. There's little advantage in knowing either the donor's or recipient's genotype in calculating the donor fraction unless the donor fraction is very low or very high.

Figure 6A:
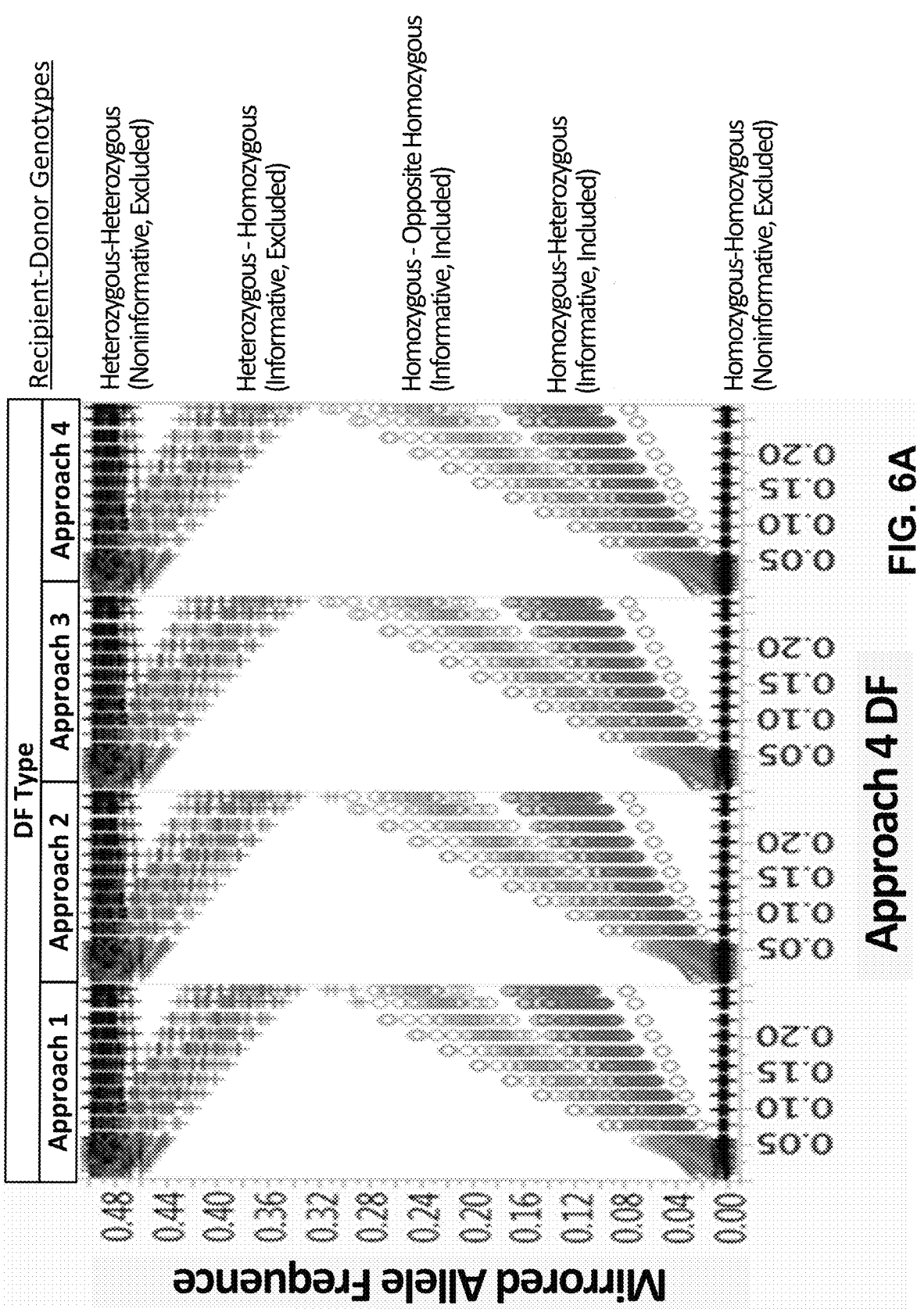
FIGS. 6A and 6B show approaches toward classifying informative SNPs.
Figure 6B:
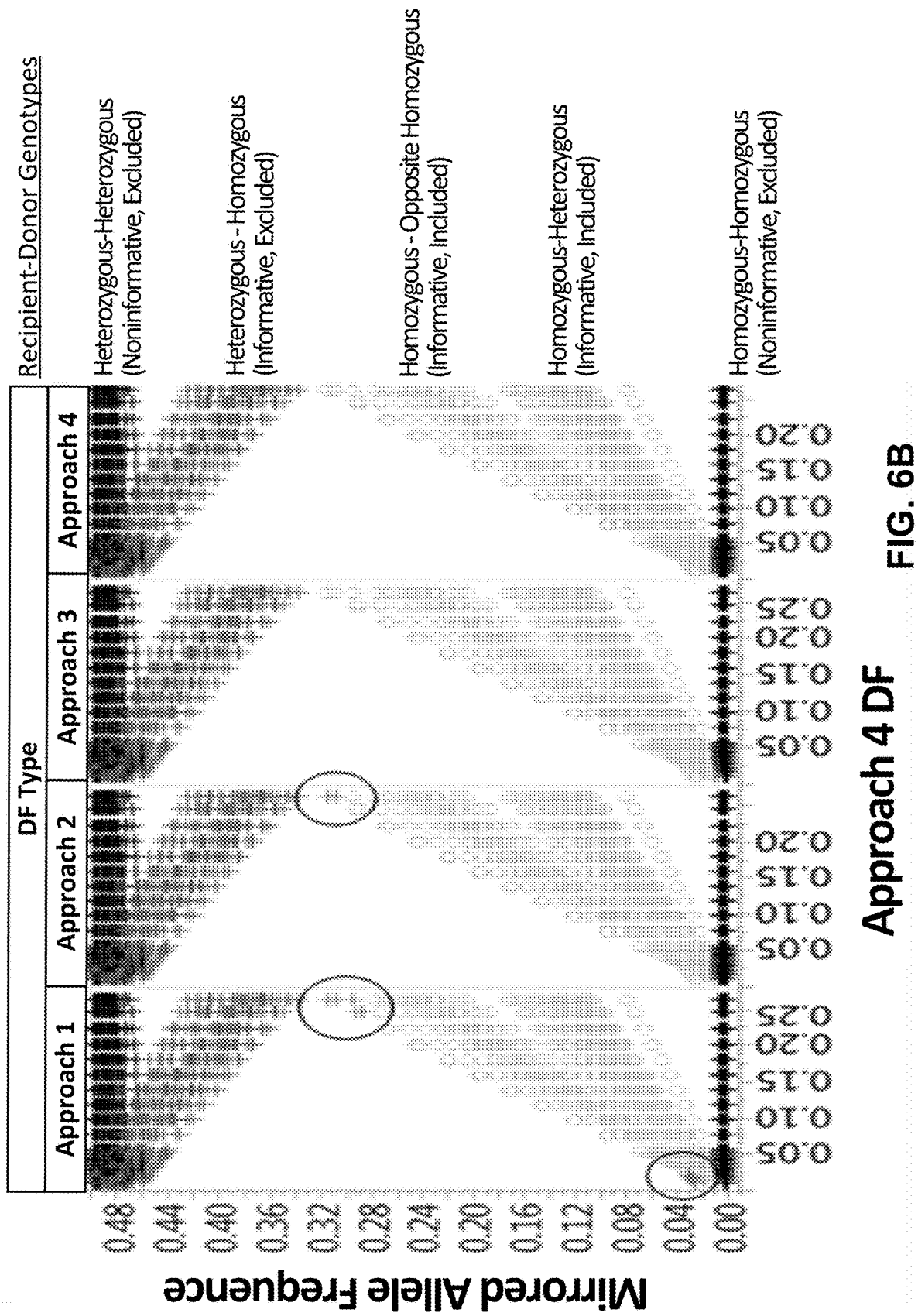
Figure 7:
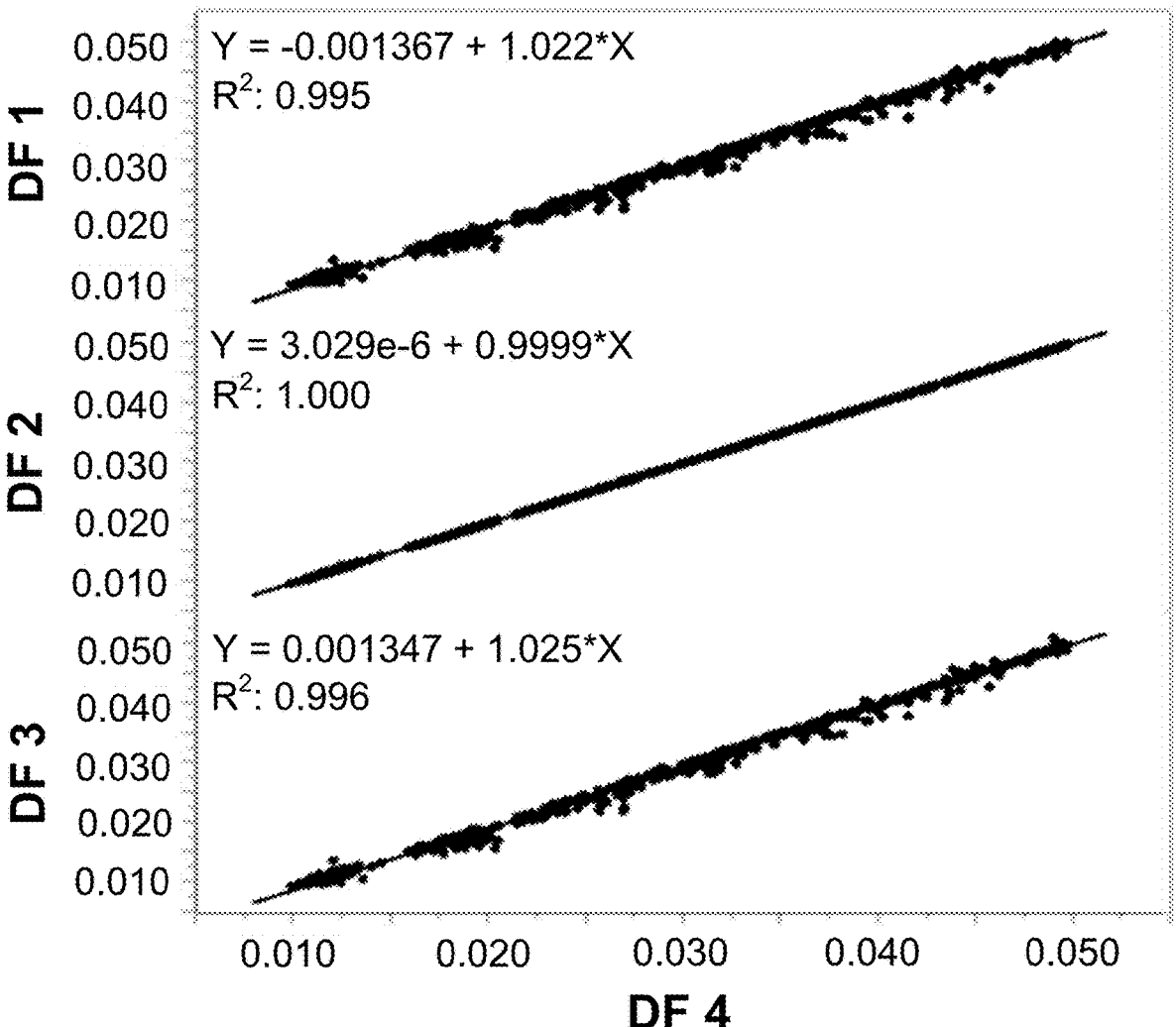
FIG. 7 shows estimation of less than 5% donor fraction using DF1, DF2, or DF3. Values on the X axis represents the donor fraction determined using DF4. Donor fraction can be overestimated for low donor fractions, but this can be mitigated through knowledge of the donor's genotype and exclusion of $AA_{recipient}/AA_{donor}$ and $BB_{recipient}/BB_{donor}$ recipient-donor's genotype combinations as is done in the calculation of DF 2.

At very low (down to 0.5%) and very high donor fractions (near 30%), where different SNP allele frequency clusters can merge into each other, there can be misclassification of informative SNPs (FIG. 6). For example, at low donor fractions, $AA_{recipient}/AB_{donor}$ SNPs could be regarded as $AA_{recipient}/AA_{donor}$ SNPs, a false negative in detecting informative SNPs. This causes an overestimation of donor fraction by an average of 2%-3% for donor fractions less than 5% (FIG. 7, DF1 and DF3 panels). Approach 2 should be more accurate here as it removes $AA_{recipient}/AA_{donor}$ and $BB_{recipient}/BB_{donor}$ combinations through knowledge of the donor's genotype. This is verified by having the slope closest to 1 in the measurement using Approach 2 (FIG. 7, DF2 panel).

Figure 8:
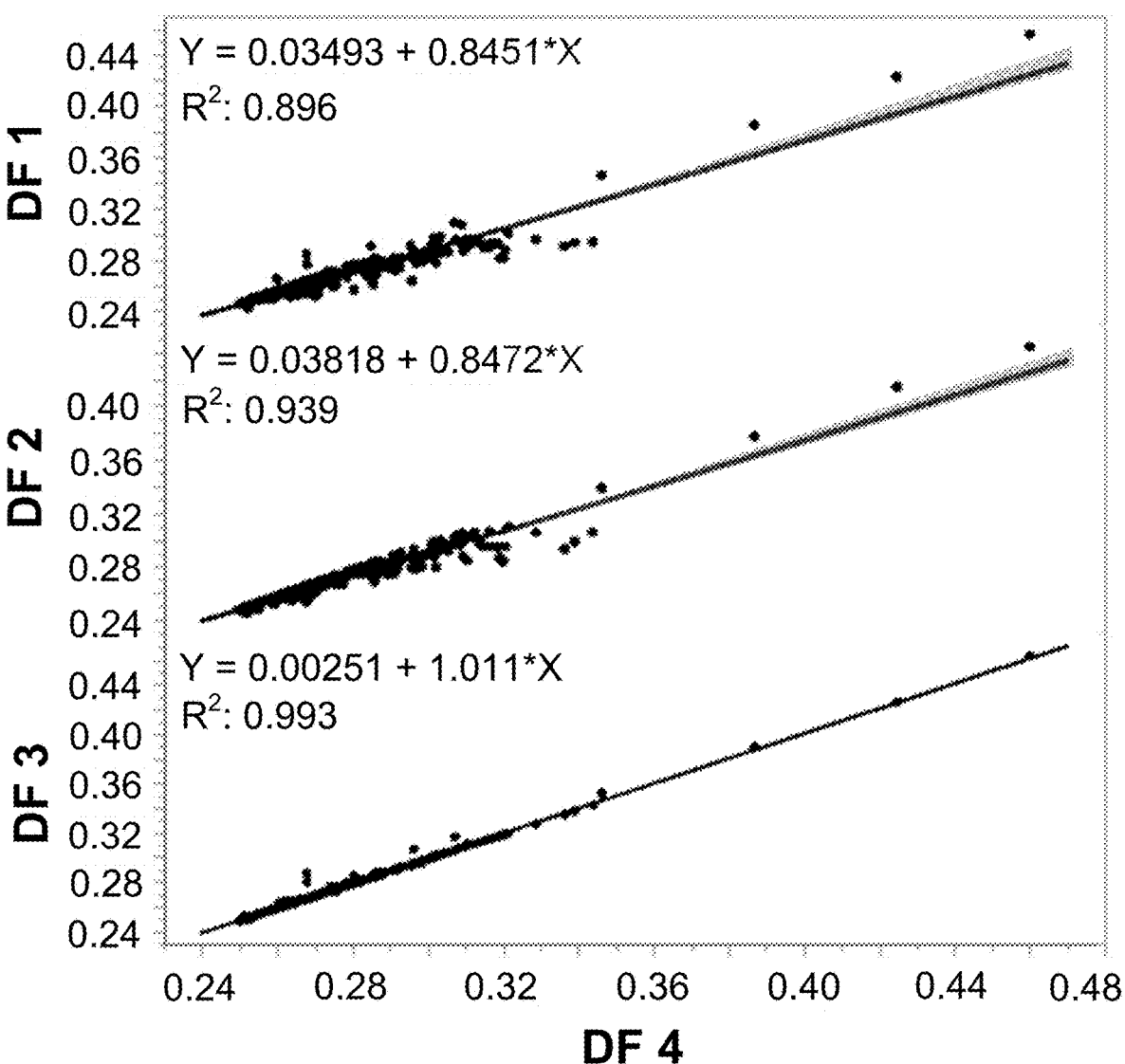
FIG. 8 shows estimation of greater than 25% donor fraction using DF1, DF2, or DF3. Values on the X axis represents the donor fraction determined using DF4. Donor fraction can be underestimated for high donor fractions, but this can be mitigated through knowledge of the recipient's genotype and exclusion of $AB_{recipient}/AA_{donor}$ and $AB_{recipient}/BB_{donor}$ donor-recipient's genotype combinations as is done in the calculation of DF 3.

At higher donor fractions, $AA_{recipient}/BB_{donor}$ SNPs could be classified as $AB_{recipient}/AA_{donor}$ SNPs and $BB_{recipient}/AA_{donor}$ SNPs could be classified as $AB_{recipient}/BB_{donor}$. Those are considered non-informative in this approach for donor fraction calculation, so another cause for false negatives. This causes a 25%-30% underestimation of donor fraction for donor fractions larger than 15% (FIG. 8). Approach 3, with knowledge of the recipient's genotype, could eliminate this issue through exclusion of $AB_{recipient}/AA_{donor}$ and $AB_{recipient}/BB_{donor}$ SNPs. This is verified by having the slope closest to 1 in the measurement using Approach 3 (FIG. 8, DF3 panel).

Determining Transplant Status

Calculating Donor-Specific Cell Free DNA Fraction ("Donor Fraction")

In some embodiments, the donor fraction is calculated as the median of the frequencies across all informative SNPs.

In some embodiments, the donor fraction is obtained by multiplying a correction factor to frequencies of informative SNPs. A correction factor of either 1 or 2 applies depending on the types of informative SNPs: if the SNP can be identified as such that the donor has one different allele from the recipient, a correction factor of 2 is applied; if the SNP can be identified as where the donor has two different alleles from the recipient, a correction factor of 1 is applied. The type of SNPs can be typically determined from analyzing the resulting allele frequency from a mixture of donor and recipient cell-free DNA, the donor's genotype is not needed to obtain such information. In some embodiments, whether the SNP is one that the donor has one or two different alleles from the recipient can be determined based on relatedness between the recipient and donor. For example, if the recipient is the parent of the donor, the donor can only have one allele different from the recipient. If the recipient and donor are unrelated, ⅓ of the SNPs will be cases where the donor has one differing allele and the correction factor will be 2 for those SNPs. The other ⅔rd of the SNPs will be cases where the donor has 2 differing alleles and the correction factor will be 1 for those SNPs. K-means clustering can be used to separate those 2 categories of SNPs, or they can be simply separated into an upper ⅓rd and lower ⅔rd groups for applying the correction factor. After correction factors are applied, the donor fraction is the median across all corrected informative SNPs.

In some embodiments, a fraction or ratio can be determined for the amount of one nucleic acid relative to the amount of another nucleic acid. In some embodiments, the fraction of donor-specific cell-free nucleic acid in a sample relative to the total amount of cell-free nucleic acid in the sample is determined. In general, to calculate the fraction of donor-specific cell-free nucleic acid in a sample relative to the total amount of the cell-free nucleic acid in the sample, the following equation can be applied:

The fraction of donor-specific cell-free nucleic acid=
(amount of donor-specific cell-free nucleic
acid)/[(amount of total cell-free nucleic acid)].

Calculating the Copy Number of Donor-Specific Cell Free DNA ("Donor Load")

In some embodiments, the total copies of genomic DNA in the cell-free DNA is determined using a reference genomic nucleic acid and a variant oligo, which is designed to contain a single nucleotide substitution as compared to the reference genomic nucleic acid and which is co-amplified with one or more polymorphic nucleic acid targets. The variant oligo is added to the amplification mixture at a known quantity. After sequencing, the number of sequences containing the variant are compared to the number of sequences containing the reference genomic nucleic acid and the ratio of the two is determined. Since the variant oligo's quantity is known, the total copies of genomic DNA can be calculated based on the quantity of the variant oligo and the ratio of the number of sequences containing the variant to the number of sequences containing the reference genomic nucleic acid. In one embodiment, the reference genomic nucleic acid is ApoE. In one embodiment, the reference genomic nucleic acid is RNasP.

In some embodiments the total copy number of the genomic DNA in cell free DNA and the donor fraction number is multiplied to generate the total copy number of donor DNA, which is used to indicate the status of transplant. The total copy number of donor DNA in some instances can be a better indicator of rejection, as a high donor genomic copy number may be masked as a low fractional concentration in a recipient having a high body mass index (BMI), or the increase of copy number of donor specific cell free DNA may be masked as a decrease or unchanged fractional concentration as the patient gains weight Determining Transplant Status Transplant status, i.e. whether the transplant is rejected or accepted, can be determined by monitoring the donor fraction or the donor load in the transplant patient.

In some embodiments, the donor fraction or donor load of the transplant patient is compared with a predetermined threshold and transplant status is determined as acceptance if the donor fraction or donor load is less than the predetermined threshold and the transplant status is determined as rejection if donor fraction or donor load is greater than the predetermined threshold. The threshold can be predetermined based on the background levels of allele frequencies in a control patient(s), for example, a patient(s) who has (have) not received an organ transplant. In some embodiments, the control patient is one who is within the same gender, age, and ethnic group as the subject for which transplantation status is to be determined and the control patient has similar BMI as the subject.

In some embodiments, the donor fraction or donor load is determined for samples taken at various time points after transplant. An increase in donor fraction or donor load over time is an indication of transplant rejection. In some embodiments, the transplant status is monitored at two or more time points. The two or more time points may comprise an earlier time point and a later time point after the first time point, both time points being post transplantation. In an embodiment, an increase in donor-specific circulating cell-free nucleic acid from the earlier time point to the later time point is indicative of developing transplant rejection. In some embodiments, the time interval between the earlier time point and the later time point is at least 7 days. In some embodiments, the earlier time point is between 0 days to one year following transplantation. In some embodiments, the later time point is between 7 days to five years following transplantation. Or other time points may be used. Sampling may vary depending upon the nature of the transplant, patient progress or other factors. In some embodiments, samples may be taken every week, once every two weeks, once every 3 weeks, once a month, once every two months, once every three months, once every four months, once every five months, once every six months, once every year, and the donor-specific cell-free nucleic acid fraction for two or more of the time points are determined; an increase in donor-specific cell-free nucleic acid fraction over time indicates transplant rejection. In some embodiments, the transplant status is monitored more frequently in the first year following transplantation than in the subsequent years. For example, samples may be taken at more than 5, more than 6, more than 7, more than 8, more than 9, or more than 10 time points for analysis of transplant status during the first year.

As described further below, in some embodiments, the amount of the reference allele or alternate allele can be determined by various assays described herein. In one embodiment, the amount of the allele (e.g., reference allele or alternate allele) corresponds to the sequence reads for that allele from sequencing reactions.

Quantification of Polymorphic Nucleic Acid Targets

In some embodiments, the amount of the polymorphic nucleic acid targets are quantified based on sequence reads. In certain embodiments the quantity of sequence reads that are mapped to a polymorphic nucleic acid target on a reference genome for each allele is referred to as a count or read density. In certain embodiments, a count is determined from some or all of the sequence reads mapped to the polymorphic nucleic acid target.

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region or other chromosomal rearrangement) and/or sometimes is a group of portions corresponding to a genome.

In some embodiments, a count is derived from raw sequence reads and/or filtered sequence reads. In certain embodiments a count is determined by a mathematical process. In certain embodiments a count is an average, mean or sum of sequence reads mapped to a target nucleic acid sequence on a reference genome for each of the two alleles (a reference allele and an alternate allele) of a polymorphic site. In some embodiments, a count is associated with an uncertainty value. A count sometimes is adjusted. A count may be adjusted according to sequence reads associated with a target nucleic acid sequence on a reference genome for each of the two alleles (a reference allele and an alternate allele) of a polymorphic site that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a target nucleic acid sequence on a reference genome for each of the two alleles (a reference allele and an alternate allele) of a polymorphic site. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Enriching Cell-Free Nucleic Acids

In some embodiments, the polymorphic nucleic acid targets are enriched before identifying the donor-specific cell free nucleic acid using methods described herein. In some embodiments, enriching comprises amplifying the plurality of polymorphic nucleic acid targets. In some cases, the enriching comprises generating amplification products in an amplification reaction. Amplification of polymorphic targets may be achieved by any method described herein or known in the art for amplifying nucleic acid (e.g., PCR). In some cases, the amplification reaction is performed in a single vessel (e.g., tube, container, well on a plate) which sometimes is referred to herein as multiplexed amplification.

The amount of donor-specific cell free nucleic acid can be quantified and used in conjunction with other methods for assessing transplant status. The amount of donor-specific nucleic acid can be determined in a nucleic acid sample from a subject before or after processing to prepare sample nucleic acid. In certain embodiments, the amount of donor-specific nucleic acid is determined in a sample after sample nucleic acid is processed and prepared, which amount is utilized for further assessment. In some embodiments, an outcome comprises factoring the fraction of donor-specific nucleic acid in the sample nucleic acid (e.g., adjusting counts, removing samples, making a call or not making a call).

In some embodiments, the cell-free nucleic acids from the sample derived from the transplant recipient who has received an organ transplant can be enriched before determining the donor-specific cell-free nucleic acids or quantifying the donor-specific fraction. In some cases, the enrichment methods can include amplification (e.g., PCR)-based approaches.

Amplification of Nucleotide Sequences

In many instances, it is desirable to amplify a nucleic acid sequence of the technology herein using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present technology, one of skill in the art will recognize that the amplification of a genomic sequence found in a recipient blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology herein, which represents a particular methylation pattern, or to quantitatively determine the amount of this particular genomic sequence in the recipient blood. For a review of branched-DNA signal amplification for direct quantitation of nucleic acid sequences in clinical samples, see Nolte, Adv. Clin. Chem. 33:201-235, 1998.

The compositions and processes of the technology herein are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

The terms "amplify", "amplification", "amplification reaction", or "amplifying" refer to any in vitro process for multiplying the copies of a nucleic acid. Amplification sometimes refers to an "exponential" increase in nucleic acid. However, "amplifying" as used herein can also refer to linear increases in the numbers of a select nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or abundance of the nucleic acid. In some embodiments a one-time primer extension may be performed as a prelude to linear or exponential amplification.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, digital PCR, combinations thereof, and the like. For example, amplification can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation). Reagents and hardware for conducting PCR are commercially available.

A generalized description of an amplification process is presented herein. Primers and nucleic acid are contacted, and complementary sequences anneal to one another, for example. Primers can anneal to a nucleic acid, at or near (e.g., adjacent to, abutting, and the like) a sequence of interest. In some embodiments, the primers in a set hybridize within about 10 to 30 nucleotides from a nucleic acid sequence of interest and produce amplified products. In some embodiments, the primers hybridize within the nucleic acid sequence of interest.

A reaction mixture, containing components necessary for enzymatic functionality, is added to the primer-nucleic acid hybrid, and amplification can occur under suitable conditions. Components of an amplification reaction may include, but are not limited to, e.g., primers (e.g., individual primers, primer pairs, primer sets and the like) a polynucleotide template, polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

PCR conditions can be dependent upon primer sequences, abundance of nucleic acid, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known in the art; see, e.g., United States Patent Application Publication no. 20070202525, filed Feb. 2, 2007, which is hereby incorporated by reference). PCR is typically carried out as an automated process with a thermostable enzyme. In this process, the temperature of the reaction mixture is cycled through a denaturing step, a primer-annealing step, and an extension reaction step automatically. Some PCR protocols also include an activation step and a final extension step. Machines specifically adapted for this purpose are commercially available. A non-limiting example of a PCR protocol that may be suitable for embodiments described herein is, treating the sample at 95° C. for 5 minutes; repeating thirty-five cycles of 95° C. for 45 seconds and 68° C. for 30 seconds; and then treating the sample at 72° C. for 3 minutes. A completed PCR reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product may include naturally occurring nucleotides, non-naturally occurring nucleotides, nucleotide analogs and the like and combinations of the foregoing. An amplification product often has a nucleotide sequence that is identical to or substantially identical to a nucleic acid sequence herein, or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

Primers

Primers useful for detection, amplification, quantification, sequencing and analysis of nucleic acid are provided. The term "primer" as used herein refers to a nucleic acid that includes a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and primer sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/ sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. Features of primers can be applied to probes and oligonucleotides, such as, for example, the competitive and inhibitory oligonucleotides provided herein.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at 3' or 5' end of the nucleotide subsequence in the primer complementary to or substantially complementary to the solid phase primer hybridization sequence).

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme and the like, as described above for labeled competitor oligonucleotides).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments, the primers are complementary to genomic DNA target sequences. In some cases, the forward and reverse primers hybridize to 5' and 3' ends of the genomic DNA target sequences. In some embodiments, primers that hybridize to the genomic DNA target sequences also hybridize to competitor oligonucleotides that were designed to compete with corresponding genomic DNA target sequences for binding of the primers. In some cases, the primers hybridize or anneal to the genomic DNA target sequences and the corresponding competitor oligonucleotides with the same or similar hybridization efficiencies. In some cases the hybridization efficiencies are different. The ratio between genomic DNA target amplicons and competitor amplicons can be measured during the reaction. For example if the ratio is 1:1 at 28 cycles but 2:1 at 35, this could indicate that during the end of the amplification reaction the primers for one target (i.e. genomic DNA target or competitor) are either reannealing faster than the other, or the denaturation is less effective than the other.

In some embodiments primers are used in sets. As used herein, an amplification primer set is one or more pairs of forward and reverse primers for a given region. Thus, for example, primers that amplify nucleic acid targets for region 1 (i.e. targets 1a and 1b) are considered a primer set. Primers that amplify nucleic acid targets for region 2 (i.e. targets 2a and 2b) are considered a different primer set. In some embodiments, the primer sets that amplify targets within a particular region also amplify the corresponding competitor oligonucleotide(s). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used.

In some cases, loci-specific amplification methods can be used (e.g., using loci-specific amplification primers). In some cases, a multiplex SNP allele PCR approach can be used. In some cases, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In some cases, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In some cases, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In some cases, a microfluidics approach can be used. In some cases, an array-based microfluidics approach can be used. For example, such an approach can involve the use of a microfluidics array (e.g., Fluidigm) for amplification at low plex and incorporation of index and capture probes, followed by sequencing. In some cases, an emulsion microfluidics approach can be used, such as, for example, digital droplet PCR.

In some cases, universal amplification methods can be used (e.g., using universal or non-loci-specific amplification primers). In some cases, universal amplification methods can be used in combination with pull-down approaches. In some cases, the method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In some cases, pull-down approaches can be used in combination with ligation-based methods. In some cases, the method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In some cases, pull-down approaches can be used in combination with extension and ligation-based methods. In some cases, the method can include molecular inversion probe (MIP) extension and ligation. For example, such an approach can involve the use of molecular inversion probes in combination with sequence adapters followed by universal amplification and sequencing. In some cases, complementary DNA can be synthesized and sequenced without amplification.

In some cases, extension and ligation approaches can be performed without a pull-down component. In some cases, the method can include loci-specific forward and reverse primer hybridization, extension and ligation. Such methods can further include universal amplification or complementary DNA synthesis without amplification, followed by sequencing. Such methods can reduce or exclude background sequences during analysis, in some cases.

In some cases, pull-down approaches can be used with an optional amplification component or with no amplification component. In some cases, the method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In some cases, the method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In some cases, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In some cases, the separated target fragments and the separated reference fragments also are isolated away from each other (e.g., isolated in separate assay compartments). In some cases, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, WI); Illumina BEADARRAY platform (Illumina, San Diego, CA); Affymetrix GENECHIP platform (Affymetrix, Santa Clara, CA); Agilent SureSelect Target Enrichment System (Agilent Technologies, Santa Clara, CA); and related platforms. Such methods typically involve hybridization of a capture oligonucleotide to a portion or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some cases, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. In such methods, a fragment size species (e.g., short fragments) nucleic acids are selectively tagged in a sample that includes long and short nucleic acids. Such methods typically involve performing a nucleic acid amplification reaction using a set of nested primers which include inner primers and outer primers. In some cases, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Assays for Detecting the Polymorphic Nucleic Acid Targets

In some embodiments, the one or more polymorphic nucleic acid targets can be determined using one or more assays that are known in the art. Non-limiting examples of methods of detection, quantification, sequencing and the like include mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, a cycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNAPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, hybridization using at least one fluorescently labeled probe, cloning and sequencing, electrophoresis, the use of hybridization probes and quantitative real time polymerase chain reaction (QRT-PCR), digital PCR, nanopore sequencing, chips and combinations thereof. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

In some embodiments, the assay is a sequencing reaction, as described herein. Sequencing, mapping and related analytical methods are known in the art (e.g., United States Patent Application Publication US2009/0029377, incorporated by reference). Certain aspects of such processes are described hereafter.

In some embodiments, the relative abundance of donor-specific cell-free nucleic acid in a recipient sample can be determined as a parameter of the total number of unique sequence reads mapped to a target nucleic acid sequence on a reference genome for each of the alleles (a reference allele and one or more alternate alleles) of a polymorphic site. In some embodiments, the assay is a high throughput sequencing. In some embodiments, the assay is a digital polymerase chain reaction (dPCR). In some embodiments, the assay is a microarray analysis.

In some embodiments, the sequencing process is a sequencing by synthesis method, as described herein. Typically, sequencing by synthesis methods comprise a plurality of synthesis cycles, whereby a complementary nucleotide is added to a single stranded template and identified during each cycle. The number of cycles generally corresponds to read length. In some cases, polymorphic targets are selected such that a minimal read length (i.e., minimal number of cycles) is required to include amplification primer sequence and the polymorphic target site (e.g., SNP) in the read. In some cases, amplification primer sequence includes about 10 to about 30 nucleotides. For example, amplification primer sequence may include about 11, 12, 13, 14, 15, 16, 17, 18, 19, 20, 21, 22, 23, 24, 25, 26, 27, 28, or 29 nucleotides, in some embodiments. In some cases, amplification primer sequence includes about 20 nucleotides. In some embodiments, a SNP site is located within 1 nucleotide base position (i.e., adjacent to) to about 30 base positions from the 3' terminus of an amplification primer. For example, a SNP site may be within 2, 3, 4, 5, 6, 7, 8, 9, 10, 11, 12, 13, 14, 15, 16, 17, 18, 19, 20, 21, 22, 23, 24, 25, 26, 27, 28, or 29 nucleotides of an amplification primer terminus. Read lengths can be any length that is inclusive of an amplification primer sequence and a polymorphic sequence or position. In some embodiments, read lengths can be about 10 nucleotides in length to about 50 nucleotides in length. For example, read lengths can be about 15, 20, 21, 22, 23, 24, 25, 26, 27, 28, 29, 30, 31, 32, 33, 34, 35, 36, 37, 38, 39, 40, or 45 nucleotides in length. In some cases, read length is about 36 nucleotides. In some cases, read length is about 27 nucleotides. Thus, in some cases, the sequencing by synthesis method comprises about 36 cycles and sometimes comprises about 27 cycles.

In some embodiments, a plurality of samples is sequenced in a single compartment (e.g., flow cell), which sometimes is referred to herein as sample multiplexing. Thus, in some embodiments, donor-specific nucleic acid fraction is determined for a plurality of samples in a multiplexed assay. For example, donor-specific nucleic acid fraction may be determined for about 10, 20, 30, 40, 50, 60, 70, 80, 90, 100, 200, 300, 400, 500, 600, 700, 800, 900, 1000, 2000 or more samples. In some cases, donor-specific nucleic acid fraction is determined for about 10 or more samples. In some cases, donor-specific nucleic acid fraction is determined for about 100 or more samples. In some cases, donor-specific nucleic acid fraction is determined for about 1000 or more samples.

Typically, sequence reads are monitored and filtered to exclude low quality sequence reads. The term "filtering" as used herein refers to removing a portion of data or a set of data from consideration and retaining a subset of data. Sequence reads can be selected for removal based on any suitable criteria, including but not limited to redundant data (e.g., redundant or overlapping mapped reads), non-informative data, over represented or underrepresented sequences, noisy data, the like, or combinations of the foregoing. A filtering process often involves removing one or more reads and/or read pairs (e.g., discordant read pairs) from consideration. Reducing the number of reads, pairs of reads and/or reads comprising candidate SNPs from a data set analyzed for the presence or absence of an informative SNP often reduces the complexity and/or dimensionality of a data set, and sometimes increases the speed of searching for and/or identifying informative SNPs by two or more orders of magnitude.

Nucleic acid detection and/or quantification also may include, for example, solid support array based detection of fluorescently labeled nucleic acid with fluorescent labels incorporated during or after PCR, single molecule detection of fluorescently labeled molecules in solution or captured on a solid phase, or other sequencing technologies such as, for example, sequencing using ION TORRENT or MISEQ platforms or single molecule sequencing technologies using instrumentation such as, for example, PACBIO sequencers, HELICOS sequencer, or nanopore sequencing technologies.

In some cases, nucleic acid quantifications generated by a method comprising a sequencing detection process may be compared to nucleic acid quantifications generated by a method comprising a different detection process (e.g., mass spectrometry). Such comparisons may be expressed using an $R^2$ value, which is a measure of correlation between two outcomes (e.g., nucleic acid quantifications). In some cases, nucleic acid quantifications (e.g., donor copy number quantifications) are highly correlated (i.e., have high $R^2$ values) for quantifications generated using different detection processes (e.g., sequencing and mass spectrometry). In some cases, $R^2$ values for nucleic acid quantifications generated using different detection processes may be between about 0.90 and about 1.0. For example, $R^2$ values may be about 0.91, 0.92, 0.93, 0.94, 0.95, 0.96, 0.97, 0.98, or 0.99.

In some embodiments, the polymorphic nucleic acid targets are restriction fragment length polymorphisms (RFLPs). RFLPs detection may be performed by cleaving the nucleic acid with an enzyme and evaluated with a probe that hybridize to the cleaved products and thus defines a uniquely sized restriction fragment corresponding to an allele. RFLPs can be used to detect donor cell-free nucleic acids. As an illustrative example, where a homozygous recipient would have only a single fragment generated by a particular restriction enzyme which hybridizes to a restriction fragment length polymorphism probe, after receiving a transplant from a heterozygous donor, the cell-free nucleic acids in the recipient would have two distinctly sized fragments which hybridize to the same probe generated by the enzyme. Therefore detecting the RFLPs can be used to identify the presence of the donor-specific cell-free nucleic acids.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present technology. Additional means suitable for detecting changes in a polynucleotide sequence for practicing the methods of the present technology include but are not limited to mass spectrometry, primer extension, polynucleotide hybridization, real-time PCR, and electrophoresis.

Use of a primer extension reaction also can be applied in methods of the technology herein. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the technology herein, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic acids using cleavable detector probes that are cleaved during the amplification process and detected by mass spectrometry, see U.S. patent application Ser. No. 11/950,395, which was filed Dec. 4, 2007, and is hereby incorporated by reference.

Various sequencing techniques that are suitable for use include, but not limited to sequencing-by-synthesis, reversible terminator-based sequencing, 454 sequencing (Roche) (Margulies, M. et al. 2005 Nature 437, 376-380), Applied Biosystems' SOLID™ technology, Helicos True Single Molecule Sequencing (tSMS), single molecule, real-time (SMRT™) sequencing technology of Pacific Biosciences, ION TORRENT (Life Technologies) single molecule sequencing, chemical-sensitive field effect transistor (CHEMFET) array, electron microscopy sequencing technology, digital PCR, sequencing by hybridization, nanopore sequencing, Illumina Genome Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53:1996-2001). Many of these methods allow the sequencing of many nucleic acid molecules isolated from a specimen at high orders of multiplexing in a parallel fashion (Dear Brief Funct Genomic Proteomic 2003; 1:397-416).

Many sequencing platforms that allow sequencing of clonally expanded or non-amplified single molecules of nucleic acid fragments can be used for detecting the donor-specific cell-free nucleic acids. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucle-otides or primers, enables sequence determination by fluorescence detection. Longer sequence reads may be obtained by including primers containing cleavable linkages that can be cleaved after label identification. Cleavage at the linker removes the label and regenerates 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemilumi-nescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleo-tide sequences by pyrosequencing methodology (e.g., Nakano et al., "Single-molecule PCR using water-in-oil emulsion;" Journal of Biotechnology 102:117-124 (2003)). Such a system can be used to exponentially amplify ampli-fication products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunc-tion with total internal reflection microscopy (TIRM). Pho-tons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluo-rophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluores-cent molecule; and capturing an image of fluorescence resonance energy transfer signals after each iteration (e.g., U.S. Pat. No. 7,169,314; Braslavsky et al., PNAS 100 (7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer—released linear amplification product complexes with the immobilized cap-ture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer—released linear amplification product complexes, the bound nucleic acids often are sequenced in parallel by the iterative steps of, a) polymerase extension in the pres-ence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53 (11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein.

Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291:1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-

233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Additional Methods for Obtaining Nucleotide Sequence Reads

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, donor-specific nucleic acid can be enriched by selecting for nucleic acid having a lower molecular weight (e.g., less than 300 base pairs, less than 200 base pairs, less than 150 base pairs, less than 100 base pairs). In some embodiments, donor-specific nucleic acid can be enriched by suppressing recipient background nucleic acid, such as by the addition of formaldehyde. In some embodiments, a portion or subset of a pre-selected pool of nucleic acids is sequenced randomly. In some embodiments, the nucleic acid is amplified prior to sequencing. In some embodiments, a portion or subset of the nucleic acid is amplified prior to sequencing.

In some cases, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some cases, a ligation-based library preparation method is used (e.g., ILLUMINA TRUSEQ, Illumina, San Diego CA). Ligation-based library preparation methods typically use a methylated adaptor design which can incorporate an index sequence at the initial ligation step and often can be used to prepare samples for single-read sequencing, paired-end sequencing and multiplexed sequencing. In some cases, a transposon-based library preparation method is used (e.g., EPICENTRE NEXTERA, Epicentre, Madison WI). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template or a single DNA molecule. High-throughput sequencing technologies include, for example, sequencing-by-synthesis with reversible dye terminators, sequencing by oligonucleotide probe ligation, pyrosequencing and real time sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in the methods provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Adaptors

In some embodiments, nucleic acids (e.g., PCR primers, PCR amplicons, sample nucleic acid) may include an adaptor sequence and/or complement thereof. Adaptor sequences often are useful for certain sequencing methods such as, for example, a sequencing-by-synthesis process described herein. Adaptors sometimes are referred to as sequencing adaptors or adaptor oligonucleotides. Adaptor sequences typically include one or more sites useful for attachment to a solid support (e.g., flow cell). Adaptors also may include sequencing primer hybridization sites (i.e. sequences complementary to primers used in a sequencing reaction) and identifiers (e.g., indices) as described below. Adaptor sequences can be located at 5' and/or 3' end of a nucleic acid and sometimes can be located within a larger nucleic acid sequence. Adaptors can be any length and any sequence, and may be selected based on standard methods in the art for adaptor design.

One or more adaptor oligonucleotides may be incorporated into a nucleic acid (e.g., PCR amplicon) by any method suitable for incorporating adaptor sequences into a nucleic acid. For example, PCR primers used for generating PCR amplicons (i.e., amplification products) may comprise adaptor sequences or complements thereof. Thus, PCR amplicons that comprise one or more adaptor sequences can be generated during an amplification process. In some cases, one or more adaptor sequences can be ligated to a nucleic acid (e.g., PCR amplicon) by any ligation method suitable for attaching adaptor sequences to a nucleic acid. Ligation processes may include, for example, blunt-end ligations, ligations that exploit 3' adenine (A) overhangs generated by Taq polymerase during an amplification process and ligate adaptors having 3' thymine (T) overhangs, and other "sticky-end" ligations. Ligation processes can be optimized such that adaptor sequences hybridize to each end of a nucleic acid and not to each other.

In some cases, adaptor ligation is bidirectional, which means that adaptor sequences are attached to a nucleic acid such that both ends of the nucleic acid are sequenced in a subsequent sequencing process. In some cases, adaptor ligation is unidirectional, which means that adaptor sequences are attached to a nucleic acid such that one end of the nucleic acid is sequenced in a subsequent sequencing process. Examples of unidirectional and bidirectional ligation schemes are as described in US20170058350, the entire disclosure is hereby incorporated by reference.

Identifiers

In some embodiments, nucleic acids (e.g., PCR primers, PCR amplicons, sample nucleic acid, sequencing adaptors) may include an identifier. In some cases, an identifier is located within or adjacent to an adaptor sequence. An identifier can be any feature that can identify a particular origin or aspect of a nucleic acid target sequence. For example, an identifier (e.g., a sample identifier) can identify the sample from which a particular nucleic acid target sequence originated. In another example, an identifier (e.g., a sample aliquot identifier) can identify the sample aliquot from which a particular nucleic acid target sequence originated. In another example, an identifier (e.g., chromosome identifier) can identify the chromosome from which a particular nucleic acid target sequence originated. An identifier may be referred to herein as a tag, index, barcode, identification tag, index primer, and the like. An identifier may be a unique sequence of nucleotides (e.g., sequence-based identifiers), a detectable label such as the labels described below (e.g., identifier labels), and/or a particular length of polynucleotide (e.g., length-based identifiers; size-based identifiers) such as a stuffer sequence. Identifiers for a collection of samples or plurality of chromosomes, for example, may each comprise a unique sequence of nucleotides. Identifiers (e.g., sequence-based identifiers, length-based identifiers) may be of any length suitable to distinguish certain target genomic sequences from other target genomic sequences. In some embodiments, identifiers may be from about one to about 100 nucleotides in length. For example, identifiers independently may be about 1, 2, 3, 4, 5, 6, 7, 8, 9, 10, 20, 30, 40, 50, 60, 70, 80, 90 or 100 nucleotides in length. In some embodiments, an identifier contains a sequence of six nucleotides. In some cases, an identifier is part of an adaptor sequence for a sequencing process, such as, for example, a sequencing-by-synthesis process described in further detail herein. In some cases, an identifier may be a repeated sequence of a single nucleotide (e.g., poly-A, poly-T, poly-G, poly-C). Such identifiers may be detected and distinguished from each other, for example, using nanopore technology, as described herein.

In some embodiments, the analysis includes analyzing (e.g., detecting, counting, processing counts for, and the like) the identifier. In some embodiments, the detection process includes detecting the identifier and sometimes not detecting other features (e.g., sequences) of a nucleic acid. In some embodiments, the counting process includes counting each identifier. In some embodiments, the identifier is the only feature of a nucleic acid that is detected, analyzed and/or counted.

Data Processing And Normalization

In some embodiments, sequence read data that are used to represent the amount of a polymorphic nucleic acid target can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or underrepresented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a micro-processor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation or genetic alteration (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments one or more processing steps can comprise one or more normalization steps. Normalization can be performed by a suitable method described herein or known in the art. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter are certain examples of normalization processes that can be utilized, such as LOESS normalization, principal component normalization, and hybrid normalization methods, for example. Aspects of certain normalization processes also are described, for example, in International Patent Application Publication No. WO2013/052913 and International Patent Application Publication No. WO2015/051163, each of which is incorporated by reference herein.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization."

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include principal component analysis, decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principal component analysis, linear discriminant analysis, quadratic discriminant analysis, bagging, neural networks, support vector machine models, random forests, classification tree models, K-nearest neighbors, logistic regression and/or smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation/genetic alteration and/or copy number alteration, depending on the status of the reference samples (e.g., positive or negative for a selected copy number alteration). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation/genetic alteration and/or copy number alteration and/or medical condition.

After data sets have been counted, optionally filtered, normalized, and optionally weighted the processed data sets can be further manipulated by one or more filtering and/or normalizing and/or weighting procedures, in some embodiments. A data set that has been further manipulated by one or more filtering and/or normalizing and/or weighting procedures can be used to generate a profile, in certain embodiments. The one or more filtering and/or normalizing and/or weighting procedures sometimes can reduce data set complexity and/or dimensionality, in some embodiments. An outcome can be provided based on a data set of reduced complexity and/or dimensionality. In some embodiments, a profile plot of processed data further manipulated by weighting, for example, is generated to facilitate classification and/or providing an outcome. An outcome can be provided based on a profile plot of weighted data, for example.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fraction of a minority species (e.g., fraction of cancer cell nucleic acid; fetal fraction). In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fraction of a minority species (e.g., fraction of cancer cell nucleic acid; fetal fraction).

In some embodiments, analysis and processing of data can include the use of one or more assumptions. A suitable number or type of assumptions can be utilized to analyze or process a data set. Non-limiting examples of assumptions that can be used for data processing and/or analysis include subject ploidy, cancer cell contribution, maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a nucleic acid quantification assay (e.g., fetal quantifier assay (FQA)), assumptions regarding twins (e.g., if 2 twins and only 1 is affected the effective fetal fraction is only 50% of the total measured fetal fraction (similarly for triplets, quadruplets and the like)), cell free DNA (e.g., cfDNA) uniformly covers the entire genome, the like and combinations thereof.

In those instances where the quality and/or depth of mapped sequence reads does not permit an outcome prediction of the presence or absence of a genetic variation/genetic alteration and/or copy number alteration at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Described in greater detail hereafter are non-limiting examples of processing steps and normalization methods that can be utilized, such as normalizing to a window (static or sliding), weighting, determining bias relationship, LOESS normalization, principal component normalization, hybrid normalization, generating a profile and performing a comparison.

Normalizing to a Window (Static or Sliding)

In certain embodiments, a processing step comprises normalizing to a static window, and in some embodiments, a processing step comprises normalizing to a moving or sliding window.

The term "window" as used herein refers to one or more portions chosen for analysis, and sometimes is used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate surrounding portions, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of microdeletions and/or microduplications. In certain embodiments, displaying cumulative sums of one or more portions is used to identify the presence or absence of regions of copy number alteration (e.g., microdeletion, microduplication).

Weighting

In some embodiments, a processing step comprises a weighting. The terms "weighted," "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with underrepresented or low quality sequence data can be "down weighted" to minimize the influence on a data set, whereas selected portions of a reference genome can be "up weighted" to increase the influence on a data set. A non-limiting example of a weighting function is [1/(standard deviation) 2]. Weighting portions sometimes removes portion dependencies. In some embodiments one or more portions are weighted by an eigen function (e.g., an eigenfunction). In some embodiments an eigen function comprises replacing portions with orthogonal eigen-portions. A weighting step sometimes is performed in a manner substantially similar to a normalizing step. In some embodiments, a data set is adjusted (e.g., divided, multiplied, added, subtracted) by a predetermined variable (e.g., weighting variable). In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

Bias Relationships

In some embodiments, a processing step comprises determining a bias relationship. For example, one or more relationships may be generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content.

In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments, a processing step comprises normalizing sequence read counts by comparing local genome bias estimates of sequence reads of a test sample to local genome bias estimates of a reference (e.g., a reference genome, or part thereof). In some embodiments, counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads may be normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

Machines, Systems, Software and Interfaces

Certain processes and methods described herein (e.g., obtaining and filtering sequencing reads, determining if a polymorphic nucleic acid target is an informative, or determining if one or more cell-free nucleic acid is a donor-specific nucleic acid, using the fixed cutoff, dynamic k-means clustering, or individual polymorphic nucleic acid target threshold) often cannot be performed without a computer, microprocessor, software, module or other machine. Methods described herein typically are computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein is a computer system configured to perform the any of the embodiments of the methods for determining transplant status disclosed herein. In some embodiments, this disclosure provides a system for determining transplant status comprising one or more processors and non-transitory machine readable storage medium and/or memory coupled to one or more processors, and the memory or the non-transitory machine readable storage medium encoded with a set of instructions configured to perform a process comprising: (a) obtaining measurements of one or more polymorphic nucleic acid targets within the circulating cell-free nucleic acids isolated from a biological sample, wherein the biological sample is obtained from an organ transplant recipient who has received an organ from an allogeneic donor; (b) detecting, by a computing system, one or more donor-specific circulating cell-free nucleic acids based on the measurements from (a); and (c) determining transplant status based on the presence or amount of said one or more donor-specific nucleic acids.

In some embodiments, the set of instructions further comprise instructions for determining whether a polymorphic nucleic acid target is informative, and/or detecting donor-specific cell-free nucleic acids in a sample from a test subject's sample according to, for example, one of more of the fixed cutoff approach, a dynamic clustering approach, and/or an individual polymorphic nucleic acid target threshold approach as described above. In some cases, the instructions to reduce experimental bias is according to a GC normalized quantification of sequence reads.

Also provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein. In some embodiments, the program module instructs the microprocessor to perform a process comprising: (a) obtaining measurements of one or more polymorphic nucleic acid targets within the circulating cell-free nucleic acids isolated from a biological sample, wherein the biological sample is obtained from an organ transplant recipient who has received an organ from an allogeneic donor; (b) detecting, by a computing system, one or more donor-specific circulating cell-free nucleic acids based on the measurements from (a); and (c) determining transplant status based on the presence or amount of said one or more donor-specific nucleic acids The executable program stored on the computer reusable storage media may further instruct the microprocessor to determine whether a polymorphic nucleic acid target is informative, and/or detect donor-specific cell-free nucleic acids in a sample from a test subject's sample according to, for example, one of more of the fixed cutoff approach, a dynamic clustering approach, and/or an individual polymorphic nucleic acid target threshold approach as described above.

In some embodiments, the disclosure provides a non-transitory machine readable storage medium comprising program instructions that when executed by one or more processors cause the one or more processors to perform a method, the method comprising: (a) obtaining measurements of one or more polymorphic nucleic acid targets within the circulating cell-free nucleic acids isolated from a biological sample, wherein the biological sample is obtained from an organ transplant recipient who has received an organ from an allogeneic donor; (b) detecting, by a computing system, one or more donor-specific circulating cell-free nucleic acids based on the measurements from (a); and (c) determining transplant status based on the presence or amount of said one or more donor-specific nucleic acids The program instructions may further comprise instructions for the one or more processors to determine whether a polymorphic nucleic acid target is informative, and/or detect donor-specific cell-free nucleic acids in a sample from a test subject's sample according to, for example, one of more of the fixed cutoff approach, a dynamic clustering approach, and/or an individual polymorphic nucleic acid target threshold approach as described above.

The non-transitory machine readable storage medium may further comprise program instructions that when executed by one or more processors cause the one or more processors to perform a method comprising: adjusting the quantified sequence reads for each of the genomic portions by an adjustment process that reduces experimental bias, wherein the adjustment process generates a normalized quantification of sequence reads for each of the polymorphic nucleic acid targets.

Thus, also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., (e.g., obtaining and filtering sequencing reads, determining if a polymorphic nucleic acid target is an informative, or determining if one or more cell-free nucleic acid is a donor-specific nucleic acid, using the fixed cutoff, dynamic k-means clustering, or individual polymorphic nucleic acid target threshold) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Sequence reads, counts, levels and/or measurements sometimes are referred to as "data" or "data sets." In some embodiments, data or data sets can be characterized by one or more features or variables (e.g., sequence based (e.g., GC content, specific nucleotide sequence, the like), function specific (e.g., expressed genes, cancer genes, the like), location based (genome specific, chromosome specific, portion or portion-specific), the like and combinations thereof). In certain embodiments, data or data sets can be organized into a matrix having two or more dimensions based on one or more features or variables. Data organized into matrices can be organized using any suitable features or variables. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine a classification outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein.

A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a part thereof, and/or padding), providing identification (e.g., identifying a copy number alteration, genetic variation/genetic alteration or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence read quantifications (e.g., counts) sometimes are accessed by a microprocessor that executes instructions configured to carry out a method described herein. Sequence read quantifications that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software comprising program instructions often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using, for example, algorithms described herein to determine donor-specific nucleic acids such as a fixed cutoff algorithm, a dynamic clustering algorithm, or an individual polymorphic nucleic acid target threshold algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation or genetic alteration.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Figure 2:
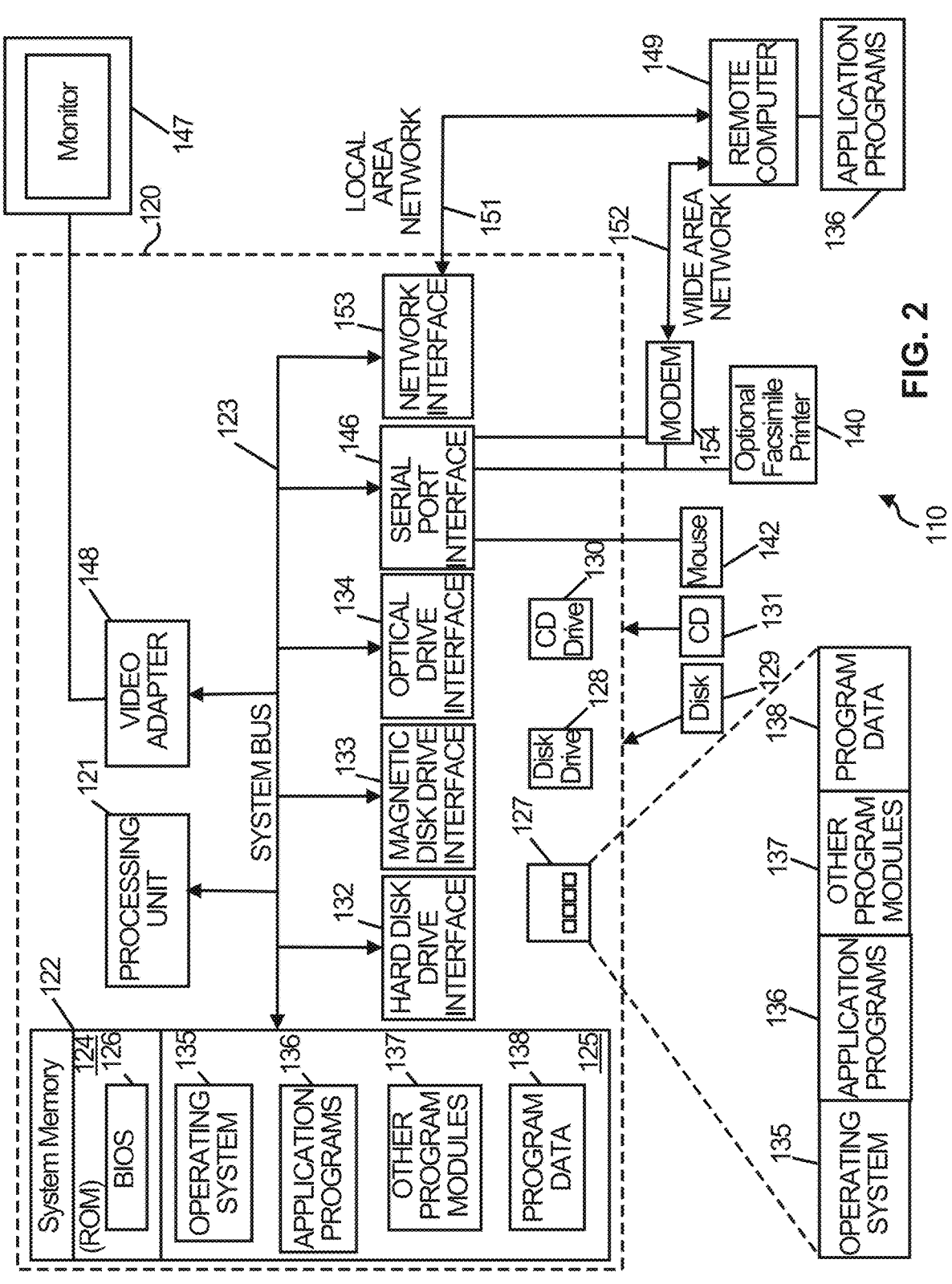
FIG. 2 shows an illustrative embodiment of a system in which certain embodiments of the technology may be implemented.

FIG. 2 illustrates a non-limiting example of a computing environment 110 in which various systems, methods, algorithms, and data structures described herein may be implemented. The computing environment 110 is only one example of a suitable computing environment and is not intended to suggest any limitation as to the scope of use or functionality of the systems, methods, and data structures described herein. Neither should computing environment 110 be interpreted as having any dependency or requirement relating to any one or combination of components illustrated in computing environment 110. A subset of systems, methods, and data structures shown in FIG. 1 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 110 of FIG. 2 includes a general purpose computing device in the form of a computer 120, including a processing unit 121, a system memory 122, and a system bus 123 that operatively couples various system components including the system memory 122 to the processing unit 121. There may be only one or there may be more than one processing unit 121, such that the processor of computer 120 includes a single central-processing unit (CPU), or a plurality of processing units, commonly referred to as a parallel processing environment. The computer 120 may be a conventional computer, a distributed computer, or any other type of computer.

The system bus 123 may be any of several types of bus structures including a memory bus or memory controller, a peripheral bus, and a local bus using any of a variety of bus architectures. The system memory may also be referred to as simply the memory, and includes read only memory (ROM) 124 and random access memory (RAM). A basic input/output system (BIOS) 126, containing the basic routines that help to transfer information between elements within the computer 120, such as during start-up, is stored in ROM 124. The computer 120 may further include a hard disk drive interface 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media.

The hard disk drive 127, magnetic disk drive 128, and optical disk drive 130 are connected to the system bus 123 by a hard disk drive interface 132, a magnetic disk drive interface 133, and an optical disk drive interface 134, respectively. The drives and their associated computer-readable media provide nonvolatile storage of computer-readable instructions, data structures, program modules and other data for the computer 120. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 129, optical disk 131, ROM 124, or RAM, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port, or a universal serial bus (USB). A monitor 147 or other type of display device is also connected to the system bus 123 via an interface, such as a video adapter 148. In addition to the monitor, computers typically include other peripheral output devices (not shown), such as speakers and printers.

The computer 120 may operate in a networked environment using logical connections to one or more remote computers, such as remote computer 149. These logical connections may be achieved by a communication device coupled to or a part of the computer 120, or in other manners. The remote computer 149 may be another computer, a server, a router, a network PC, a client, a peer device or other common network node, and typically includes many or all of the elements described above relative to the computer 120, although only a memory storage device 125 has been illustrated in FIG. 2. The logical connections depicted in FIG. 2 include a local-area network (LAN) 151 and a wide-area network (WAN) 152. Such networking environments are commonplace in office networks, enterprise-wide computer networks, intranets and the Internet, which all are types of networks.

When used in a LAN-networking environment, the computer 120 is connected to the local network 151 through a network interface or adapter 153, which is one type of communications device. When used in a WAN-networking environment, the computer 120 often includes a modem 154, a type of communications device, or any other type of communications device for establishing communications over the wide area network 152. The modem 154, which may be internal or external, is connected to the system bus 123 via the serial port interface 146. In a networked environment, program modules depicted relative to the personal computer 120, or portions thereof, may be stored in the remote memory storage device. It is appreciated that the network connections shown are non-limiting examples and other communications devices for establishing a communications link between computers may be used.

Transformations

As noted above, data sometimes is transformed from one form into another form. The terms "transformed," "transformation," and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's nucleic acid.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fragment size (e.g., length of circulating cell-free fragments, reads or a suitable representation thereof (e.g., FRS)), fragment sequence, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., allele frequencies, normalized values, Z-scores, p-values); reduction of multiple analysis methods to probability plots or single points; principal component analysis of derived quantities; and the like or combinations thereof.

Exemplary Embodiments of the Invention

1. A method of determining transplant status comprising:
(a) obtaining a biological sample from an organ transplant recipient who has received an organ from a donor;
(b) isolating cell-free nucleic acids from the biological sample;
(c) measuring the amount of each allele of one or more polymorphic nucleic acid targets in the biological sample;
(d) identifying donor specific allele using a computer algorithm based on the measurements of the one or more polymorphic nucleic acid targets, whereby detecting one or more donor-specific circulating cell-free nucleic acids
(e) detecting tissue injury based on the presence or amount of said one or more donor-specific nucleic acids, whereby determining transplant status.

2. The method of embodiment 1, wherein the organ is a solid organ from an allogeneic source.

2.1 The method of embodiment 1 or 2, the method further comprising determining a donor-specific nucleic acid fraction based on the amount of the polymorphic nucleic acid targets that are specific for donor and the total amount of the polymorphic nucleic acid targets in circulating cell-free nucleic acids in the biological sample.

3. The method of embodiments 1-2, wherein said polymorphic nucleic acid targets comprises (i) one or more SNPs, (ii) one or more restriction fragment length polymorphisms (RFLPs), (iii) short tandem repeats (STRs), (iv) variable number of tandem repeats (VNTRs), (v) copy number variants, (vi) insertion/deletion variants, or (vii) a combination of any of (i)-(vi) thereof.

4. The method of embodiment 3, wherein the combination of any of items (i) to (vii) is a deletion insertion variants combined with a short tandem repeat (DIP-STR).

5. The method of embodiment 3, wherein said polymorphic nucleic acid targets comprises one or more SNPs 5.1 The method of embodiment 5, wherein the one or more SNPs does not comprise a SNP for which the reference allele and alternate allele combination is selected from the group consisting of A_G, G_A, C_T, and T_C.

6. The method of embodiment any of embodiments 1-5, wherein each polymorphic nucleic acid target has a minor population allele frequency of 15%-49%.

7. The method of any of embodiments 3, 5 or 6, wherein the SNPs comprise at least one, two, three, or four or more SNPs of SEQ ID NOs in Table 1 or Table 6.

8. The method of any of embodiments 1-7, wherein the biological sample from an organ transplant recipient is a bodily fluid.

9. The method of embodiment 1-7, wherein the bodily fluid is one or more of blood, serum, plasma, saliva, tears, urine, cerebralspinal, fluid, mucosal secretion, peritoneal fluid, ascitic fluid, vaginal secretion, breast fluid, breast milk, lymph fluid, cerebrospinal fluid, sputum, and stool.

10. The method of any of embodiments 1-9, wherein the organ donor's genotype is not known for the one or more polymorphic nucleic acid targets prior to the transplant status determination.

10.1 The method of embodiment 10, wherein the recipient's genotype is known for the one or more polymorphic nucleic acid targets prior to the transplant status determination, wherein the (d) identifying donor-specific allele and/or determining the donor-specific nucleic acid fraction comprises:
IV) filtering out 1) polymorphic nucleic acid targets which are present in the recipient and the donor in a genotype combination of $AB_{recipient}/AB_{donor}$, $AB_{recipient}/AA_{donor}$, and $AB_{recipient}/BB_{donor}$,
V) performing the computer algorithm on a data set consisting of measurements of the remaining polymorphic nucleic acid targets to form a first cluster and a second cluster,
wherein the first cluster comprises polymorphic nucleic acid targets that are present in the recipient and the donor in a genotype combination of $AA_{recipient}/AB_{donor}$, Or $BB_{recipient}/AB_{donor}$, and
wherein the second cluster comprises SNPs that are present in the recipient and the donor in a genotype combination of $AA_{recipient}/BB_{donor}$ or $BB_{recipient}/AA_{donor}$; and
detecting the donor specific allele based on the presence of the remaining polymorphic nucleic acid targets in the one or more polymorphic nucleic acid targets in the biological sample.

11. The method of embodiments 1-10, wherein the recipient's genotype is not known for the one or more polymorphic nucleic acid targets prior to the transplant status determination.

11.1 The method of embodiment 11, wherein the donor's genotype is known for the one or more polymorphic nucleic acid targets prior to the transplant status determination, wherein the (d) detecting the donor specific allele comprise:
I) filtering out 1) polymorphic nucleic acid targets which are present in the recipient and the donor in a genotype combination of $AA_{recipient}/AA_{donor}$ or $AB_{recipient}/AA_{donor}$ and the donor allele frequency is less than 0.5, and 2) SNPs which are present in the recipient and the donor in a genotype combination of $BB_{recipient}/BB_{donor}$, and $AB_{recipient}/BB_{donor}$, and the donor allele frequency is larger than 0.5; and II) detecting the donor specific alleles based on the presence of the remaining polymorphic nucleic acid targets in the biological sample.

12. The method of embodiments 1-11, wherein neither the recipient nor the organ donor's genotype is known for the one or more polymorphic nucleic acid targets prior to the transplant status determination.

12.1 The method of embodiment 12, wherein the (d) detecting donor-specific allele and/or determining donor-specific nucleic acid fraction comprises:

I) performing the computer algorithm on a data set consisting of measurements of the amounts of the one or more polymorphic nucleic acid targets to form a first cluster and a second cluster, wherein the first cluster comprises polymorphic nucleic acid targets that are present in the recipient and the donor in a genotype combination of $AA_{recipient}/AB_{donor}$, $BB_{recipient}/AB_{donor}$, $AA_{recipient}/BB_{donor}$, or $BB_{recipient}/AA_{donor}$, and wherein the second cluster comprises polymorphic nucleic acid targets that are present in the recipient and the donor in a genotype combination of $AB_{recipient}/AB_{donor}$, $AB_{recipient}/AA_{donor}$, Or $AB_{recipient}/BB_{donor}$; and II) detecting the donor specific allele based on the presence of the polymorphic nucleic acid targets in the first cluster.

13. The method of any of embodiments 1-12, wherein the algorithm is one or more of the following: (i) a fixed cutoff, (ii) a dynamic clustering, and (iii) an individual polymorphic nucleic acid target threshold.

14. The method of embodiment 13, wherein the fixed cutoff algorithm detects donor-specific nucleic acids if the deviation between the measured frequency of a reference allele of the one or more polymorphic nucleic acid targets in the cell-free nucleic acids in the sample and the expected frequency of the reference allele in a reference population is greater than a fixed cutoff, wherein the expected frequency for the reference allele is in the range of:

0.00-0.03 if the recipient is homozygous for the alternate allele, 0.40-0.60 if the recipient is heterozygous for the alternate allele, or 0.97-1.00 if the recipient is homozygous for the reference allele.

15. The method of embodiment 14, wherein the recipient is homozygous for the reference allele, and the fixed cutoff algorithm detects donor-specific nucleic acids if the measured allele frequency of the reference allele of the one or more polymorphic nucleic acid targets is less than the fixed cutoff.

15.1. The method of embodiment 15, wherein the recipient is homozygous for the alternate allele, and the fixed cutoff algorithm detects donor-specific nucleic acids if the measured allele frequency of the reference allele of the one or more polymorphic nucleic acid targets is greater than the fixed cutoff.

16. The method of any of embodiments 13-15.1, wherein the fixed cutoff is based on the homozygous allele frequency of the reference or alternate allele of the one or more polymorphic nucleic acid targets in a reference population.

17. The method of embodiment 13-15.1, wherein the fixed cutoff is based on a percentile value of distribution of the homozygous allele frequency of the reference or alternate allele of the one or more polymorphic nucleic acid targets in the reference population.

18. The method of embodiment 17, wherein the percentile is at least 90.

19. The method of embodiment 13, wherein identifying one or more cell-free nucleic acids as donor-specific nucleic acids using the dynamic clustering algorithm comprises (i) stratifying the one or more polymorphic nucleic acid targets in the cell-free nucleic acids into recipient homozygous group and recipient heterozygous group based on the measured allele frequency for a reference allele or an alternate allele of each of the polymorphic nucleic acid targets;

(ii) further stratifying recipient homozygous groups into non-informative and informative groups; and (iii) measuring the amounts of one or more polymorphic nucleic acid targets in the informative groups.

20. The method of embodiment 19, wherein the dynamic clustering algorithm is a dynamic K-means algorithm.

21. The method of embodiment 13, wherein the individual polymorphic nucleic acid target threshold algorithm identifies the one or more nucleic acids as donor-specific nucleic acids if the allele frequency of each of the one or more of the polymorphic nucleic acid targets is greater than a threshold.

22. The method of embodiment 21, wherein the threshold is based on the homozygous allele frequency of each of the one or more polymorphic nucleic acid targets in a reference population.

23. The method of embodiment 22, wherein the threshold is a percentile value of a distribution of the homozygous allele frequency of each of the one or more polymorphic nucleic acid targets in the reference population.

25. The method of any of the preceding embodiments, wherein the amount of one or more circulating cell-free nucleic acids from said transplant donor is detected by measuring the one or more polymorphic nucleic acid targets in at least one assay, and wherein the at least one assay is high-throughput sequencing, capillary electrophoresis or digital polymerase chain reaction (dPCR).

26. The method of embodiment 25, wherein the high-throughput sequencing comprises targeted amplification using a forward and a reverse primer designed specifically for the SNP or targeted hybridization using a probe sequence that contains the SNP.

27. The method of embodiment 26, wherein the method further comprises targeted amplification using a forward and a reverse primer designed specifically for a native genomic nucleic acid and a variant oligo that contains a single nucleotide substitution as compared to the native sequence, wherein the variant oligo is added to the amplification reaction in a known amount wherein the method further comprises:

determining the ratio of the amount of the amplified native genomic nucleic acid to the amount of the amplified variant oligo, determining the total copy number of genomic DNA by multiplying the ratio with the amount of the variant oligo added to the amplification reaction.

28. The method of any of embodiments 1-27, wherein the method further comprises determining total copy number of genomic DNA in circulating cell-free nucleic acids in the biological sample and determining the copy number of the donor-specific nucleic acid by multiplying the donor-specific nucleic acid fraction and the total copy number of genomic DNA.

29. The method of embodiment 25, wherein the amount of one or more polymorphic nucleic acid target is determined based on sequence reads for each allele of each of the one or more polymorphic nucleic acid targets.

30. The method of any of embodiments 1-29, wherein the allogeneic source is from at least one of kidney, heart, lung, pancreas, intestine, stomach, and liver transplants.

31. The method of embodiment 24, wherein the transplant status is determined as rejection if the donor-specific nucleic acid fraction is greater than a predetermined threshold; wherein the transplant status is determined as acceptance if the donor-specific nucleic acid fraction is less than a predetermined threshold.

32. The method of any of embodiments 1-30, wherein the transplant status is determined as rejection if the copy number of the donor-specific nucleic acid is greater than a predetermined threshold;

wherein the transplant status is determined as acceptance if the copy number of the donor-specific nucleic acid is less than a predetermined threshold.

33. A method of detecting transplant status of any of the preceding embodiments, wherein the transplant status is monitored at one or more time points comprising an earlier time point and a later time point after the earlier time point, all time points being post transplantation, and wherein an increase in donor-specific circulating cell-free nucleic acid fraction or an increase in the copy number of donor-specific circulating cell-free nucleic acid from the earlier time point to later time point is indicative of developing transplant rejection, wherein the time interval between the earlier time point and the later time point is at least 7 days.

34. The method of embodiment 33, wherein the earlier time point is between 0 days to one year following transplantation.

35. The method of embodiment 33, wherein the later time point is between 7 days to five years following transplantation.

36. The method of any one of the preceding embodiments, further comprising advising administration of immunosuppressive therapy to the organ transplant recipient or advising the modification of the organ transplant recipient's immunosuppressive therapy.

37. A system to perform the method in any one of the preceding embodiments.

38 A system for determining transplant status comprising one or more processors; and memory coupled to one or more processors, the memory encoded with a set of instructions configured to perform a process comprising:

(a) obtaining measurements of one or more polymorphic nucleic acid targets within the circulating cell-free nucleic acids isolated from a biological sample, wherein the biological sample is obtained from an organ transplant recipient who has received an organ from an allogeneic donor;

detecting, a presence or absence of one or more donor-specific circulating cell-free nucleic acids based at least on the measurements of the one or more polymorphic nucleic acid targets from (a); and (c) determining a transplant status of the organ transplant recipient based at least on the determined presence or amount of said one or more donor-specific nucleic acids.

39. The system of embodiment 38, wherein said polymorphic nucleic acid targets comprises (i) one or more SNPs, (ii) one or more restriction fragment length polymorphisms (RFLPs), (iii) one or more short tandem repeats (STRs), (iv) one or more variable number of tandem repeats (VNTRs), (v) one or more copy number variants, (vi) one or more insertion/deletion variants, or (vii) a combination of any of (i)-(vii) thereof.

40. The system of embodiment 38, wherein said polymorphic nucleic acid targets comprises one or more SNPs.

40.1 The system of embodiment 40, wherein the one or more SNPs does not comprise a SNP for which the reference allele and alternate allele combination is selected from the group consisting of A_G, G_A, C_T, and T_C.

41. The system of embodiment 38, wherein each of the polymorphic nucleic acid targets has a minor population allele frequency of 15%-49%.

42. The system of any of embodiments 38-41, wherein the SNPs comprise at least one, two, three, or four or more SNPs of SEQ ID NOs in Table 1 or Table 6.

43. The system of any of embodiments 38-42, wherein the biological sample from an organ transplant recipient is selected from the group consisting of blood, serum, plasma, saliva, tears, urine, cerebralspinal fluid, mucosal secretion, peritoneal fluid, ascitic fluid, vaginal secretion, breast fluid, breast milk, lymph fluid, cerebrospinal fluid, sputum, and stool.

44. The system of any of embodiments 38-43, wherein the organ donor's genotype is not known for the one of more polymorphic nucleic acid targets prior to the transplant status determination.

44.1 The system of embodiment 44, wherein the recipient's genotype is known for the one or more polymorphic nucleic acid targets prior to the transplant status determination, and identifying donor-specific allele and/or determining the donor-specific nucleic acid fraction is by DF3.

45. The system of any of embodiments 38-44, wherein the recipient's genotype is not known for the one of more polymorphic nucleic acid targets prior to transplant status determination.

45.1 The system of embodiment 45, wherein the donor's genotype is known for the one or more polymorphic nucleic acid targets prior to the transplant status determination, wherein the method comprises identifying donor-specific allele and/or determining donor-specific nucleic acid fraction by DF2.

46. The system of any of embodiments 38-45, wherein neither the recipient nor the donor's genotype is known for the one of more polymorphic nucleic acid targets prior to the transplant status determination.

46.1 The system of embodiment 46, wherein identifying donor-specific allele and/or determining donor-specific nucleic acid fraction is by DF1.

47. The system of embodiment 38 or embodiment 46, wherein the donor-specific nucleic acids is detected using one or more of the following: (i) a fixed cutoff approach, (ii) a dynamic clustering approach, and (iii) an individual polymorphic nucleic acid target threshold approach.

48. The system of embodiment 47, wherein the fixed cutoff approach detects donor-specific nucleic acids if the deviation between the measured frequency of a reference allele of the one or more polymorphic nucleic acid targets in the cell-free nucleic acids in the sample and the expected allele frequencies of the allele is greater than a fixed cutoff, the expected frequency for the reference allele is in the range of:

0.00-0.03 if the recipient is homozygous for the alternate allele, 0.40-0.60 if the recipient is heterozygous for the alternate allele, or 0.97-1.00 if the recipient is homozygous for the reference allele.

49. The system of embodiment 47, wherein the recipient is homozygous for the reference allele, and the fixed cutoff approach detects donor-specific nucleic acids if the measured allele frequency of the reference allele of the one or more polymorphic nucleic acid targets is greater than the fixed cutoff.

50. The system of embodiment 47, wherein the fixed cutoff is based on the homozygous allele frequency of the reference or alternate allele of the one or more polymorphic nucleic acid targets in a reference population.

51. The system of any of embodiments 47-50, wherein the fixed cutoff is based on a percentile value of distribution of the homozygous allele frequency of the reference or alternate allele of the one or more polymorphic nucleic acid targets in the reference population.

52. The system of embodiment 51, wherein the percentile is 90.

53. The system of embodiment 47, wherein identifying one or more cell-free nucleic acids as donor-specific nucleic acids using the dynamic clustering approach comprises (i) stratifying the one or more polymorphic nucleic acid targets in the cell-free nucleic acids into recipient homozygous group and recipient heterozygous group based on the measured allele frequency for a reference allele or an alternate allele of each of the polymorphic nucleic acid targets;

(ii) further stratifying recipient homozygous groups into non-informative and informative groups; and (iii) measuring the amounts of one or more polymorphic nucleic acid targets in the informative groups.

54. The system of embodiment 47, wherein the dynamic clustering approach uses a dynamic K-means algorithm.

55. The system of embodiment 48, wherein the individual polymorphic nucleic acid target threshold approach identifies the one or more nucleic acids as donor-specific nucleic acids if the allele frequency of each of the one or more of the polymorphic nucleic acid targets is greater than a threshold.

56. The system of embodiment 55, wherein the threshold is based on the homozygous allele frequency of each of the one or more polymorphic nucleic acid targets in a reference population.

57. The system of any of embodiments 55-56, wherein the threshold is a percentile value of a distribution of the homozygous allele frequency of each of the one or more polymorphic nucleic acid targets in the reference population.

58. The system of any of embodiments 38-57, the system further comprising determining a donor-specific nucleic acid fraction based on the amount of the polymorphic nucleic acid targets that are specific for donor and the total amount of the polymorphic nucleic acid targets in circulating cell-free nucleic acids in the biological sample.

59 The system of any of embodiments 38-58, wherein the determining of the amount of one or more circulating cell-free nucleic acids from said transplant donor is performed by measuring the one or more polymorphic nucleic acid profile in at least one assay, and wherein the at least one assay is high-throughput sequencing, capillary electrophoresis or digital polymerase chain reaction (dPCR).

60. The system of embodiment 59, wherein the high-throughput sequencing comprises targeted amplification using a forward and a reverse primer designed specifically for the SNP or targeted hybridization using a probe sequence that contains the SNP.

61. The system of embodiment 38, wherein the transplant status is determined as rejection if the donor-specific nucleic acid fraction is greater than a predetermined threshold;

wherein the transplant status is determined as acceptance if the donor-specific nucleic acid fraction is less than a predetermined threshold.

62. A system of detecting transplant status of embodiment 38, wherein the transplant status is monitored at a first time and a second time point after the first time point, both time being post transplantation, and wherein an increase in donor-specific circulating cell-free nucleic acid from the first time point to the second time point is indicative of developing transplant rejection, wherein the time interval between the first time point and the second time point is at least 7 days.

63. The system of embodiment 62, wherein the first time point is between 7 days to one year following transplantation.

64. The system of embodiment 62 or 63, wherein the second time point is between 14 days to two years following transplantation.

65. A non-transitory machine readable storage medium comprising program instructions that when executed by one or more processors cause the one or more processors to perform a method of determining transplant status, the method comprising:

(a) obtaining measurements of one or more polymorphic nucleic acid targets within the circulating cell-free nucleic acids isolated from a biological sample, wherein the biological sample is obtained from an organ transplant recipient who has received an organ from an allogeneic donor;

(b) detecting, by a computing system, one or more donor-specific circulating cell-free nucleic acids based on the measurements from (a); and (c) determining transplant status based on the presence or amount of said one or more donor-specific nucleic acids.

The following examples of specific aspects for carrying out the present invention are offered for illustrative purposes only, and are not intended to limit the scope of the present invention in any way.

Example 1 Developing SNP Panels for Determining Transplant Rejection

Blood samples are drawn from a liver transplant recipient at various time points: prior to the transplantation, two days, and nine days after the transplantation. The blood samples are placed in a tube containing EDTA or a specialized commercial product such as Vacutainer SST (Becton Dickinson, Franklin Lakes, and N.J.) to prevent blood clotting. Cells are removed from plasma by centrifugation for 10 minutes at 1,000-2,000×g using a refrigerated centrifuge. The resulting supernatant, which is plasma, is immediately transferred into a clean vial with a sterile pipette. Plasma samples are stored at −20° C. and thawed at use.

The plasma samples are processed using QIAamp Circulating Nucleic Acid (QCNA) kit to produce cell free DNA.

A PCR reaction is set up with primers that are specific to the SNP panels (the sequences of the SNPs and respective primers (the first primer and the second primer) are provided in Table 3 and Table 4) to amplify the SNPs. In addition, an RNAsP variant oligo that has a single nucleotide substitution relative to the native RNAsP, and ApoE variant oligo that has a single nucleotide substitution relative to the native ApoE, also added in the PCR reaction at known amounts to be amplified simultaneously with the SNP panel. The RNAsP and ApoE variant oligo sequences are provided in Table 5.

Each of the SNPs is sequenced using a primer pair consisting of a first primer and a second primer, the sequences of which are provided in Table 5. The amplification products are sequenced and copy numbers of the amplification products comprising the SNPs are determined to calculate the relative frequencies of the reference allele and alternative allele for each of the SNPs.

A SNP is chosen as informative SNP i) if the frequency distribution of the alleles for the SNP indicates that the recipient is homozygous for the reference allele and that the donor is homozygous or heterozygous for the alternative allele, and ii) if the alternative allele frequency is greater than a fixed cutoff frequency, which is expressed as a percent (%) shift of the alternative allele frequency from an expected frequency. Donor fraction is then determined based on the frequencies of the alternative alleles of the selected, informative SNPs.

The amplified native RNAsP and the RNAsP variant and the amplified native ApoE and the ApoE variant are quantified by sequencing, and the ratios of the respective native nucleic acids to the variant oligos are calculated. The total copies of genomic DNA in the cf DNA is determined based on the following formula:

> Total copy number of genomic DNA in the cfDNA=ratio of the amount of amplified native ApoE (or RNAsP) to the amount of amplified ApoE (or RNAsP) variant×the amount of the variant oligos added before amplification.

> The copy number of the donor-specific cell-free nucleic acid=total copy number of genomic DNA in the cfDNA×donor-specific nucleic acid fraction The amount of donor-specific cell-free nucleic acids from plasma samples derived from blood samples drawn at various time points are determined as above and compared. If the amount of donor-specific cell-free nucleic acids in samples posttransplant are greater than the baseline level of the pre-transplant sample and the amount of the of donor-specific cell-free nucleic acids increases over time, i.e., the level in the sample from later time point is greater than the level in the sample from the earlier time point post transplantation, the transplant is being rejected.

TABLE 3

| | Panel A SNPs and amplification primers | | | |
|---|---|---|---|---|
| SNP | SEQ ID NO | First Primer Sequence | SEQ ID NO | Second Primer Sequence |
| rs38062 | 1 | AAAAACTGCTTGCCTTCTTCTT | 2 | TCTATGGGTTCTCACAACTCAAC |
| rs163446 | 3 | TGGACAAAAATACCATCATCA | 4 | AGATCATCCTGAACATAAGGT |
| rs226447 | 5 | CATCTAAATACATGAAAAAGGAG | 6 | TCAAGTATCCAGGACTTGTTCG |
| rs241713 | 7 | GGACCCAAGATCTGATTCTAGC | 8 | AGGGTGAGCTGTTCTCAGGA |
| rs253229 | 9 | TCCCCAGACTAATTATGGAAAAA | 10 | TCACTTTACTGTTCACCAAACG |
| rs309622 | 11 | GGATTTTAGGGCACTAGGAAGG | 12 | GAGAGTTTTTAAAGAGTGTCGTT |
| rs376293 | 13 | TGTATTTGCCTAAAAGTAAGAGG | 14 | GGCAGAGTTCTCTTGACGTG |
| rs387413 | 15 | CAGCTAAAGGAAAACTATTAATGC | 16 | TCTCTTTGTCTGTTAGGGTTTT |
| rs427982 | 17 | TCATCTGTGAAATAGGGACACC | 18 | GCTCTTAAAACTCATCCCAAGC |
| rs511654 | 19 | AGAAATTATTCAGGACACAGAGA | 20 | TCCTGACAAGACAGTTATCATCT |
| rs517811 | 21 | GAGAAGAATGATTAGACCTTGCT | 22 | ACAAGAGTACACGAGAGAAAAA |
| rs582991 | 23 | TGATGTGGAATAGTTTAGGTGA | 24 | TCCAAAAGGTAATTCCAATATGC |
| rs602763 | 25 | GGATATGCCGCTTTTCCTCT | 26 | GCTAAGTAAATAATTTGGCAGTT |
| rs614004 | 27 | TCACAGTGTTTCTCATAGTTTTA | 28 | CAGCAGCTAGTGTTGCACTAAT |
| rs686106 | 29 | GGTTCACAGAGCCCAAGTTAC | 30 | TGAGTCTCTTACTGATCCTGTGAC |
| rs723211 | 31 | GAGTCACTCTTGGGGTATCA | 32 | GATGCCCAGCCTCTTCTCTC |
| rs751128 | 33 | AGAGATCTCCGCATCCTGTG | 34 | GGGGGCCAATAACTATGCTC |
| rs756668 | 35 | AGTGTGATGTTTGAGTGAGG | 36 | GTCCTATCATCTTTTATTTCCAA |
| rs765772 | 37 | TTCCTTGGCATTTTAGTTTCC | 38 | TCCCATGTAACACCTTTCAGA |

TABLE 3-continued

| SNP | SEQ ID NO | First Primer Sequence | SEQ ID NO | Second Primer Sequence |
|-----|-----------|----------------------|-----------|------------------------|
| rs792835 | 39 | TCACCCATTCTTCATACTCTTTG | 40 | AACTTTTCAGGTCGGCAGTG |
| rs863368 | 41 | GGAGAGAATCCCTTACCCTTG | 42 | GGAATTTTATTAGATGTTGAGG |
| rs930189 | 43 | CAGCCCAGATTTTCTCTTTCA | 44 | TCGAGGTAAATAGGCCCACA |
| rs955105 | 45 | TTCAGCTCTTCTACTCTGGACTG | 46 | TGAAACAAGAGAAGACTGGATTTG |
| rs967252 | 47 | GTTATATCTCTTTTGTTTCTCTCC | 48 | TTGGATTGTTAGAGAATAACG |
| rs975405 | 49 | TGGACAAGAGAGACTTCAGGAG | 50 | GCTGAGCCTTTTAGATAGTGCTG |
| rs1002142 | 51 | TCCAACTGGAAAACACCTCA | 52 | GAGCCACCTTCAAGACTCTTTC |
| rs1002607 | 53 | TTTAAATCTTTCCAGGGGGTTT | 54 | TGATTCTCAGCCTGGAGTTT |
| rs1030842 | 55 | AGGATTCAGCCATCCATCTG | 56 | TCTGCCATGGGAGGTATAGA |
| rs1145814 | 57 | AAAACATAATTGAACACCTAGCA | 58 | AATAGGAGGCTGCTCTATGC |
| rs1152991 | 59 | TGATTCACTTCCAGTTCTTGACA | 60 | AGTGACCTTGCTGGTTTGTG |
| rs1160530 | 61 | GGGTACCATATGAGGCCAGTT | 62 | TCTTCTTCCCAATGTCATGGA |
| rs1281182 | 63 | CCAGGCTTCCAAGATTATTGT | 64 | AAGGCATCTCAGGTGTTATTTT |
| rs1298730 | 65 | CCTCGCTGTCCCTGCATAC | 66 | AAGTGCTGACTCTGTTCTGG |
| rs1334722 | 67 | GAATATCTGTCTCGGAATACCA | 68 | GGGATGTGTGATTTCTGAAGG |
| rs1341111 | 69 | GAACAACATCTATCATTCATCTCT | 70 | CACCACTCTAAAGTAGACCATTG |
| rs1346065 | 71 | GCTTTGGGGTTATAGCTGGA | 72 | AGATGGCCATTAGCTAGGAA |
| rs1347879 | 73 | GCACATAGAGGTCTCTCTCTTCT | 74 | CTATATTAGAACACTCAGCAGCTA |
| rs1390028 | 75 | AGGGCTGAACAAGGAACTGA | 76 | CTCATCCTGAGCTCTCGTGTA |
| rs1399591 | 77 | TCACTCATGTTTTACCTTTTAGC | 78 | TGAGTCAGATTCTTCATAACTTT |
| rs1442330 | 79 | TACTGCCAACAGACAACTCG | 80 | TTAGACCGCAGACCTTTAGAA |
| rs1452321 | 81 | GGGGCAGATCAGAAATGTTG | 82 | GGCTGTTCTCAATGGTGTCA |
| rs1456078 | 83 | CCCCATATGTAACCCATCACA | 84 | TCTTTGGAAGAGAAATGTGATTCT |
| rs1486748 | 85 | GGAATGTATTTCTGCTGTGCTG | 86 | TCACTATTCCTTACTCCAGGTGA |
| rs1510900 | 87 | CCATTCACGTGGCACTTTTT | 88 | CACCTTACTGCTTCCTGCTACC |
| rs1514221 | 89 | CCAAAGGCTGTATTATTTATGC | 90 | GTGTTGAAGTGATGTAATTCAG |
| rs1562109 | 91 | TGAACATATCAGCTGGCCATT | 92 | AAAGCCCAGAATTGACTTGG |
| rs1563127 | 93 | CAAACCTCCAGGGTAGTAGACA | 94 | GGGGTTCATAAGGGAAACCA |
| rs1566838 | 95 | TCTCAGAGCAACATGTACCAAAA | 96 | GCCCAATCAGACATCAATCC |
| rs1646594 | 97 | GTTTCCCAGCAAATTCCCTA | 98 | TCATCAAAATGGATCATAACAG |
| rs1665105 | 99 | TTTGGAGTGGGTCTCTTCACT | 100 | AAAGAGTACATTCTGCCTTGCT |
| rs1795321 | 101 | GCTCACTGTTACCCTACTACTCTC | 102 | ACCACACAAATGATTATGGTA |
| rs1821662 | 103 | CCACACACTGAAAAGAATTTGTG | 104 | AGTGGGCTGGATATATGAAAA |
| rs1879744 | 105 | AGGCATGTGTTAAACTAGAAAAA | 106 | GGAGGAAGCTGTGTTCTTTTCA |
| rs1885968 | 107 | GGGGATCTTAAAAGCACCAA | 108 | GACACTCCCACTTCTGCCTA |
| rs1893691 | 109 | CAGCCTAAATTTCCAGTCTT | 110 | AGTTATGAGTAATGAAGGAAGG |
| rs1894642 | 111 | ATTTCTTCAAGTGTATACAGAGC | 112 | CAGGCAAACATTCCCTTGTA |

TABLE 3-continued

| | | | | |
|---|---|---|---|---|
| | SEQ | | SEQ | |
| | ID | | ID | |
| SNP | NO | First Primer Sequence | NO | Second Primer Sequence |
| rs1938985 | 113 | TGTCTTTGCTCAGTTATGAAGAGA | 114 | TTGTAAATTTTTCTCTAGGTGTG |
| rs1981392 | 115 | GGCATGGCAATACTCTTCTGA | 116 | GATTTTCACATCTAATTTTCACC |
| rs1983496 | 117 | ACAATGAGCTATTTTAACTCCA | 118 | ACTAACTTTGCAAGATACAGATT |
| rs1992695 | 119 | TGGCCACTTGCTTATTTGAA | 120 | TGTTCTTAAGTTGCCCATAA |
| rs2049711 | 121 | CCCACTTTCACAATTTGAATCC | 122 | GAAGAAATACAAAGCAGTTGCTAA |
| rs2051985 | 123 | GCTTAGGAAGGTGTGGAGAGC | 124 | CCACTATTTATGTTTATTGAGTGC |
| rs2064929 | 125 | GAGTCATTTTGTCCACCAACC | 126 | GCTCATAGTTAGAAGTGGCAGCA |
| rs2183830 | 127 | GCAATGATAACAAGAACACAGCA | 128 | TGGAGCCAAAGGGAGTAATA |
| rs2215006 | 129 | TTGCTGGCTTACATTCATTCC | 130 | TACAGCTCAGCCAGTTCTGC |
| rs2251381 | 131 | GAAAGGGATGATGGTTCCAA | 132 | CCCATGAACACATTCACAGC |
| rs2286732 | 133 | GTCTGTCCCTGGGCCATTAT | 134 | CACGATTCAGTAAATGGCTTG |
| rs2377442 | 135 | TGGAGACATGACACTATGAATTT | 136 | CCATCCTGGGATTACCAATCT |
| rs2377769 | 137 | TTCTGTGTTCTACAATGTCTAGGG | 138 | TCATCCATTTGAGTTTTCCAA |
| rs2388129 | 139 | TATGAGCTGTGGCCAATGAA | 140 | CCTGAAGTGTCCCCTAGAAGG |
| rs2389557 | 141 | TTTGCAGACAGGTTAAGATGC | 142 | TGCACCAAGATGTGTTCTGTC |
| rs2400749 | 143 | CCTACAGTCCAGGGGGTCTT | 144 | TCTAGATAAGGAGAATCTGGTG |
| rs2426800 | 145 | CGGAATTGAGCTAACCGTCT | 146 | CACTGGCCTGAGGCTACTTC |
| rs2457322 | 147 | AAGTCCTGGATTTCACCAGAG | 148 | TCCCAAGATCTGCACTAAACG |
| rs2509616 | 149 | CCCTCCAGAGCTAACTGCAT | 150 | TGGATTTATTCTTCATGTTGCTT |
| rs2570054 | 151 | TTTCCAGGAGTATAAAGGAGTGAA | 152 | AACCAACACTTAGGAAAACAAATG |
| rs2615519 | 153 | GAAGCTTCTGTCCCTTCTGT | 154 | CCTGCTGATTTCATCCTTCC |
| rs2622744 | 155 | TCACATCAGTAACCTCCTTCTTG | 156 | TCCAGAAGCCTTTCTTCCTG |
| rs2709480 | 157 | GGCATAGGAACCATATTATTGTCA | 158 | CCTTCTCAACATAGTTCTAATTCC |
| rs2713575 | 159 | CCACAAGCTCATCATCTATTCG | 160 | TTTCTGAGGCTGATAACTGAA |
| rs2756921 | 161 | GAAGGAACATCAAACAAGGAAA | 162 | TGCATATCACAGTCTCCAAGG |
| rs2814122 | 163 | GAGCAGGTAGCTACAATGACA | 164 | TGCCACCCAGATCTCTTTTC |
| rs2826676 | 165 | CCTGATCTGGAAACTCATGAAA | 166 | TGGGGATGTGGGTAAGTTAAT |
| rs2833579 | 167 | GCAACTGGTCTTGTTCCACA | 168 | GCTAAGCCAATGTCTACATCTTC |
| rs2838046 | 169 | TGGTGTGTTAGGGATCTGGAG | 170 | TGACATTGGTTATTGGCAGA |
| rs2863205 | 171 | CGTATTCATTATCCACAGGGACT | 172 | TGCAGTGAAGGATTGCAAAG |
| rs2920833 | 173 | CCCTTCCTGGACTTCACATAG | 174 | GCATCTAGATCTTTACCATTGC |
| rs2922446 | 175 | GGAGAACATTTAGTGCCTCTGC | 176 | ACACTCGGAACGATCTCTGC |
| rs3092601 | 177 | AAACCCACGGAGGTCATTTT | 178 | TGGGTCTCCTATTTCTGTGTCC |
| rs3118058 | 179 | TGTTAGGACTACCTTATGCAGTT | 180 | TGGTATGTCTCCTTTGATCTTT |
| rs3745009 | 181 | CTGAGCGGGAGCTTGTAGAT | 182 | GCTCCTGACGACCAATAACC |
| rs4074280 | 183 | GGACCACTGTCTAGACCAAGC | 184 | TGTGTCTGGTGAGGAAGATGA |
| rs4076588 | 185 | GGGATGAAACCAAACCTCCT | 186 | TTTTAGGAAACCTCACCAGGAC |

TABLE 3-continued

| | SEQ ID | | SEQ ID | |
|---|---|---|---|---|
| SNP | NO | First Primer Sequence | NO | Second Primer Sequence |
| rs4147830 | 187 | TCTCTGTTCGTGTCTCTGTCTTG | 188 | TTGAGTTGGCCTAAAACCAGA |
| rs4262533 | 189 | CCCGACCACTAAAAGGCATA | 190 | TTGCCTCTAAAATCTAGAATAGCC |
| rs4282978 | 191 | TCTTAGGAATGACTCACACTGGTC | 192 | CACTGAATATTGAAAACTAATGG |
| rs4335444 | 193 | GCATGTTATAATTTTACAAGCTC | 194 | TCACACAGGTTAGGATGTTTGTG |
| rs4609618 | 195 | GCACCCTAGGAGCAAACTGA | 196 | GCAGTTGCCTTGAAAGGAGT |
| rs4687051 | 197 | GCAAATAAAATGACTCTGGGAAC | 198 | GGGGTTGAGATACAACATCTTCA |
| rs4696758 | 199 | GATTCTTGGGGCATCAAGTG | 200 | GGACGTGGGTGACTATCAGG |
| rs4703730 | 201 | TCTAGCTCCTAAGTTGATTGATTC | 202 | TCCATTATAGTTCAGTCTTCAAT |
| rs4712253 | 203 | CAGGAGAAAAGCAGAGACCAA | 204 | AGCGAGAGCAGGCTCATAAT |
| rs4738223 | 205 | TGACAAGGGATTAGGGCAAA | 206 | GAAACTACCTCTGAGTGTTACAGA |
| rs4920944 | 207 | GAATCCTGGACGGTCAGAAA | 208 | TGAAAATGAGTAGTGGACATCTG |
| rs4928005 | 209 | AAAATGTGAAGATAAGTGAACAGC | 210 | CCCTAACTTATTCAACATCACTGC |
| rs4959364 | 211 | ACATATTCCAGGAGCATGAC | 212 | CATTGAGTTCATTGGCCTGT |
| rs4980204 | 213 | CTCTCGTGGTGGATTGAACA | 214 | CCAACAAGTACTCTGAACCAATTT |
| rs6023939 | 215 | AAGGAGGGCTTAGCTAGTTG | 216 | GCTCTTTCTCATCTTAAGGCTTC |
| rs6069767 | 217 | GTTAAAATTACTGTTCCAGTTGT | 218 | CAGGCAACCAAATAATAACAAAA |
| rs6075517 | 219 | CCCATTTCCATTTACCGTTTT | 220 | TTGTATTTACAATAGCCATCCA |
| rs6075728 | 221 | TGAAAGTATCAGGAAAAATGGATG | 222 | AGCAGTCAAAGTGAGGATATGTT |
| rs6080070 | 223 | GCAGTAACAAATAACCCCAACAG | 224 | ACCAGCCTTTGTTGTTGAGC |
| rs6434981 | 225 | GGGTTCCAGCAATATTCTACCTT | 226 | GGTAATGAAGAAAGACAAAACA |
| rs6461264 | 227 | TCTAATGCCTCACCAAGCAA | 228 | GCACAGCAGAAACCCAGATT |
| rs6570404 | 229 | CACTAGTCCGGCTTGTGTAAAA | 230 | TGGTGATTACAGAATACCACCAG |
| rs6599229 | 231 | ACAGGAGCGGACAATGAGAG | 232 | TGATGTGCATGTGTCTCAGC |
| rs6664967 | 233 | TGGTCCTCTGCTTCCCTAAG | 234 | CATACATGAGGTGACTACCACCA |
| rs6739182 | 235 | CATCAGATTCCCAACATTGCT | 236 | AGCTCATCCCAATCATCACA |
| rs6758291 | 237 | AAGGGCCATGAGGGTACTTT | 238 | AACCCAAACGTCTAACAAGATACA |
| rs6788448 | 239 | CATCGATAGTATTAGGCCCACA | 240 | TGTGATTTCTTTCTATAGGAGGTT |
| rs6802060 | 241 | GGAAGGAAAGCTCTTTTGGAA | 242 | TTCCAGCCCTGAATAACAACTT |
| rs6828639 | 243 | TGATCATTGCTGTGATGTATT | 244 | AGGATACCATGATTTTGTAGTGC |
| rs6834618 | 245 | CTTCCCTGCACATCCTTTTG | 246 | CTGTTTAGGAAGAGTCATGTAACC |
| rs6849151 | 247 | AACTGTTTTGTCAGCTGCTCAT | 248 | AAAAGACCACTTGATTCAGCTT |
| rs6850094 | 249 | TGAGCACACACATATGGAAGC | 250 | TGCAATGTACATGTGGAGAATC |
| rs6857155 | 251 | CCCGTTCTCCATTCTGGTTA | 252 | CCCAGGGAAGAAAATTGGTA |
| rs6927758 | 253 | TGAAATAGTGCTTATTGCATCG | 254 | AGCCACTCCAGCATTCACTT |
| rs6930785 | 255 | CCACATGTTTCTGAGTGAAGGA | 256 | GGAGTTACAGTTATCAAATGCAGA |
| rs6947796 | 257 | GGAAAGAAGGGAGAATGGTCA | 258 | TTGCATATTCTGGACCTCATCT |
| rs6981577 | 259 | GGAGGCAAAGAAGTTAGGGAGT | 260 | TTTTACCTCCCTGCCCTAGT |

TABLE 3-continued

| | SEQ ID | | SEQ ID | |
|---|---|---|---|---|
| SNP | NO | First Primer Sequence | NO | Second Primer Sequence |
| rs7104748 | 261 | AGGAAATGTAGTCAGGTCTAGGA | 262 | GCAGCTTGAAAACAGCCAGT |
| rs7111400 | 263 | CATGGTAAGTATGCTGTTAAATC | 264 | GCTGAGCAGAAAACATAAGCA |
| rs7112050 | 265 | CAAACCCACACTGTGTTAGCTG | 266 | AGCTAATCTTTGGTACTTCAATCT |
| rs7124405 | 267 | CAAGCATCTTGCTGAATTTCC | 268 | AGTGCAAAGTGAAGATAATGACA |
| rs7159423 | 269 | AGTGTCTGTCTTCCAGTTCC | 270 | CATTCATCCCATCTTCTAACTTCA |
| rs7229946 | 271 | GCAAACATGTAAAGTGTGAGAG | 272 | GCAGTCTTCTGTGATTITATATT |
| rs7254596 | 273 | CAGAAGGAAGGGGTAAGACACA | 274 | TCCCCTCAGGTAACTTCCATC |
| rs7422573 | 275 | GATTTCTGTGTTGTGCCACAGT | 276 | TTGGTGTCTTACATGTATTGTGA |
| rs7440228 | 277 | GCTGTAGCACATCCAAAAACC | 278 | GAACTGAAAAAGGAATAAAGTAGG |
| rs7519121 | 279 | GGCATAAGCAGATACAGACAGC | 280 | TGAAACCTATAAGCCACTGAGC |
| rs7520974 | 281 | TCCAAAAAGACAGCTGAAAGAA | 282 | AAGCCATGCAGTGGGTATCT |
| rs7608890 | 283 | TCCATACAGGAAGATCCATTAAGA | 284 | GTGCAGTTTGGGCTACAAGA |
| rs7612860 | 285 | TCACACATCATTGGTGAAGG | 286 | AAGTGTCAGAGGGTTAGTGATTCC |
| rs7626686 | 287 | CACCTAAAGATTTCCCCACAA | 288 | GACTTACGGCCTAACCCTTT |
| rs7650361 | 289 | GAACAAGTATACTAGCAAAACGAA | 290 | TTTGTCTAAAGAATTTGACAGTGG |
| rs7652856 | 291 | TCTTGAGAAGCCTTTTCTTACCA | 292 | GCATGAGTGTGTGTCTATGCAG |
| rs7673939 | 293 | TTCTGGACTCTCCACTCTATTTCA | 294 | TGGCATAAGATAGACATATTCACC |
| rs7700025 | 295 | GCATCTATGTCACCAAGCATTT | 296 | GCCGTTAAGCACTGAGCTGT |
| rs7716587 | 297 | TCCACTACTTCTTGGAGTTCA | 298 | TCTTGAATAGCACCCACAAGAG |
| rs7767910 | 299 | GACACTACTGTCCTCAAACG | 300 | GCCCAAAGACCAAGTTTTAGA |
| rs7917095 | 301 | CGTGTCTGTGAGCTCCTTTCT | 302 | AGGTTGTGAAAGACACTGATGG |
| rs7925970 | 303 | TCCAAGCTGTTTCTCATGTTTG | 304 | CAGTGGGCTCACAGTAATGG |
| rs7932189 | 305 | GCAATTCCAGATATCTCTTTAT | 306 | TTATCTACCCATGCTTCTCTC |
| rs8067791 | 307 | AACAGATCACTTACCGCTTTG | 308 | CCCTACATGCATTATCTCCTTT |
| rs8130292 | 309 | TGGTGCCATCCTAGAGTTCTG | 310 | AGTGTGCACTTGCTCATGACT |
| rs9293030 | 311 | CCAGGGATTTCATCTTCACC | 312 | ATGTCTATGCCCTGCCTCAT |
| rs9298424 | 313 | TGTAGTCGAAGCAATGAGATGTG | 314 | TTTCACTCCCTTCTGTATTTAGCC |
| rs9397828 | 315 | AAATGCTTTGCTGCATGTCT | 316 | TCAATGGCAATTTGAGGAGA |
| rs9432040 | 317 | TGAGGAAGTGACAAGTTCAGA | 318 | TTTTCTCCCCATCTGTTACTA |
| rs9479877 | 319 | CAATTTTACATCCAACAGAAGA | 320 | TGGGATTATAAGGAGGTCAAGAA |
| rs9678488 | 321 | TGGTGAGTTTCTTCCCTAGGTT | 322 | CTTGACACCATAGTGGTCACCT |
| rs9682157 | 323 | TTTACTTCTGAGCTGAAGGTACTC | 324 | CACGCAGGCAATAGTAGGAA |
| rs9810320 | 325 | AGCACCAAAGGCAAGTTCAA | 326 | GGATGCCAAGATTGCAAATA |
| rs9841174 | 327 | TTCTTTCTACCCAGGTACTTATCA | 328 | TTTCAAGATGCAAAGGCTTG |
| rs9864296 | 329 | CGAAATCCATAGGACCTACA | 330 | AGCTACACTATTTCCATGTGAC |
| rs9867153 | 331 | CGTCGGTTGTTTTATCATTGC | 332 | GGACAGGTTGTGCATAACTAAGA |
| rs9870523 | 333 | CCTCACTTAAGGAGAACAGTTAGA | 334 | TGCTAATCATCCCTTATTATTGC |

TABLE 3-continued

Panel A SNPs and amplification primers

| SNP | SEQ ID NO | First Primer Sequence | SEQ ID NO | Second Primer Sequence |
|-----|-----------|----------------------|-----------|------------------------|
| rs9879945 | 335 | TGACCTACTAGACATCAAGCCTTA | 336 | TGCCAGTAACTTAATCCATAGC |
| rs9924912 | 337 | CCAGACAGGCACATACAGTCA | 338 | GGGAACTGAGTATCTCTGTGTGA |
| rs9945902 | 339 | GAGGTCGAAGTTGTAGGCTTG | 340 | TCAACTTAGTTACAGGTCACACA |
| rs10033133 | 341 | TCAATTTTTGTTGTGGTTTACCT | 342 | AGGTTTTCCTAATAAGACTGCT |
| rs10040600 | 343 | TCAGAGTAGGAATGAACAATTT | 344 | CTCAGGGCCTAAACTTGCAC |
| rs10089460 | 345 | GCACTCATGTGAGTTTGCAC | 346 | CACAGTGAAGTATGTATAAATTGC |
| rs10133739 | 347 | GCCTAGCTGTGCGATTCTTC | 348 | TGATACCAGTTGATGCCACA |
| rs10134053 | 349 | TGACTGAACTCAATTCAAACAGC | 350 | TGGCATCTAGGGTATAGGAAGA |
| rs10168354 | 351 | GGCCACCATCTCCTGTTCTA | 352 | CCTTGTTTGTCTGTATCTGAGC |
| rs10232758 | 353 | CCAACTCTGATTGTGCGACT | 354 | GCTCCAAGCCATAGATCCAG |
| rs10246622 | 355 | GGTGTGTGTATGAGGCTTGG | 356 | AACCGCCAGCATAGCTTCT |
| rs10509211 | 357 | GGTAGGAAGGGGTTGTCGTT | 358 | TTTCTTTCTACTTCTCATCACTCT |
| rs10518271 | 359 | GGACATCAGCACTAACTGAAGTG | 360 | TTCTCTTGTGTGAACCATCCTC |
| rs10737900 | 361 | GCCAGCGTGTAAGACACAAG | 362 | TGGCATTTGTTTACAGACTTATC |
| rs10758875 | 363 | TCCTCCACATTGGTAATTAGGG | 364 | GGTGTCCCCCTCAAATTGTA |
| rs10759102 | 365 | CAAGTTTGTACCTCAGCTTTCA | 366 | TGAGATACTGTTGTCCTCTGC |
| rs10781432 | 367 | TTCCCTTCTTATGTAATCTCC | 368 | GAGGGTTACTGAACTAGGATAATG |
| rs10790402 | 369 | TCCTGAGAGCATGGTAAGATGT | 370 | TGCAGGGCATTCTATGTGAA |
| rs10881838 | 371 | TACAGCTGAGCAATAACGTG | 372 | TGGCTGGCCAAATCTTTCTA |
| rs10914803 | 373 | AAACTATAAAAGGACCTAGGAAA | 374 | AAGTCTAGTGAATTTCTTGTTAGG |
| rs10958016 | 375 | CTTAATGATTTTGTAATGTCAGG | 376 | ATTTGAGAGGTTGCCAGAGC |
| rs10980011 | 377 | GAGGTTCTCATTCCCTCACC | 378 | AGAGGGGCTCACCTGAGAGT |
| rs10987505 | 379 | CACACTAGTGGGTCCTGATTAGA | 380 | TTGCGGTTTCCTCATTCTTC |
| rs11074843 | 381 | CGTGATGGGTAGGTCAGTCC | 382 | CGCCTCTGGGGATAACTAAA |
| rs11098234 | 383 | GGAATTGCCACTCTGGAGAA | 384 | AGTGGTCCCCAACAACTTGA |
| rs11099924 | 385 | ATAACAATGTCTAGCAACAGG | 386 | GATCAACACTTCAAAATTATGGT |
| rs11119883 | 387 | TCAGATAAAACAATTCCAGTTAC | 388 | ACCCACAGAGGAAAGCCTTG |
| rs11126021 | 389 | CAGCATATATTACCTTTTCTTTG | 390 | TGTGCCCAGAAAGTTTTAGCA |
| rs11132383 | 391 | TCAACTGACACTGGTGTTTCTC | 392 | GTGAAGGGAGGACAAAATCG |
| rs11134897 | 393 | CAAGTGATCTGATGGGGTGA | 394 | TGCTGAGTTTGAGAAACTTGGT |
| rs11141878 | 395 | GTAGGACTTAGGGCGCTCAT | 396 | GCATTACTGCCGAGGGATCT |
| rs11733857 | 397 | TGACAAAGCCTAGAGTGAACTGA | 398 | TCCTAGAGTACTCCTCTTTGTCCA |
| rs11738080 | 399 | GTACAGAGTCCCTGTCTCACA | 400 | CATGATCTGTCTCTCTCACTGAA |
| rs11744596 | 401 | GCATTTTCTCACAGCCACAG | 402 | TGGCCTAAAAATTCACCACTG |
| rs11785007 | 403 | AACATTTGCACATTATCAGC | 404 | GCAAGGATCAGTCAGACTACGA |
| rs11925057 | 405 | TGTCCATCAATCTCAAAAGTCG | 406 | CTGATTTCTACCAGTTACTTACCA |
| rs11941814 | 407 | GCATGAGCCACCCTAAATCT | 408 | TGCAGACCATGAGGAATGTT |

TABLE 3-continued

Panel A SNPs and amplification primers

| SNP | SEQ ID NO | First Primer Sequence | SEQ ID NO | Second Primer Sequence |
|---|---|---|---|---|
| rs11953653 | 409 | AGGATTCCTTATACACTGACCTC | 410 | ACCAAATAATGGTCTACTCCT |
| rs12036496 | 411 | AAGACATTCTCTGCCTTTCTCA | 412 | GGCTCTACTATGGGGAAAATTCA |
| rs12045804 | 413 | GCAAATCACTAGGAAAGCTCA | 414 | GAGGTTCACTCTATTTCTGTTCC |
| rs12194118 | 415 | CTAGAAACGGCTGCCAGGTA | 416 | CCCTGCACTTGTACCAGCTT |
| rs12286769 | 417 | AGGACATTCTTTTGTGTATTCAAG | 418 | ATCCCATATAGGCACTTGCT |
| rs12321766 | 419 | CAAATAATCACCCCAATACAATCA | 420 | GCTTTCAGTGCCCTCATCTC |
| rs12553648 | 421 | AAGATGATCAAAGTTTTGAGAGCA | 422 | CACTCCTAAAGAACAAGATGTCAA |
| rs12603144 | 423 | GACAAGAACTGAAGGCAAAGG | 424 | GGGAGGAACAGAACAACCTTC |
| rs12630707 | 425 | CCCTTGCAATACCCAGCATA | 426 | AGTTATCTGAGTTGGCTTACC |
| rs12635131 | 427 | TCGCAGTCTTTTGCATCATT | 428 | TCCAATAGCTACCTTCACCAGAA |
| rs12902281 | 429 | TGGAAAAACACAGGCATATTCTC | 430 | CCAAAAGCATCTAAAAACAGGA |
| rs13019275 | 431 | CAAATATACTGATTCTGTGGCAAA | 432 | TGATGCATTGAGATTTTGATGA |
| rs13026162 | 433 | TAGCCTTTGGATAACAGTCC | 434 | GAGGGAGGAAATGGTCAACTT |
| rs13095064 | 435 | AGGCAAAGAACTAGACAACTCT | 436 | AGACGTGCTGGGTTCCTAGA |
| rs13145150 | 437 | GGCATGAAGATGTTAACCTACCA | 438 | TTGTCTGGTCTTCATCAAGTCTCT |
| rs13171234 | 439 | TTGCCATGCAGCAGTACTTAG | 440 | TGACTTTTCATTGCTAGTATCCA |
| rs13383149 | 441 | GCAACAAGAACAGGAACCAAG | 442 | TGTTTTGACATTGTCCTGTGTG |
| rs16843261 | 443 | CAGTGAGGTGTGATGTATAAAGAG | 444 | GAGAACACATATTCATTCCTCTCC |
| rs16864316 | 445 | GTGGGGTCCAGCAGTAAATC | 446 | GAACTTCTCACATCACCTCAAGC |
| rs16950913 | 447 | TCTATTAACCCTAATCAATCTCCT | 448 | TTGCTAAATTTCAGGCACCTC |
| rs16996144 | 449 | CCTTTGACTCTGGCCTCATC | 450 | AGTGAATAACCAGCCTTAGTTG |
| rs17520130 | 451 | AAATAAGGACATCTGGAAAACAA | 452 | GTGCCAGCTACAAACAATGG |

TABLE 4

Panel B SNPs and amplification primers

| SNP | SEQ ID NO | First Primer Sequence | SEQ ID NO | Second Primer Sequence |
|---|---|---|---|---|
| rs196008 | 453 | GTGCCTCATCAAAATGCAAC | 454 | ACACAGATGACTTCAGCTGG |
| rs243992 | 455 | AACTCAAACCTAAGTGCCCC | 456 | GGAATGGAATAGTGTGTGGG |
| rs251344 | 457 | ACACTGGTCTCAAGCTCCC | 458 | CACACCTGTAATTCTAGCCC |
| rs254264 | 459 | AGAAGGAAGGATCAGAGAAG | 460 | AGCTTTCCTCCCCACACTG |
| rs290387 | 461 | GCTGTGTGGAGCCCTATAAA | 462 | GAATGAAATGGAGTTTGCAG |
| rs321949 | 463 | CCTCAGCCACCACTTGTTAG | 464 | GTGTTGGTCAGACAGAAAGG |
| rs348971 | 465 | GCCAATTACCCCATAATTAG | 466 | ATGCACACTTACACACGCAC |
| rs390316 | 467 | AAGGAAGTAAAGGTATGTGC | 468 | AGGCTAACTCTAACATCCTG |
| rs425002 | 469 | AAGAGTGTCTCCTCCCTCTG | 470 | AACTGGAGGCTGTGTTAGAC |
| rs432586 | 471 | CGCTCTTTTCTGACTAGTCC | 472 | TTGCAGCAGTCACAGGAAAC |

TABLE 4-continued

| | | Panel B SNPs and amplification primers | | |
| --- | --- | --- | --- | --- |
| SNP | SEQ ID NO | First Primer Sequence | SEQ ID NO | Second Primer Sequence |
| rs444016 | 473 | CTCTCTGTGCACAAAAAACC | 474 | GGAAGACACTGCCTTCAAAC |
| rs447247 | 475 | AAAAACCCCAGGCTCCATTG | 476 | ATGTCCAGCTGCTTCTTTTC |
| rs484312 | 477 | TCCAAGTCAGAAGCTATGGG | 478 | AGTCTGCAGACCTAACATGG |
| rs499946 | 479 | ATGGCTTGTACTTCCTCCTC | 480 | TTCGGTGGAATAGCAGCAAG |
| rs500090 | 481 | CATAATCTCAGGGCTACAT | 482 | TTCACCTGGCCTTGAGGGTC |
| rs500399 | 483 | GTTTATTGATGAACTGGTGC | 484 | GGGCAGAGTGATATCACAG |
| rs505349 | 485 | ACTGGCAAGTCCAGGTCTTC | 486 | AAGGCTCAGGGCAGAAGCAC |
| rs505662 | 487 | TCCTCATCCGGTGTGGCAA | 488 | CAGCAAAGAGAGAGAGGTTCC |
| rs516084 | 489 | AGTATGCCATCATGAAAGCC | 490 | CTTCTTTGACTAAGGCTGAC |
| rs517316 | 491 | CTCTGCCTATTCTCCTCTTC | 492 | TAGACCTCAAGGCCTAGAGC |
| rs517914 | 493 | AGTAAGAGCTCCCTTGGTTG | 494 | GCTCATAACAATCTCTCCCC |
| rs522810 | 495 | TCCCCTCTACCCCTTGAAGC | 496 | CAGCACTGATGACATCTGGG |
| rs531423 | 497 | AAGAACACAGGCCTGGTTGG | 498 | TATGGCTCTGGGGCTCTATA |
| rs537330 | 499 | AACAGAGAGAATGAGGAGGG | 500 | TCATTCTAAAAGGGCTGCCG |
| rs539344 | 501 | GAAAGGTATTCAGGGTGGTG | 502 | GATGCTCTGAGACAATCCTG |
| rs551372 | 503 | TTAACTGTGAGGCGTTCACC | 504 | GATCATGGGACTATCCACAC |
| rs567681 | 505 | CCAGCCCTGCTCCTTTAATC | 506 | GGAGAAGATCCTACACTCAG |
| rs585487 | 507 | CCAACTTCTTCCCAGTCTGT | 508 | CTGGAGCTGAAGGACCCCA |
| rs600933 | 509 | GGAGAAATCCTTCCCTAGAG | 510 | TTCAAGGTGCTGCAGGTTTG |
| rs619208 | 511 | CCCCCTCTACAGGAAAATTC | 512 | TTCTGAATTCTTCAGCCAGC |
| rs622994 | 513 | CATCCTACCTCTAGGTACAC | 514 | GGTGTCTTAGTTACATGTGC |
| rs639298 | 515 | TGGTGACGCAAGGACTGGAC | 516 | ATACTGTGCTGCTCTTCAGG |
| rs642449 | 517 | CAGCTGCTGTTCCCTCAGA | 518 | CCAAAAAACCATGCCCTCTG |
| rs677866 | 519 | TAATTGGTACAGGAGGTGGG | 520 | AGGCATGGGACTCAGCTTG |
| rs683922 | 521 | GTGCAGGTCATTGTGCTGAG | 522 | AAACACTCCACGTTAAAGGG |
| rs686851 | 523 | CAGCTGAGAAAACTGAGACC | 524 | TTTACAGACTAGCGTGACGG |
| rs870429 | 525 | TGCTGCTCCGCCATGAAAGT | 526 | ATGCAGGGAGAGCAGCAGCC |
| rs949312 | 527 | GCTGAGAGTTAAGTGGCCAA | 528 | CTGTGGCCATATTTCTGCTG |
| rs970022 | 529 | GCAATCAGGCCCAGCTTATG | 530 | TTGTCTGGACTCTCTTCATC |
| rs985462 | 531 | CGCCTAATTTCCAGCAAGAA | 532 | GACTTGCAAAAGCTCTCTGG |
| rs1115649 | 533 | GTCTGGCTGAGGAATGCTAC | 534 | AAGGGCAGCATGAGCTTGGG |
| rs1444647 | 535 | GTCTACTTCAAATCATGCCTC | 536 | CTACATGCATATCTGGAGAC |
| rs1572801 | 537 | CAGAGATGCAAGCAGCCAAG | 538 | AGGAATGGGGCTGCCATCT |
| rs1797700 | 539 | GAGACAGGCAAAGATGCAAC | 540 | ACCACGCCTGGCCAGAACT |
| rs1921681 | 541 | GGGTTTAGTCTCCTTACCCC | 542 | AATGTCCCTGGCACAGCTCA |
| rs1958312 | 543 | GCTTCAGTTGTCACTGTGAG | 544 | CTCAGATGATGTCCCTTCTT |
| rs2001778 | 545 | CGATGCAAGCTTCCATTCTA | 546 | GGACAGAGAATGGCCTGCTA |
| rs2323659 | 547 | TTAAAACAGCCCTGCAACC | 548 | TGATGAGAACAGAGCTGAG |

TABLE 4-continued

| | SEQ ID | | SEQ ID | |
|---|---|---|---|---|
| SNP | NO | First Primer Sequence | NO | Second Primer Sequence |
| rs2427099 | 549 | CTGAAGCTATGTCCTGTTAG | 550 | AGGTGGCACGGCACGTTCAT |
| rs2827530 | 551 | CTGAAGTGCAGGAAGCTTGG | 552 | ACCCTAGAACTTGACACTGC |
| rs3944117 | 553 | AAGGAGCTGGCAAGGCCCTA | 554 | ACATAGGCACAATGAGATGG |
| rs4453265 | 555 | TACCTTTCAAGCTCAAGTGC | 556 | TTTGGATGGAACGTTTGCAG |
| rs4745577 | 557 | GCTACCCTTTAATGTGTCTC | 558 | ATGAAGAGCAGCTGGTCAAC |
| rs6700732 | 559 | CAGCCCTTGTGTGCATAAAG | 560 | TACAGTGGTGGACAAGGTGG |
| rs6941942 | 561 | CTTGTTTTGCAGGCTGATTG | 562 | TCAATCATCCCCATCCCCAC |
| rs7045684 | 563 | GCACATCACAAGTTAAGAGG | 564 | CCCCAGTAGGGAACACACTT |
| rs7176924 | 565 | CAGGATGCACTTTTTGGATG | 566 | GGCTTCTCCCAGAAAATCTC |
| rs7525374 | 567 | ACTGCAGTGCCGGGAAAAGT | 568 | TITGCTCACCCTACCCCAC |
| rs9563831 | 569 | TGATAACAGCCTCCATTTCC | 570 | TAGGGATGCAAGATGAAAGG |
| rs10413687 | 571 | GATGCAGGAGGGCGTCCCA | 572 | TCCAGCCACTCTGAGCTGC |
| rs10949838 | 573 | TCTGCTGTTTGATGGATGTG | 574 | TGGGAGATCAGCTAGGAATG |
| rs11207002 | 575 | GCTGGGATCCCATCTCAAAG | 576 | TGAATGTCTTGCTTGAGACC |
| rs11632601 | 577 | TTCCCTTGTTTGGAACCCTG | 578 | CAGCTTCCACCCTCTCCAC |
| rs11971741 | 579 | TGGCCTTAAACATGCATGCT | 580 | GGTGACAATCTAGAGAGGTG |
| rs12660563 | 581 | AGGTCAGCTCAGGGTGAAGT | 582 | GCTCCATTGAAGGGTAAAGG |
| rs13155942 | 583 | GAGGGTACCTTTCTTTCTCC | 584 | GCTCAGTGTCTGACAAAAGC |
| rs17773922 | 585 | AGCCATGTTTCAGGGTTCAG | 586 | CAGTGCCTGACAGGGAAAGT |

TABLE 5 reference nucleic acids and oligos and primers

| | |
|---|---|
| RNaseP Loci PCR forward primer sequence | TCTTTCCCTACACGACGCTCTTCCGATCTCTCCCACATG TAATGTGTTG (SEQ ID NO: 1337) |
| RNaseP Loci PCR reverse primer sequence | GTGACTGGAGTTCAGACGTGTGCTCTTCCGATCTCATA CTTGGAGAACAAAGGAC (SEQ ID NO: 1338) |
| RNaseP variant (rev_comp)* | CTCCCACATGTAATGTGTTGAAAAAGCATGGATAACGGT GTCCTTTGTTCTCCAAGTATG (SEQ ID NO: 1339) |
| ApoE Loci PCR forward primer sequence | TCTTTCCCTACACGACGCTCTTCCGATCTCCAGGAATGT GACCAGCAAC (SEQ ID NO: 1340) |
| ApoE Loci PCR reverse primer sequence | GTGACTGGAGTTCAGACGTGTGCTCTTCCGATCTCAAT CACAGGCAGGAAGATG (SEQ ID NO: 1341) |
| ApoE variant (rev_comp)* | CCAGGAATGTGACCAGCAACGCAGCCCACAAAACCTTC ATCTTCCTGCCTGTGATTG (SEQ ID NO: 1342) |

*The underlined nucleotide is one that is different from the native sequences.

Example 2. Design SNP Panels with Improved Sensitivity

The Transplant Monitoring v1 228plex panel, which include the 226 SNPs in Panel A described above is a highly multiplexed PCR-based target enrichment designed for non-invasive detection of donor-derived cell-free DNA (dd-cfDNA) in organ transplant patients. The panel targets 226 SNPs for measuring donor fraction and 2 synthetic competitors for measuring the total amount of copies of DNA input. The donor fraction, the percent of cfDNA that is donor-derived in recipient plasma, is used as a biomarker for organ injury and acute rejection. During the course of a transplant rejection and subsequent cell damage in a graft, dd-cfDNA is released and the donor fraction increases. The total copies are used as a quality control metric for the donor fraction measurement as the measurement of donor fraction will lose accuracy if there are insufficient amounts of DNA used in the PCR reaction.

The key variable used for measuring both total copies and donor fraction is the allele frequency of each of 228 targets. This is the ratio of counts of the reference allele to the sum of both reference and alternate allele counts. In a pure sample, with DNA from a single individual, a biallelic SNP can only have an allele frequency of 0 (homozygous for alternate allele), 0.5 (heterozygous for reference and alternate allele), or 1 (homozygous for reference allele). For an organ transplant patient, cfDNA is a mixture of donor and recipient cfDNA. Donor fraction is determined from "informative" SNPs—where the allele frequency is shifted from 0, 0.5, or 1 due to a difference in donor and recipient's genotype. This occurs for example when the recipient is homozygous for an allele (e.g. AA) and the recipient is either heterozygous (e.g. AB) or homozygous for a different allele (e.g. BB).

Figure 10:
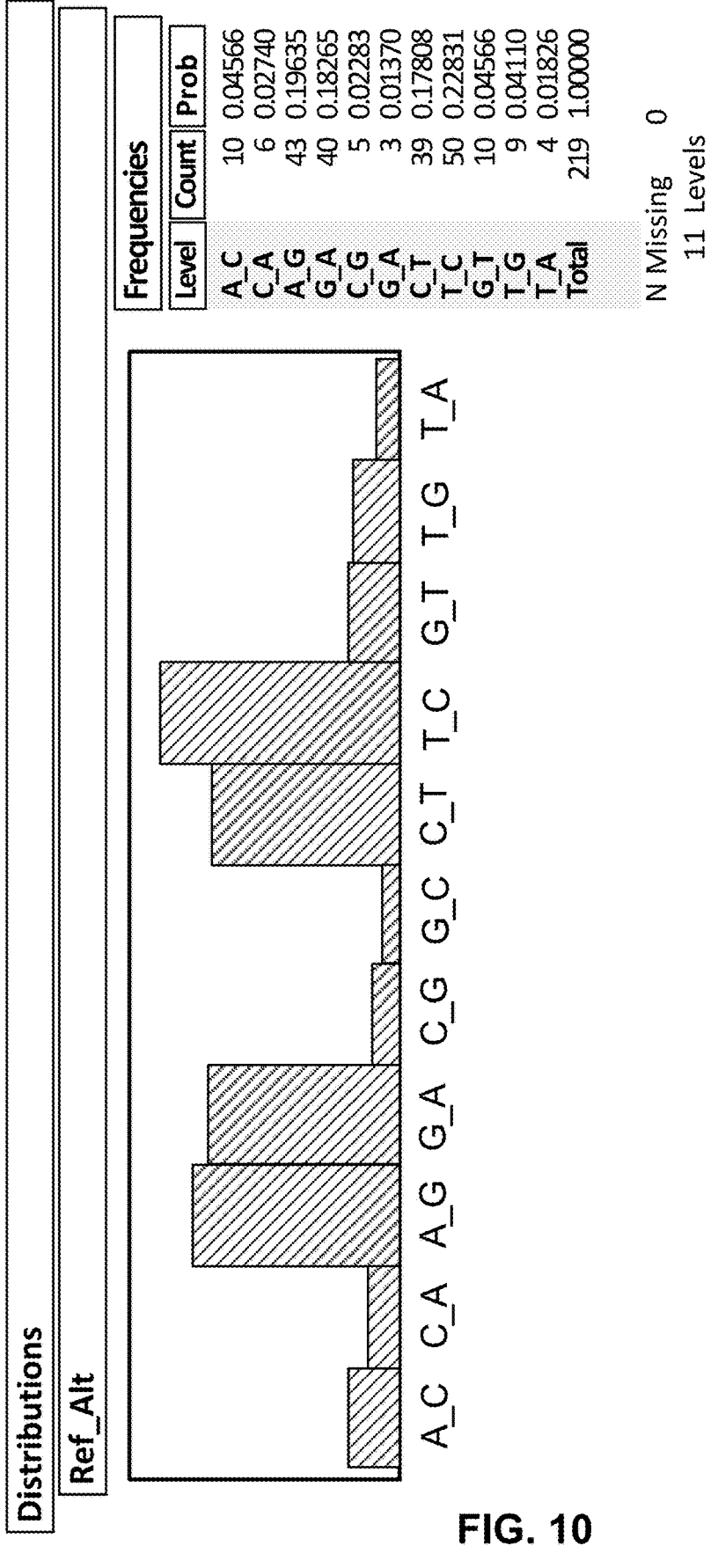
FIG. 10 shows that distribution of Ref_Alt combinations. A_G, G_A, C_T, and T_C are the most frequent combinations of reference and alternate allele in a v1.1 panel (i.e. a combination of subsets of Panel A and Panel B as disclosed in Table 1), occurring in 79.5% of the panel's targets (172 out of the 219 donor fraction assays).

During characterization of the v1 panel (the v1 panel refers to the SNP panel A in Table 1 and two synthetic competitors for measuring the total amount of copies of DNA input, as described in Example 2), it was determined that certain categories of SNPs had higher amount of bias and variability in their allele frequencies. For a homozygous SNP, the allele frequency should be equal to 0 or 1. Background is defined as a median bias away from 0 or 1. This is caused in part by sequencing error or PCR error. The variability is the median absolute deviation (MAD) of the homozygous allele frequencies—in an error free measurement, this would be 0. When these biallelic SNPs are categorized by their combinations of reference and alternate alleles (abbreviated as Ref_Alt), it is observed that A_G, G_A, C_T, and T_C have the highest median and MAD for homozygous SNPs FIG. 9) and represent 78.5% of the panel (FIG. 10). These Ref_Alt combinations serve as a lower limit to the donor fraction that can be detected.

This motivated the development of a v2 panel that has only lower background Ref_Alt combinations in order to improve sensitivity for low levels of donor fraction. The v2 panel retains 47 SNPs from the v1 panel and adds in 328 new assays that all have the desired Ref_Alt combinations (not any of A_G, G_A, C_T, or T_C).

The first step in the design process is to identify SNPs that can serve as a universal individual identification panel. The goal is to be able to distinguish dd-cfDNA from recipient cfDNA regardless of the population (e.g. Asian, European, African, etc.). The ALlele FREquency Database (ALFRED, site: http://afred.med.yale.edu/afred/sitesWithfst.asp) provides allele frequency data on human populations. The Fixation Index (FST) is the proportion of total genetic variance contained in a subpopulation relative to the total genetic variance. A low value is desirable for obtaining a SNP that will have similar genetic variance in most populations. The first step in panel development was to filter this database to obtain SNPs with a FST lower than 0.06 based on a minimum of 50 populations. The SNPs were further filtered to ensure a minimum average heterozygosity of 0.4 (the maximum possible is 0.5). This increases the proportion of SNPs in the panel that will be "informative," increasing the confidence in the measurement of donor fraction. This filtering resulted in 3618 SNPs.

FASTA sequences were obtained for these SNPs from dbSNP On average, this provided a 1001 bp flanking sequence that included the SNP plus 500 bp both upstream and downstream of the SNP. These sequences were used in the primer design tool BatchPrimer3 along with the parameters indicated in FIG. 11 to obtain candidate primers for each SNP.

Processing through BatchPrimer3 resulted in 2645 assays that met the design criteria. These SNPs were further filtered based on additional characteristics obtained from the dbSNP database. SNPs were selected if they met all of the following criteria:

1. Biallelic.
2. The SNP is not located within the primer annealing regions.
3. Validated by the 1000 Genomes Project.
4. The ref_alt combination is not any of A_G, G_A, C_T or T_C.
5. minor allele frequency is at least 0.3.
6. The sequence for amplified target region is unique and cannot be found elsewhere in the genome.

The result is a 377plex panel that includes the 2 assays for total copy calculation and 375 assays for donor fraction measurement. The donor fraction assays consist of 47 primers from the v1 panel and 328 newly designed primers. This panel was further filtered to obtain a 198plex (2 for total copies, 196 for donor fraction) (Table 6) after removing assays with low depth, high allele frequency bias (deviation from 0, 0.5, or 1 in a test with pure samples), or having a significant role in lowering the alignment or on-target rate (determined from re-aligning unaligned or off-target reads to first 18 bp of each of the primers). Table 7 lists the excluded SNPs and provides reasons for their exclusion. The first primer and the second primer were used as a primer pair to amplify the region containing the SNP in the same row in Tables 6 and 7.

TABLE 6

| | | Panel v2 | | |
|---|---|---|---|---|
| SNP | SEQ ID NO | First Primer Sequence | SEQ ID NO | Second Primer Sequence |
| rs150917 | 587 | CTGTTTTCTCAGAAGGGACTTT | 588 | TCGAAAGAAAACACTGAGAATCAA |
| rs163446 | 589 | TGGACAAAAATACCATCATCA | 590 | AGATCATCCTGAACATAAGGT |
| rs191454 | 591 | TTCCCTCTTCAGTTTACCTGTTT | 592 | CACCAAGAAGGGAATGAAAAT |
| rs224870 | 593 | TGAAGAAAGCAAGGGACAGAA | 594 | AAGCCGCGTGTTATTGAAAC |
| rs232504 | 595 | TTCAGTGCTTTCCGTTGGA | 596 | CACACACACGCACTAAGCAA |
| rs258679 | 597 | TCACCTCATACATGTTTTCTTTT | 598 | AATACCTCAAAGGACTGTAATG |

TABLE 6-continued

Panel v2

| SNP | SEQ ID NO | First Primer Sequence | SEQ ID NO | Second Primer Sequence |
|---|---|---|---|---|
| rs260097 | 599 | TGCTGCATTCATTTGTCAAC | 600 | GAACTCTGGTGTTCCTAGTG |
| rs376293 | 601 | TGTATTTGCCTAAAAGTAAGAGG | 602 | GGCAGAGTTCTCTTGACGTG |
| rs390316 | 603 | AAGGAAGTAAAGGTATGTGC | 604 | AGGCTAACTCTAACATCCTG |
| rs468141 | 605 | ACTTAAAACCAAACCCTCA | 606 | TTATTGGGTGTTGCAAGTGT |
| rs500399 | 607 | GTTTATTGATGAACTGGTGC | 608 | GGGCAGAGTGATATCACAG |
| rs522810 | 609 | TCCCCTCTACCCCTTGAAGC | 610 | CAGCACTGATGACATCTGGG |
| rs534665 | 611 | ACGGGGTCTTATGGTTCCTC | 612 | GCCTGAGAAGCAATTAACCTG |
| rs535468 | 613 | TGCTAACCTGTGAAGTCCATTC | 614 | TTTATTTGCATTGGTCTTTGC |
| rs535689 | 615 | GCATAATTTGAAAGCTCTGTTTG | 616 | CGATTATGCCCATTGATATTTTT |
| rs535923 | 617 | TCAAGGGATTGCTCCAATGT | 618 | CTCCAAACCAATACCTAAAAA |
| rs567681 | 619 | CCAGCCCTGCTCCTTTAATC | 620 | GGAGAAGATCCTACACTCAG |
| rs570626 | 621 | GCTTCTCATCTGTGTGCATTT | 622 | CCTAGAATATGATGCCCAAACA |
| rs580581 | 623 | CCTCCTCTACTAGACCTCTGACG | 624 | TGTAGAATAAGAAGGCAGTCCAA |
| rs600810 | 625 | ACCTAGGGAAGGGGTCAC | 626 | AAGCCAGGGTTCATCTGC |
| rs622994 | 627 | CATCCTACCTCTAGGTACAC | 628 | GGTGTCTTAGTTACATGTGC |
| rs698459 | 629 | TCCAAAATTCCTTGATGTGTCA | 630 | TCAACCTCCTACAGCAACAAA |
| rs707210 | 631 | GGTTCACTACAGAGCGTCTCAA | 632 | ATGTACCTTTTGGGCCTTGC |
| rs729334 | 633 | CCACCAACCTGCCTCTGG | 634 | TGATTTGTGATCAGTCTTCCTCTT |
| rs747190 | 635 | ATTCTTCCTCCTGCAATCCA | 636 | TTTGGAAGTCGGTGCTAACC |
| rs751137 | 637 | GGCTTGCTTAACATGTGCTG | 638 | CAAAGATTGCAGATAAAGTGCT |
| rs765772 | 639 | TTCCTTGGCATTTTAGTTTCC | 640 | TCCCATGTAACACCTTTCAGA |
| rs810834 | 641 | TTTGCATTCTCCTGTCTCTTTTT | 642 | GGAACCACTACAGGAAACGAA |
| rs827707 | 643 | TTTTGCCAAGCTATTCACAG | 644 | CTCCATCGAGGGATTATCAGA |
| rs876901 | 645 | GCACCTATTCACAGACAGTTTGA | 646 | AGAATCTTCCGATTCTGCAT |
| rs895506 | 647 | GCCCCTATAATCCTTGGAGTC | 648 | GAGGAGCCAAAGAGCTGAAA |
| rs930698 | 649 | GGTTTCATTACTCTATGCTTCTTC | 650 | AGGAGATGTGCATTTCAGCA |
| rs937799 | 651 | CAGGACAGGAATTAGTGTTGC | 652 | TTTTAAATACTACGGAGTCAAAC |
| rs955456 | 653 | GCCCTTGAAAAGAGGGCTTA | 654 | GCAGGATATTCTCTGACTGCAA |
| rs974807 | 655 | AAAGAGTATAGGGATGGACACTGA | 656 | CGTGTAGTAGTCACCCGGTTT |
| rs994770 | 657 | GAAAGCCTACACGCCCAAG | 658 | TTTTCAGTGTCCTCACCTCTGA |
| rs1002142 | 659 | TCCAACTGGAAAACACCTCA | 660 | GAGCCACCTTCAAGACTCTTTC |
| rs1017972 | 661 | CAAAATTTCCAGCGCATTCT | 662 | ACTGATTCCTCGCAGCCTTG |
| rs1057501 | 663 | ACTGCATTGTGGCGGTATCT | 664 | AAAAGTACATGATGCATTTAAGC |
| rs1145814 | 665 | AAAACATAATTGAACACCTAGCA | 666 | AATAGGAGGCTGCTCTATGC |
| rs1278329 | 667 | CGCTGGTAAATACTTAGAGATAAA | 668 | ACATGTTCCCCATTGCTCA |
| rs1336661 | 669 | CAGTCTTGTTGTATTCCCTAAAGA | 670 | GCAACTGAGAGGATGAGGTTG |
| rs1340562 | 671 | GACCTAAGACTAGTGCCGTGAA | 672 | GTGCAAAGGAAACCAGGAGA |
| rs1356258 | 673 | GGAATAATATATGTGGACTGCTT | 674 | TTACCCTTAAAAATTCCTTGG |

TABLE 6-continued

| | | | | |
|---|---|---|---|---|
| | | Panel v2 | | |
| SNP | SEQ ID NO | First Primer Sequence | SEQ ID NO | Second Primer Sequence |
| rs1396798 | 675 | AAAGCAAATGGTTAAATAGCAGA | 676 | TTGGTTCTTTCTCTTTAATTGTG |
| rs1406275 | 677 | CAGAGAGAAAGCAGTTTGAATTTG | 678 | CCAAGATACCTTGCCTTCTGA |
| rs1437753 | 679 | CATCATATTCCTAACTGTGCTCAT | 680 | TCCTTGGTAAAGAGGGTAAAGAAA |
| rs1442330 | 681 | TACTGCCAACAGACAACTCG | 682 | TTAGACCGCAGACCTTTAGAA |
| rs1444647 | 683 | GTCTACTTCAAATCATGCCTC | 684 | CTACATGCATATCTGGAGAC |
| rs1482873 | 685 | ACTGAGGAGTAATTCATGAGG | 686 | TGGTTTTACCTTTCTGAAAAACA |
| rs1512820 | 687 | CACCTCCTAAGACAAAATGGCTA | 688 | CCTAATCCAGCAGACCATGT |
| rs1517350 | 689 | GGAGGCAGAAATTGCATCAG | 690 | GCATAGCCAGCCATTAGCAT |
| rs1566838 | 691 | TCTCAGAGCAACATGTACCAAAA | 692 | GCCCAATCAGACATCAATCC |
| rs1584254 | 693 | CCTCAAGGCCTCTCCATTG | 694 | GAAGAGTTTTGACTTTTTCTGAGG |
| rs1610367 | 695 | ATCCCCAAGCCCAAGAAG | 696 | ACAGCCATGAACGAAGCATT |
| rs1714521 | 697 | GGCTCATGAACTAAGATAGTTTGG | 698 | AAGAAAGATTGTGGGATTAGACA |
| rs1769678 | 699 | CCATCAGAGCTTAGGGTTGAA | 700 | TTGGAGGAGAAAGGCATCAG |
| rs1979581 | 701 | CCATCTTAGTTGGAAATAGCAACC | 702 | CCATCTTCTTTTCCCAAGCA |
| rs1990103 | 703 | ACATGCTCCTAGGGTGCTTC | 704 | TTCTTGACGGTGTTCTGTTTTT |
| rs2004187 | 705 | CCCTTGTTGGGGAAATAACA | 706 | CCCTATTTCCTACTGAACGCTTA |
| rs2010151 | 707 | TTGGAATGTCCATCCTTTGAG | 708 | CAAACCCATGGCCTTGAA |
| rs2022962 | 709 | GGTATGTATGTGGGAAGGGAAT | 710 | AAGGTTATGTAAGAAAGATGTCA |
| rs2038784 | 711 | AAGGAAGAATTCTCAATGACCT | 712 | TGGGGCTAAAAGTCAGACCA |
| rs2040242 | 713 | TTTAAGATATGCTCTCTCCTGACT | 714 | CTATTAGTTAGGTTTCCAGTTGA |
| rs2055451 | 715 | AGGAAATCTGTGAGTAACTATCAT | 716 | CCTAATAGACCTAACCAAGGATGC |
| rs2183830 | 717 | GCAATGATAACAAGAACACAGCA | 718 | TGGAGCCAAAGGGAGTAATA |
| rs2204903 | 719 | TCTCTCCACCTTTCCACACTG | 720 | TGTGTGAAACCTGTGACTTGC |
| rs2244160 | 721 | CATATTCATACCTTCAAGCCAAC | 722 | TGTGGAAACACAGCCCATT |
| rs2251381 | 723 | GAAAGGGATGATGGTTCCAA | 724 | CCCATGAACACATTCACAGC |
| rs2252730 | 725 | CAGGAACTCGCTGAATACCC | 726 | CAGAGGAGCACCAGCCTATG |
| rs2270541 | 727 | GCCATGAATTAGGAGCCTTG | 728 | CAATCCAACGAAGATGACCA |
| rs2291711 | 729 | ACCATGACCTGGCTTGAAGT | 730 | GGACGATCAGGTTACACCTAAAA |
| rs2300857 | 731 | TCCACCTCCTAACCAAGGAC | 732 | CAGCTGAACACTGAGATTTTT |
| rs2328334 | 733 | AAGCCCTGTTTCCCTGTTTT | 734 | CATCTGCAGAAGACAGACTC |
| rs2373068 | 735 | ATCATTCCCGGAGCTCACA | 736 | GACACAATGTGCCTTGAAA |
| rs2407163 | 737 | GTACAGCTGGAATGGCCAAG | 738 | CCCAGTTTCCATCCTCAGTC |
| rs2418157 | 739 | AACAATTTGCTCTGAGAACCTC | 740 | TCTTGGCCTTCAGGGTTTC |
| rs2469183 | 741 | CCTTTGTTACTAAGAATTGAAGTG | 742 | TCGTTTCTTATTGTCTTCTGTT |
| rs2530730 | 743 | CTCCCAATATCCGACAGCTC | 744 | CCACCTCAGGACAGGAGAGT |
| rs2622244 | 745 | TGGATTGATGGCAGAACATT | 746 | CTGAGGGCTTTTTGGCTAAC |
| rs2794251 | 747 | TTTTATTTTTCTCACAAGCCTGA | 748 | TCAGAGAGATAAAGAAGGAAAGGA |

TABLE 6-continued

| | | | | |
|---|---|---|---|---|
| | | Panel v2 | | |
| SNP | SEQ ID NO | First Primer Sequence | SEQ ID NO | Second Primer Sequence |
| rs2828829 | 749 | TCTAATTAAGCCATGACTCC | 750 | GGCTGTGGTATGGCTAGCAG |
| rs2959272 | 751 | CACAGAGAAAGAACAGAATCTGAA | 752 | AGGCAGACAGATGGACACAT |
| rs3102087 | 753 | GAGCTTTGCATGCAGTAGGG | 754 | CCCAGCCTCTCTGTCTATGG |
| rs3103810 | 755 | TGACTTCTATCACCCCTACC | 756 | GTGCAGGAGAGGAAAGCAGA |
| rs3107034 | 757 | GTTGATGACACCCACATTCA | 758 | GCACGACGTACGAATGAGTC |
| rs3128687 | 759 | AGCACCAGGCTTTGGCTAT | 760 | GAAGGATGTGAGAAAAGACCTG |
| rs3756508 | 761 | GCATGGTCACTGAGTTTTGC | 762 | CAAGCCACAAGAGGTGATGA |
| rs3786167 | 763 | CACAGAACAGCTTGTGAAAATCA | 764 | TGGTACTAAGACCCACCAAAA |
| rs3902843 | 765 | AAAACCCTCTAACTAGGCATTGAA | 766 | GCTTGCTCTTATTATTTTGACGTT |
| rs4290724 | 767 | AGAATTTGGAACTCACTTTGG | 768 | AAACAGATCCTATTGTGTCTGGAA |
| rs4305427 | 769 | ACCTCATGCACCAGCCCTTA | 770 | AAGTGTTGCTCCCTGCTGTC |
| rs4497515 | 771 | AAAGGTCTTTCAGGAGAATTTG | 772 | AGGTGGCCATACACATGCTT |
| rs4510132 | 773 | GGTTGTCCATGTCCCCAAG | 774 | TTTGCAGTGTTTATGCCACA |
| rs4568650 | 775 | TCATGGCAATTTAAATGATGAG | 776 | TTTAAATGGTGCCTTGTTTCTT |
| rs4644241 | 777 | CAGGGCACTAACTGAAAAAT | 778 | GGGATATGGATTATCTTTCTCAT |
| rs4684044 | 779 | AGCCCCAAACTAAGTGCTGA | 780 | CCCAGAGCCAGTGCATTTA |
| rs4705133 | 781 | TGATGAGAAAACACAGAAATGC | 782 | CCTGGCTGAATCAAGGAAGA |
| rs4712565 | 783 | CAGTGACAGTTTTCTCATTAAGC | 784 | TAGGAACAATCCCCAATCCA |
| rs4816274 | 785 | TGAGAAACTCACTTGGGGTCA | 786 | TGACAGCAATTCTGGTCTGC |
| rs4846886 | 787 | AGGCTTGAAGAAAAGCTTCAT | 788 | CTTTTTCATATCCAGTATTTCAG |
| rs4910512 | 789 | CAGCTAGAATCTATACAAGGAAGG | 790 | GGATACAACAGGAACTAGGATCAA |
| rs4937609 | 791 | CCCATTATTATGCTGTTATGCTG | 792 | TCTGAGAGTTAAATCCTTGGTGA |
| rs6022676 | 793 | CACCTCTTAACAGTTTCATTTT | 794 | GGCCGACAGCTTCTACTTTA |
| rs6023939 | 795 | AAGGAGGGCTTAGCTAGTTG | 796 | GCTCTTTCTCATCTTAAGGCTTC |
| rs6069767 | 797 | GTTAAAATTACTGTTCCAGTTGT | 798 | CAGGCAACCAAATAATAACAAAA |
| rs6102760 | 799 | GGATTCTGCAGACCCTCAGT | 800 | CACCTTGCCACTCACTGTTG |
| rs6434981 | 801 | GGGTTCCAGCAATATTCTACCTT | 802 | GGTAATGAAGAAAGACAAAACA |
| rs6489348 | 803 | CTGTGTGGCTGGGGAAGC | 804 | GCACATAACCTCAGAACCAG |
| rs6496517 | 805 | GGAGCCCCAACCCTAATTT | 806 | ATCCTCATCCTCCGCACA |
| rs6550235 | 807 | CGGTAGCTAAGTATCTGCTTTTT | 808 | GGGCAGGAATTATTATGTTCCA |
| rs6720308 | 809 | GGATGTTTTTGCAGTTTATT | 810 | ACTTGCTCTGATACCTAAATGA |
| rs6723834 | 811 | CGGCTCTCTCCTCATTCTGT | 812 | GCATTGCCACTGAGACATGA |
| rs6755814 | 813 | AAGAGGAGGGCTTTGAGTCC | 814 | TTTAGTAGAGCTACTGATCATTCC |
| rs6768883 | 815 | CAATTAAGTCAGGTAATAATGCTG | 816 | AAGCCATTCATTTGGGTTTG |
| rs6778616 | 817 | TTGATTCCTATTGAGCTTTCA | 818 | GGCCTCTGACATCACTCTCA |
| rs6795216 | 819 | GGCAAGGGTTTAGGACTTGG | 820 | GGATTGCGCCTCAAAATAAA |
| rs6834618 | 821 | CTTCCCTGCACATCCTTTTG | 822 | CTGTTTAGGAAGAGTCATGTAACC |
| rs6840915 | 823 | TGGCCTATTTCTCAAATGCAG | 824 | CTGCAAGGCACGATCTATGA |

TABLE 6-continued

| | | | | |
|---|---|---|---|---|
| | | Panel v2 | | |
| SNP | SEQ ID NO | First Primer Sequence | SEQ ID NO | Second Primer Sequence |
| rs6848817 | 825 | GTGATTCTAACAGGTATGTAATGA | 826 | TGCATGTTAACACCACATTGAG |
| rs6872422 | 827 | GGAGACCATACTGAAGTTATTTT | 828 | TTTCGAGTTGGTGGTAATTT |
| rs6902640 | 829 | TCGAAGGTAGAATTAAATGTTTC | 830 | GATAGTGACTTATAACAACTCCAA |
| rs6979000 | 831 | TGAATTGAAGGGTTTTGGAC | 832 | GCACACGTTAAGATGGTTTGAA |
| rs7006018 | 833 | GGGGAGGGAGACGTAAAAAC | 834 | TCCAGATTTTCCTGTTCATGATT |
| rs7045684 | 835 | GCACATCACAAGTTAAGAGG | 836 | CCCCAGTAGGGAACACACTT |
| rs7176924 | 837 | CAGGATGCACTTTTTGGATG | 838 | GGCTTCTCCCAGAAAATCTC |
| rs7215016 | 839 | GGGGAGGCCCTACAAGTTAT | 840 | GAAGGGAGGGGCATCTTTA |
| rs7321353 | 841 | AAAATCACATCTGCTAAATATCC | 842 | TGGACGATAGAACTTGTTAGTGC |
| rs7325480 | 843 | CCATTAAGCAGACACACCTACG | 844 | CTCCTTTGAAAGTGGATCAAA |
| rs7539855 | 845 | TCTGAAAATGGGGCTAAAACTT | 846 | TCCTTAAAGCAGCCCTAAAA |
| rs7568190 | 847 | AGTTTAGATTTCAGTCTATGCAA | 848 | TGGAGAATAGCTCCTGCAGTT |
| rs7580218 | 849 | TCTTTCTGGAGACACTCAGG | 850 | CTGGAATCTAGAAAGAAAAAGAA |
| rs7609643 | 851 | CAAAGATAGATGAGATGCTTTT | 852 | CTGACATTGAAAACTTGAAAGAA |
| rs7632519 | 853 | AGCCCTCCTCCACCGTTAG | 854 | GCCCAGCTACGATTTCTCCT |
| rs7660174 | 855 | TTTTATGCAGCCTGTGATGG | 856 | CCCTTAGTTCAATCAAGCCAAC |
| rs7711188 | 857 | CACTCTTGCAATCTCCCTCAG | 858 | CTGACCCTTGTGGGATTCAT |
| rs7765004 | 859 | CTTTTATGATATCCACCAAGACT | 860 | TGGATCATCTGTCCAAAGTCA |
| rs7816339 | 861 | CCAAAACCTGCTCTCCAAGA | 862 | AAGACTACTGAGGTTGTGCAAAGA |
| rs7829841 | 863 | TTCAACTTGGTACCCTGAAAAA | 864 | AGTCAGTTAGTATGCAGTACTTGG |
| rs7916063 | 865 | TCTTAAAAGTGTCTTGACTGAAA | 866 | GGTCAATGGCTAAATCATTCG |
| rs7932189 | 867 | GCAATTCCAGATATCTCTTTAT | 868 | TTATCTACCCATGCTTCTCTC |
| rs7968311 | 869 | GCATAAACAAATGTGTAACGTGGT | 870 | TGTTTTCGTAGTCTTTATTGCT |
| rs8006558 | 871 | TGCTAGCTATATGTAGGTCAGTT | 872 | CGTTAGTTCCCTGGAAAGATCA |
| rs8054353 | 873 | TTGCATAGATGTAGCAGTATTTC | 874 | GACTTTCTTAAAGCTGCACAATCA |
| rs8084326 | 875 | GTTTGCTTGCTTTTACTTTG | 876 | TGTGAAGCACCATTTCTGTTT |
| rs8097843 | 877 | AACAGTGAGGCTCTCCTGTAGC | 878 | CCCATTGTCACCGAGGATA |
| rs9289086 | 879 | CAGAGAGCTCACTTCTAGTTCTGC | 880 | GCTATCTTGGGTCATGAATTTG |
| rs9310863 | 881 | CCTCATGCAATTCAAAGGAA | 882 | CATTTCCCCTAGGTTTGTGC |
| rs9311051 | 883 | GTGGGGCACACAGTGTCTT | 884 | CTTAGATTTGTTCATCTGATGGT |
| rs9356755 | 885 | TTGGGTAGATGCAATGCAAG | 886 | AACCCATATGACTAAGGTGAA |
| rs9544749 | 887 | GCTGAAAATTCACACTGTGGTC | 888 | TGTCATAATGAAGAGCTAGTTGC |
| rs9547452 | 889 | GAGAGGTAAGAGAGAGTATCTTTG | 890 | GAGTTATTTCCCTTAAAAACCAG |
| rs9814549 | 891 | GCTACGCTTGACACCCTTACA | 892 | GGATGCTGTGAGTGCTAAATGA |
| rs9861140 | 893 | GGCACTGCGTCAGCATACTA | 894 | CTGGCTCCTTGCCATCAT |
| rs9919234 | 895 | TAGGCCTCAGAAAGAACGAG | 896 | TGCTAGGCTTACTTCGTTTTC |
| rs9955796 | 897 | AAAATAATTCCCTTTGGTATGC | 898 | CATCATGAATTCTCCCAATGC |

TABLE 6-continued

| | | Panel v2 | | |
| --- | --- | --- | --- | --- |
| SNP | SEQ ID NO | First Primer Sequence | SEQ ID NO | Second Primer Sequence |
| rs10073918 | 899 | TTGGGTAAATGTGTGACTACGC | 900 | TACCTGGGGCCCTGATTTAT |
| rs10096021 | 901 | GCACTGAAAATGTTAGTGATT | 902 | CCTTAGTGAGGTATTTAGGTTACA |
| rs10197959 | 903 | AGGGAGTTATGATGCCAAGG | 904 | TGATCAGGGGTAGAAGAGATTT |
| rs10233000 | 905 | CGGCTTCCAATCGTATCTTG | 906 | GACAAGTCAGAGAACAAGCTG |
| rs10444584 | 907 | TCATCTGTAACTAATGAACCTTG | 908 | TCAGGAAAGAATGCTACTCA |
| rs10473372 | 909 | AATTGGATGCTGTTTTAACC | 910 | TGCCACATGACAAATTATCACA |
| rs10777309 | 911 | CCAAGGTTTAGCTACATGTATAA | 912 | CTGATAGAAAAATTTCTGTTGTG |
| rs10783507 | 913 | ATTCCTTCCCGCCTTGCT | 914 | ATTCCTGCACAGGCTCAGAC |
| rs10802949 | 915 | AAATGTTCAGTGTAAAAGGCTACA | 916 | AAAGGACTAGCAGCATGTAACTC |
| rs10816273 | 917 | CACTACTTCCCCTTCCCAAA | 918 | AAGATCTGGTAGAAATAAATGGA |
| rs10817141 | 919 | GCTTCCAGGCTAAAAGAAGG | 920 | AAAAAGAAAAGCTGGTTAGG |
| rs10892855 | 921 | CACCTCTATGGTTTAGTCCACTCC | 922 | CCTGGGATTGAAAGCACCTA |
| rs11098234 | 923 | GGAATTGCCACTCTGGAGAA | 924 | AGTGGTCCCCAACAACTTGA |
| rs11119883 | 925 | TCAGATAAAACAATTCCAGTTAC | 926 | ACCCACAGAGGAAAGCCTTG |
| rs11157734 | 927 | CCTGCTGGCACACGTAAGTT | 928 | CCATGGGAATTTGAACCACT |
| rs11166916 | 929 | AACCACAATCCACCTCTTGC | 930 | GCCAAGTCATTAACACAAAGTGA |
| rs11223738 | 931 | CCCACTCTTCTGCTTTACTCCA | 932 | GAGAAGGGGAAAGAGAACAAA |
| rs11247709 | 933 | GGCTTTTTCCACCCAGCTTA | 934 | AGTGGGCAATAATAAACCTT |
| rs11611055 | 935 | GGTGGCTGGAGAAATTGAGA | 936 | AAAGACAATTTGGCTGGTGTTT |
| rs11627579 | 937 | GCTAAGTTGCCTCCAAGCTG | 938 | TTCCCTATTTCTGCCAAAGC |
| rs11636944 | 939 | TTCATGGAGATTTGACCAGTG | 940 | CAGATACTCCTTTTTGGAGAGTCA |
| rs11643312 | 941 | CAGCTAATGCATAAGGGAGATG | 942 | CCAGAACATTTCATCACTCCAA |
| rs11738080 | 943 | GTACAGAGTCCCTGTCTCACA | 944 | CATGATCTGTCTCTCTCACTGAA |
| rs11750742 | 945 | GTGGCAGAACTGACATGCAA | 946 | TGTGGGGGCAGACAGACT |
| rs11774235 | 947 | TCCACCAGAAACCCTTTGG | 948 | CCTCTGTGGAAAGGAAGGAA |
| rs11785511 | 949 | CCCGCTCCAGGTTATTCTC | 950 | AAGAAATCTGAAAAGCAGAGG |
| rs11924422 | 951 | AACTGATTCACATGAGGTTGC | 952 | TTTGAGAGGCAACATTAACAA |
| rs11928037 | 953 | AGTCTGTACAAGGGGCCACA | 954 | TAAGGCTCCTGTGGTAGACG |
| rs11943670 | 955 | CATCATGGAAGGTCCCTCAC | 956 | CAAGATCAAGGCATTGGTAG |
| rs12332664 | 957 | AGGTTCAGATTCTATTTCTGTCA | 958 | CCTTGCCTAAGATAACACAACCA |
| rs12470927 | 959 | TGTTTTGTAATTCCTTTCAGTCA | 960 | CCTCAAATACTGAAGATAGCAAGC |
| rs12603144 | 961 | GACAAGAACTGAAGGCAAAGG | 962 | GGGAGGAACAGAACAACCTTC |
| rs12635131 | 963 | TCGCAGTCTTTTGCATCATT | 964 | TCCAATAGCTACCTTCACCAGAA |
| rs12669654 | 965 | GGTTAAATTCTACTTCGCAACCA | 966 | GCAGTGTAGTCTAACTAGCTGTGT |
| rs12825324 | 967 | CAGCTTCCCAGTTTCTCACA | 968 | AATTGCTACATTCCTGTCTATTG |
| rs12999390 | 969 | GCGGAAAGACATTCCATGTT | 970 | TGCATCTCAATGATATTGCTTTT |
| rs13125675 | 971 | TCTCTGAGAGCAAAGACACT | 972 | TGTGCAATAGTAATAATGGGTCT |
| rs13155942 | 973 | GAGGGTACCTTTCTTTCTCC | 974 | GCTCAGTGTCTGACAAAAGC |

TABLE 6-continued

| | | Panel v2 | | |
|---|---|---|---|---|
| SNP | SEQ ID NO | First Primer Sequence | SEQ ID NO | Second Primer Sequence |
| rs17361576 | 975 | TGGCTGCCTAAAATTATTTACGA | 976 | AAGCAAATAAGGCCATCTAAGAA |
| rs17648494 | 977 | TCAAACAAAAACAGTGTAGGCATT | 978 | GAAAAGTTAAGTCAGAGGCTATCG |

TABLE 7

| | | Excluded SNPs | | | |
|---|---|---|---|---|---|
| SNP | SEQ ID NO | First Primer Sequence | SEQ ID NO | Second Primer Sequence | Reasons for exclusion |
| rs31036 | 979 | AAGTCACCTAAATGGCATGA | 980 | AGACACAGCAAGATGCAAAA | High Unmapped Reads |
| rs42101 | 981 | CAGCAACCCTTTGAAGCAAT | 982 | TGTTTTCTCTTCAAATGCAA | High Unmapped Reads |
| rs164301 | 983 | TGACTCAGTGGTGAACTGTCT | 984 | GCAGCCCATTAATACTAGCACA | High Unmapped Reads |
| rs232474 | 985 | TGCATTCAAGAGGAAGAAAGG | 986 | TCAGGACGAATTCACAGGAT | Low Depth |
| rs235854 | 987 | ATGAAGGCCAGGCTGTAGG | 988 | GAACATTCACTGCCTTACTCTCA | High Off-Target Reads, Low Depth, High Unmapped Reads |
| rs238925 | 989 | TTCAGTGAAGGGATGGACCT | 990 | GGCCACAGGATCTCCTATCT | High Unmapped Reads |
| rs242656 | 991 | CCAAGTAATCACTTCAACCCTCT | 992 | GCTAGCTACGCCCACGAGAT | High Unmapped Reads |
| rs243992 | 993 | AACTCAAACCTAAGTGCCCC | 994 | GGAATGGAATAGTGTGTGGG | Low Depth, High Unmapped Reads |
| rs251344 | 995 | ACACTGGTCTCAAGCTCCC | 996 | CACACCTGTAATTCTAGCCC | High Off-Target Reads |
| rs254264 | 997 | AGAAGGAAGGATCAGAGAAG | 998 | AGCTTTCCTCCCCACACTG | High Off-Target Reads |
| rs265518 | 999 | TAACAAATTTGCATGTCATC | 1000 | AGAAGCCAGGTGCTGAAGTG | High Off-Target Reads |
| rs290387 | 1001 | GCTGTGTGGAGCCCTATAAA | 1002 | GAATGAAATGGAGTTTGCAG | High Unmapped Reads |
| rs357678 | 1003 | GGCAGTGTTTAAGGTGTTGG | 1004 | AGGTAGTGATTTCTAGGCTTATCA | High Unmapped Reads |

TABLE 7-continued

| | | | | | |
|---|---|---|---|---|---|
| | | | | | Excluded SNPs |

| SNP | SEQ ID NO | First Primer Sequence | SEQ ID NO | Second Primer Sequence | Reasons for exclusion |
|---|---|---|---|---|---|
| rs378331 | 1005 | CCTGGAAGTATTCATTCATGT GG | 1006 | GGGACATCTGGGTAGCACTG | High Off-Target Reads |
| rs425002 | 1007 | AAGAGTGTCTCCTCCCTCTG | 1008 | AACTGGAGGCTGTGTTAGAC | High Off-Target Reads |
| rs447247 | 1009 | AAAAACCCCAGGCTCCATTG | 1010 | ATGTCCAGCTGCTTCTTTTC | High Off-Target Reads |
| rs499946 | 1011 | ATGGCTTGTACTTCCTCCTC | 1012 | TTCGGTGGAATAGCAGCAAG | High Unmapped Reads |
| rs516084 | 1013 | AGTATGCCATCATGAAAGCC | 1014 | CTTCTTTGACTAAGGCTGAC | High Unmapped Reads |
| rs602182 | 1015 | GATCTTCCAGGGGGCACT | 1016 | TCATTTTGGTITCGTTCATT | Low Depth |
| rs621425 | 1017 | CCTTTTGTGGCTTTTCCTCA | 1018 | GGCATTCCAACATGAAAAGG | High Off-Target Reads |
| rs642449 | 1019 | CAGCTGCTGTTCCCTCAGA | 1020 | CCAAAAAACCATGCCCTCTG | High Unmapped Reads |
| rs686106 | 1021 | GGTTCACAGAGCCCAAGTTAC | 1022 | TGAGTCTCTTACTGATCCTGT GAC | High Unmapped Reads |
| rs751834 | 1023 | CTTCCCTCTGCCTCTTTTAGA | 1024 | CCAAAGAGCTCAGGTCTCCA | High Unmapped Reads |
| rs755467 | 1025 | AGGTGAGCATGGGGTTGATA | 1026 | ACCTCTTCCTTCCTCACCAA | High Unmapped Reads |
| rs842274 | 1027 | GGCAGCTCCACACACCTTAG | 1028 | TCATCTTTTGGTTTTAGATTG TG | High Off-Target Reads, High Unmapped Reads |
| rs893226 | 1029 | CAACTGCCCGCTTATCCTT | 1030 | AAGACAGCTTGAAGATTCTG G | High Bias |
| rs898212 | 1031 | AAGGTCTAAGGGGGCACAAG | 1032 | ATGGCCACGCTCTTTGTC | High Unmapped Reads |
| rs949771 | 1033 | CCAGATTATCTTCTTCGCCCTA | 1034 | TGATTAGGGTTGGGAAGTG G | High Off-Target Reads |
| rs955105 | 1035 | TTCAGCTCTTCTACTCTGGACT G | 1036 | TGAAACAAGAGAAGACTGG ATTTG | High Unmapped Reads |
| rs959964 | 1037 | CAAGTTAGTGAGAAACAGAG TCG | 1038 | GGCCTCTACTCCAAGAAAGC | High Bias |
| rs967252 | 1039 | GTTATATCTCTTTTGTTTCTCT CC | 1040 | TTGGATTGTTAGAGAATAAC G | High Bias |
| rs1007433 | 1041 | GTCCAGCTGTGTGATTATCT | 1042 | AGAGGGAGATGGAATAAAA A | Low Depth |

TABLE 7-continued

| | | | | | |
|---|---|---|---|---|---|
| | | | | | Excluded SNPs |

| SNP | SEQ ID NO | First Primer Sequence | SEQ ID NO | Second Primer Sequence | Reasons for exclusion |
|---|---|---|---|---|---|
| rs1062004 | 1043 | AAAAATAAACATCCCTGTGG | 1044 | ACATAGCCACCAGCCACACT | High Off-Target Reads, High Unmapped Reads |
| rs1080107 | 1045 | TGCTCTTTTTCTCACAAATGA | 1046 | ATATTGGTCAGTGGGGCAAA | High Off-Target Reads |
| rs1242074 | 1047 | GCACATGAGCTGAGACTGGA | 1048 | TGGCAGTATTACCTGAGCAA | High Off-Target Reads, High Unmapped Reads |
| rs1263548 | 1049 | GCAGCGTCTTGCCTCCTT | 1050 | GCCCAGCTCTTAACACAACA | Low Depth |
| rs1286923 | 1051 | AAAAGGCTGGAGGATGAAGG | 1052 | TCAGAAGGCACCTCTGTCAC | High Off-Target Reads, High Unmapped Reads |
| rs1353618 | 1053 | TGCAACCAAAACTCAGTTATCTA | 1054 | TCCCTTGCCTATCATTGCTT | High Unmapped Reads |
| rs1355414 | 1055 | TTCCCAGCCTTCCAGGAG | 1056 | TACAATGGCTGACTGAGCAC | Low Depth |
| rs1418232 | 1057 | TGATTTAAACCTGATCTTGGTGA | 1058 | ATTCCTGTCCACCCTGGTC | High Off-Target Reads, High Unmapped Reads |
| rs1474408 | 1059 | CCTTTGATCACAAGCAACCA | 1060 | TTACTCTTGGGTCAGGTGCAT | High Unmapped Reads |
| rs1496133 | 1061 | ATGGCAGAAGAGCCCAGAG | 1062 | CGATGCTGACCTTCTGGAGT | High Unmapped Reads |
| rs1500666 | 1063 | GCTGAAAAACCCAGGAATCA | 1064 | GGAGTTGAGGGAGAGGGTCT | High Bias |
| rs1514644 | 1065 | GACAGAATGAAATGCTGTGT | 1066 | CTTTCTAATCCAGCAGCCTCT | High Off-Target Reads, High Unmapped Reads |
| rs1565441 | 1067 | CTGATCCCCGTAAGATCAGC | 1068 | CAGGATGAAACGGTGCAG | High Bias |
| rs1674729 | 1069 | TCTCTGACCTGCTTCCTCGT | 1070 | TAAGGCAATAGGCACCAAGC | High Off-Target Reads |
| rs1858587 | 1071 | AGCAATGGGGTCAGAGTCC | 1072 | AGCTGATTCCTTCCCTGGAT | High Off-Target Reads |
| rs1884508 | 1073 | CCTGATGGAGGATCCACTTG | 1074 | CTGCAAAGCTTCCCATCCT | High Off-Target Reads |
| rs1885968 | 1075 | GGGGATCTTAAAAGCACCAA | 1076 | GACACTCCCACTTCTGCCTA | High Off-Target Reads |

TABLE 7-continued

Excluded SNPs

| SNP | SEQ ID NO | First Primer Sequence | SEQ ID NO | Second Primer Sequence | Reasons for exclusion |
|---|---|---|---|---|---|
| rs1894642 | 1077 | ATTTCTTCAAGTGTATACAGA GC | 1078 | CAGGCAAACATTCCCTTGTA | High Bias |
| rs1915616 | 1079 | CACTGTTGACTCCAAAACAAA AA | 1080 | CTTCCCACAACAATGAGCTG | High Off-Target Reads, High Unmapped Reads |
| rs1998008 | 1081 | GCAGCTAAGAAAGACTCTCC AA | 1082 | TCTTTGCTCCCCACCTATT | High Unmapped Reads |
| rs2056123 | 1083 | TGAATTCAACTGATGGCACA | 1084 | AAGATTTAATCCTITGAGAT GC | High Unmapped Reads |
| rs2126800 | 1085 | TGAAAGGACCCACCAAATGT | 1086 | TTTTGTTGTGTGTTTGCTTT | Common Deletion in Primer Binding Region |
| rs2215006 | 1087 | TTGCTGGCTTACATTCATTCC | 1088 | TACAGCTCAGCCAGTTCTGC | High Off-Target Reads |
| rs2226114 | 1089 | TGGTTGGTATGGTTATTATTG G | 1090 | GCCTTAGTTTCTCTTTCTGTA AAA | Low Depth |
| rs2241954 | 1091 | GGCCAGCACAAACACACC | 1092 | TCCTAGGACTCTCCCTTTAGA | High Unmapped Reads |
| rs2278441 | 1093 | AATGGGCAGATGAGAGCAAG | 1094 | CCAGTACCTACCCCATGTCC | High Unmapped Reads |
| rs2285545 | 1095 | TCCTTTTGACAGGTCCACATC | 1096 | TGGCCCAATTTTCAGTAACTT C | High Unmapped Reads |
| rs2288344 | 1097 | CACCAGGGGTAGAAGTAAGA CG | 1098 | GAGTATCCATGCCCAGAACC | High Bias |
| rs2292467 | 1099 | TGCATGTCTGTATGTGTGTTG G | 1100 | ATGCTCCCACTGCATCCTTA | Low Depth, High Unmapped Reads |
| rs2300669 | 1101 | AAATGAAGAGCCAGCAGCAT | 1102 | CCCACCAACACTAACCTAGC A | High Off-Target Reads |
| rs2300855 | 1103 | ACATCTAGCTGAGGTCAGAA | 1104 | TGTGCAGATTTATGCAAATC AA | High Unmapped Reads |
| rs2362540 | 1105 | GGGAATTTCTCTGGTTGGAG | 1106 | AAACACAGCTTCATGACAAG | High Off-Target Reads, High Unmapped Reads |
| rs2376382 | 1107 | GGACTGAGCATATGTGGAAA | 1108 | CCTGAATTTTTACTTCTTTGCT T | High Unmapped Reads |
| rs2430989 | 1109 | TTGCTGAGTAACAGGAAAAC AA | 1110 | TGCTAAACCATTAAATAATCT GG | High Bias |

TABLE 7-continued

Excluded SNPs

| SNP | SEQ ID NO | First Primer Sequence | SEQ ID NO | Second Primer Sequence | Reasons for exclusion |
|---|---|---|---|---|---|
| rs2442572 | 1111 | GATGCTAAGCCCATCTCCTG | 1112 | AGGGTAGGAAGGATGCAATG | High Unmapped Reads |
| rs2509973 | 1113 | GGAGCGACCACTCTTCATTT | 1114 | CTGAAGGGCTCCCAGGCTA | High Off-Target Reads |
| rs2518112 | 1115 | GAAGATTTTGTAGCTGGTCTTGG | 1116 | CCACAATGGTTTGTAAGATTT | Low Depth |
| rs2545450 | 1117 | TGCGTTCTTTGGAGATAAGACC | 1118 | CACATTTCTCACCCATGTCAA | Common SNPs in Primer Binding Region |
| rs2569456 | 1119 | GTTCCCTCATCTGCCCTTC | 1120 | TGTGAGATGAGTGGAGAGCAA | Low Depth |
| rs2632051 | 1121 | TAAATGTGCCTGGCTTGATG | 1122 | CCCTTTCCTTCCTTGGATGT | High Off-Target Reads, High Unmapped Reads |
| rs2732954 | 1123 | TGCAAGGACACCAGAACAGA | 1124 | CATTTGCACAGCATCTGACC | High Bias |
| rs2786951 | 1125 | GGGTGAGATCAAATTCTTAGGC | 1126 | TTCTAATATGTATTTGGGAGAGAG | High Unmapped Reads |
| rs2822493 | 1127 | GCCATGTITTCATCTTGTGG | 1128 | TCTGTAAAGGACTTCATGTTTCAT | High Unmapped Reads |
| rs2881380 | 1129 | TCCTGCCATCTTAATAGTCTCACA | 1130 | CTTGTGGCCTCTCATTCTCC | High Unmapped Reads |
| rs2906967 | 1131 | TGTTAATGTAAAATTGCCTCGAT | 1132 | GAGCTCTGGCATTTCTCTGC | High Off-Target Reads |
| rs2920653 | 1133 | TGCTGGAAAGTCATTTTGA | 1134 | TTGGCATTATTTGTGATCC | High Bias |
| rs2993998 | 1135 | CCACACTCCCCAGACCAG | 1136 | GGGAAGACCAGAACTTCAGAAA | Low Depth |
| rs3736590 | 1137 | CTCTTGCCTTCTCATTCACAA | 1138 | CTTTCCTCCCTTTGGGACTC | High Unmapped Reads |
| rs3750880 | 1139 | CCCACGCACTGTACCACA | 1140 | TCAGGGCGAGATACACCTTT | High Unmapped Reads |
| rs3778354 | 1141 | GCCAGCTCAGCTCCTCTCT | 1142 | GAGGGAAATTCGAGCATCAG | High Off-Target Reads, High Unmapped Reads |
| rs3907130 | 1143 | GGCACTCAATAAACATTGACACA | 1144 | GGGAGAGAGGTGTTCTCAGC | High Unmapped Reads |
| rs4075073 | 1145 | CGCAATACCTTCAACAGCAG | 1146 | GGTGGGCTGCATTCATAAAG | High Off-Target Reads |

TABLE 7-continued

| | | | | | |
|---|---|---|---|---|---|
| | | | | | Excluded SNPs |

| SNP | SEQ ID NO | First Primer Sequence | SEQ ID NO | Second Primer Sequence | Reasons for exclusion |
|---|---|---|---|---|---|
| rs4313714 | 1147 | TGCCAAGAATCCACTCCAAG | 1148 | GGGGAGGGAGAATTGGACTA | High Unmapped Reads |
| rs4502972 | 1149 | CAAAGAAACAGAATGAAAAAGTGG | 1150 | CACCAACCTGGAATGCTTACT | High Unmapped Reads |
| rs4642852 | 1151 | TGACTGCTCTAAAATCTTTGTCA | 1152 | ATACGCCAAACAGTGAGATG | High Unmapped Reads |
| rs4708055 | 1153 | TGACCTATCTATAACCTGTCCAC | 1154 | TGGGAATTTTAGTTTCTCTGTCT | High Unmapped Reads |
| rs4717565 | 1155 | ATTGATCTATGTGTCTGTAGCTT | 1156 | AATTAAGACAGTGTGGTATTGG | High Off-Target Reads |
| rs4768760 | 1157 | TTCAGAGAGGGACACCCTTG | 1158 | TTCTTCGCAACCACACTTTG | High Bias |
| rs4793426 | 1159 | GAGGCTCTCTGGGGCTTG | 1160 | AGCCTTCCACCTGATTGAAA | High Unmapped Reads |
| rs4845835 | 1161 | AGAGTCATGCATCCTTCATT | 1162 | TGGTGGAGACACAGATCCAA | High Off-Target Reads |
| rs4880544 | 1163 | GCAGCAGGAACCATTCACA | 1164 | CACTTGTGTCCTCCAACATT | High Unmapped Reads |
| rs4903401 | 1165 | CCCCTCAGAGTGATGACTGG | 1166 | CTCCTGACCCAGCCACTTT | High Unmapped Reads |
| rs4909472 | 1167 | GAAAATCTTGTGGAGCCTGAA | 1168 | AGAGAGGAGATGGGGGAAAG | High Unmapped Reads |
| rs4909666 | 1169 | TGAGCCTACACTAACACATCA | 1170 | GCCCTAATGTAAACTAAAGACGTT | Low Depth |
| rs4927069 | 1171 | GGAAATGTGACCCTCACAGG | 1172 | TTTTCCATACCTAAAGAACG | Low Depth, High Unmapped Reads |
| rs4945026 | 1173 | CATCATCTCTTCCTTATGTTCTCC | 1174 | GGCCTGGGGGTGCTAATG | High Off-Target Reads |
| rs5009912 | 1175 | GGGTGGTCTGGTGATGTGTT | 1176 | GCTATGCCAAGGGAACCTAGA | Low Depth |
| rs6082979 | 1177 | GGGAGTACTCTCCAAAGC | 1178 | CCTCCTGTCACTTTCCCTCA | High Off-Target Reads, High Unmapped Reads |
| rs6088301 | 1179 | TGCTCCACAGATGACACAGT | 1180 | TGGAATGTGATGGATGAGA | High Bias |
| rs6124059 | 1181 | AGCCCTGCTTCAGCTTCTG | 1182 | TTGACTACTGGAACTTGGAGAGG | High Unmapped Reads |
| rs6134639 | 1183 | TGGAAACTTCTTGTGGACCT | 1184 | GTGGGTGGAAGACTTGCTCT | High Unmapped Reads |

TABLE 7-continued

Excluded SNPs

| SNP | SEQ ID NO | First Primer Sequence | SEQ ID NO | Second Primer Sequence | Reasons for exclusion |
|---|---|---|---|---|---|
| rs6499618 | 1185 | TITCTGGGCCACCTACAAGT | 1186 | CCCAAGGTTCTGGGCTAAG | High Off-Target Reads |
| rs6538276 | 1187 | CCTCCTCCTCACACTGCTTC | 1188 | CCCTTTCTTAGCTCCTGACCA | High Off-Target Reads, High Unmapped Reads |
| rs6560430 | 1189 | GGTCTAAAGGGAGAGTAGGA GGTC | 1190 | GAATGGTCTTTTCGTCATTCC | High Unmapped Reads |
| rs6602240 | 1191 | CTTTCCCAAAACCCCACACT | 1192 | CACACACAAGGAAAAACAG GA | High Unmapped Reads |
| rs6681073 | 1193 | GCTGGATGGAGGGTGAGG | 1194 | TGCCTGCCTGTTAGAACATC | Low Depth |
| rs6682943 | 1195 | GGCAATCCGAAGTCTAAGAG A | 1196 | TGGAACCAACAACCTATCAT CA | High Bias |
| rs6700298 | 1197 | GACTGGTACTTCCCCAAGGA | 1198 | TGAAAATCCATTTGGTAGTT GCT | High Unmapped Reads |
| rs6714809 | 1199 | AAAATGACTGTCCCCTATCT | 1200 | TGGTAAGTGGGATGATACTG AGC | High Unmapped Reads |
| rs6728087 | 1201 | AAGCATAGAAGGAAAAACAG ATTG | 1202 | CCCCTGAATGAAACTATTGA GC | High Bias |
| rs6765108 | 1203 | AGCAAGGGAGGGAAGACAC C | 1204 | TTGTCAATCCTTGCTCTACCC | High Off-Target Reads, High Unmapped Reads |
| rs6788750 | 1205 | TGAAGGGTAGATATGAAGTT TTTC | 1206 | TAATCTTTGGACTCCTTGAA | High Bias |
| rs6863383 | 1207 | TGATCCCATGTATTTAAACCT | 1208 | CCCCTGAAATGAGAGTCACC | High Bias |
| rs6893628 | 1209 | CAAAATAAACCCAGGCAAAA A | 1210 | CTTTAACAAATATAGGGCGA TTT | High Bias |
| rs6986644 | 1211 | AAGTACCAAAAAGGCACATC G | 1212 | TCCCCCTAAGATCAGGAACA | High Unmapped Reads |
| rs6994806 | 1213 | TGGAACAGCAACTTGCAAAC | 1214 | AAGAGTGTAAATGGGTCCTG A | High Unmapped Reads |
| rs7098657 | 1215 | CTCCCCTGAACCTGAGTGAC | 1216 | TGCTCACATTTCATTGACCAG | High Off-Target Reads |
| rs7133402 | 1217 | TGAGGTGGGAAGAAACACAA | 1218 | TGCGACTGGATACTATTTTTG G | High Unmapped Reads |
| rs7157032 | 1219 | AGTTGCATGGAGTGGCTGA | 1220 | TGTTGGTGCATTCAGAGAGC | High Unmapped Reads |
| rs7195624 | 1221 | CAAGTAATTCTTACCAGCCTT T | 1222 | AGGCTACAAAAAGGCAGCA G | High Unmapped Reads |

TABLE 7-continued

| | | | | | |
|---|---|---|---|---|---|
| | | | | | Reasons |
| | SEQ | | SEQ | | for |
| | ID | | ID | | exclusion |
| SNP | NO | First Primer Sequence | NO | Second Primer Sequence | |
| rs7251148 | 1223 | AAGGAAACGGCCCCAGAG | 1224 | GACCCTGTGGACTGAGAACC | High Unmapped Reads |
| rs7479857 | 1225 | TCAGAGCACTCTGCATTCCA | 1226 | CTTTTTAAAGCCAGAAAAT GG | High Unmapped Reads |
| rs7521976 | 1227 | AGAATCATATGACACATGGA A | 1228 | CAGCTTATCTTTATCTGTTTG CTT | High Unmapped Reads |
| rs7564063 | 1229 | CACTTTGCAGCCAATCCATA | 1230 | CAGATCTGATTTCCTGGAG | High Bias |
| rs7608890 | 1231 | TCCATACAGGAAGATCCATTA AGA | 1232 | GTGCAGTTTGGGCTACAAGA | Low Depth |
| rs7684457 | 1233 | TGCTGCCAGAAGCAACCTAC | 1234 | AGAAAGTTGTGCCAAGTGCT | High Off-Target Reads, High Unmapped Reads |
| rs7745188 | 1235 | TGTCTGGAAATCATTGCTTCA | 1236 | CATAAAGCTAAAAGATTGGA CA | High Off-Target Reads |
| rs7763061 | 1237 | CAAATCAGTGTGCCCCAAC | 1238 | GTTTTGCCCAGAGGTCATGT | High Unmapped Reads |
| rs7820286 | 1239 | GCTCTTCCCTCAGTGGCTTA | 1240 | CTATCATTTCTCCCCAACACA | High Unmapped Reads |
| rs7830700 | 1241 | CTGGATTTCAAATTGTTTCA | 1242 | TCAAGTATCTAGTTGTGATA GCC | High Bias |
| rs7833328 | 1243 | TAGAGCAGCTAGGGGACTGC | 1244 | CGAGACTGTTCACCCTTTGG | High Off-Target Reads, High Unmapped Reads |
| rs7982170 | 1245 | ATGCCAGACTTCACCACTGC | 1246 | TTTCAGTTTTGTTATGTGGCT A | High Off-Target Reads |
| rs8053194 | 1247 | TTGAAGTTAGTTCTTTGTGGA TGG | 1248 | ATCAACTCCCCACCTGGAAG | High Unmapped Reads |
| rs9300647 | 1249 | TTTTCCCTCATTAGCTGCATT | 1250 | TGATTCCAGTTCACAGTAGTC CA | High Unmapped Reads |
| rs9371705 | 1251 | CATTTCCAGCTGACTGGTTA | 1252 | ACCCTGAGGAGGGGCTAGT | High Bias |
| rs9377381 | 1253 | GCCCAGTAGCACTGCTCTTC | 1254 | AGATCACCAAGGCAGAAACC | High Off-Target Reads |
| rs9405991 | 1255 | CCGAGAACGCTCTGAGTTG | 1256 | GGCAGCAACAGGAAATAGC A | High Bias |
| rs9522306 | 1257 | ACAGGAGTGGCTCGGTCA | 1258 | CACTGCAGGAAATGCAGCTT | High Unmapped Reads |
| rs9864296 | 1259 | CGAAATCCATAGGACCTACA | 1260 | AGCTACACTATTTCCATGTGA C | High Unmapped Reads |

TABLE 7-continued

| | | | | | |
|---|---|---|---|---|---|
| | | | | | Excluded SNPs |

| SNP | SEQ ID NO | First Primer Sequence | SEQ ID NO | Second Primer Sequence | Reasons for exclusion |
|---|---|---|---|---|---|
| rs9881075 | 1261 | AACAAGAAAGGCAGGGAAG G | 1262 | CTGGGTCACGCCTCTTGA | High Unmapped Reads |
| rs10041720 | 1263 | TACAAACAGTGGGGCAACAA | 1264 | GCCAGGCATGGGCTTAAT | High Bias |
| rs10106215 | 1265 | TTCGTCTTTCAGCAATTTGA | 1266 | AACAGAAAGAGAGTTACATC TACA | High Bias |
| rs10142058 | 1267 | CCTCATGACCTAACCACCTC | 1268 | CCCCCAATGCAAGAGTGTT | High Off-Target Reads |
| rs10444986 | 1269 | TTTCACAGTGGAATGAATCG | 1270 | GCCCAGGACACACAAAAA | High Unmapped Reads |
| rs10765992 | 1271 | CTGGTCCTCTGTGAATTGAA | 1272 | CACCGAATCTATATCTGTGA GG | Low Depth, High Unmapped Reads |
| rs10787889 | 1273 | TCTTTATGTGGCCTTCACTTG | 1274 | TATGCTGAAGCTGCCATCCT | High Off-Target Reads |
| rs10790395 | 1275 | GGGCAGGAAACAGGGACTA | 1276 | GCTGTCCTATTTCAGGTTGCA T | High Unmapped Reads |
| rs10800542 | 1277 | TCCACTGGAATTGGTAGACA GA | 1278 | AGCAATCATCCTAGGAGGTC A | High Unmapped Reads |
| rs10815682 | 1279 | TTCTGACTTCACAGAGGGTA | 1280 | GGGCAAGTCACTTAGCATTT | High Unmapped Reads |
| rs10874506 | 1281 | TTCTCAGACTTCAAAGCAAAG G | 1282 | TGAAAAGATACCTAAAATCA AGG | High Unmapped Reads |
| rs10906984 | 1283 | GAGAAGAACCAGACAGAACA CG | 1284 | ATTTCTGCAGCCCTGTGACT | High Unmapped Reads |
| rs10952780 | 1285 | CATGAAAAATAAGGAAATGC TGA | 1286 | TCCTAAGTTTTTCTGATCTGT GG | High Unmapped Reads |
| rs11058137 | 1287 | GCCTCAGTTTCCTCCTCAGA | 1288 | CCTCTCAACAACCCAGGTACT | High Bias |
| rs11153132 | 1289 | ACTGTGGCTCCAGCATGAA | 1290 | AGTCCAGGCACCACTGCTAC | High Off-Target Reads |
| rs11216096 | 1291 | GCTGGAAGGAGAGAAACACG | 1292 | ATGGCCACTAGAGGGGAGTC | High Off-Target Reads, High Unmapped Reads |
| rs11705789 | 1293 | GCATCCTGTGGTGGGAAG | 1294 | TGGTCAATAAGCCTGTTCCA | High Bias |
| rs11714718 | 1295 | GGTCAGGACCTGTTTTCTCAA | 1296 | TCAATAACTGCTGGAGATGT GG | High Off-Target Reads, High Unmapped Reads |

TABLE 7-continued

Excluded SNPs

| SNP | SEQ ID NO | First Primer Sequence | SEQ ID NO | Second Primer Sequence | Reasons for exclusion |
|---|---|---|---|---|---|
| rs11745637 | 1297 | GCCCAATCTAATCATGTGAGG | 1298 | GCAGCCAAGAAAGGCTGT | Low Depth, High Unmapped Reads |
| rs11786747 | 1299 | GGAAAGCAGTGAAGACAGCA | 1300 | TCCTCTTCCCCAGAACTTGA | High Unmapped Reads |
| rs12210929 | 1301 | GTTGGGGCAGTACTCAGCAG | 1302 | TCCTTTACTACATCATGGGTCA | Low Depth |
| rs12287505 | 1303 | GGCCTCCCCTTCATTCAA | 1304 | TTGAACTAGTTTATACACCCAGAA | High Off-Target Reads |
| rs12321981 | 1305 | CACACATACACAAAATAAAGGT | 1306 | CAAAGAAGAAGGAGCAAGG | High Unmapped Reads |
| rs12349140 | 1307 | TTATCCAGGACAGGAAGCTG | 1308 | CCCGGTGATAACAGAACGAT | High Off-Target Reads, High Unmapped Reads |
| rs12448708 | 1309 | CATGGGACTCTAGAGGTAGAA | 1310 | TTTTAATCTCTCTTGCTCTCC | Low Depth, High Unmapped Reads |
| rs12500918 | 1311 | TCATAGAGTAAGCCAGATATAAGC | 1312 | TTTACCAGCCAGCTCAGTCC | High Off-Target Reads, High Unmapped Reads |
| rs12554667 | 1313 | TCCTGAAGGGTAAGCAGGAA | 1314 | ACCAAGGTCTTCCCTCTGC | High Off-Target Reads, Low Depth |
| rs12660563 | 1315 | AGGTCAGCTCAGGGTGAAGT | 1316 | GCTCCATTGAAGGGTAAAGG | High Off-Target Reads |
| rs12711664 | 1317 | TGGAATAGAATGCAATCCTGA | 1318 | AGCCCACACAGGTTGGTAAG | High Unmapped Reads |
| rs12881798 | 1319 | CAGATGCTGCAGGAAACAGA | 1320 | GTGGATCACAGGGTCACCTC | High Off-Target Reads, High Unmapped Reads |
| rs12917529 | 1321 | CCTCAAGCTGGCCTGCAA | 1322 | AAGGCAGGCAAGACGTAGC | Low Depth, High Unmapped Reads |
| rs13019275 | 1323 | CAAATATACTGATTCTGTGGCAAA | 1324 | TGATGCATTGAGATTTTGATGA | High Unmapped Reads |
| rs13042906 | 1325 | CGTCTCCCACATTCTTITGG | 1326 | GGTAGGCTTTGTAACTTGCACTG | High Bias |

TABLE 7-continued

| | | | | | |
|---|---|---|---|---|---|
| | | Excluded SNPs | | | |
| SNP | SEQ ID NO | First Primer Sequence | SEQ ID NO | Second Primer Sequence | Reasons for exclusion |
| rs13267077 | 1327 | TGAATCCTGGCTGGGAAA | 1328 | GCCTCACCTACAAAGCTTATT CA | High Unmapped Reads |
| rs13362486 | 1329 | TGCAGTTTGCTATGCAGTCTT T | 1330 | TGAAGCTACACAGATAAGAA GC | High Unmapped Reads |
| rs17077156 | 1331 | TCATTCTGGGTTACCCTTTTG | 1332 | GCCAGGAAAAGACAGTGCAT | High Unmapped Reads |
| rs17382358 | 1333 | TCTCAGCACAGAGAAGGTGC T | 1334 | GCACATTTATTCACTCAGCAA A | Low Depth |
| rs17699274 | 1335 | TGTCCTCTGTAAACCAGACAA | 1336 | CATTTTCCAAGGTTGTTTCTG T | High Unmapped Reads |

What is claimed is:

1. A method of determining transplant status comprising:

(a) obtaining a biological sample from an organ transplant recipient who has received an organ from a donor;

(b) isolating cell-free nucleic acids from the biological sample;

(c) performing multiplex PCR to amplify one or more SNPs, wherein the one or more SNPs is rs150917, rs163446, rs191454, rs224870, rs232504, rs258679, rs260097, rs376293, rs390316, rs468141, rs500399, rs522810, rs534665, rs535468, rs535689, rs535923, rs567681, rs570626, rs580581, rs600810, rs622994, rs698459, rs707210, rs729334, rs747190, rs751137, rs765772, rs810834, rs827707, rs876901, rs895506, rs930698, rs937799, rs955456, rs974807, rs994770, rs1002142, rs1017972, rs1057501, rs1145814, rs1278329, rs1336661, rs1340562, rs1356258, rs1396798, rs1406275, rs1437753, rs1442330, rs1444647, rs1482873, rs1512820, rs1517350, rs1566838, rs1584254, rs1610367, rs1714521, rs1769678, rs1979581, rs1990103, rs2004187, rs2010151, rs2022962, rs2038784, rs2040242, rs2055451, rs2183830, rs2204903, rs2244160, rs2251381, rs2252730, rs2270541, rs2291711, rs2300857, rs2328334, rs2373068, rs2407163, rs2418157, rs2469183, rs2530730, rs2622244, rs2794251, rs2828829, rs2959272, rs3102087, rs3103810, rs3107034, rs3128687, rs3756508, rs3786167, rs3902843, rs4290724, rs4305427, rs4497515, rs4510132, rs4568650, rs4644241, rs4684044, rs4705133, rs4712565, rs4816274, rs4846886, rs4910512, rs4937609, rs6022676, rs6023939, rs6069767, rs6102760, rs6434981, rs6489348, rs6496517, rs6550235, rs6720308, rs6723834, rs6755814, rs6768883, rs6778616, rs6795216, rs6834618, rs6840915, rs6848817, rs6872422, rs6902640, rs6979000, rs7006018, rs7045684, rs7176924, rs7215016, rs7321353, rs7325480, rs7539855, rs7568190, rs7580218, rs7609643, rs7632519, rs7660174, rs7711188, rs7765004, rs7816339, rs7829841, rs7916063, rs7932189, rs7968311, rs8006558, rs8054353, rs8084326, rs8097843, rs9289086, rs9310863, rs9311051, rs9356755, rs9544749, rs9547452, rs9814549, rs9861140, rs9919234, rs9955796, rs10073918, rs10096021, rs10197959, rs10233000, rs10444584, rs10473372, rs10777309, rs10783507, rs10802949, rs10816273, rs10817141, rs10892855, rs11098234, rs11119883, rs11157734, rs11166916, rs11223738, rs11247709, rs11611055, rs11627579, rs11636944, rs11643312, rs11738080, rs11750742, rs11774235, rs11785511, rs11924422, rs11928037, rs11943670, rs12332664, rs12470927, rs12603144, rs12635131, rs12669654, rs12825324, rs12999390, rs13125675, rs13155942, rs17361576, or rs17648494, thereby obtaining one or more targeted amplification products (d) obtaining a measurement of an amount of each allele of one or more SNPs in the targeted amplification products, wherein (i) none of the SNPs has a reference allele and alternate allele combination of A_G, G_A, C_T, and T_C, (ii) each of the one or more SNPs has a minor population allele frequency of 15%-49%;

(e) detecting a donor specific allele using a computer algorithm based on the measurement of the one or more SNPs targets, whereby detecting one or more donors specific circulating cell-free nucleic acids; and (f) detecting tissue injury based on a presence or amount of said one or more donor-specific circulating nucleic acids, whereby determining transplant status.

2. The method of claim 1, wherein the organ is a solid organ from an allogeneic source.

3. The method of claim 1, the method further comprising determining a donor-specific circulating nucleic acid fraction based on the amount of the SNPs targets that are specific for donor and a total amount of the SNPs targets in the circulating cell-free nucleic acids in the biological sample.

4. The method of claim 1, wherein the biological sample from an organ transplant recipient is a bodily fluid, wherein the bodily fluid comprises one or more of blood, serum, plasma, saliva, tears, urine, cerebral, spinal, fluid, mucosal secretion, peritoneal fluid, ascitic fluid, vaginal secretion, breast fluid, breast milk, lymph fluid, cerebrospinal fluid, sputum, and stool.

5. The method of claim 1, wherein the organ donor's genotype is not known for the one or more SNPs targets prior to the transplant status determination, wherein a recipient's genotype is known for the one or more SNPs prior to the transplant status determination, wherein the (e) identifying donor specific allele and/or determining a donor-specific circulating nucleic acid fraction comprises:

I) filtering out 1) SNPs which are present in the recipient and the donor in a genotype combination of $AB_{recipient}$ $AB_{donor}$, $AB_{recipient}$ $AA_{donor}$, and $AB_{recipient}$ $BB_{donor}$;

II) performing the computer algorithm on a data set consisting of measurements of the remaining SNPs to form a first cluster and a second cluster, wherein the first cluster comprises SNP targets that are present in the recipient and the donor in a genotype combination of $AA_{recipient}$ $AB_{donor}$, or $BB_{recipient}$ $AB_{donor}$, and wherein the second cluster comprises SNPs that are present in the recipient and the donor in a genotype combination of $AA_{recipient}$ $BB_{donor}$ or $BB_{recipient}$ $AA_{donor}$; and III) detecting the donor specific allele based on the presence of the remaining SNPs in the one or more SNPs targets in the biological sample.

6. The method of claim 1, wherein the recipient's genotype for the one or more SNPs prior to the transplant status determination is not known, wherein a donor's genotype for the one or more SNPs targets is known prior to the transplant status determination, wherein the (e) detecting the donor specific allele comprise:

I) filtering out 1) SNPs targets which are present in the recipient and the donor in a genotype combination of $AA_{recipient}/AA_{donor}$ or $AB_{recipient}$ $AA_{donor}$ and a donor allele frequency is less than 0.5, and 2) SNPs which are present in the recipient and the donor in a genotype combination of $BB_{recipient}/BB_{donor}$ and $AB_{recipient}$ $BB_{donor}$, and the donor allele frequency is larger than 0.5; and I) detecting the donor specific alleles based on the presence of the remaining SNPs in the biological sample.

7. The method of claim 1, wherein neither the recipient nor the organ donor are genotyped for the one or more SNPs targets prior to the transplant status determination, wherein the (e) detecting donor-specific allele and/or determining donor-specific nucleic acid fraction comprises:

I) performing the computer algorithm on a data set consisting of measurements of the amounts of the one or more SNPs to form a first cluster comprising informative SNPs and a second cluster comprising non-informative SNPs, wherein the informative SNP are present in the recipient and the donor in a genotype combination of $AA_{recipient}/AB_{donor}$, $BB_{recipient}$ $AB_{donor}$, $AA_{recipient}/BB_{donor}$, or $BB_{recipient}$ $AA_{donor}$ and wherein the non-informative SNPs are present in the recipient and the donor in a genotype combination of $AB_{recipient}/AB_{donor}$, $AB_{recipient}$ $AA_{donor}$, Or $AB_{recipient}/BB_{donor}$; and II) detecting the donor specific allele based on the presence of the informative SNPs in the first cluster.

8. The method of claim 1, wherein the algorithm comprises one or more of the following: (i) a fixed cutoff algorithm, (ii) a dynamic clustering algorithm, and (iii) an individual SNP target threshold algorithm.

9. The method of claim 8, wherein the fixed cutoff algorithm detects donor-specific nucleic acids if a deviation between a measured frequency of a reference allele of the one or more SNPs in the cell-free nucleic acids in the sample and an expected frequency of the reference allele in a reference population is greater than the fixed cutoff, wherein the expected frequency for the reference allele is in a range of 0.00-0.03 if the recipient is homozygous for the alternate allele, 0.40-0.60 if the recipient is heterozygous for the alternate allele, or 0.97-1.00 if the recipient is homozygous for the reference allele.

10. The method of claim 9, wherein the recipient is homozygous for the reference allele, and the fixed cutoff algorithm detects the donor-specific nucleic acids if the measured allele frequency of the reference allele of the one or more SNPs is less than the fixed cutoff, or wherein the recipient is homozygous for the alternate allele, and the fixed cutoff algorithm detects donor-specific nucleic acids if the measured allele frequency of the reference allele of the one or more SNPs is greater than the fixed cutoff.

11. The method of claim 8, wherein the fixed cutoff is based on a homozygous allele frequency of a reference or alternate allele of the one or more SNPs in a reference population, or wherein the fixed cutoff is based on a percentile value of distribution of a homozygous allele frequency of the reference or alternate allele of the one or more SNPs in a reference population.

12. The method of claim 11, wherein the percentile is at least 90.

13. The method of claim 8, wherein identifying one or more cell-free nucleic acids as donor-specific nucleic acids using the dynamic clustering algorithm comprises (i) stratifying the one or more SNPs in the cell-free nucleic acids into recipient homozygous group and recipient heterozygous group based on a measured allele frequency for a reference allele or an alternate allele of each of the SNPs;

(ii) further stratifying recipient homozygous groups into non-informative and informative groups; and (iii) measuring the amounts of one or more SNPs in the informative groups.

14. The method of claim 13, wherein the dynamic clustering algorithm is a dynamic Kmeans algorithm.

15. The method of claim 8, wherein the individual SNPs target threshold algorithm identifies the one or more nucleic acids as donor-specific nucleic acids if the allele frequency of each of the one or more of the SNPs is greater than a threshold.

16. The method of claim 15, wherein the threshold is based on the homozygous allele frequency of each of the one or more SNPs in a reference population, or wherein the threshold is a percentile value of a distribution of the homozygous allele frequency of each of the one or more SNPs in the reference population.

17. The method of claim 1, wherein the amount of each allele of the one or more SNPs in the targeted amplification products is detected by at least one assay selected from the group consisting of high-throughput sequencing, capillary electrophoresis and digital polymerase chain reaction (dPCR).

18. The method of claim 17, wherein the method further comprises targeted amplification using a forward and a reverse primer designed specifically for a native genomic nucleic acid and a variant oligonucleotide that contains a single nucleotide substitution as compared to a native sequence, wherein the variant oligonucleotide is added to the amplification reaction in a known amount wherein the method further comprises:

determining a ratio of an amount of the amplified native genomic nucleic acid to the amount of the amplified variant oligonucleotide, determining a total copy number of genomic DNA by multiplying the ratio with the amount of the variant oligonucleotide added to the amplification reaction.

19. The method of claim 1, wherein the method further comprises determining a total copy number of genomic DNA in the circulating cell-free nucleic acids in the biological sample and determining a copy number of the donor-specific nucleic acid by multiplying a donor specific circulating nucleic acid fraction and the total copy number of genomic DNA.

20. The method of claim 3, wherein the transplant status is determined as rejection if the donor-specific circulating nucleic acid fraction is greater than a predetermined threshold, and wherein the transplant status is determined as acceptance if the donor-specific circulating nucleic acid fraction is less than a predetermined threshold.

21. The method of claim 19, wherein the transplant status is determined as rejection if the copy number of the donor-specific nucleic acid is greater than a predetermined threshold, and wherein the transplant status is determined as acceptance if the copy number of the donor-specific nucleic acid is less than a predetermined threshold.

22. The method of claim 1, further comprising monitoring the transplant status at different times post-translation, wherein the transplant status is monitored at one or more time points comprising an earlier time point and at least one later time point wherein all time points are post transplantation, and wherein an increase in the donor-specific circulating cell-free nucleic acid fraction or an increase in a copy number of the donor-specific circulating cell-free nucleic acid from the earlier time point as compared to the at least one later time point is indicative of developing transplant rejection, wherein the time interval between the earlier time point and the at least one later time point is at least 7 days.

23. The method of claim 22, wherein the earlier time point is between 0 days to one year following transplantation, and/or wherein the later time point is between 7 days to five years following transplantation.

24. The method of claim 22, further comprising advising administration of immunosuppressive therapy to the organ transplant recipient or advising modification of the organ transplant recipient's immunosuppressive therapy if the monitoring indicates that the organ transplant recipient develops transplant rejection.

\* \* \* \* \*